United States Patent [19]
Jarrell

[11] Patent Number: 6,150,141
[45] Date of Patent: Nov. 21, 2000

[54] INTRON-MEDIATED RECOMBINANT TECHNIQUES AND REAGENTS

[75] Inventor: Kevin A. Jarrell, Lincoln, Mass.

[73] Assignee: Trustees of Boston University, Boston, Mass.

[21] Appl. No.: 08/814,412

[22] Filed: Mar. 11, 1997

Related U.S. Application Data

[63] Continuation-in-part of application No. 08/488,015, Jun. 7, 1995, Pat. No. 5,780,272, which is a continuation-in-part of application No. 08/119,512, Sep. 10, 1993, Pat. No. 5,498,531.

[51] Int. Cl.$^7$ .......................... C12P 19/34; C12N 15/64; C07H 21/04
[52] U.S. Cl. .................... 435/91.31; 435/91.1; 435/91.3; 435/91.4; 435/91.5; 536/23.1
[58] Field of Search .............................. 435/91.31, 172.1, 435/172.3, 91.5, 91.32, 91.3, 69.1, 91.1, 235.1, 91.42, 91.4, 91.51; 536/23.1, 23.2, 24.1, 23.5, 23.7, 23.53

[56] References Cited

U.S. PATENT DOCUMENTS

| | | | |
|---|---|---|---|
| 4,935,357 | 6/1990 | Szybalski | 435/91.53 |
| 5,498,531 | 3/1996 | Jarrell | 435/91.31 |
| 5,523,221 | 6/1996 | Weiner | 435/91.2 |
| 5,595,895 | 1/1997 | Miki et al. | 435/488 |
| 5,605,793 | 2/1997 | Stemmer | 435/6 |
| 5,641,673 | 6/1997 | Hazeloff et al. | 435/325 |
| 5,667,969 | 9/1997 | Sullenger et al. | 435/6 |
| 5,688,670 | 11/1997 | Szostak et al. | 435/91.21 |
| 5,780,272 | 7/1998 | Jarrell | 435/91.31 |

FOREIGN PATENT DOCUMENTS

| | | |
|---|---|---|
| 0 773 294 A2 | 5/1997 | European Pat. Off. . |
| 0 773 294 A3 | 9/1997 | European Pat. Off. . |
| WO 91/02077 | 2/1991 | WIPO . |
| WO 94/16736 | 8/1994 | WIPO . |
| WO 95/07351 | 3/1995 | WIPO . |
| WO 95/13379 | 5/1995 | WIPO . |

OTHER PUBLICATIONS

Agabian et al., "Trans Splicing of Nuclear Pre–mRNAs" *Cell*, vol. 61, pp. 1157–1160, Jun. 29, 1990.
Augustin et al., "Reverse self–splicing of group II introl RNAs in vitro" *Nature*, vol. 343, pp. 383–386, Jan. 25, 1990.
Beaudry et al., "Directed Evolution of an RNA Enzyme" *Science*, vol. 257, pp. 635–641, Jul. 31, 1992.
Been et al., "One Binding Site Determines Sequence Specificity of Therahymena Pre–rRNA Self–Splicing, Trans–Splicing, and RNA Enzyme Activity" *Cell*, vol. 47, pp. 207–216, Oct. 24, 1986.
Blumenthal et al., "Cis and trans mRNA splicing in *C. elegans*" *TIG*, vol. 4(11), pp. 305–308, Nov. 1988.
Blumenthal, Tom, "Mammalian Cells Can Trans–splice. But Do They?" *BioEssays*, vol. 15(5), pp. 347–348, May, 1993.
Blumenthal, Thomas, "Trans–splicing and polycistronic transcription in *Caenorhabditis elegans*" *TIG*, vol. 11(4), pp. 132–136, Apr., 1995.

Bonen et al., "Trans–splicing of pre–mRNA in plants, animals and protists" the *FASEB Journal*, vol. 7, pp. 40–46, Jan. 1993.
Buckler et al., "Exon amplication; A strategy to isolate mammalian genes based on RNA splicing" *Proceedings of The National Academy of Sciences*, vol. 88, pp. 4005–4009, May 1991.
Burgess et al., "A Mechanism to Enhance mRNA Splicing Fidelity: The RMA–Dependent ATPase Prp16 Usage of a Discard Pathway for Aberrant Lariant Intermediates" *Cell*, vol. 73, pp. 1377–1391, Jul. 2, 1993.
Burke et al., "Sequences and Classification of Group I and Group II Introns" *Methods in Enzymology*, vol. 180, pp. 533–545, 1989.
Bryk et al., "Spontaneous shuffling of domains between introns of phage T4" *Nature*, vol. 346, pp. 394–396, Jul. 26, 1990.
Burke John M., "Sequences and Classification of Group I and Group II Introns" *Proc. Natl. Acad. Sci. U.S.A.*, vol. 85, pp. 533–545, 1988.
Campbell et al., "Alternative Approaches for the Application of Ribozymes as Gene Therapies for Retroviral Infections" *Advances in Pharmacology*, vol. 33, pp. 143–178, 1995.
Cech et al., "Self–Splicing of Group I Introns" *Annu. rev. Biochem.*, vol. 59, pp. 543–568, 1990.
Chapdelaine et al., "The Wheat Mitochondrial Gene for Subunit I of the NADH dehydrogenase Complex: A Trans–splicing Model for This Gene–in–Pieces" *Cell*, vol. 65, pp. 465–472, May 3, 1991.
Conklin et al., "Multiple trans–splicing events are required to produce a mature nad1 transcript in a plant mitrochondrin" *Genetics and Devel., Cornell Univ., Ithaca, NY 14853, USA*, pp. 1–9, May 31, 1991.
Conrad et al., "Conversion of a trans–spliced *C. elegans* gene into a conventional gene by introduction of a spice doner site" the *EMBO J.*, vol. 12(3), pp. 1249–1255, 1993.
Conrad et al., Insertion of Part of an Intron into the 5' Untrasnlated Region of a *Caenorhabditis elegans* Gene Converts It into a trans–Spliced Gene, *Molec. and Cellul. Biol.*, vol. 11(4) pp. 1921–1926, Apr. 1991.

(List continued on next page.)

*Primary Examiner*—Nancy Degen
*Attorney, Agent, or Firm*—Choate, Hall & Stewart; Sam Pasternack; Brenda Herschbach Jarrell

[57] ABSTRACT

The present invention makes available methods and reagents for novel manipulation of nucleic acids. As described herein, the present invention makes use of the ability of intronic sequences, such as derived from group I, group II, or nuclear pre-mRNA introns, to mediate specific cleavage and ligation of discontinuous nucleic acid molecules. For example, novel genes and gene products can be generated by admixing nucleic acid constructs which comprise exon nucleic acid sequences flanked by intron sequences that can direct trans-splicing of the exon sequences to each other. The flanking intronic sequences can, by intermolecular complementation, form a reactive complex which promotes the transesterification reactions necessary to cause the ligation of discontinuous nucleic acid sequences to one another, and thereby generate a recombinant gene comprising the ligated exons.

19 Claims, 64 Drawing Sheets

OTHER PUBLICATIONS

Cotten et al., "Ribozyme mediated destruction of RNA in vivo" the *EMBO J.*, vol. 8(12), pp. 3861–3866, 1989.

Couto et al., "A trans–acting suppressor restores splicing of a yeast intron with a branch point mutation" *Genes & Development, Cold Spring Harbor Lab.*, pp. 445–455, 1987.

Chuat et al., "Can Ribosymes Be Used to Regulate Procaryote Gene Expression?" *Biochem. and Biophys. Res. Commun.*, vol. 162(3), pp. 1025–1029, 1989.

Cripe et al., "Structure of the Gene for Human Coagulation Factor V" *Biochemistry*, vol. 31, pp. 3777–3785, 1992.

Da'Dara et al., "A novel trans–spliced mRNA from *Onchocerca volvulus* encodes a functional S–adenosylmethionine decarboxylase" *Biochem. J.* vol. 320, pp. 519–530, 1996.

Davis et al., RNA Trans–splicing in Flatworms *J. Biol. Chem.*, vol. 270(37), pp. 21813–21819, Sep. 15, 1995.

De Giorgi et al., "A silent trans–splicing signal in the cuticlin–encoding gene of the plant–parasitic nematode Meloidogyne artiellia." *Gene*, vol. 170(2), pp. 261–265, 1996.

De Vries et al., "Artificial Exon Shuffling between Tissue–Type Plasminogen Activator (t–PA) and Urokinase (u–PA): A comparative Study on the Fibrinolytic Properties of t–PA/U–PA Hybrid Proteins" *Biochemistry*, vol. 27, pp. 2565–2572, 1988.

Dib–Hajj, "Domain 5 interacts with domain 6 and influences the second transesterification reaction of group II intron self–splicing", *Nucleic Acids Res.*, vol. 21(8), pp. 1797–1804, Apr. 25, 1993.

Dorit et al., "How Big Is the Universe of Exons?" *Science*, vol. 250, pp. 1377–1382, Dec. 7, 1990.

Doudna et al., "RNA structure not sequence, determines the 5' splice–site specificity of a group I intron" *Proceedings of the National Academy of Sciences*, vol. 86, pp. 7402–7406, Oct. 1989.

Eul, et al., "Experimental evidence for RNA trans–spicing in mammalian cells", *EMBO J.*, vol. 14(13), pp. 3226–3235, Jul. 3, 1995.

Eul et al., "Trans–splicing and alternative–tandem–cis–splicing: two ways by which mammalian cells generate a truncated SV40 T–antigen" *Nucleic Acids Res.*, vol. 24(9), pp. 1653–1661, May 1, 1996.

Fedorov et al., "Analysis of nonuniformity in intorn phase distribution" *Nucleic Acid Research*, vol. 20(10), pp. 2553–2557, 1992.

Franzen et al. "Kinetic analysis of the 5' splice junction hydrolysis of a group II intron promoted by domain 5" *Nucleic Acid Research*, vol. 21(3), pp. 627–634, 1993.

Galloway et al., "Deletion–tolerance and Trans–splicing of the Bacteriophage T4 td Intron" *J. Mol. Biol.* vol. 211, pp. 537–549, 1990.

Garriga et al., "Mechanism of recognition of the 5' splice site in self–splicing group I introns" *Nature*, vol. 322, pp. 86–89, Jul. 3, 1986.

Ghetti et al., "In vitro trans–splicing in Saccharomyces cerevisiae" *Proc. Natl. Acad. Sci. USA*, vol. 92(25), pp. 11461–11464, Dec. 5, 1995.

Goldschmidt–Clermont et al., "A Small Cholorplast RNA May Be Required for Trans–Splicing in *Chlamydomonas reinhardtii*" *Cell*, vol. 65, pp. 135–143, Apr. 5, 1991.

Goldschmiti–Clermont et al., "Trans–splicing mutants of *Chlamydomonas reinhardtii*" *Mol. Gen.Genet.*, vol. 223, pp. 417–425, Sep. 1990.

Hall et al., "Exon shuffling by recombination between self–splicing introns of bacteriophage T4" *Nature*, vol. 340, pp. 574–576, Aug. 17, 1989.

Herrin et al., "trans–splicing of transcripts for the chloroplast psaA1 gene" *J. Biol. Chem.*, vol. 263(29), pp. 14601–14604, Oct. 15, 1988.

Herzog et al., "Overlapping Gene Structure of the Human Neuropeptide Y Receptor Subtypes Y1 and Y5 Suggests Coordinate Transcriptional Regulation" *Genomics*.vol. 41(3), pp. 315–319, May 1997.

Hetzer et al., "Trans–activation of group II intron splicing by nuclear U5 snRNA" *Nature*, vol. 386(6623), pp. 417–420, Mar. 27, 1997.

Holländer et al., "Splicing of the mitochondrial group–II intron rl1: conserved intron–exon interactions diminish splicing efficiency" *Curr Genet.vol.* 33(2), pp. 117–123, Feb. 1998.

Jacquier et al., "Efficient Trans–Splicing of a Yeast Mitochondrial RNA Group II Intron Implicates a Strong 5' Exon–Intron Interaction" *Science*, vol. 234, pp. 1099–1104, Nov. 28, 1986.

Jacquier et al., "Multiple Exon–Binding Sites in Class II Self–Splicing Introns" *Cell*, vol. 50, pp. 17–29, Jul. 3, 1987.

Jarrell et al., "Group II Intron Domain 5 Facilitates a trans–Splicing Reaction" *Molecular and Cell. Biol.*, vol. 8, No. 6, pp. 2361–2366, Jun. 1988.

Jarrell et al., "Group II Intron Self–splicing" *J. Biol. Chem.*, vol. 263(7), pp. 3432–3439, Mar. 5, 1988.

Jones et al., "Evaluating and enhancing ribozyme reaction efficiency in mammalian cells" *Nature Biotech.*, vol. 15, pp. 902–905, Sep. 1997.

Jones et al., "Tagging ribozyme reaction sites to follow trans–splicing in mammalian cells" *Nat. Med.*, vol. 2(6), pp. 643–648, Jun. 1996.

Kim et al., "Pre–mRNA splicing within an assembled yeast spliceosome requires an RNA–dependent ATPase and ATP hydrolysis" *Proc.Natl. Acad. Sci.*, vol. 90, pp. 888–892, Feb. 1993.

Knoop et al., "A tripartite group II intron in mitochondria of an angiosperm plant" *Mol Gen Genet.*, vol. 255(3), pp. 269–276, Dec. 1996.

Knoop et al, "Promiscuous mitochondrial group II intron sequences in plant nuclear genomes" *J Mol Evol.*, vol. 39(2), pp. 144–150, Aug. 1994.

Knoop et al., "Trans splicing integrates an exon of 22 nucleotides into the nad5 mRNA in higher plant mitochondria" *EMBO J.*, vol. 10(11), pp. 3483–3493, 1991.

Koch et al., "Group II Introns Deleted for Multiple Substructures Retain Self–Splicing Activity" *Molec.and Cell. Biol.*, vol. 12(5), pp. 1950–1958, May 1992.

Kohchi et al., "A nicked group II intron and trans–splicing in liverwort, *Marchantia polymorpha*, chloroplasts" *Nucleic Acids Res.*, vol. 16(21), pp. 10025–10036, Nov. 11, 1988.

Koller et al., "Evidence for In Vivo Trans Splicing of Pre–mRNAs in Tobacco Chloroplasts" *Cell*, vol. 48(1), pp. 111–119, Jan. 16, 1987.

Konarska et al., "Trans Splicing of mRNA Precursors In Vitro" *Cell*, vol. 42, pp. 165–171, Aug. 1985.

Lan et al., "Ribozyme–Mediated Repair of Sickle β–Globin mRNAs in Erythrocyte Precursors" *Science*, vol. 280(5369), pp. 1593–1596, Jun. 5, 1998.

Langer–Safer et al., "Replacement of Finger and Growth Factor Domains of Tissue Plasminogen Activator with Plasminogen Kringle 1" *The Journal of Biological Chemistry*, vol. 266(6), pp. 3715–3723, Feb. 25, 1991.

Lee et al, "Conservation of gene organization and trans-splicing in the glyceraldehyde -3-phosphate dehydrogenase-encoding genes of *Caenorhabditis briggsae*" *Gene.*, vol. 121(2), pp. 227-235, Nov. 16, 1992.

Lücke et al., "Spliced leader RNA of trypanosomes: in vivo mutational analysis reveals extensive and distinct requirements for trans splicing and cap4 formation" *EMBO J.*, vol. 15(16), pp. 4380-4391, 1996.

Malek, et al., "Evolution of trans-splicing plant mitochondrial introns in pre-Permain times", *Proc. Natl. Acad. Sci. USA.*, vol. 94(2), pp. 553-558, Jan. 21, 1997.

Maroney et al., "Intramolecular base pairing between the nematode spliced leader and its 5' splice site is not essential for trans-splicing in vitro", *EMBO J.*, vol. 10(12), pp. 3869-3875, Dec. 1991.

Metzenberg et al., "Human and fungal 3' splice sites are used by *Trypanosoma brucei* for trans splicing" *Mol Biochem Parasitol.*, vol. 83(1), pp. 11-23, Dec. 2, 1996.

Michel et al., "Comparative and functional anatomy of group II catalytic introns: a review" *Gene*, vol. 82, pp. 5-30, 1989.

Miller et al., "trans splicing in *Leishmaina enrietti* and identification of ribonucleoprotein complexes containing the spliced leader and U2 equivalent RNAs" *Mol Cell Biol.*, vol. 8(6), pp. 2597-2603, Jun. 1988.

Mohr et al., "Integration of a group I intron into a ribosomal RNA sequence promoted by a tyrosyl-tRNA synthetase" *Nature*, vol. 354(6349), pp. 164-167, Nov. 14, 1991.

Morawala-Patell et al., "Cis- and trans-splicing and RNA editing are required for the expression of nad2 in wheat mitochondria" *Mol Gen Genet.*, vol. 258(5), pp. 503-511.

Mörl et al., "Group II intron RNA-catalyzed recombination of RNA in vitro" *Nucleic Acids Research*, vol. 18(22), pp. 6545-6551, 1990.

Mörl et al., "New reactions Catalyzed by Group II Intron Ribozyme with RNA and DNA Substrates" *Cell*, vol. 70, pp. 803-810, Sep. 4, 1992.

Mörl et al., "Integration of Group II Intron bl1 into a Foreign RNA by Reversal of the Self-Slicing Reaction In Vitro" *Cell*, vol. 60, pp. 629-636, Feb. 23, 1990.

Mohr et al., "Integration of a group I intron into a ribosomal RNA sequence promoted by a tyrosyl-tRNA synthetase" *Nature*, vol. 354, pp. 164-167, Nov. 14, 1991.

Mueller et al., "Group II Intron RNA Catalysis of Progressive Nucleotide Insertion: A Model for RNA Editing" *Science*, vol. 261, pp. 1035-1037, Aug. 20, 1993.

Murphy et al., "Identification of a Novel Y Branch Structure as an Intermediate in Trypanosome mRNA Processing: Evidence for Trans Splicing" *Cell*, vol. 47(4), pp. 517-525, Nov. 21, 1986.

Ny et al., "The structure of the human tissue-type plasonogen activator gene: Gorrelation of intron and exon structures to functional and structural domains" *Proceedings of the National Academy of Sciences*, vol. 81, pp. 5355-5359, Sep. 1984.

Patthy et al., "Intron-dependent evolution: preferred types of exons and introns" *FEBS Letters*, vol., 214(1), pp. 1-7, Apr. 1987.

Peebles et al., "Group II Intron Selt-splicing: Development of Alternative Reaction Conditions and Identification of a Predicted Intermediate" *Cold Spring Harbor Symposia on Quantitative Biology*, vol. LII, pp. 223-232, 1987.

Peebles et al., "Mutation of the Conserved First Nucleotide of a Group II Intron from Yeast Mitochondrial DNA Reduces the Rate But Allows Accurate Splicing" *The Journal of Biological Chemistry*, vol. 268(16), pp. 11929-11938, Jun. 5, 1993.

Pereia de Souza et al., "A trans-splicing model for the expression of the tripartite nad5 gene in wheat and maize mitochondria" *Plant Cell*, vol. 3(12), pp. 1363-1378, Dec., 1991.

Phylactou et al., "Ribozyme-mediated trans-splicing of a trinucleotide repeat" *Nat Genet.*, vol. 18(4), pp. 378-381, Apr. 1998.

Puttaraju et al., "Group I permuted intron-exon (PIE) sequences self-splice to produce circular exons" *Nucleic Acids Res.*, vol. 20(20), pp. 5357-5364, 1992.

Saldanha et al., "Group I and group II introns" *The FASEB Journal*, vol. 7, pp. 15-24, Jan. 1993.

Salvo et al., "Deletion-tolerance and trans-splicing of the bacteriophage T4 td intron" *J Mol Biol.*, vol. 211(3), pp. 537-549, Feb. 5, 1990.

Sargueil et al., "A Shortened Form of the *Tetrahymena thermophila* Group I Intron Can Catalyze the Complete Splicing Reaction in trans" *J Mol Biol.*, vol. 233(4), pp. 629-643, Oct. 20, 1993.

Sarver et al., "Ribozyme trans-splicing and RNA tagging: Following the messenger" *Nat Med.*, vol. 2(6), pp. 641-642, Jun. 1996.

Schmeizer et al., "Self-Splicing of Group II Introns In Vitro: Mapping of the Branch Point and Mutation Inhibition of Lariat Formation" *Cell*, vol. 46, pp. 557-565, Aug. 15, 1986.

Schroeder et al., "Splice-Site Selection and Decoding: Are They Related?" *Science*, vol. 260, pp. 1443-1444, Jun. 4, 1993.

Seidel et al., "Exons as Microgenes?" *Science*, vol. 257, pp. 1489-1490, Sep. 11, 1992.

Sharp et al., "On the Origin of RNA Splicing and Introns" *Cell*, vol. 42, pp. 397-400, Sep. 1985.

Sharp et al., "Trans Splicing: Variation on the Familiar Theme?"*Cell*, vol. 50, pp. 147-148, Jul. 17, 1987.

Solnick et al., "Trans Splicing of mRNA Precursors" *Cell*, vol. 42, pp. 157-164, Aug. 1985.

Steitz et al., "Splicing Takes a Holiday" *Science*, vol. 257, pp. 888-889, Aug. 14, 1992.

Suchy et al., "Restoration of the Self-splicing Activity of a Defective Group II Intron by a Small Trans-acting RNA" *Institut für Genetik Mikrobiologie der Universität München*, pp. 179-187, Academic Press Limited 1991.

Sutton et al., "Trypanosome trans-splicing utilized 2'-5' branches and a corresponding debranching acitivity" *EMBO J.*, vol. 7(5), pp. 1431-1437, 1988.

Sturm et al., "Efficient trans-splicing of Mutated Spliced Leader Exons in *Leishmania tarentolae*" *J. Biol. Chem.*, vol. 273(30), pp. 18689-18692, Jul. 24, 1998.

Sullenger et al., "Colocalizing Ribozymes with Substrate RNSs to Increase Their Efficacy as Gene Inhibitors"*Applice Biochem. and Biotech.*, vol. 54, pp. 57-61, 1995.

Sullenger et al., "Ribozymes-mediated repair of defective mRNA by targeted trans-splicing" *Nature*, vol. 371, Oct. 13, 1995.

Sullenger et al., "Tethering Ribozymes to a Retroviral Packaging Signal for Destruction of Viral RNA" *Science*, vol. 262, pp. 1566-1569, Dec. 3, 1993.

Szostak et al., "Enzymatic activity of the conserved core of a group I self-splicing intron" *Nature*, vol. 322, pp. 83-86, Jul. 3, 1986.

Tasiouka et al., "A modified group I intron can function as both a ribozyme and a 5' exon in a trans–exon ligation reaction" *Gene*, vol. 144, pp. 1–7, 1994.

Tschudi et al., "Destruction of U2, U4, or U6 Small Nuclear RNA Blocks Trans Splicing in Trypanosome Cells" *Cell*, vol. 61, pp. 459–466, May 4, 1990.

Turmel et al., "The trans–spliced intron 1 in the psaA gene of the Chlamydomonas chloroplast: a comparative analysis" *Curr Genet.*, vol. 27, pp. 270–279, 1995.

Ullu et al., "Permeable trypanosome cells as a model system for transcription and trans–splicing" *Nucleic Acids Res.*, vol. 18(11), pp. 3319–3326, 1990.

Von Ahesen et al., "Footprinting the Sites of Interaction of Antibiotics with Catlytic Group I Intron RNA" *Science*, vol. 260(12), 1500–1503, Jun. 4, 1993.

Wallasch et al., "Structural requirements for section of 5'- and 3' splice sites of group II introns" *Nucleic Acids Research*, vol. 19(12), pp. 3307–3314, 1991.

Wang et al., "Movement of the Guide Sequece During RNA Catalysis by a Group I Ribozyme" *Science*, vol. 260, pp. 504–508, Apr. 23, 1993.

Watakabe et al., "The role of exon sequences in splice site selection" *Genes & Devel., Cold Spring Harbor Laboratory Press*, vol. 7, pp. 407–418, 1993.

Winter et al., "The mechanism of group I self–splicing: an internal guide sequence can be provided in trans" *EMBO J.*, vol. 9(6), pp. 1923–1928, 1990.

Wissinger et al., "Trans Splicing in *Oenothera Mitochondria*: nad1 mRNAs Are Edited in Exon and Trans–Splicing Group II Intron Sequences" *Cell.* vol. 65(3),pp. 473–482, May 3, 1991.

Woodson et al., "Reverse Self–Splicing of the Tetrahymena Group I Intron: Implication of the Directionality of Splicing and for Intron Transposition" *Cell*, vol. 57, pp. 335–345, Apr. 21, 1989.

Xiang et al., "Sequence Specificity of a Group II Intron Ribozyme: Multiple Mechanisms for Promoting Unusually High Discrimination against Mismatched Targets" *Biochem.*, vol. 37, pp. 3839–3849, Feb. 27, 1998.

Dube et al., (1989) Biochemistry, vol. 28(14), pp. 5703–5707.

Beaudry et al., (1992) Science, vol. 257, pp. 635–641.

Capel et al., "Circular transcripts of the testis–determining gene sry in adult mouse testis", Cell, vol. 73, pp. 1019–1030, Jun. 4, 1993.

Curcio et al., "Hetrohoming: cDNA–mediated mobility of group II introns requires a catalytic RNA", Molecular Genetics Program, Wadsworth Center, NY State Dept. of Health.

Mörl et al., "New reactions catalyzed by a group II intron ribozyme with RNA and DNA substrates", Cell, vol. 70, pp. 803–810, Sep. 4, 1992.

Pasman et al., "Exon circulation in mammalian nuclear extracts", RNA, 2:603–610, 1996.

Yang et al., "Efficient integration of an intron RNA into double–stranded DNA by reverse splicing", Nature, vol. 381, May 23, 1996.

Zimmerly et al., "Group II intron mobility occurs by target DNA–primed reverse transcription", Cell, vol. 82, pp. 545–554, Aug. 25, 1995.

Zimmerly et al., "A Group II intron RNA is a catalytic component of a DNA endonuclease involved in intron mobility", Cell, vol. 83, pp. 529–538, Nov. 17, 1995.

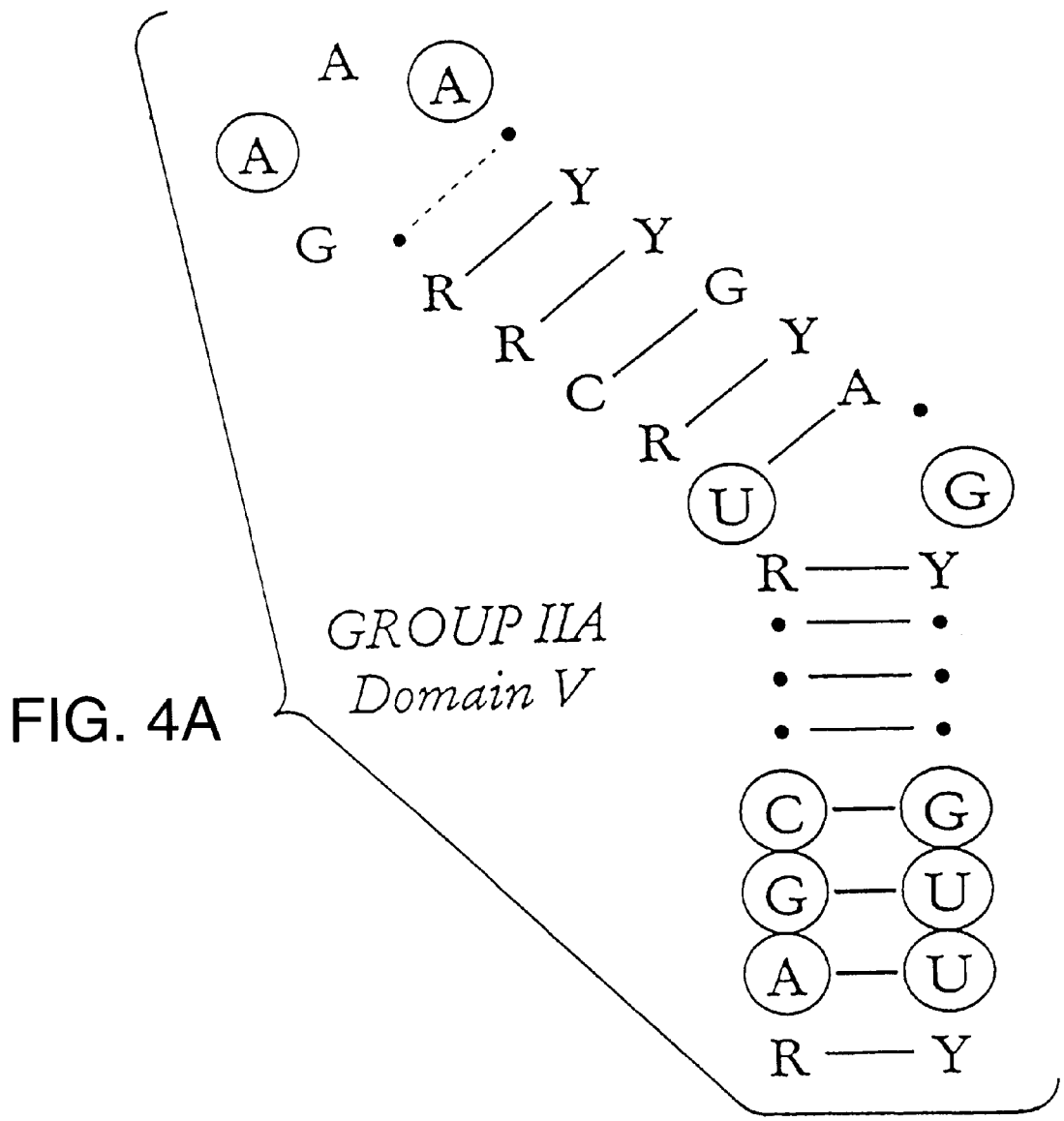
FIG. 4A GROUP IIA Domain V

GROUP IIB
Domain V

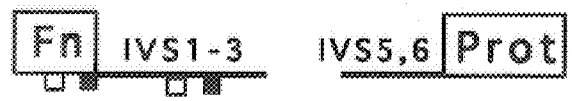
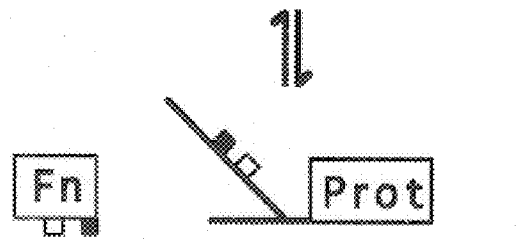
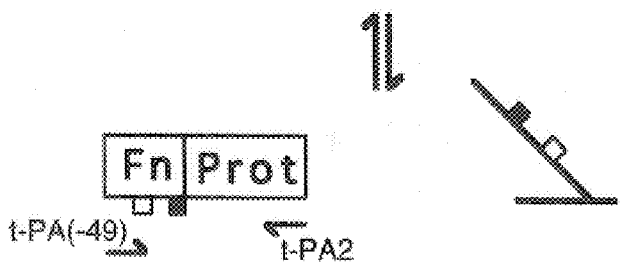
FIG. 16A
OBSERVED
SPLICE
POINT
SEQUENCES          FREQUENCY
| 5'-CAAA | ACCT |    21/24
| 5'-CAA | ACCT |    3/24
FIG. 16C
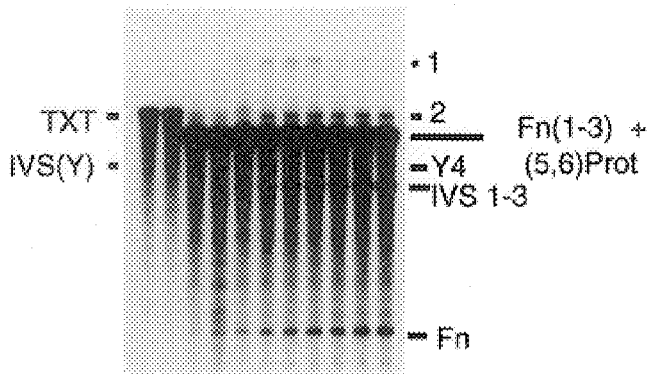
FIG. 16B

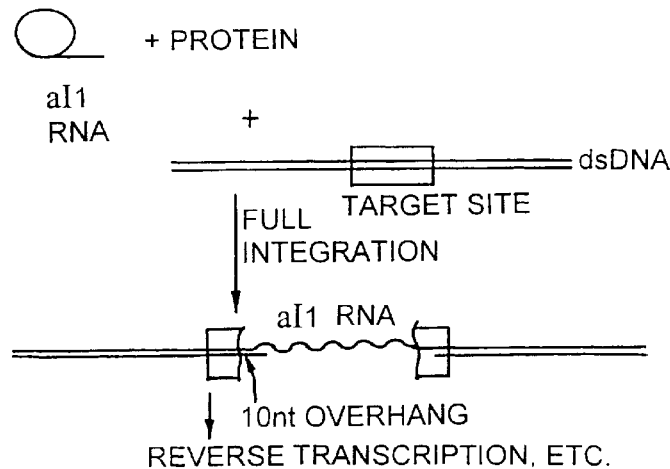
FIG. 22A
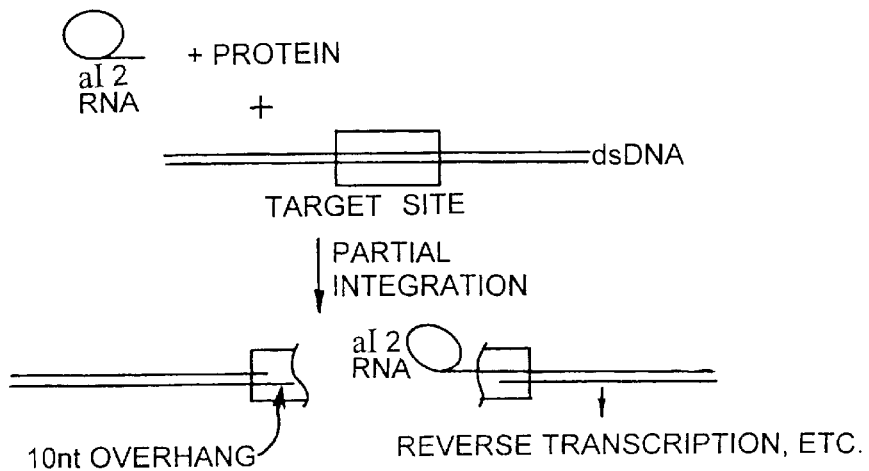
FIG. 22B
FIG. 22

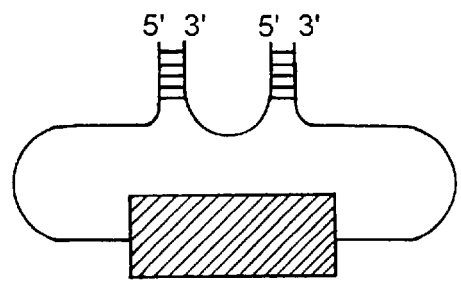
FIG. 36A
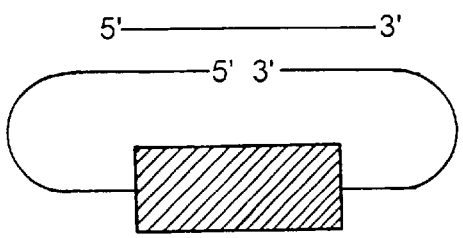
FIG. 36B
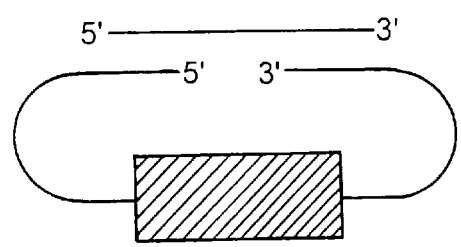
FIG. 36C
FIG. 36

| RNA | IBS2 | IBS1 | EBS2 | EBS1 | $\Delta G°_{37}$ EBS2 IBS2 | $\Delta G°_{37}$ EBS1 IBS1 | Sum of values |
|---|---|---|---|---|---|---|---|
| PY1 | GUGGUG | CAUUUC | CACCAC | GGAAAUG | -11.9 | -7.4 | -19.3 |
| PY8 | ugccug | ugaggga | CACCAC | ucccuca | -2.3 | -14.7 | -17.0 |
| PY9 | ugccug | ugaggga | caggca | ucccuca | -12.2 | -14.7 | -26.9 |

FIG. 38B

1. PY8 and PY9
   1070 nt

2. IVS(Y)
   803 nt

3. K1$_d$(IVS1-3)
   756 nt

4. IVS1-3
   712 nt 5. (IVS5,6)K1
   358 nt 6. (IVS5,6)K1$_u$
   314 nt

7. K1(C)
   267 nt

8. K1
   267 nt

| | $\Delta G°_{37}$ EBS2 IBS2 | $\Delta G°_{37}$ EBS1 IBS1 | Sum of values | Relative splicing rate | Time course data |
|---|---|---|---|---|---|
| PY1 EBS2  CACCAC-5'<br>             \|\|\|\|\|\|<br>EXON 5'-GUGGUGGGACAUUUUC<br>                    \|\|\|\|\|·\|<br>EBS1           GUAAAGG-5' | -11.9 | -7.4 | -19.3 | 100 | 0 1 3 5 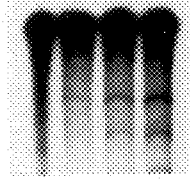 |
| PY2 EBS2  CACCAC-5'<br>             \|\|\|\|\|\|<br>EXON 5'-GUGGUGGGAUGUCAAA<br>                    \|\|\|\|\|\|\|<br>EBS1           ACAGUUU-5' | -11.9 | -10.6 | -22.5 | 10 | 0 10 20 40 |
FIG. 42A
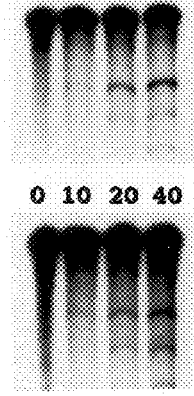

WT

| Ionic reaction conditions | Rate (min⁻¹) | Lariat Intron | Linear Intron |
|---|---|---|---|
| (NH₄)₂SO₄ | .03399 | .769 | .231 |
| NH₄Cl | .06274 | .684 | .316 |
| KCl | .07397 | .204 | .796 |

PY1

| Ionic reaction conditions | Rate (min⁻¹) | Y-Branch Intron | Linear Intron |
|---|---|---|---|
| (NH₄)₂SO₄ | .01795 | .846 | .154 |
| NH₄Cl | .02588 | .705 | .295 |
| KCl | .05187 | .247 | .753 |

PY2

| Ionic reaction conditions | Rate (min⁻¹) | Y-Branch Intron | Linear Intron |
|---|---|---|---|
| (NH₄)₂SO₄ | .00203 | .630 | .370 |
| NH₄Cl | .00795 | .562 | .438 |
| KCl | .03019 | .104 | .896 |

PY3

| Ionic reaction conditions | Rate (min⁻¹) | Y-Branch Intron | Linear Intron |
|---|---|---|---|
| (NH₄)₂SO₄ | .00052 | .684 | .316 |
| NH₄Cl | .00676 | .658 | .342 |
| KCl | .01337 | .158 | .842 |

FIG. 43A

| | Ionic reaction conditions | Rate (min$^{-1}$) | Y-Branch Intron | Linear Intron |
|---|---|---|---|---|
| PY4 | (NH$_4$)$_2$SO$_4$ | .00192 | .652 | .348 |
| | NH$_4$Cl | .01154 | .578 | .422 |
| | KCl | .02255 | .119 | .881 |

| | Ionic reaction conditions | Rate (min$^{-1}$) | Y-Branch Intron | Linear Intron |
|---|---|---|---|---|
| PY5 | (NH$_4$)$_2$SO$_4$ | .00110 | .643 | .357 |
| | NH$_4$Cl | .00486 | .553 | .447 |
| | KCl | .01173 | .253 | .747 |

| | Ionic reaction conditions | Rate (min$^{-1}$) | Y-Branch Intron | Linear Intron |
|---|---|---|---|---|
| PY6 | (NH$_4$)$_2$SO$_4$ | .00112 | .765 | .235 |
| | NH$_4$Cl | .00721 | .707 | .293 |
| | KCl | .01625 | .216 | .784 |

| | Ionic reaction conditions | Rate (min$^{-1}$) | Y-Branch Intron | Linear Intron |
|---|---|---|---|---|
| PY7 | (NH$_4$)$_2$SO$_4$ | .00077 | .613 | .387 |
| | NH$_4$Cl | .00487 | .524 | .476 |
| | KCl | .01288 | .152 | .848 |

FIG. 43B

|  | Ionic reaction conditions | Rate (min⁻¹) | Y-Branch Intron | Linear Intron |
|---|---|---|---|---|
| PY8 | (NH₄)₂SO₄ | .00017 | .605 | .395 |
|  | NH₄Cl | .00361 | .412 | .588 |
|  | KCl | .01571 | .080 | .920 |

|  | Ionic reaction conditions | Rate (min⁻¹) | Y-Branch Intron | Linear Intron |
|---|---|---|---|---|
| PY9 | (NH₄)₂SO₄ | .00052 | .619 | .381 |
|  | NH₄Cl | .00393 | .534 | .466 |
|  | KCl | .01696 | .095 | .905 |

FIG. 43C

IN VITRO GENETICS

CIRCULAR TARGET random sequence enriched for G and U nucleotides

+

ENZYME

EBS I random A and C nucleotides

REVERSE REACTION primer 1     primer 2
EBS I site

INTRON-MEDIATED RECOMBINANT TECHNIQUES AND REAGENTS

PRIOR APPLICATIONS

The present application is a Continuation-in-part of U.S. Ser. No. 08/488,015, filed Jun. 7, 1995 now U.S. Pat. No. 5,780,272, which is a Continuation-in-part of U.S. Ser. No. 08/119,572, filed Sep. 10, 1993, now U.S. Pat. No. 5,498,531. Each of these applications is incorporated herein by reference.

GOVERNMENT RIGHTS

The development of the present invention was supported by grant number MCB-9400562 from the National Science Foundation. The government may have certain rights in the invention.

BACKGROUND OF THE INVENTION

Most eukaryotic genes are discontinuous with proteins encoded by them, consisting of coding sequences (exons) interrupted by non-coding sequences (introns). After transcription into RNA, the introns are removed by splicing to generate the mature messenger RNA (mRNA). The splice points between exons are typically determined by consensus sequences that act as signals for the splicing process.

Structural features of introns and the underlying splicing mechanisms form the basis for classification of different kinds of introns. Since RNA splicing was first described, four major categories of introns have been recognized. Splicing of group I, group II, nuclear pre-mRNA, and tRNA introns can be differentiated mechanistically, with certain group I and group II introns able to be autocatalytically excised from a pre-RNA in vitro in the absence of any other protein or RNA factors. In the instance of the group I, group II and nuclear pre-mRNA introns, splicing proceeds by a two-step transesterification mechanism.

To illustrate, the nuclear rRNA genes of certain lower eukaryotes (e.g., *Tetrahymena thermophila* and *Physarum polycephalum*) contain group I introns. This type of intron also occurs in chloroplast, yeast, and fungal mitochondrial rRNA genes; in certain yeast and fungal mitochondrial mRNA; and in several chloroplast tRNA genes in higher plants. Group I introns are characterized by a linear array of conserved sequences and structural features, and are excised by two successive transesterifications. Splicing of the Tetrahymena pre-rRNA intron, a prototypic group I intron, proceeds by two transesterification reactions during which phosphate esters are exchanged without intermediary hydrolysis. Except for the initiation step, promoted by a free guanosine, all reactive groups involved in the transesterification reactions are contained within the intron sequences. The reaction is initiated by the binding of guanosine to an intron sequence. The unshared pair of electrons of the 3'-hydroxyl group of the bound guanosine can act as a nucleophile, attacking the phosphate group at the 5' exon-intron junction (splice site), resulting in cleavage of the precursor RNA. A free 3'-hydroxyl group is generated at the cleavage site (the end of the 5'exon) and release of the intron occurs in a second step by attack of the 5' exon's $3^1$-hydroxyl group on the 3' splice site phosphate.

Group II introns, which are classed together on the basis of a conserved secondary structure, have been identified in certain organellar genes of lower eukaryotes and plants. The group II introns also undergo self-splicing reactions in vitro, but in this instance, a residue within the intron, rather than added guanosine, initiates the reaction. Another key difference between group II and group I introns is in the structure of the excised introns. Rather than the linear products formed during splicing of group I introns, spliced group II introns typically occur as lariats, structures in which the 5'-phosphoryl end of the intron RNA is linked through a phoshodiester bond to the 2'-hydroxyl group of an internal nucleotide. As with group I introns, the splicing of group II introns occurs via two transesterification steps, one involving cleavage of the 5' splice site and the second resulting in cleavage of the 3' splice site and ligation of the two exons. For example, 5' splice site cleavage results from nucleophilic attack by the 2'-hydroxyl of an internal nucleotide (typically an adenosine) located upstream of the 3' splice site, causing the release of the 5' exon and the formation of a lariat intermediate (so called because of the branch structure of the 2',5' phosphodiester bond thus produced). In the second step, the 3'-end hydroxyl of the upstream exon makes a nucleophilic attack on the 3' splice site. This displaces the intron and joins the two exons together.

Eukaryotic nuclear pre-mRNA introns and group II introns splice by the same mechanism; the intron is excised as a lariat structure, and the two flanking exons are joined. Moreover, the chemistry of the two processes is similar. In both, a 2 hydroxyl group within the intron serves as the nucleophile to promote cleavage at the 5' splice site, and the 3' hydroxyl group of the upstream exon is the nucleophile that cleaves the 3' splice site by forming the exon-exon bond. However, in contrast to the conserved structural elements that reside within group I and II introns, the only conserved features of nuclear pre-mRNA introns are restricted to short regions at or near the splice junctions. In yeast, these motifs are (i) a conserved hexanucleotide at the 5' splice, (ii) an invariant heptanucleotide, the UACUAAC Box, surrounding the branch point A, (iii) a generally conserved enrichment for pyrimidine residues adjacent to the invariant AG dinucleotide at the 3' splice site. Further characteristics of nuclear pre-mRNA splicing in vitro that distinguish it from autocatalytic splicing are the dependence on added cell-free extracts, and the requirement for adenosine triphosphate (ATP). Another key difference is that nuclear pre-mRNA splicing generally requires multiple small nuclear ribonucleoproteins (snRNPs) and other accessory proteins, which can make-up a larger multi-subunit complex (splicesome) that facilitates splicing.

SUMMARY OF THE INVENTION

The present invention makes available methods and reagents for novel manipulation of nucleic acids. As described herein, the present invention makes use of the ability of intronic sequences, such as derived from group I, group II, or nuclear pre-mRNA introns, to mediate specific cleavage and ligation of discontinuous nucleic acid molecules. For example, novel genes and gene products can be generated by admixing nucleic acid constructs comprising "exon" nucleic acid sequences flanked by intron sequences that can direct trans-splicing of the exon sequences to each other. The flanking intronic sequences, by intermolecular complementation between the flanking intron sequences of two different constructs, form a functional intron which mediates the transesterification reactions necessary to cause the ligation of the discontinuous nucleic acid sequences to one another, and thereby generate a recombinant gene comprising the ligated exons. As used herein, the term exon denotes nucleic acid sequences, or exon "modules", that can, for instance, encode portions of proteins or polypeptide chains, such as corresponding to naturally occurring exon sequences or naturally occurring exon sequences which have been mutated (e.g. point mutations, truncations, fusions), as well as nucleic acid sequences from "synthetic exons" including sequences of purely random construction. However, the term "exon", as used in the present invention, is not limited to protein-encoding sequences, and may comprises nucleic acid sequences of other function, including nucleic acids of "intronic origin" which give rise to, for example, ribozymes or other nucleic acid structure having some defined chemical function.

As described herein, novel genes and gene products can be generated, in one embodiment of the present method, by admixing nucleic acid constructs which comprise a variegated population of exon sequences. As used herein, "variegated" refers to the fact that the population includes nucleic acids of different nucleotide compositions. When the interactions of the flanking introns are random, the order and composition of the internal exons of the combinatorial gene library generated is also random. For instance, where the variegated population of exons used to generate the combinatorial genes comprises N different internal exons, random trans-splicing of the internal exons can result in $N^y$ different genes having y internal exons. However, the present trans-splicing method can also be utilized for ordered gene assembly such that nucleic acid sequences are spliced together in a predetermined order, and can be carried out in much the same fashion as automated oligonucleotide or polypeptide synthesis. In similar fashion, an ordered combinatorial ligation can be carried out in which particular types of exons are added to one and other in an ordered fashion, but, at certain exon positions, more than one type of exon may be added to generate a library of combinatorial genes.

Furthermore, the present invention makes available methods and reagents for producing circular RNA molecules. In particular, exon constructs flanked by either group II or nuclear pre-mRNA fragments can, under conditions which facilitate exon ligation by splicing of the flanking intron sequences, drive the manufacture of circularly premuted exonic sequences in which the 5' and 3' ends of the same exon are covalently linked via a phosphodiester bond. Circular RNA moieties generated in the present invention can have several advantages over the equivalent "linear" constructs. For example, the lack of a free 5' or 3' end may render the molecule less susceptible to degradation by cellular nucleases. Such a characteristic can be especially beneficial, for instance, in the use of ribozymes in vitro, as might be involved in a particular gene therapy. The circularization of mature messenger-RNA transcripts can also be beneficial, by conferring increased stability as described above, as well as potentially increasing the level of protein translation from the transcript.

DESCRIPTION OF DRAWINGS

FIG. 16A presents a schematic of a trans-splicing reaction involving Fn(1–3) and (5,6)Prot.

FIG. 16B shows the products of the trans-splicing reaction schematically represented in FIG. 16A.

FIG. 16C gives the observed splice junction sequences in products of the trans-splicing reaction.

FIG. 22 is a schematic representation of group II intron integration into double-stranded DNA.

FIG. 22A presents the complete integration achieved by intron aI1;

FIG. 22B presents the partial integration achieved by intron aI2.

FIG. 36A shows a nucleic acid construct, designated (IVS5,6)-exon-(IVSI-3), which can mediate trans-splicing between heterologous exons, as well as be used to generate circular RNA transcripts.

FIGS. 36B–C depict two examples of nucleic acid constructs, designated (3'half-IVS)-exon-(5'-half-IVS), which can mediate trans-splicing between heterologous exons, as well as be used to generate circular RNA transcripts.

FIG. 38B presents the EBS1 and EBS2 sites in the substrates of FIG. 38A, as well as their $\Delta G°37$ values.

FIG. 39 shows inverse splicing reactions and products with the substrates of FIG. 38A.

FIG. 40 shows various experiments characterizing the products observed in FIG. 39.

FIG. 41 shows an analysis of the K1(C) ligation point achieved in the reactions of FIG. 39A.

DETAILED DESCRIPTION OF PREFERRED EMBODIMENTS OF THE INVENTION

Figure 1:
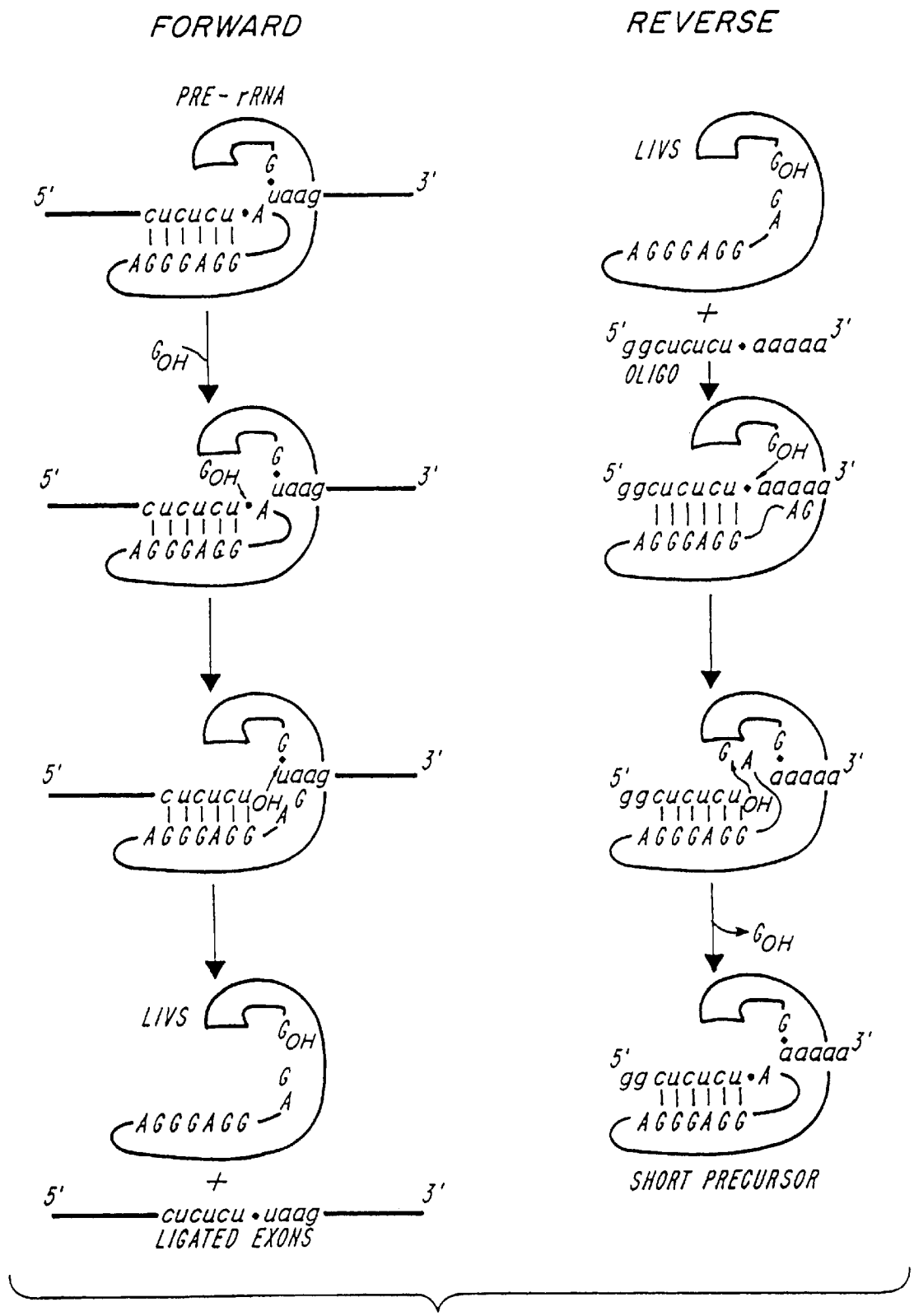
FIG. 1 is a schematic representation of an illustrative group I splicing reaction, as well as a reverse-splicing reaction.

Biological selections and screens are powerful tools with which to probe protein and nucleic acid function and to isolate variant molecules having desirable properties. The technology described herein enables the rapid and efficient generation and selection of novel genes and gene products. The present combinatorial approach, for example, provides a means for capturing the vast diversity of exons, and relies on the ability of intron sequences to mediate random splicing between exons.

As described below, novel genes and gene products can be generated, in one embodiment of the present combinatorial method, by admixing a variegated population of exons which have flanking intron sequences that can direct trans-splicing of the exons of each other. Under conditions in which trans-splicing occurs between the exons, a plurality of genes encoding a combinatorial library are generated by virtue of the ability of the exons to be ligated together in a random fashion. Where the initial variegated exon population are ribonucleotides (i.e. RNA), the resulting combinatorial transcript can be reverse-transcribed to cDNA and cloned into an appropriate expression vector for further manipulation or screening.

In another embodiment of the present combinatorial method, a variegated population of single-stranded DNA molecules corresponding to exon sequences of both (+) and (−) strand polarity, and which have flanking intron sequences capable of mediating cis-splicing, are provided together such that a portion of the nucleic acid sequence in the flanking intron of an exon of one polarity (e.g. a (+) strand) can base pair with a complementary sequence in the flanking intron of another exon of opposite polarity (e.g. a (−) strand). Using standard techniques, any single-stranded regions of the concatenated exon/intron sequences can be subsequently filled-in with a polymerase, and nicks covalently closed with a ligase, to form a double-stranded chimeric gene comprising multiple exons interrupted by intron sequences. Upon transcription of the chimeric gene to RNA, cis-splicing can occur between the exons of the chimeric gene to produce the mature RNA transcript, which can encode a chimeric protein.

As used herein, the term exon denotes nucleic acid sequences, or exon "modules", that can, for instance, encode portions of proteins or polypeptide chains. The exons can correspond to discrete domains or motifs, as for example, functional domains, folding regions, or structural elements of a protein; or to short polypeptide sequences, such as reverse turns, loops, glycosylation signals and other signal sequences, or unstructured polypeptide linker regions. The exons modules of the present combinatorial method can comprise nucleic acid sequences corresponding to naturally occurring exon sequences or naturally occurring exon sequences which have been mutated (e.g. point mutations, truncation, fusions), as well as nucleic acid sequences from "synthetic exons" including sequences of purely random construction, that is, nucleic acid sequences not substantially similar to naturally occurring exon sequences. In some instances, the exon module can correspond to a functional domain and the module may comprise a number of naturally occurring exon sequences spliced together, with the intron sequences flanking only the exon sequences disposed at the extremity of the module.

Moreover, the term "exon", as used in the present invention, is not limited to protein-encoding sequences, and may comprises nucleic acid sequences of other function, including nucleic acids of "intronic origin" which give rise to, for example, ribozymes or other nucleic acid structure having some defined chemical function. As illustrated below, group II intron domains (e.g. domains 1–6) and group I intron domains (e.g. paired regions P1–P10) can themselves be utilized as "exons", each having flanking intronic sequences that can mediate combinatorial splicing between different group I or group II domains to produce novel catalytic intron structures. In another illustrative embodiment, the exon can comprise a cloning or expression vector into which other nucleic acids are ligated by an intron-mediated trans-splicing reaction.

With respect to generating the protein-encoding exon constructs of the present invention, coding sequences can be isolated from either cDNA or genomic sources. In the instance of cDNA-derived sequences, the addition of flanking intronic fragments to particular portions of the transcript can be carried out to devise combinatorial units having exonic sequences that correspond closely to the actual exon boundaries in the pre-mRNA. Alternatively, the choice of coding sequences from the cDNA clone can be carried out to create combinatorial units having "exon" portions chosen by some other criteria. For example, as described below with regard to the construction of combinatorial units from either antibody or plasminogen activator cDNA sequences, the criteria for selecting the exon portions of each splicing construct can be based on domain structure or function of a particular portion of the protein.

Several strategies exist for identifying coding sequences in mammalian genomic DNA which can subsequently be used to generate the present combinatorial units. For example, one strategy frequently used involves the screening of short genomic DNA segments for sequences that are evolutionarily conserved, such as the 5' splice site and branch acceptor site consensus sequences (Monaco et al. (1986) Nature 323:646–650; Rommens et al. (1989) Science 245:1059–1065; and Call et al. (1990) Cell 60:509–520). Alternative strategies involve sequencing and analyzing large segments of genomic DNA for the presence of open reading frames (Fearson et al. (1990) Science 247:49–50), and cloning hypo-methylated CpG islands indicative of 5' transcriptional promoter sequences (Bird et al. (1986) Nature 321:209–213). Yet another technique comprises the cloning of isolated genomic fragments into an intron which is in turn disposed between two known exons. The genomic fragments are identified by virtue of the ability of the inserted genomic sequences to direct alternate splicing which results in the insertion into a mature transcript of at least one genomic-derived exon between the two know exons (Buckler et al. (1991) PNAS 88:4005–4009).

Exons identified from genomic DNA can be utilized directly as combinatorial units by isolating the identified exon and appropriate fragments of the flanking intron sequences normally associated with it. Alternatively, as with the cDNA derived exons, the genomic-derived exon can be manipulated by standard cloning techniques (Molecular Biology: A Laboratory Manual, eds. Sambrook, Fritsch and Maniatis (New York: CSH Press, 1989); and Current Protocols in Molecular Biology, Eds. Ausebel et al. (New York: John Wiley & Sons, 1989)) into vectors in which appropriate flanking intronic sequences are added to the exon upon transcription. In yet another embodiment, the reversal of splicing reactions, described below for the various intron groups, can be used to specifically add flanking intron fragments to one or both ends of the exonic sequences, and thereby generate the combinatorial units of the present invention.

Furthermore, generating the splicing units useful in the present combinatorial methods, one skilled in the art will recognize that in the instance of protein-encoding exons, particular attention should be payed to the phase of the intronic fragments. Introns that interrupt the reading frame between codons are known as "Phase 0" introns; those which interrupt the codons between the first and second nucleotides are known as "Phase 1" introns; and those interrupting the codons between the second and third nucleotides are known as "Phase 2" introns. In order to prevent a shift in reading frame upon ligation of two exons, the phase at both the 5' splice site and 3' splice site must be the same. The phase of the flanking intronic fragments can be easily controlled during manipulation, especially when reverse splicing is utilized to add the intronic fragments, as the each insertion site is known. However, as described below, when the variegated population of combinatorial units comprises flanking intronic fragments of mixed phase, particular nucleotides in the intronic sequences can be changed in such a manner as to lower the accuracy of splice site choice. In addition, the splicing reaction conditions can also be manipulated to lower the accuracy of splice site choice.

I. Intronic Sequences

The present invention makes use of the ability of introns to mediate ligation of exons to one and other in order to generate a combinatorial library of genes from a set of discontinuous exonic sequences. This method is not limited to any particular intron or class of introns. By way of example, the intronic sequences utilized can be selected from group I, group II, or nuclear pre-mRNA introns. Furthermore, in light of advancement made in delineating the critical and dispensable elements in each of the classes of introns, the present invention can be practiced with portions of introns which represent as little as the minimal set of intronic sequences necessary to drive exon ligation.

Group I introns, as exemplified by the Tetrahymena ribosomal RNA (rRNA) intron, splice via two successive phosphate transfer, transesterification reactions. As illustrated in FIG. 1, the first transesterfication is initiated by nucleophilic attack at the 5' junction by the 3' OH of a free guanosine nucleotide, which adds to the 5' end of the intron and liberates the 5' exon with a 3' OH. The second transesterification reaction is initiated by nucleophilic attack at the 3' splice junction by the 3' OH of the 5' exon, which results in exon ligation and liberates the intron.

Figure 2B:
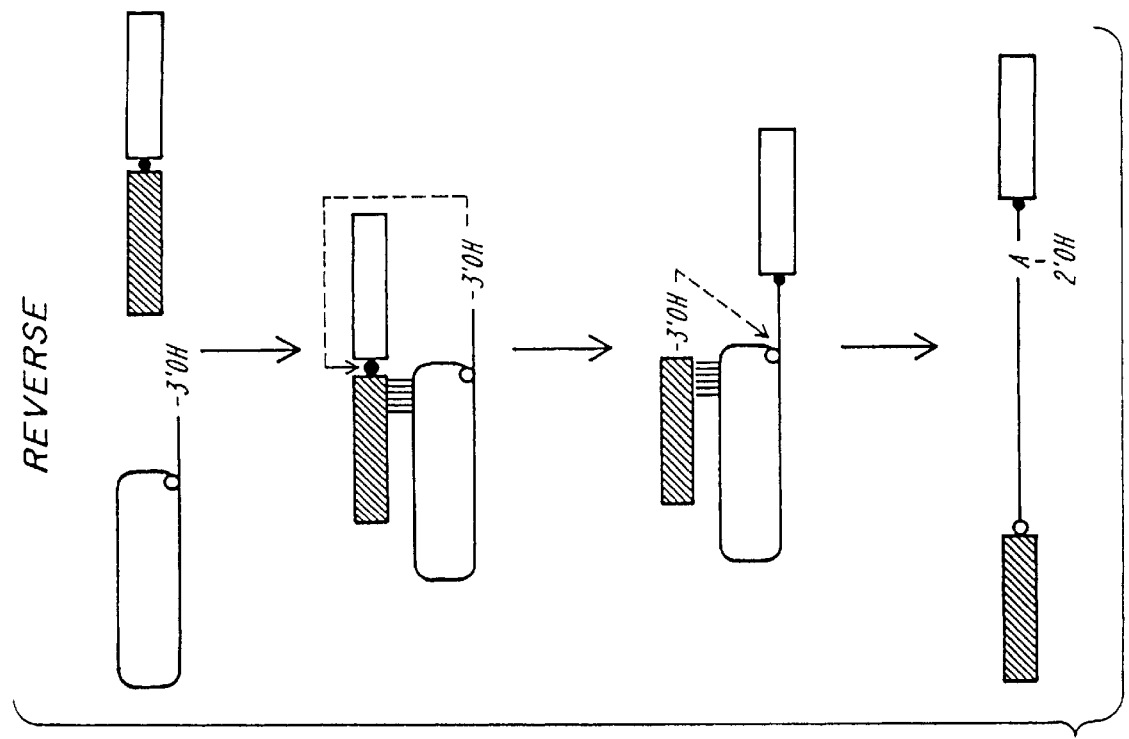
FIG. 2 is a schematic representation of the group II splicing reaction, as well as the reverse-slicing reaction.
Figure 2A:
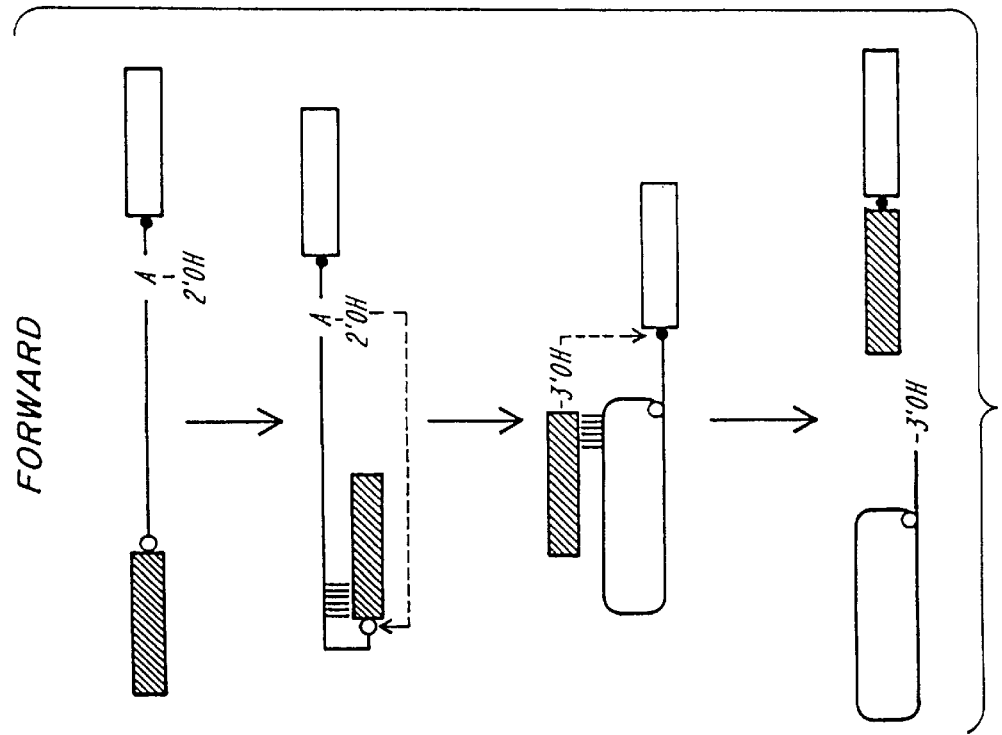

Group II introns also splice by way of two successive phosphate transfer, transesterification reactions (see FIG. 2). There is, however, one prominent difference between the reaction mechanisms proposed for group I and group II introns. While cleavage at the 5' junction in group I splicing is due to nucleophilic attack by a free guanosine nucleotide, cleavage at the 5' junction in group II splicing is typically due to nucleophilic attack by a 2'-OH from within the intron. This creates a lariat intermediate with the 5' end of the intron attached through a 2', 5'-phosphodiester bond to a residue near the 3' end of the intron. Subsequent cleavage at the 3' junction results in exon ligation and liberates the "free" intron in the form of a lariat. The nature of the initiating nucleophile notwithstanding, the two self-splicing mechanism appear quite similar as both undergo 5' junction cleavage first, and subsequently 3' junction cleavage and exon ligation as a consequence of nucleophilic attack by the 5' exon. Furthermore, nuclear pre-mRNA, in similar fashion to group II—intron splicing, also proceed through a lariat intermediate in a two-step reaction.

All three intron groups share the feature that functionally active introns able to mediate splicing can be reconstituted from intron fragments by non-covalent interactions between the fragments (and in some instances other trans-acting factors). Such "trans-splicing" by fragmented introns, as described herein, can be utilized to ligate discontinuous exon sequences to one and other and create novel combinatorial genes. Moreover, autocatalytic RNA (i.e. group I and group II introns) are not only useful in the self-splicing reactions used generate combinatorial libraries, but can also catalyze reactions on exogenous RNA.

The following description of each of the group I, group II, and nuclear pre-mRNA intronic sequences is intended to illustrate the variation that exists in each group of introns. Moreover, the descriptions provide further insight to one skilled in the art to devise exon constructs useful in the present splicing methods, using as little as a minimal set of intronic-fragments.

A. Group II Introns

Group II introns, which are classed together on the basis of a conserved secondary structure, are found in organellar genes of lower eukayotes and plants. Like introns in nuclear pre-mRNA, group II introns are excised by a two-step splicing reaction to generate branched circular RNAs, the so-called intron lariats. A remarkable feature of group II introns is their self-splicing activity in vitro. In the absence of protein or nucleotide cofactors, the intronic RNA catalyzes two successive transesterfication reactions which lead to autocatalytic excision of the intron-lariat from the pre-mRNA and concomitantly to exon ligation (see FIG. 2).

Figure 3:
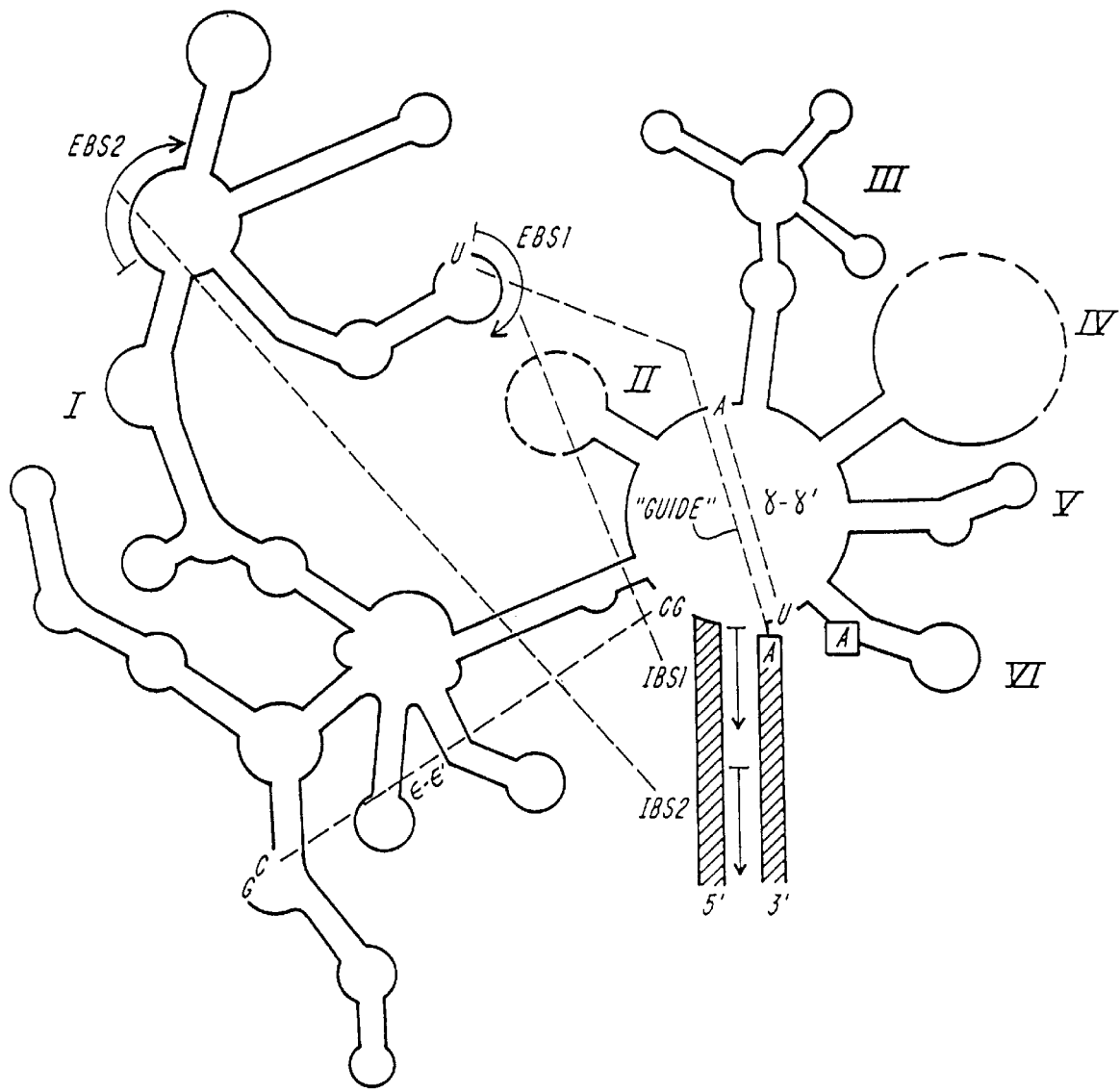
FIG. 3 illustrates the domain structure of a group II intron.

More than 100 group II intron sequences from fungal and plant mitochondria and plant chloroplasts have been analyzed for conservation of primary sequence, secondary structure and three-dimensional base pairings. Group II introns show considerable sequence homology at their 3' ends (an AY sequence), and have a common $G_1W_2G_3Y_4G_5$ motif at their 5' ends, but do not show any other apparent conserved sequences in their interior parts. However, group II introns are generally capable of folding into a distinctive and complex secondary structure typically portrayed as six helical segments or domains (designated herein as domains 1–6) extending from a central hub (see FIG. 3). This core structure is believed to create a reactive center that promotes the transesterification reactions.

However, mutational analysis and phylogenetic comparison indicate that certain elements of the group II intron are dispensable to self-splicing. For example, several group II introns from plants have undergone some rather extensive pruning of peripheral and variable stem structures. Moreover, while the group II intron can be used to join two exons via cis-splicing, a discontinuous group II intron form of trans-splicing can be used which involves the joining of independently transcribed coding sequences through interactions between intronic RNA pieces. In vitro studies have shown that breaks, for example within the loop region of domain IV, can be introduced without disrupting self-splicing. The ability of group II intron domains to reassociate specifically in vivo is evidenced by trans-spliced group II introns, which have been found, for example, in the rps-12 gene of higher plant ctDNA, the psaA gene in *Chlamydomonas reinhardtii* ctDNA, and the nad1 and nad5 genes in higher plant mtDNA (Michel et al. (1989) *Gene* 82:5–30; and Sharp et al. (1991) *Science* 254:663). These genes consist of widely separated exons flanked by 5'- or 3'-segments of group II introns split in either domains 3 or 4. The exons at different loci are transcribed into separate precursor RNAs, which are trans-spliced, presumably after the association of the two segments of the group II intron. Moreover, genetic analysis of trans-splicing of the *Chlamydomonas reinhardtii* psaA gene has demonstrated that the first intron of this gene is split into three segments. The 5' exon is flanked by parts of domain 1 and the 3' exon by parts of domains 4 to 6, respectively. The middle segment of the intron is encoded at a remote locus, tscA, and consists of the remainder of domains 1 to 4. This tscA segment can apparently associate with the other two intron segments to reconstitute an intron capable of splicing the two exons (Goldschmidt et al. (1991) *Cell* 65:135–143).

The functional significance to self-splicing of certain control structural elements have been further deduced by analysis of minimal trans-splicing sets, and found to generally comprise an exon-binding site and intron-binding site, a structural domain 5, and (though to lesser extent) a "branch-site" nucleotide involved in lariat formation. Domain 1 contains the exon-binding sequences. Domain 6 is a helix containing the branch site, usually a bulged A residue. Domain 5, the most highly conserved substructure, is required for catalytic activity and binds to at least a portion of domain 1 to form the catalytic core.

The 5' splice sites of group II introns are defined by at least three separate tertiary base pairing contacts between nucleotides flanking the 5' splice site and nucleotides in substructures of domain I. The first interaction involves a loop sequence in the D sub-domain of domain 1 (axon binding site 1 or EBS 1) that base pairs with the extreme 3' end of the 5' exon (intron binding site 1 or IBS 1). The second interaction involves the conserved dinucleotide-$G_3Y_4$-(designated ε) that base pairs with a dinucleotide in the C1 subdomain of domain I (designated ε'). The third interaction involves base pairing between intron binding site (IBS 2), a sequence located on the 5' side of IBS 1, with exon binding site 2 (EBS 2), a loop sequence of the D subdomain of domain 1 near EBS 1. Of the two exon-binding sites identified in group II introns, only EBS 1 is common to all group II members. The EBS 1 element comprises a stretch of 3 to 8 consecutive residues, preferably 6, located within domain 1, which are complementary to the last 3 to 8 nucleotides of the 3' exon end of the 5' exon. The EBS 2-IBS 2 pairing also typically consists of two 4–8 nucleotide stretches. Its exonic component (IBS 2) lies from 0 to 3 nucleotides upstream from the IBS 1 element, and the intronic component (EBS 2) also lies within domain 1. However, while IBS 2-EBS 2 pairing can improve the efficiency of 5' splice site use, particularly in trans, it is subject to many more variations from the IBS 1-EBS 1 interaction, such as reduced length, presence of bulging nucleotides or a mismatch pair. Disrupting the IBS 2-EBS 2 pairing, in the Sc.aS group II intron for example, is essentially without effect on the normal splicing reaction, and in at least twelve group II introns analyzed, the IBS 2-EBS 2 interaction seems to be missing altogether and is apparently less important than the IBS 1-EBS 2 interaction. As already noted, only that pairing is absolutely constant in (typical) group II introns, and always potentially formed at cryptic 5' splice sites.

Further studies, while confirming that the EBS 1-IBS 1 base pairing is necessary for activation of the 5' junction, indicate that this interaction alone is not always sufficient for unequivocal definition of the cleavage site. Is have been established that altering the first nucleotide of the group II intron (e.g., $G_1$ of $G_1W_2G_3Y_4G_5$) can reduce the self-splicing rate in vitro. Characterization of the products of self-splicing from $G_1 \rightarrow N$ mutant transcripts have demonstrated that the relative order of function is G>U>A>C. It is also suggested that the 5' G of the intron helps to position the cleavage site precisely (Wallasch et al. (1991) *Nuc. Acids Res.* 19:3307–3314). For example, the presence of an additional adenosine following IBS 1 can lead to ambiguous hydrolytic cleavages at the 5' intron/exon boundary. As described herein, such ambiguity can be used to address exon phasing.

Another well conserved feature of group II introns is the bulging A located 7 to 8 nt upstream from the 3' intron-exon junction on the 3' side of helix VI. This is the nucleotide which participates in the long range, 2'-5' lariat bond (Van der Veen et al. (1986) *Cell* 44:225–234; Schmelzer et al. (1986) *Cell* 46:557–565; Jacquier et al. (1987) *Cell* 50:17–29; Schmelzer et al. (1987) *Cell* 51:753–762). Evidence from electron microscopy, attempts at reverse transcription of circular introns, and treatment with the 2',5'-phosphodiesterase of HeLa cells indicate that group II introns are excised as lariats (Van der Veen et al. (1986) *Cell* 44:225–234; Schmitt et al. (1987) *Curr. Genet.* 12:291–295; Kroller et al. (1985) *Embo J.* 4:2445–2450). However, lariat formation is not absolutely essential for correct exon ligation to occur. Cleavage at the 5' splice site, presumably mediated by free hydroxide ions rather than a 2'-OH group, followed by normal exon ligation, has been observed both in trans-splicing reactions (Jacquier and Rosbash (1986) *Science* 234:1099–1104; and Koch et al. (1992) *Mol. Cell Biol.* 12:1950–1958) and, at high ionic strength, in cis-splicing reactions with molecules mutated in domain 6 (Van der Veen et al. (1987) *Embo. J.* 12:3827–3821). Also, several group II introns lack a bulging A on the 3' side of helix VI. For instance, all four CP tRNA-VAL introns of known sequence have a fully paired helix VI, and their 7th nucleotide upstream from the 3' intron-exon junction is a G, not an A. Furthermore, correct lariat formation has been observed with a mutant of intron Sc.bI whose helix VI should be fully paired, due to the insertion of an additional nucleotide (a U) at the site facing the normally bulging A (Schmelzer and Muller (1987) *Cell* 51:753–762).

Figure 4B:
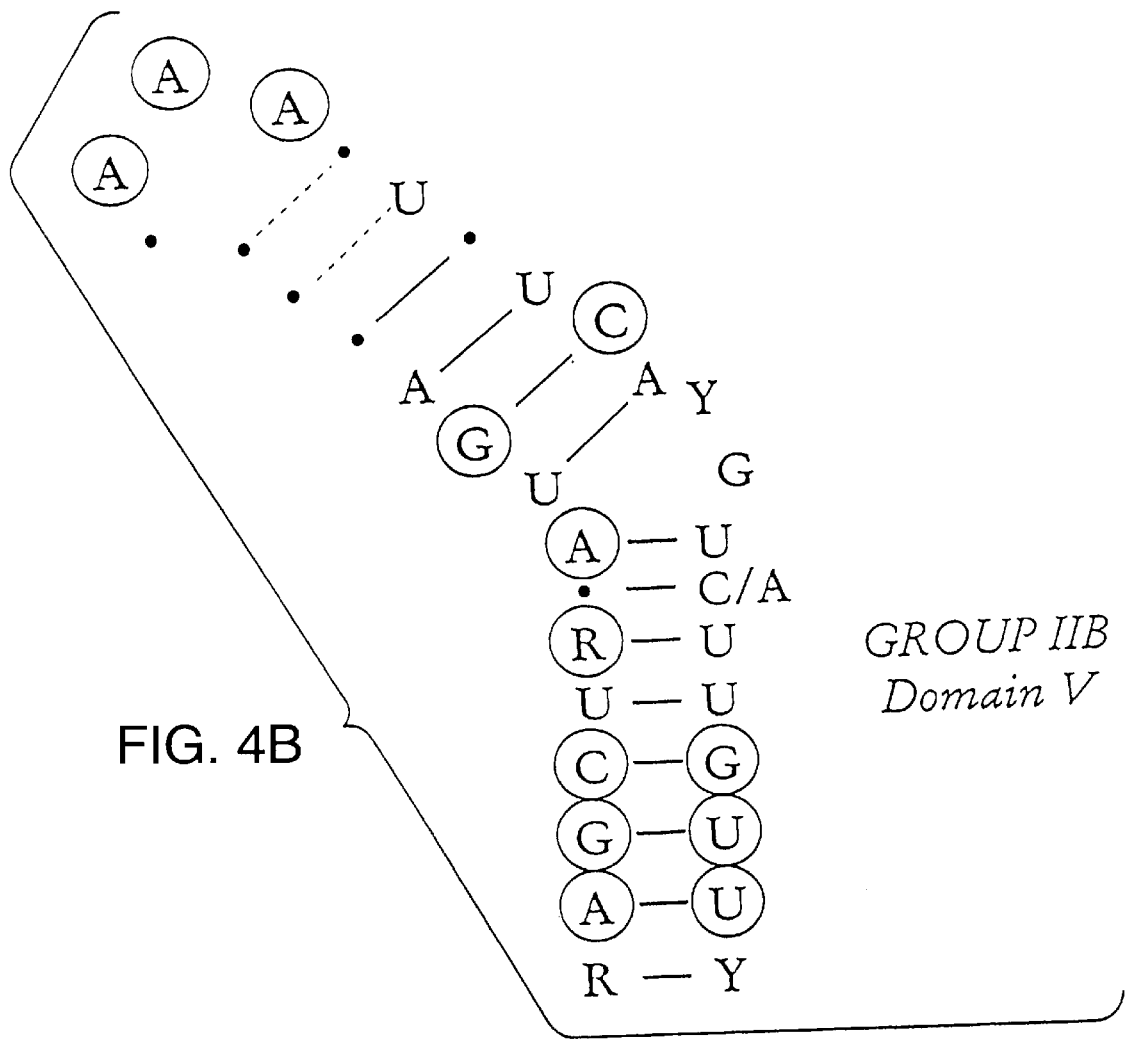
FIG. 4 illustrates the consensus sequence for group IIA and IB domain V.

Perhaps one of the best conserved structural elements of group II introns is domain 5. The typical domain 5 structure contains 32–34 nucleotides and is predicted to fold as a hairpin. The hairpin is typically an extended 14 base pair helix, capped by a four base loop involving 15–18, and punctuated by a 2 base bulge at positions 25 and 26. Comparative sequence analysis (Michel et al. (1989) *Gene* 82:5–30) has shown that group II introns can generally be classified into one of two classes (e.g. group IIA and IIB). FIG. 4 shows the consensus sequences of domain 5 for each of the IIA and IIB introns. Base pairs that are highly conserved are indicated by solid lines. Dashed lines indicate less well conserved base pair interactions. The unpaired loop at the apex of the hairpin is typically an NAAA sequence, where N is most often a G for IIA introns. Nucleotides which are highly conserved are circled, while less conserved nucleotides are uncircled. A black dot indicates a lack of discernible sequence consensus.

Degenerate group II introns can be functional despite lacking some domains. Euglena ctDNA, for example, contains a large number of relatively short group II introns which sometimes lack recognizable cognates of domain 2,3, or 4 The view that the only group II structures required for splicing activities are domains 1 and 5 is supported by a detailed mutational analysis of a yeast mitochondrial group II intron in which various domains were deleted, either singly or in combinations (Koch et al. (1992) *Mol. Cell. Biol.* 12:1950–1958). For example, the removal or disruption of the domain 6 helix simply reduces 3' splice site fidelity and reaction efficiency. This analysis has led to the belief that domain 5 probably interacts with domain 1 to activate the 5' splice site, since a transcript lacking domains 2–4, and 6, but retaining domain 1 and domain 5 was capable of specific hydrolysis of the 5' splice junction.

With regard to 3' splice-site selection, two weak contacts are believed to play a role in defining the 3' splice-site but are, however, not essential to splicing. The first of these contacts is a lone base pair, termed γ/γ', between the 3' terminal nucleotide of the introns and a single base between domains 2 and 3. (Jacquier et al. (1990) *J. Mol. Biol.* 13:437–447). A second single base pair interaction, termed the internal guide, has been defined between the first base of the 3' exon and the nucleotide adjacent to the 5' end of EBS 1 (Jacquier et al. (1990) *J. Mol. Biol.* 219:415–428).

In addition to the ability of autocatalytic RNAs such as group I and group II introns to excise themselves from RNA and ligate the remaining exon fragments, ample evidence has accumulated demonstrating that the autocatalytic RNAs can also catalyze their integration into exogenous RNAs. For example, both group I and group II introns can integrate into foreign RNAs by reversal of the self-splicing reactions. The mechanism of the group II intron reverse-splicing reaction is shown in FIG. 2. In the first step of the reverse reaction, the attack of the 3'-OH group of the intron 3' terminus at the junction site of the ligated exons yields a splicing intermediate, the intron-3' exon lariat, and the free 5' exon. In the second step, the 5' exon, which is still bound to the lariat via the EBS 1/EBS 1 base pairing, can attack the 2'–5' phosphodiester bond of the branch. This transesterification step leads to reconstitution of the original precursor. The analogous reaction of the intron with a foreign RNA harboring an IBS 1 motif results in site-specific integration downstream of the IBS 1 sequence.

The exon constructs of the present invention, whether comprising the group II intronic sequences described above or the group I or nuclear pre-mRNA intronics described below, can be generated as RNA transcripts by synthesis in an in vitro transcription system using well known protocols. For example, RNA can be transcribed from a DNA template containing the exon construct using a T3 or T7 RNA polymerase, in a buffer solution comprising 40 mm Tris-HCl (pH 7.5), 6 mM $MgCl_2$, 10 mM dithiothreitol, 4 mM spermridine and 500 mM each ribonucleoside triphosphate. In some instances, it will be desirable to omit the spermidine from the transcription cocktail in order to inhibit splicing of the transcribed combinatorial units.

Several reaction conditions for facilitating group II-mediated splicing are known. For example, the reaction can be carried out in "Buffer C" which comprises 40 mM Tris-HCl (pH 7.0), 60 mM $MgCl_2$, 2 mM spermidine, and 500 mM KCl (Wallasch et al. (1991) *Nuc. Acid Res.* 19:3307–3314; and Suchy et al. (1991) *J. Mol. Biol.* 222:179–187); or "Buffer S" which comprises 70 mM $Tris-SO_4$ (pH 7.5) 60 mM $MgSO_4$, 2 mM spermidine, and 500 mM $(NH_4)2\ SO_4$ (Morl et al. (1990) *Nuc. Acid Res.* 18:6545–6551; and Morl et al. (1990) *Cell* 60:629–636). The group II ligation reactions can be carried out, for instance, at 45° C., and the reaction stopped by EtOH precipitation or by phenol:chloroforrn (1:1) extraction. Suitable reaction conditions are also disclosed in, for example, Jacquier et al. (1986) *Science* 234:1099–1104; Franzer et al. (1993) *Nuc. Acid Res.* 21:627–634; Schmelzer et al. (1986) *Cell* 46:557–565; Peebles et al. (1993) *J. Biol. Chem.* 268:11929–11938; Jarrell et al. (1988) *J. Biol. Chem.* 263:3432–3439; and Jarrell et al. (1982) *Mol. Cell Biol.* 8:2361–2366. Moreover, manipulation of the reaction conditions can be used to favor certain reaction pathways, such as reverse-splicing reaction (e.g., by increasing the $MgSO_4$, concentration to 240 mM in Buffer S); bypassing the need for a branch nucleotide acceptor (e.g. high salt); and decreasing the accuracy of splice-site choice (Peebles et al. (1987) *CSH Symp. Quant. Biol.* 52:223–232).

B. Group I Introns

Group I introns are present in rRNA, tRNA, and protein-coding genes. They are particularly abundant in fungal and plant mitochondrial DNAs (mtDNAs), but have also been found in nuclear rRNA genes of Tetraphymena and other lower eukaryotes, in chloroplast DNAs (ctDNAs), in bacteriophage, and recently in several tRNA genes in eubacteria.

As first shown for the Tetrahymena large rRNA intron, group I introns splice by a mechanism involving two transesterification reactions initiated by nucleophilic attack of guanosine at the 5' splice site (see FIG. 1). The remarkable finding for the Tetrahymena intron was that splicing requires only guanosine and $Mg^{2+}$. Because bond formation and cleavage are coupled, splicing requires no external energy source and is completely reversible. After excision, some group I introns circularize via an additional transesterfication, which may contribute to shifting the equilibrium in favor of spliced products.

The ability of group I introns to catalyze their own splicing is related to their highly conserved secondary and tertiary structures. The folding of the intron results in the formation of an active site juxtaposing key residues that are widely separated in primary sequence. This RNA structure catalyzes splicing by bring the 5' and 3' splice sites and guanosine into proximity and by activating the phosphodiester bonds at the splice sites. Different group I introns have relatively little sequence similarity, but all share a series of the short, conserved sequence elements P, Q, R, and S. These sequence elements always occur in the same order and basepair with one another in the folded structure of the intron (see FIG. 5). Element R [consensus sequence (C/G) YUCA(GA/AC)GACUANANG; SEQ ID NO: 1] and S [consensus AAGAUAGUCY; SEQ ID NO: 2] are the most highly conserved sequences within group I introns, and typically serve as convenient "landmarks" for the identification of group I introns. The boundaries of group I introns are marked simply by a U residue at the 3' end of the 5' exon and a G residue at the 3' end of the intron. (see, for example, Michel et al. (1990) *J Mol Biol* 216:585–610; Cech, T R (1990) *Annu Rev Biochem* 59:543–568; Cech, T R (1988) *Gene* 73:259–271; Burke (1989) Methods in Enzymology 190:533–545; and Burke et al. (1988) *Gene* 73:273–294).

The conserved group I intron secondary structure was deduced from phylogenetic comparisons, and specific features have been confirmed by analysis of in vivo and in vitro mutations and by structure mapping. The structure, shown in FIG. 5, consists of a series of paired regions, denoted P1–P10, separated by single-stranded regions (denoted J) or capped by loops (denoted L), from the core of the structure. The fundamental correctness of the model is supported by the observation that a vast number of group I intron sequences can be folded into this basis structure.

P1 and P10, which contain the 5' and 3' splice sites, respectively, are formed by base pairing between an internal guide sequence (IGS), generally located just downstream of the 5' splice site, and exon sequences flanking the splice sites. Group I introns have been classified into four major subgroups, designated IA to ID, based on distinctive structural and sequence features. Group IA introns, for example, contain two extra pairings, P7.1/P7.1a or P7.1/P7.2, between P3 and P7, whereas many group IB and IC introns may contain additional sequences, including open reading frames (ORFs), in positions that do not disrupt the conserved core structure. Indeed, many of the peripheral stem-loops can be completely deleted without major loss of splicing function. For example, the phage I4 sunY intron has been re-engineered to contain as few as 184 nucleotides while still retaining greater than 10-percent activity. Presumably, if the criterion for activity were lowered, the minimal size one could achieve would be decreased.

The region of the Tetrahymena intron required for enzymatic activity, the catalytic core, consists of P3, P4, P6, P7, P8, and P9.0. Mutation of a nucleotide involved in one of these core structural elements typically decreases the maximum velocity of splicing, increase $K_m$ for guanosine, or both. In those instances where the primary importance of the nucleotide is its contribution to the formation of a duplex region, a second-site mutations that restores base-pairing also restores splicing function. Studies using Fe(II)-EDTA, a reagent that cleaves the sugar-phosphate backbone, have shown that parts of the core are buried in the structure inaccessible to the solvent, that $Mg^{2+}$ is necessary for folding of the intron, and that individual RNA domains fold in a specific order as $Mg^{2+}$ is increased. All group I introns have fundamentally similar core structures, but subgroup-specific structures such as P7.1, P7.2, and P5abc appear to participate in additional interactions that stabilize the core structure in different ways (Michel et al. (1990) *J. Mol. Biol.* 216:585–610; and Michel et al. (1992) *Genes Dev.* 6:1373–1385).

A three dimensional model of the group I intron catalytic core has been developed by Michel and Westhof (Michel et al. (1990) *J. Mol. Biol.* 216:585–610) through comparative sequence analysis. In the Michel-Westhof model, the relative orientation of the two helices is constrained by a previously proposed triple helix involving parts of J3/4–P4–P6-J6/7 and by potential tertiary interactions identified by co-variation of nucleotides that are not accounted for by secondary structure. A number of these binding sites accounts for the known splicing mechanism, which requires appropriate alignments of guanosine and the 5' and 3' exons in the first and second steps of splicing. Deoxynucleotide and phosphorothioate substitution experiments suggest that finctionally important $Mg^{2+}$ ions are coordinated at specific positions around the active site (e.g., P1 and J8/7) where they may function directly in phosphodiester bond cleavage (Michel et al. (1990) *J. Mol. Biol.* 216:585–610; and Yarus, M (1993) *FASEB J.* 7:31–9). Basic features of the predicted three-dimensional structure have been supported by mutant analysis in vitro and by the use of specifically positioned photochemical cross-linking and affinity cleavage reagents.

Figure 5:
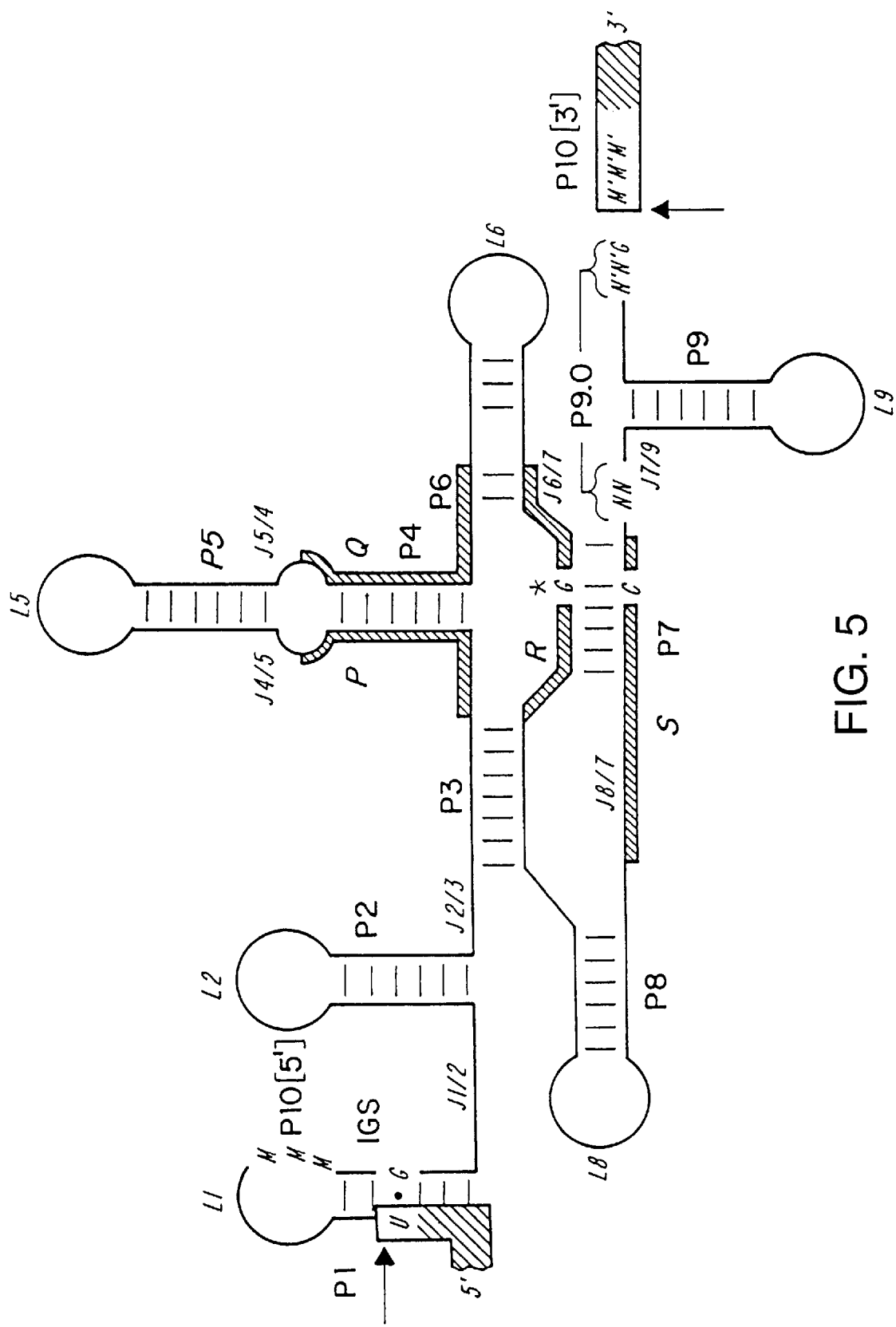
FIG. 5 illustrates the secondary structure of a group I intron.

The 5' and 3' splice sites of group I introns are substrates that are acted on by the catalytic core, and they can be recognized and cleaved by the core when added on separate RNA molecules (Cech (1990) *Annu. Rev. Biochem.* 59:543–568). In group I introns the last 3–7 nucleotides of the 5' exon are paired to a sequence within the intron to form the short duplex region designated P1. The intron-internal portion of P1 is also known as the 5' exon-binding site and as a portion of the internal guide sequences, IGS. The P1s of different group I introns vary widely in sequence. Neither the sequence nor length of P1 is fixed, but the conserved U at the 3' end of the 5' exon always forms a wobble base pair with a G residue in the IGS (FIG. 5). The conserved U:G is one important recognition element that defines the exact site of guanosine attack. In general, other base combinations do not substitute well. One exception is C:G, which maintains the accuracy of splicing but decreases the $K_{cat}/K_m$ by a factor of 100. Another exception is C:A; the ability of this pair to substitute well for U:G has been interpreted as an indication that disruption of P1 by a wobble base pair is a key element in recognition of the splice site. Position within the P1 helix is another determinant of 5' splice site. Analysis of in vitro mutants has shown that the distance of the U:G pair from the bottom of the P1 helix is critical for efficient cleavage in the Tetrahymena intron and that J1/2 and P2 also play a role in the positioning of P1 relative to the core (Michel et al. (1990) *J. Mol. Biol.* 216:585–610; Young et al. (1991) *Cell* 67:1007–1019; and Salvo et al. (1992) *J. Biol. Chem.* 267:2845–2848). The U:G pair is most efficiently used when located 4–7 base pairs from the base of the P1.

The positioning of the 3' splice site in group I introns depends on at least three interactions, whose relative importance differs in different introns. These are the P10 pairing between the IGS and the 3' exon, binding of the conserved G residue at the 3' end of the intron to the G-binding site in the second step of splicing, and an additional interaction, P9.0, which involves base paring between the two nucleotides preceding the terminal G of the intron and two nucleotides in J7/9 (Cech (1990) *Annu. Rev. Biochem.* 59:543–568).

Group I introns have $K_m$ values for guanosine that are as low as 1 $\mu$M and readily discriminate between guanosine and other nucleosides. The major component of the guanosine-binding site corresponds to a universally conserved CG pair in P7. Guanosine was initially proposed to interact with this base pair via formation of a base triple, but the contribution of neighboring nucleotides and the binding of analogs are also consistent with a model in which guanosine binds axially to the conserved G and flanking nucleotides. The guanosine-binding site of group I introns can also be occupied by the guanidino groups of arginine or antibiotics, such as streptomycin, which act as competitive inhibitors of splicing (von Ahsen et al. (1991) *Nuc. Acids Res.* 19:2261–2265).

Group I introns can also be utilized in both trans-splicing and reverse-splicing reactions. For example, the ribozyme core of a group I intron can be split in L6, and through intermolecular complementation, a functional catalytic core can be reassembled from intronic fragments (i.e. P1–6.5 and P6.5–10) on separately transcribed molecules (Galloway et al. (1990) J. Mol. Biol. 211:537–549).

Furthermore, as described for group II intron constructs, combinatorial units comprising group I introns can be transcribed from DNA templates by standard protocols. The group I self-splicing reaction has an obligatory divalent cation requirement, which is commonly met by $Mg^{2+}$. The reaction can be in fact be stopped using a chelating agent such as EDTA. The group I-mediated splicing of exonic sequences can be carried out, for example, in a buffer comprising 100 mM $(NH_4)_2SO_4$, 50 mM HEPES (pH 7.5), 10 mM $MgCl_2$, and 25 $\mu$M GTP, at a temperature of 42° C. (Woodson et al. (1989) *Cell* 57:335–345). In another embodiment, the reaction buffer comprises 50 mM Tris-HCl (pH 7.5), 50 mM $NH_4Cl$, 3 mM $MgCl_2$, 1 mM spermidine, and 100 mM GTP, and the reaction proceeds at 55° C. (Salvo et al. (1990) *J. Mol. Biol.* 211:537–549). To form the reverse-splicing reaction, the $Mg^{2+}$ concentration can be increased (e.g., to 25 mM) and the GTP omitted. Typically, the reversal of splicing reaction is favored by high RNA concentrations, high magnesium and temperature, and the absence of guanosine. Other examples of useful reaction conditions for group I intron splicing can be found, for example, in Mohr et al. (1991) *Nature* 354:164–167; Guo et al. (1991) *J. Biol.Chem.* 266:1809–1819; Kittle et al. (1991) *Genes Dev.* 5:1009–1021; Dounda et al. (1989) PNAS 86:7402–7406; and Pattanju et al. (1992) *Nuc. Acid Res.* 20:5357–5364.

The efficiency of splicing of group II and group I introns can often be improved by, and in some instances may require, the addition of protein and/or RNA co-factors, such as maturases. (Michel et al. (1990) *J. Mol. Biol.* 216:585–610; Burke et al. (1988) *Gene* 71:259–271; and Lambowitz et al. (1990) *TIBS* 15:440–444). This can be especially true when more truncated versions of these introns are used to drive ligation by trans-splicing, with the maturase or other co-factor compensating for structural defects in the intron structure formed by intermolecular complementation by the flanking intron fragments. Genetic analysis of mitochondrial RNA splicing in Neurospora and yeast has shown, for example, that some proteins involved in splicing group I and group II introns are encoded by host chromosomal genes, whereas others are encoded by the introns themselves. Several group I and group II introns in yeast mtDNA, for instance, encode maturases that function in splicing the intron that encodes them. These include group I introns Cob-I2, -I3, and -I4, and group II introns cox1-I1 and -I2. Thus, the conditions for splicing of group I and group II introns can further comprise maturases and other co-factors as necessary to form a functional intron by the flanking intron sequences.

C. Nuclear pre-mRNA introns

Nuclear pre-mRNA splicing, like group II intron-mediated splicing, also proceeds through a lariat intermediate in a two-step reaction. In contrast to the highly conserved structural elements that reside within group II introns, however, the only conserved features of nuclear pre-mRNA introns are restricted to short regions at or near the splice junctions. For instance, in yeast motifs are (i) a conserved hexanucleotide at the 5' splice, (ii) an invariant heptanucleotide, the UACUAAC box, surrounding the branch point A (underlined), and (iii) a generally conserved enrichment for pyrimidine residues adjacent to an invariant AG dinucleotide at the 3' splice site.

Two other characteristics of nuclear pre-mRNA splicing in vitro that distinguish it from autocatalytic splicing are the dependence on added cell-free extracts and the requirement for adenosine triphosphate (ATP). Once in vitro systems had been established for mammalian and yeast pre-mRNA splicing, it was found that a group of trans-acting factors, predominately made up of small nuclear ribonucleoprotein particles (snRNP's) containing U1, U2, U4, U5 and U6 RNA's was essential to the splicing process. Together with the discovery of autocatalytic introns, the demonstration that snRNAs were essential, trans-acting components of the spliceosome argued strongly that group II self-splicing and nuclear pre-mRNA splicing occurring by fundamentally equivalent mechanisms. According to this view, the snRNAs compensate for the low information content of nuclear introns and, by the formation of intermolecular RNA—RNA interactions, achieve the catalytic capability inherent in the intramolecular structure of autocatalytic introns.

Figure 6A:
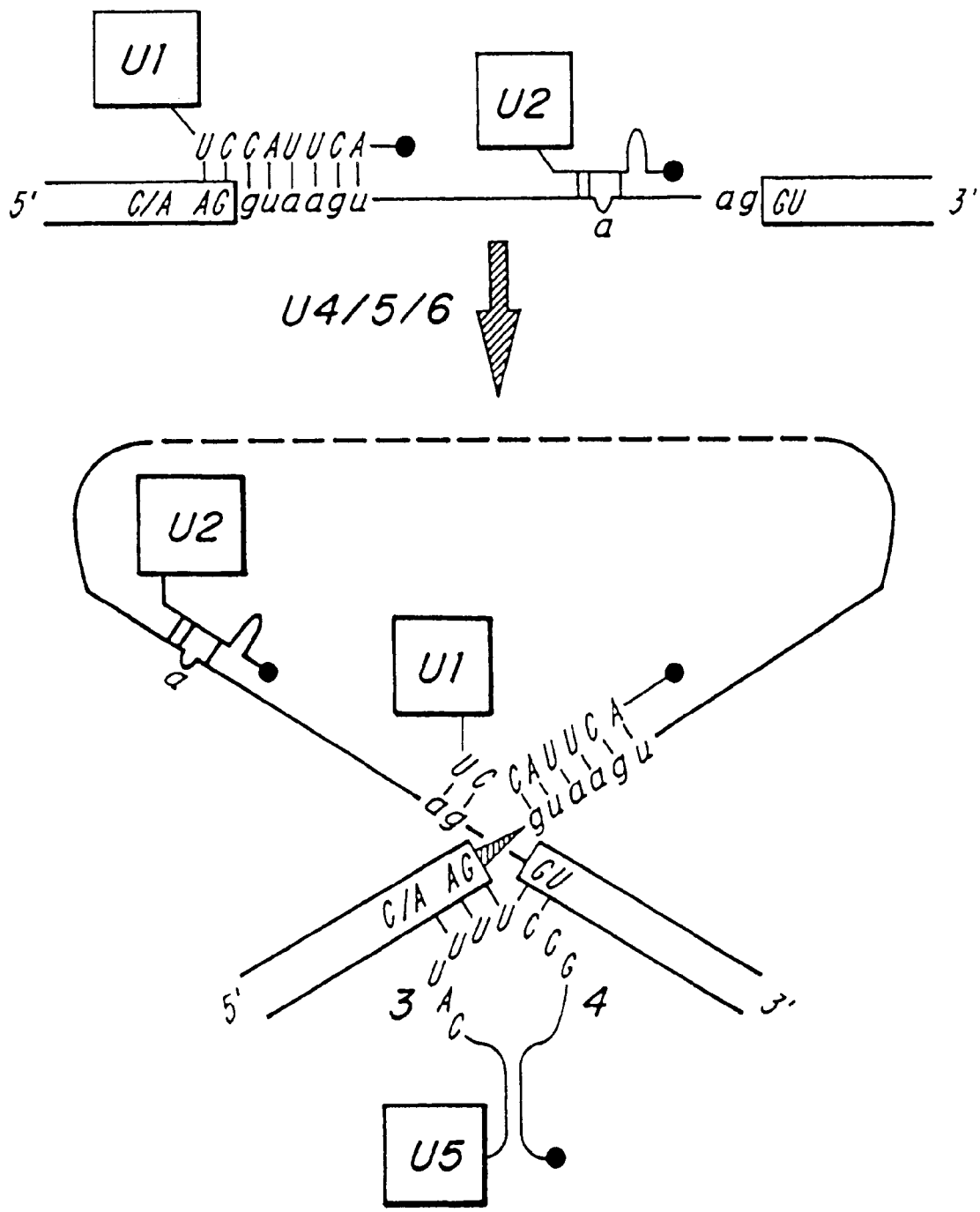
FIG. 6A illustrates the interaction between nuclear pre-mRNA introns and snRNPs.

As illustrated in FIG. 6A, consensus sequences of the 5' splice site and at the branchpoint are recognized by base pairing with the U1 and U2 snRNP's, respectively. The original proposal that the U1 RNA interacted with the 5' splice site was based solely on the observed nine-base-pair complementarity between the two mammalian sequences (Rogers et al. (1980) *Nature* 283:220). This model has since been extensively verified experimentally (reviewed in Steitz et al., in *Structure and Function of Major and Minor snRNP Particles*, M. L. Bimstiel, Ed. (Springer-Verlag, New York, 1988)). Demonstration of the Watson-Crick interactions between these RNAs was provided by the construction of compensatory base pair changes in mammalian cells (Zhuang et al. (1986) *Cell* 46:827). Subsequently, suppressor mutations were used to prove the interaction between U1 and 5' splice site in yeast (Seraphin et al. (1988) *EMBO J.* 7:2533).

The base pairing interaction between U2 and sequences surrounding the branchpoint was first tested in yeast (Parker et al. (1987) *Cell* 49:229), where the strict conservation of the branchpoint sequence readily revealed the potential for complementarity. The branchpoint nucleotide, which carries out nucleophilic attack on the 5' splice site, is thought to be unpaired (FIG. 6A), and is analogous to the residue that bulges out of an intramolecular helix in domain 6 of group II introns. The base pairing interaction between U2 and the intron has also been demonstrated genetically in mammalian systems (Zhaung et al. (1989) *Genes Dev.* 3:1545). In fact, although mammalian branchpoint sequences are notable for their deviation from a strict consensus, it has been demonstrated that a sequence identical to the invariant core of the yeast consensus, CUAAC is the most preferred (Reed et al. (1989) *PNAS* 86:2752).

Genetic evidence in yeast suggests that the intron base pairing region at the 5' end of U1 RNA per se is not sufficient to specify the site of 5' cleavage. Mutation of the invariant G at position 5 of the 5' splice site not only depresses cleavage efficiency at the normal GU site but activates cleavage nearby; the precise location of the aberrant site varies depending on the surrounding context (Jacquier et al. (1985) *Cell* 43:423; Parker et al. (1985) *Cell* 41:107; and Fouser et al. (1986) *Cell* 45:81). Introduction of a U1 RNA, the sequence of which has been changed to restore base pairing capability at position 5, does not depress the abnormal cleavage event; it enhances the cleavage at both wild-type and aberrant sites. These results indicate that the complementarity between U1 and the intron is important for recognition of the splice-site region but does not determine the specific site of bond cleavage (Seraphin et al. (1988) *Genes Dev.* 2:125; and Seraphin et al. (1990) *Cell* 63:619).

With regard to snRNPs, genetic experiments in yeast have revealed that the U5 snRNP is an excellent candidate for a trans-acting factor that functions in collaboration with U1 to bring the splice sites together in the spliceosome. U5 is involved in the fidelity of the first and the second cleavage-ligation reactions. For example, a number of U5 mutants exhibit a distinct spectrum of 5' splice-site usage; point mutations with the invariant nine-nucleotide loop sequence (GCCUUUUAC) in U5 RNA allows use of novel 5' splice sites when the normal 5' splice site was mutated. For instance, splicing of detective introns was restored when positions 5 or 6 of the invariant U5 loop were mutated so that they were complementary to the nucleotides at positions 2 and 3 upstream of the novel 5' splice site when the normal 5' splice site was mutated. For instance, splicing of defective introns was restored when positions 5 or 6 of the invariant U5 loop were mutated so that they were complementary to the nucleotides at positions 2 and 3 upstream of the novel 5' splice site. Likewise, mutational analysis has demonstrated the role of the U5 loop sequence in 3' splice site activation. For example, transcripts which are defective in splicing due to nucleotide changes in either one of the first two nucleotides of the 3' exon were subsequently rendered functional by mutations in positions 3 or 4 of the U5 loop sequence which permitted pairing with the mutant 3' exon. (See Newman et al. (1992) *Cell* 68:1; and Newman et al. (1991) *Cell* 65:115). It is suggested that first U1 base pairs with intron nucleotides at the 5' splice site during assembly of an early complex (also including U2). This complex is joined by a tri-snRNP complex comprising U4, U5 and U6 to form a Holliday-like structure which serves to juxtaposition the 5' and 3' splice sites, wherein U1 base pairs with intronic sequences at both splice site. (Steitz et al. (1992) *Science* 257:888–889).

While each of the U1, U2 and U5 snRNPs appear to be able to recognize consensus signals within the intron, no specific binding sites for the U4–U6 snRNP has been identified. U4 and U6 are well conserved in length between yeast and mammals and are found base paired to one another in a simple snRNP (Siliciano et al. (1987) *Cell* 50:585). The interaction between U4 and U6 is markedly destablized specifically at a late stage in spliceosome assembly, before the first nucleolytic step of the reaction (Pikienly et al. (1986) *Nature* 324:341; and Cheng et al. (1987) *Genes Dev.* 1:1014). This temporal correlation, together with an unusual size and sequence conservation of U6, has lead to the understanding that the unwinding of U4 and U6 activates U6 for participation in catalysis. In this view, U4 would function as an antisense negative regulator, sequestering U6 in an inert conformation until it is appropriate to act (Guthrie et al. (1988) *Annu Rev. Genet.* 22:387). Recent mutational studies demonstrate a functional role for U6 residues in the U4–U6 interaction domain in addition to base pairing (Vanken et al. (1990) *EMBO J* 9:3397; and Madhani et al. (1990) *Genes Dev.* 4:2264).

Mutational analysis of the spliceosomal RNAs has revealed a tolerance of substitutions or, in some cases, deletion, even of phylogentically conserved residues (Shuster et al. (1988) *Cell* 55:41; Pan et al. (1989) *Genes Dev.* 3:1887; Liao et al. (1990) *Genes Dev.* 4:1766; and Jones et al. (1990) *EMBO J* 9:2555). For example, extensive mutagenesis of yeast U6 has been carried out, including assaying the function of a mutated RNA with an in vitro reconstitution system (Fabrizo et al. (1990) *Science* 250:404), and transforming a mutagenized U6 gene into yeast and identifying mutants by their in vivo phenotype (Madhani et al. (1990) *Genes Dev.* 4:2264). Whereas most mutations in U6 have little or no functional consequence (even when conserved residues were altered), two regions that are particularly sensitive to nucleotide changes were identified: a short sequence in stem I (CAGC) that is interrupted by the *S. prombe* intron, and a second, six-nucleotide region (ACAGAG) upstream of stem I.

Figure 6B:
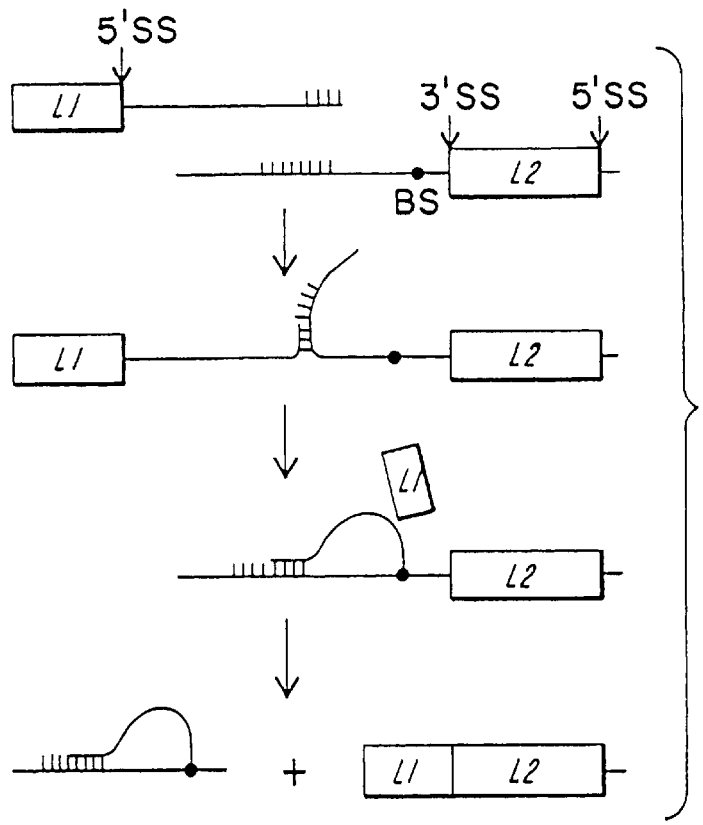
FIGS. 6B and 6C illustrate two embodiments for accomplishing nuclear pre-mRNA intron mediated trans-splicing.
Figure 6C:
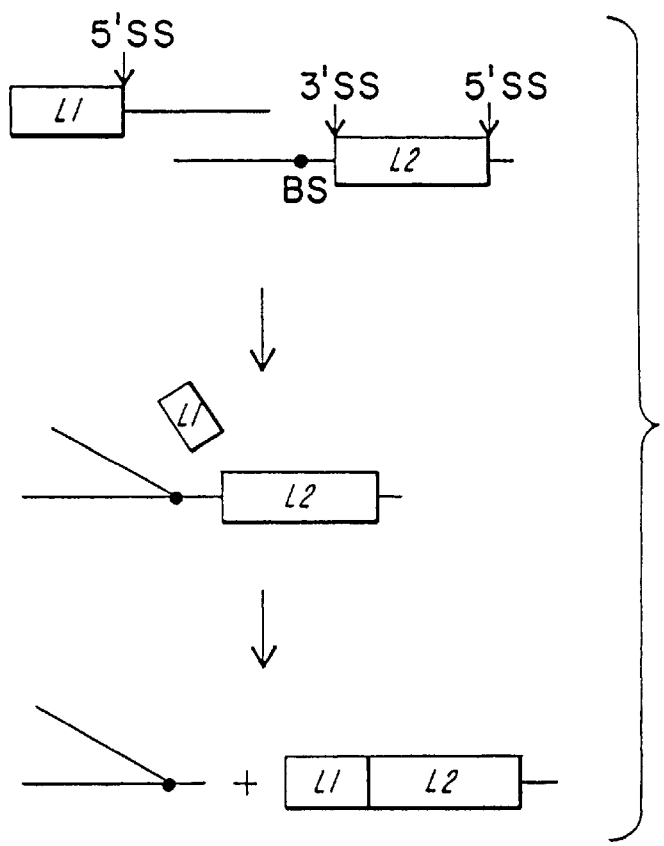

As described above for both group I and group II introns, exonic sequences derived from separate RNA transcripts can be joined in a trans-splicing process utilizing nuclear pre-mRNA intron fragments (Konarska et al. (1985) *Cell* 42:165–171; and Solnick (1985) *Cell* 42:157–164). In the trans-splicing reactions, an RNA molecule, comprising an exon and a 3' flanking intron sequences which includes a 5' splice site, is mixed with an RNA molecule comprising an exon and 5' flanking intronic sequences, including a 3' splice site, and a branch acceptor site. As illustrated in FIGS. 6B and 6C, upon incubation of the two types of transcripts (e.g. in a cell-free splicing system), the exonic sequences can be accurately ligated. In a preferred embodiment the two transcripts contain complementary sequences which allow base-pairing of the discontinuous intron fragments. Such a construct, as FIG. 6B depicts, can result in a greater splicing efficiency relative to the scheme shown in FIG. 6C in which no complementary sequences are provided to potentiate complementation of the discontinuous intron fragments.

The exon ligation reaction mediated by nuclear pre-mRNA intronic sequences can be carried out in a cell-free splicing system. For example, combinatorial exon constructs can be mixed in a buffer comprising 25 mM creatine phosphate, 1 mM ATP, 10 mM $MgCl_2$, and a nuclear extract containing appropriate factors to facilitate ligation of the exons (Konarska et al. (1985) *Nature* 313:552–557; Krainer et al. (1984) *Cell* 36:993–1005; and Dignam et al. (1983) *Nuc. Acid Res* 11:1475–1489). The nuclear extract can be substituted with partially purified spliceosomes capable of carrying out the two transesterification reactions in the presence of complementing extracts. Such spliceosomal complexes have been obtained by gradiant sedimentation (Grabowski et al. (1985) *Cell* 42:345–353; and Lin et al. (1987) *Genes Dev.* 1:7–18), gel filtration chromatography (Abmayr et al. (1988) *PNAS* 85:7216–7220; and Reed et al. (1988) *Cell* 53:949–961), and polyvinyl alcohol precipitation (Parent et al. (1989) *J. Mol. Biol.* 209:379–392). In one embodiment, the spliceosomes are activated for removal of nuclear pre-mRNA introns by the addition of two purified yeast "pre-mRNA processing" proteins, PRP2 and PRP16 (Kim et al. (1993) *PNAS* 90:888–892; Yean et al. (1991) *Mol. Cell Biol.* 11:5571–5577; and Schwer et al. (1991) *Nature* 349:494–499).

II. Trans-splicing Combination of Exons

A. Exon Shuffling

In one embodiment of the present combinatorial method, the intronic sequences which flank each of the exon modules are chosen such that gene assembly occurs in vitro through ligation of the exons, mediated by a trans-splicing mechanism. Conceptually, processing of the exons resembles that of a fragmented cis-splicing reaction, though a distinguishing feature of trans-splicing versus cis-splicing is that substrates of the reaction are unlinked. As described above, breaks in the intron sequence can be introduced without abrogating splicing, indicating that coordinated interactions between different portions of a functional intron need not depend on a covalent linkage between those portions to reconstitute a functionally-active splicing structure. Rather, the joining of independently transcribed coding sequences results from interactions between fragmented intronic RNA pieces, with each of the separate precursors contributing to a functional trans-splicing core structure.

The present trans-splicing system provides an active set of reagents for trans-splicing wherein the flanking intronic sequences can interact to form a reactive complex which promotes the transesterification reactions necessary to cause the ligation of discontinuous exons. In one embodiment, the exons are flanked by portions of one of a group I or group II intron, such that the interaction of the flanking intronic sequences is sufficient to produce an autocatalytic core capable of driving ligation of the exons in the absence of any other factors. While the accuracy and/or efficiency of these autocatalytic reactions can be improved, in some instances, by the addition of trans-acting protein or RNA factors, such additions are not necessary.

In another embodiment, the exon modules are flanked by intronic sequences which are unable, in and of themselves, to form functional splicing complexes without involvement of at least one trans-acting factor. For example, the additional trans-acting factor may compensate for structural defects of a complex formed solely by the flanking introns. As described above, domain 5 of the group II intron class can be removed from the flanking intronic sequences, and added instead as a trans-acting RNA element. Similarly, when nuclear pre-mRNA intron fragments are utilized to generate the flanking sequences, the ligation of the exons requires the addition of snRNPs to form a productive splicing complex.

Figure 7:
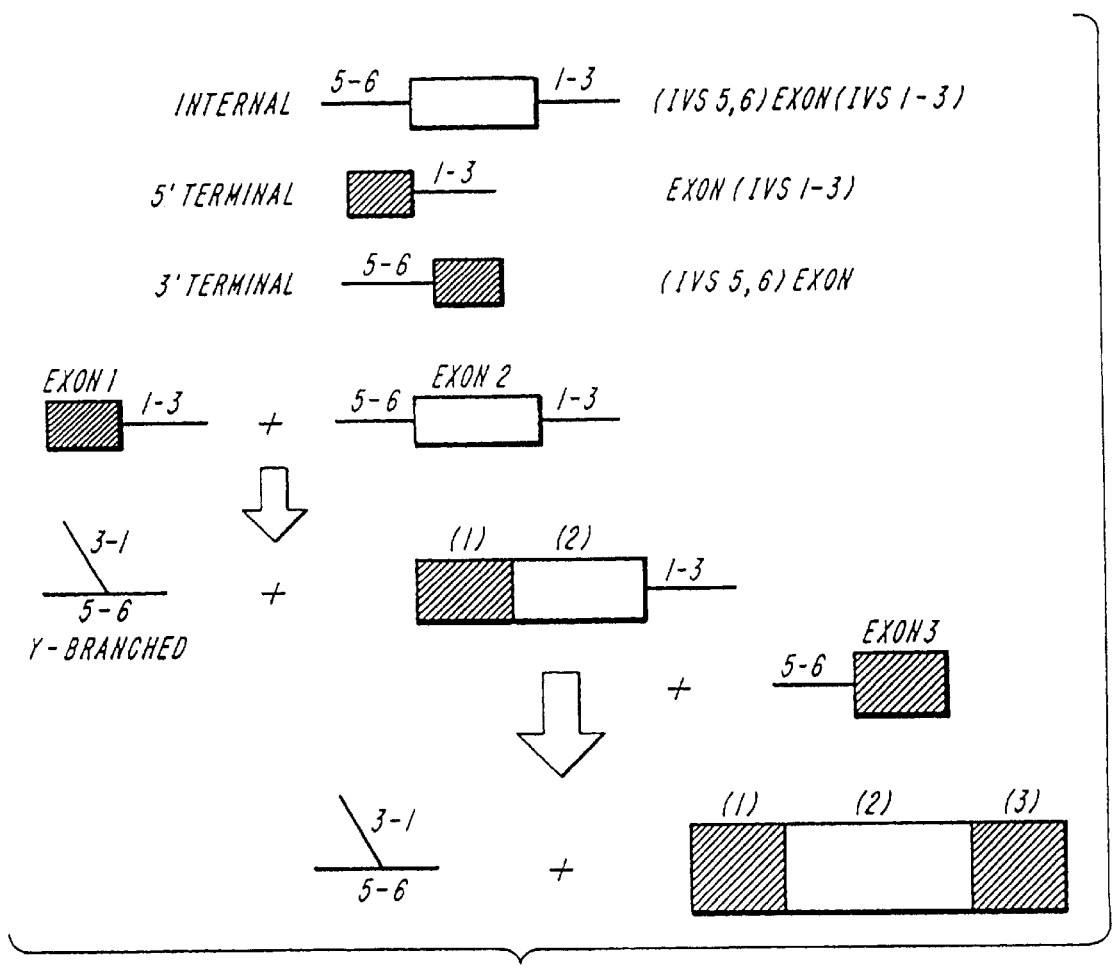
FIG. 7 is a schematic representation of a trans-splicing reaction between discontinuous exon sequences.

In an illustrative embodiment, the present combinatorial approach can make use of group II intronic sequences to mediate trans-splicing of exons. For example, as depicted in FIG. 7, internal exons can be generated which include domains 5 and 6 at their 5' end, and domains 1–3 at their 3' end. The nomenclature of such a construct is (IVS5,6) Exon(IVS 1–3), representing the intron fragments and their orientation with respect to the exon. Terminal exons are likewise constructed to be able to participate in trans-splicing, but at only one end of the exon. A 5' terminal exon, in the illustrated group II system, is one which is flanked by domains 1–3 at its 3' end [Exons(IVS1–3)] and is therefore limited to addition of further exonic sequences only at that end; and a 3' terminal exon is flanked by intron sequences (domains 5 and 6) at only its 5' end [(IVS5,6)Exon]. Under conditions which favor trans-splicing, the flanking intron sequences at the 5' end of one exon and the 3' end of another exon will associate to form a functionally active complex by intermolecular complementation and ligate the two exons together. Such trans-splicing reactions can link the 5' terminal exon directly to the 3' terminal exon, or alternatively can insert one or more internal exons between the two terminal exons.

In some cases, trans-splicing reactions by intron-flanked internal exons may be inhibited by a competing inverse-splicing reaction that such internal exons can undergo. As described below and depicted in FIG. 8A, intron-flanked internal exons can participate in intramolecular "inverse-splicing" reactions in which the 3' end of the exon is spliced to its own 5' end, so that the exon is circularized (and the intronic sequences are released as a Y-branched ribozyme). Because inverse-splicing is an intramolecular reaction, it can sometimes compete effectively with any trans-splicing reactions, so that few trans-splicing products are produced. In such cases, the inverse-splicing reaction can be inhibited by provision of an antisense nucleic acid that binds to one or the other of the flanking intronic elements. Of course, the antisense nucleic acid will also block one of the trans-splicing reactions that would otherwise be available to the internal exon. Accordingly, use of antisense nucleic acids to control inverse-splicing also limits trans-splicing experiments to a series of sequential reactions. FIG. 9 depicts one embodiment of such a controlled, sequential trans-splicing reaction according to the present invention.

Figure 10:
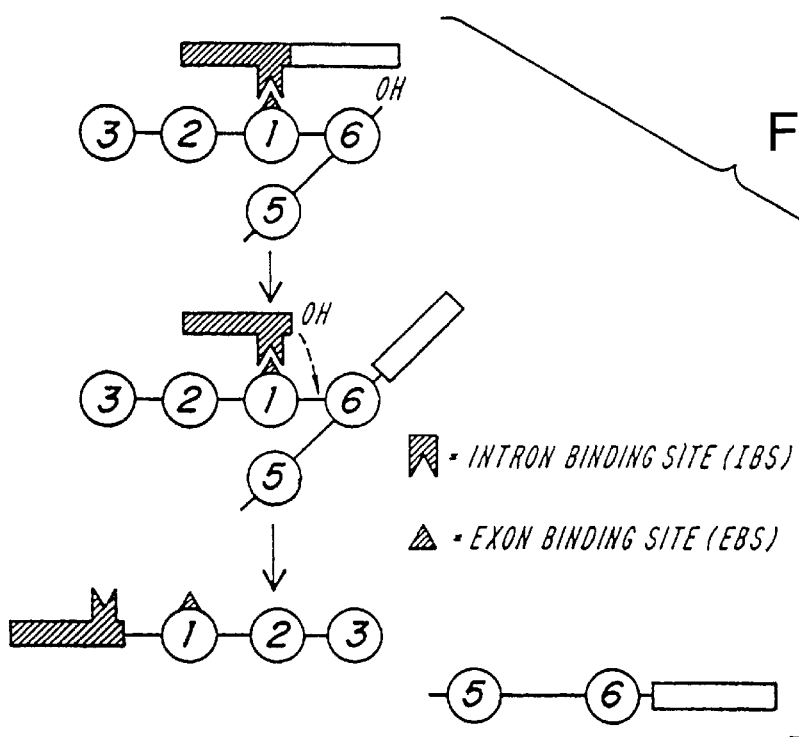
FIG. 10 illustrates how a reverse-splicing reaction can be utilized to activate exons for subsequent combinatorial trans-splicing.

In another embodiment of the present trans-splicing combinatorial method, the exons, as initially admixed, lack flanking intronic sequences at one or both ends, relying instead on a subsequent addition of flanking intronic fragments to the exons by a reverse-splicing reaction. Addition of the flanking intron sequences, which have been supplemented in the exon mixture, consequently activates an exon for trans-splicing. FIG. 10 illustrates how the reverse-splicing reaction of group II introns can be used to add domains 1–3 to the 3' end of an exon as well as domains 5–6 to the 5' end of an exon. As shown in FIG. 10, the reversal reaction for branch formation can mediate addition of 3' flanking sequences to an exon. For example, exon modules having 5' intron fragments (e.g. domains 5-6) can be mixed together with little ligation occurring between exons. These exons are then mixed with a 2'–5' Y-branched intron resembling the lariat-IVS, except that the lariat is discontinuous between domains 3 and 5. The reverse-splicing is initiated by binding of the IBS 1 of the 5' exon to the EBS 1 of the Y-branched intron, followed by nucleophilic attack by the 3'-OH of the exon on the 2'–5' phosphodiester bond of the branch site. This reaction, as depicted in FIG. 10, results in the reconstitution of the 5' splice-site with a flanking intron fragment comprising domains 1–3.

While FIG. 10 depicts both a 5' exon and 3' exon, the reverse splicing reaction can be carried out without any 3' exon, the IBS sequence being at the extreme 3' end of the transcript to be activated. Alternatively, to facilitate addition of 5' flanking sequences, an exon can be constructed so as to further include a leader sequence at its 5' end. As shown in FIG. 10, the leader (e.g. the 5' exon) contains an IBS which defines the splice junction between the leader and "mature" exon. The leader sequence can be relatively short, such as on the order of 2-3 amino acid residues (e.g. the length of the IBS). Through a reverse self-splicing reaction using a discontinuous 2'–5' branched intron, the intronic sequences can be integrated at the splice junction by reversal of the two transterfication steps in forward splicing. The resulting products includes the mature exon having a 5' flanking intron fragment comprising domains 5 and 4.

Addition of intronic fragments by reverse-splicing and the subsequent activation of the exons presents a number of control advantages. For instance, the IBS:EBS interaction can be manipulated such that a variegated population of exons is heterologous with respect to intron binding sequences (e.g. one particular species of exon has a different IBS relative to other exons in the population). Thus, sequential addition of intronic RNA having discrete EBS sequences can reduce the construction of a gene to non-random or only semi-random assembly of the exons by sequentially activating only particular combinatorial units in the mixture. Another advantage derives from being able to store exons as part of a library without self-splicing occurring at any significant rate during storage. Until the exons are activated for trans-splicing by addition of the intronic sequences to one or both ends, the exons can be maintained together in an effectively inert state.

When the interactions of the flanking introns are random, the order and composition of the internal exons of the combinatorial gene library generated is also random. For instance, where the variegated population of exons used to generate the combinatorial genes comprises N different internal exons, random trans-splicing of the internal exons can result in $N^y$ different genes having y internal exons. Where 5 different internal exons are used (N=5) but only constructs having one exon ligated between the terminal exons are considered (i.e. y=1) the present combinatorial approach can produce 5 different genes. However, where y=6, the combinatorial approach can give rise to 15,625 different genes having 6 internal exons, and 19,530 different genes having from 1 to 6 internal exons (e.g. $N^1+N^2 \ldots +N^{y-1}+N^y$. It will be appreciated that the frequency of occurrence of a particular exonic sequence in the combinatorial library may also be influenced by, for example, varying the concentration of that exon relative to other exons present, or altering the flanking intronic sequences of that exon to either diminish or enhance its trans-splicing ability relative to the other exons being admixed.

Figure 11:
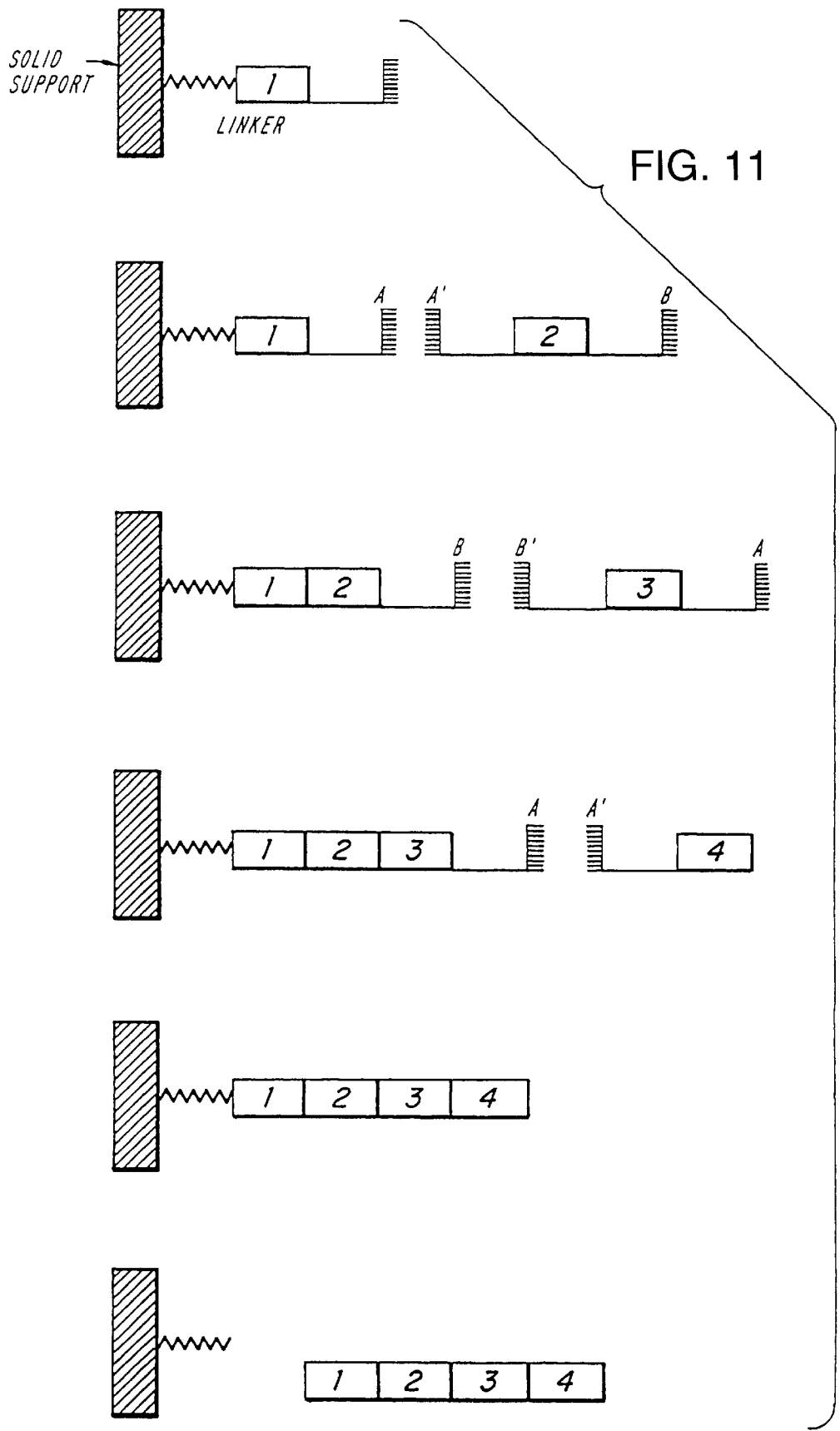
FIG. 11 illustrates an ordered gene assembly mediated by trans-splicing of exons flanked with nuclear pre-mRNA intron fragments.

However, the present trans-splicing method can be utilized for ordered gene assembly, and carried out in much the same fashion as automated oligonucleotide or polypeptide synthesis. FIG. 11 describes schematically the use of resin-bound combinatorial units in the ordered synthesis of a gene. In the illustrated example, mammalian pre-mRNA introns are used to flank the exon sequences, and splicing is catalyzed by addition by splicing extract isolated from mammalian cells. The steps outlined can be carried out manually, but are amenable to automation. The 5' terminal exon sequence (shown as exon 1 in FIG. 11) is directly followed by a 5' portion of an intron that begins with a 5' splice-site consensus sequence, but does not include the branch acceptor sequence. The flanking intron fragment further includes an added nucleotide sequence, labeled "A" in the diagram, at the 3' end of the downstream flanking intron fragment. The 5' end of this terminal combinatorial unit is covalently linked to a solid support.

In the illustrated scheme, exon 2 is covalently joined to exon 1 by trans-splicing. The internal shuffling unit that contains exon 2 is flanked at both ends by intronic fragments. Downstream of exon 2 are intron sequences similar to those downstream of exon 1, with the exception that in place of sequence A the intronic fragment of exon 2 has an added sequence B that is unique, relative to sequence A. Exon 2 is also preceded by a sequence complementary to A (designated A'), followed by the nuclear pre-mRNA intron sequences that were not included downstream of exon 1, including the branch acceptor sequence and 3' splice-site consensus sequence AG.

To accomplish the trans-splicing reaction, the shuffling units are allowed to anneal by hydrogen bonding between the complementary intronic sequences (e.g. A and A'). Then, trans-splicing is catalyzed by the addition of a splicing extract which contains the appropriate snRNPs and other essential splicing factors. The Y-branched intron that is generated, and any other by-products of the reaction, are washed away, and a ligated exon 1 and 2 remain bound to the resin. A second internal shuffling unit is added. As shown in FIG. 11, the exon (exon 3) has flanking intronic fragments which include a sequence B' in the upstream fragment and a sequence A in the downstream fragment. The nucleotide sequence B' is unique relative to sequence A', and is complementary to sequence B. As above, the RNA is allowed to anneal through the B:B' sequences, splicing of the intervening sequences is catalyzed by the addition of extract, and reaction by-products other than the resin bound exons are washed away. While FIG. 11 depicts a non-random assembly of a gene, it is understood that semi-random assembly can also be carried out, such as would occur, for example, when exon 3 is substituted with a variegated population of exons combinatorial units.

This procedure can be continued with other exons, and may be terminated by ligation of a 3' terminal shuffling unit that contains an exon (exon 4 in FIG. 11) with upstream intron sequence (and either the A' or B' sequence, as appropriate), but lacking any downstream intron sequences. After the 3' terminal exon is added, the assembled gene can be cleaved from the solid support, reverse transcribed, and the cDNA amplified by PCR and cloned into a plasmid by standard methods.

Figure 12:
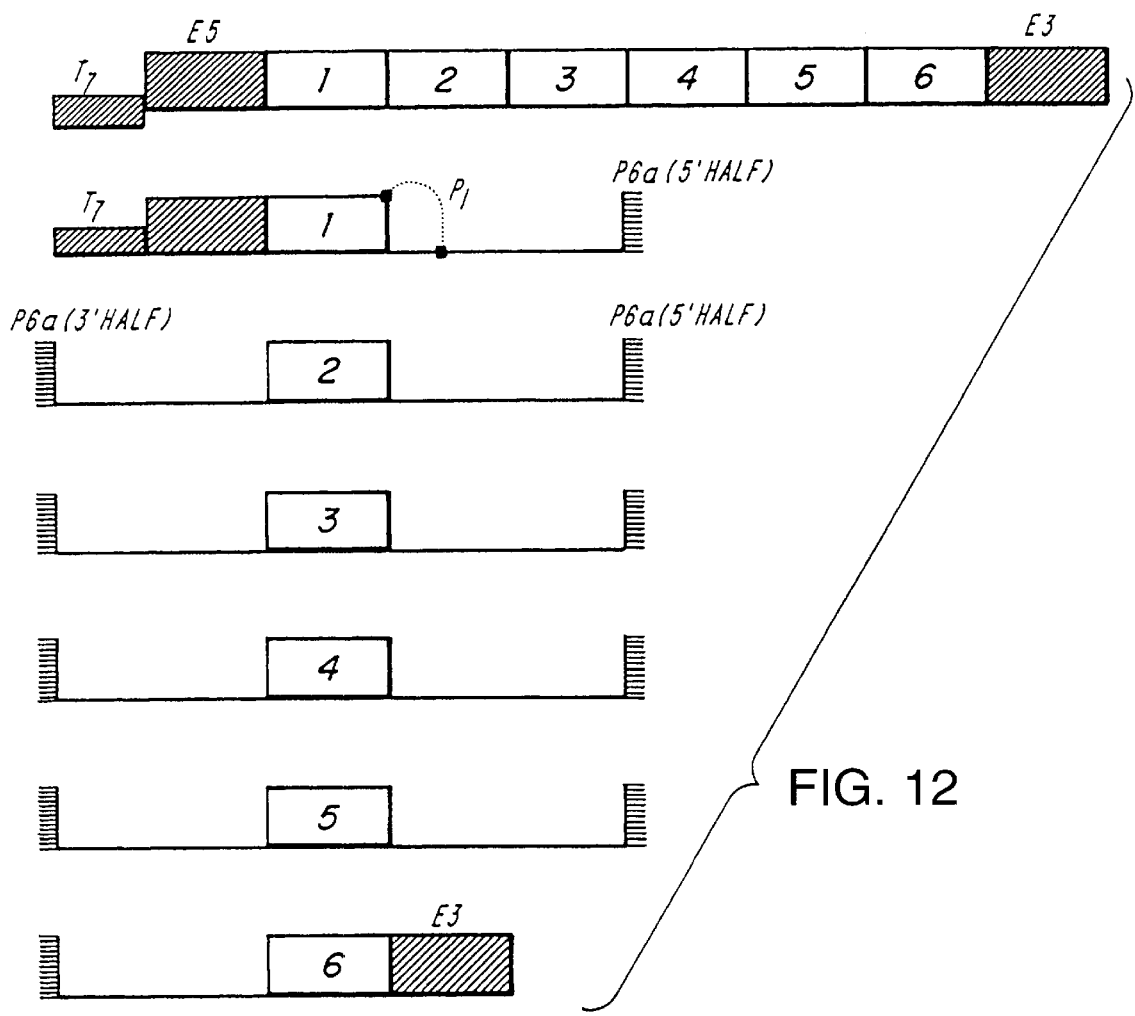
FIG. 12 depicts one example of how group I intron sequences can be used to shuffle group II intron domains.

The domain shuffling experiments described to yield novel protein coding genes can also be used to create new ribozymes. FIG. 12 depicts one example of how group I intron sequences can be used to shuffle group II intron domains. In the illustrative embodiment, the group II intron consists of 6 domains and is flanked by exon (E5 and E3); in this instance, E5 is shown to include a T7 promoter. The six shuffling competent constructs diagramed in FIG. 12 can be made either by standard site directed mutagenesis and cloning or by the reversal of splicing. The 5' terminal exon is followed by sequences from the T4 td intron, beginning with the first nucleotide of the intron and including the internal guide sequence, and continuing through the 5' half of the P6a stem (i.e. including half of L6). The last nucleotide of the exon is a U. The internal guide sequence of the intron is changed by site directed mutagenesis so that it is complementary to the last 6 nt of the exon. This will allow the P1 stem to form. The U at the end of the exon is based paired with a G in the internal guide sequence. The 3' terminal "exon", in this case, consists of group II intron domain 6 plus E3. The 3' terminal exon is preceded by the T4 id intron, beginning with the 3' half of P6a and continuing through to the end of the intron. The last nucleotide of the intron is followed by the first nucleotide of group II intron domain 6. The internal exons each consist of a group II intron domain but, in contrast to the terminal exons, each internal exon is flanked by group I intron sequences on both sides. In each case, the internal guide sequence of the group I intron is changed so as to be complementary to the last 6 nts of the exon and, in each case, the last nucleotide of the exon is a U.

Constructing a library of group II domains flanked by group I intronic sequence allows new group II ribozymes to be assembled from these units by random exon shuffling using conditions that allow for efficient trans-splicing of "exons" flanked by these group I intron sequences. For instance, if only one E5:d1 and d6:E3 are used, but a variegated population of d2–d5, the assembled genes will all have the same 5' and 3' terminal exons, but will have different arrangements and numbers of internal exons. An E3 specific primer plus reverse transcriptase can be used to make cDNA of the library of recombined transcript. T7 and E3 specific primers can be used to amplify the assembled genes by PCR, and RNA transcripts of the assembled gene can be generated using T7 polymerase. The RNA can be incubated under self splicing conditions appropriate for group II splicing. Molecules that are capable of self splicing will yield intron lariats that migrate anomalously slow on denaturing polyacrylamide gels. The lariats can be gel purified and represent active ribozyymes. The isolated lariats can be specifically debranched with a HeLa debranching activity. Reverse transcription and PCR can be used to make and amplify cDNA copies of the ribozymes. The primers used for the PCR amplification will include exon sequences so that each amplified intron will be flanked by a 5' and a 3' exon. The last 6 nt of the 5' exon will be complementary to EBS 1. The amplified DNA can be cloned into a plasmid vector and individual interesting variants isolated and studied in detail.

EXAMPLE 1

Use of Engineered Ribozymes to Catalyze Chimeric Gene Assembly

Engineered group II introns were utilized to catalyze linkage of human exons by trans-splicing (see Mikheeva et al. (1996), *PNAS* 93:7486–7490, incorporated herein by reference). Specifically, group II intron derivatives were designed that insert into selected sites in the human tissue plasmnogen activator (t-PA) mRNA. The insertion reaction linked (t-PA) sequences to the group II intron sequences so that trans-splicing reactions catalyzed by the intron sequences shuffled the (t-PA) sequences.

Figure 13A:
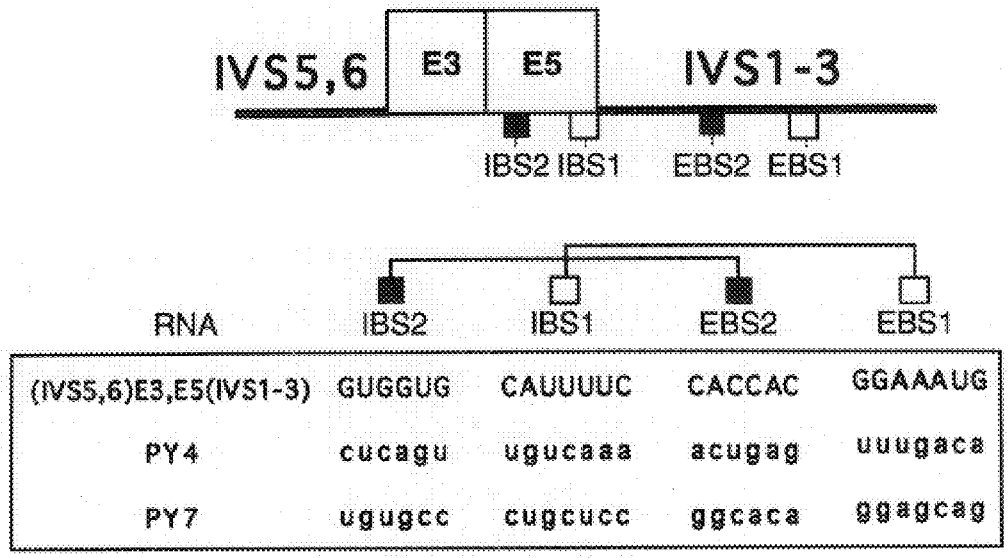
FIG. 13A depicts various inverse-splicing constructs in accordance with the present invention.

The three inverse-splicing precursors used in this study were as follows: (IVS5, 6)E3,E5(IVS1–3), PY4, and PY7. These precursors were made by transcription in vitro, using T7 RNA polymerase, of plasmids pINV1, pY4, and pY7, respectively. The three inverse-splicing precursors were identical, except for the indicated base substitutions in the EBS and IBS sequences of PY4 and PY7 (see FIG. 13). The base substitutions were made by site-directed mutagenesis of pINV1 (Jarrell (1993) *PNAS* 90, 8624–8627) DNA using the method of Kunkel, as described (Jarrell et al. (1988) *Mol. Cell. Biol.* 8:2361–2366). Prior to inverse-splicing, full-length splicing precursors were purified from an acrylamide gel. Inverse-splicing reactions were conducted in buffer containing 40 mM Tris hydrochloride (pH 7.6), 100 mM $MgCl_2$, and 1.2 M $(NH_4)_2SO_4$.

The substrate RNAs that were attacked by Y-branched ribozymes were made by transcription in vitro of plasmids pFn and pProt. Both pFn and pProt are subclones of plasmid pKS$^+$t-PA. The pKS$^+$t-PA plasmid was derived from pET-PFR (Pennica et al. (1983) *Nature* 301:214–221). The cDNA region of pETPFR was amplified using PCR primers t-PA1 (5'-ACGATGCATGCTGGAGAGAAAACCTCTGCG [SEQ ID NO: 3]) and t-PA2 (5'ACGATGCATTCTGTAGAGAAGCACTGCGCC [SEQ ID NO: 4]). Both primers included recognition sites for NsiI. The amplified DNA was cut with NsiI and ligated into the KS$^+$ vector that had been cut with PstI. A recombinant plasmid was identified with the insert in the sense orientation, relative to the start of T7 transcription. The pFn plasmid was generated by deleting the t-PA sequences between the StyI site of t-PA and the EcoRI site of the vector. Specifically, the pKS+t-PA plasmid was cut with StyI and EcoRI, treated with Klenow fragment to blunt the EcoRI end and with ligase to join the StyI end to the blunted EcoRI end of the vector. The pProt plasmid was generated by subdloning the ScaI-HindIII fragment into the pBS⁻ vector. Specifically, the pKS+t-PA plasmid was cut with ScaI and HindiI. The 922-bp fragment was isolated and ligated into pBS⁻ that had been cut with SmaI and HindIII. Ribozyme integration reactions were done in the same buffer that was used for the inverse-splicing reactions (see above).

The reverse transcription (RT)-PCR experiments were done as described (Jarrell (1993) *PNAS* 90:8624–8627). A total of five primers were used in RT-PCR experiments. The nucleotide sequences of primers t-PA1 and t-PA2 are given above. Other primers include I654 (5'-ACGAAGCTTC-CTATAGTATAAGTTAGCAGAT [SEQ ID NO: 5]); I5,6 (5'-GCGAATTCGAGCTCGTGAGCCGTAT [SEQ ID NO: 6]); and t-PA(49) (5'-ACGGGTACCGAAAGGGAAG-GAGCAAG-CCGTG [SEQ ID NO: 7]).

The trans-splicing reaction was done in buffer that was identical to that used for ribozyme integration and inverse-splicing, except the 1.2 M (NH$_4$)$_2$SO$_4$ was replaced by 1.2 M NH$_4$Cl. NH$_4$Cl was included in the trans-splicing buffer because pilot experiments showed that the rate of trans-splicing was about 10-fold higher in NH$_4$Cl was included in the trans-splicing was about 10-fold higher in NH$_4$Cl buffer than in (NH$_4$)$_2$SO$_4$ buffer (data not shown). However, the added NH$_4$Cl may have reduced the fidelity of the trans-splicing reaction: NH$_4$Cl is known to stimulate certain side reactions, such as ribozyme catalyzed site specific RNA hydrolysis (Peebles et al. (1987) *CSH Symp. Quant. Biol.* 52:223–232.; Jarrell et al. (1988) *J. Biol. Chem.* 263:3432–3439; Koch et al. (1992) *Mol. Cell. Biol.* 12:1950–1958; Wallasch et al. (1991) *Nuc.* 19:3307–3314; and Jacquier et al. (1991) *J. Mol. Biol.* 219:415–428). Trans-splicing reactions conducted in the presence of (NH$_4$)$_2$SO$_4$ may occur with higher fidelity.

The first step in our study involved identification of an efficient means of producing Y-branched ribozymes of altered specificity. Y-branched products can be produced in forward trans-splicing and inverse-splicing reactions. We chose to produce Y-branched ribozymes by inverse-splicing because that reaction, being unimolecular, is more efficient than trans-splicing.

Having decided on our strategy, we initiated our experiments to produce Y-branched ribozymes that were engineered to target t-PA sequences. Using site-directed mutagenesis on DNA plasmids that contained the aI5γ group II intron and its natural exons in inverse-splicing orientation, we produced two plasmids, pY4 and pY7, from which inverse-splicing substrates containing altered EBS1, IBS1, EBS2, and IBS2 sequences could be transcribed (FIG. 13). The EMS1 and EBS2 sequences of pY4 and pY7 were designed to hybridize to sequences within the t-PA gene, and the IBS1 and IBS2 sequences were made complementary to the mutated EBS1 and EBS2 sequences. Transcripts were produced from pY4 and pY7, and from the original inverse-splicing construct (pINV1) and were incubated under splicing conditions.

Figure 13B:
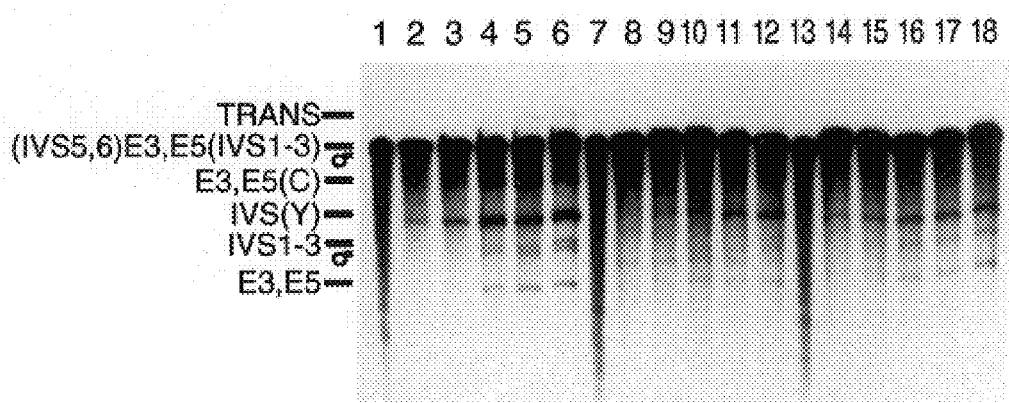
FIG. 13B shows time-course data of inverse-splicing reactions performed with the constructs of FIG. 13A.

FIG. 13B shows that all three transcripts spliced to produce an excised exon circle [E3,E5(C)] and a Y-branched intron [IVS(Y)]. Although both mutated transcripts spliced more slowly than did the control, the reactions readily produced useful quantities of Y-branched ribozymes with altered EBS1 and EBS2 sequences. For the purpose of exon shuffling, efficiency is unimportant; all that is required is that the inverse-splicing reactions produce enough Y-branched product for the subsequent integration reactions.

Figure 14A:
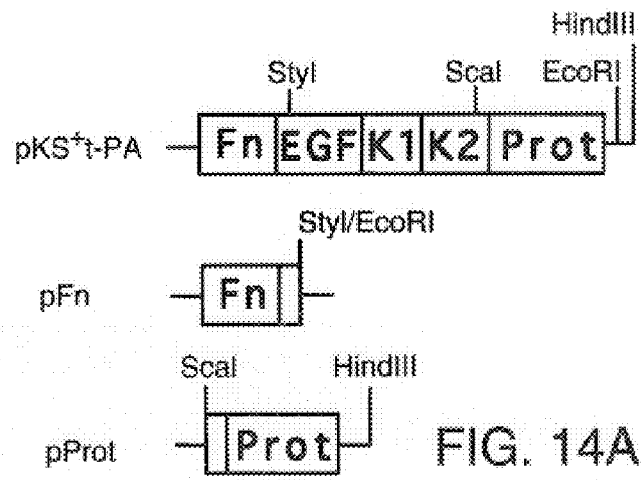
FIG. 14A depicts substrates utilized in Y-branched ribozyme insertion reactions according to the present invention.

Having produced Y-branched ribozymes with altered EBS1 and EBS2 sequences, we tested whether these ribozymes (Y4 and Y7) would insert specifically into RNA transcripts corresponding to portions of the t-PA transcript. The full-length t-PA transcript encodes five domains (FIG. 14A). We tested the ability of Y4 to integrate into a transcript, Fn txt, comprising the sequence encoding the fibronectin (Fn) domain followed by part of the sequence encoding the EGF domain. Likewise, we tested the ability of the Y7 ribozyme to integrate into the Prot txt transcript, which encodes part of a kringle domain (K2) and the protease domain (Prot).

Y4 was designed to insert precisely between the Fn and EGF sequences. Thus, for the purposes of this experiment, the last 16 nt of Fn, 5'-CUCAGUgccUGUCAAA (SEQ ID NO: 8), comprise its IBS2 and IBS1 (uppercase letters) sites, respectively. The EBS2 and EBS1 sites of Y4 were made complementary to these sequences (see FIG. 13A). Likewise, the Y7 ribozyme was engineered to insert precisely between K2 and Prot. Thus, the last 16 nt of K2, 5'-UGUGCCcucCUGCUCC (SEQ ID NO: 9), comprise its IBS2 and IBS1 sequences.

Both the Y4 ribozyme and the Y7 ribozyme were designed to insert at sites that, at the genomic level, are occupied by natural introns (Ny et al. (1984) *PNAS* 81:5355–5359). However, unlike the natural introns, which disrupt codons, the Y-branched ribozymes were designed to insert between codons, so that a subsequent trans-splicing reaction would create an in-frame fusion (see below).

Y4 was incubated with Fn txt under splicing conditions. Precise integration of Y4 into Fn txt was expected to yield two products, one corresponding to Fn joined to intron domains 1–3[Fn(1–3)], and one corresponding to intron domains 5 and 6 joined to the remainder of the Fn transcript [(5,6)E]. The Fn(1–3) product was expected to be 1034 nt; the 803-nt Y4 RNA and the RNAs in lane 5 were used in a size standards.

Figure 14B:
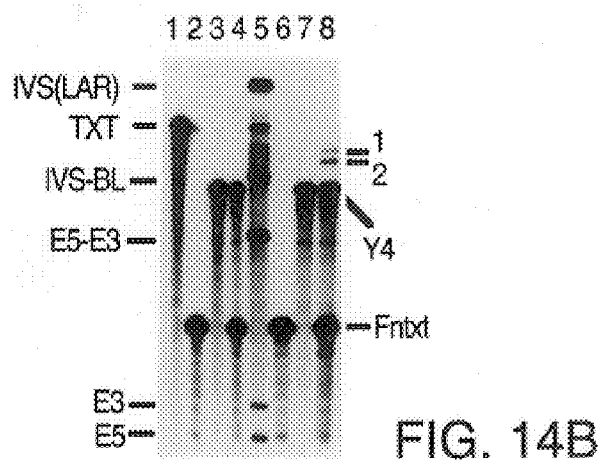
FIG. 14B shows insertion of Y-branched ribozyme Y4 into an Fn txt RNA.

As shown in FIG. 14B, lane 8, we observed two products (products 1 and 2) that migrated more slowly than Y4. Product 1 was the expected size of Fn(1–3). Both product 1 and product 2 were isolated for further analysis (see below). No attempt was made to identify or characterize the (5,6)E product, which, due to its size, was not retained within the gel.

Figure 14C:
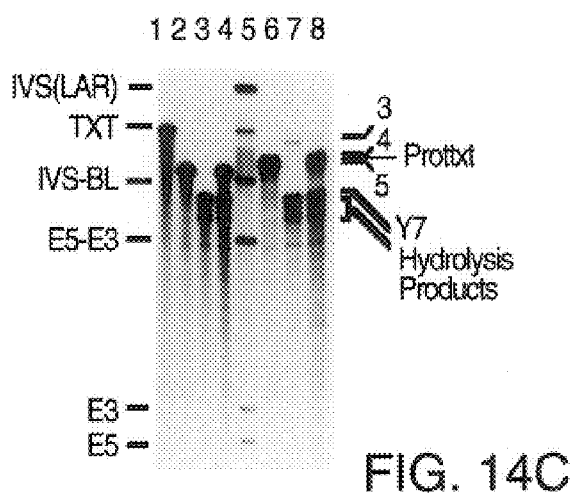
FIG. 14C shows insertion of Y-branched ribozyme Y7 into a Prot txt RNA.

In a parallel experiment, Y7 was incubated with the Prot txt RNA under splicing conditions. As was the case with Y4 and Fn txt, precise integration by the Y7 ribozyme into the Prot txt target was expected to yield two products: K(1–3) and (5,6)Prot. Our aim was to clone the (5,6)Prot product. Unfortunately, as shown in FIG. 14C, lane 8, we were not able to separate the 1000-nt (5,6)Prot product from the 955-nt Prot txt. Similarly, the 758-nt K(1–3) product was not separable from hydrolysis products of Y7. We therefore isolated three regions of the gel in order to detect any (5,6)Prot product that had been produced. We isolated the large minor triplet of bands, product 3, and also products 4 and 5 (from the Prot txt region of the gel). We did not expect product 3 to be (5,6)Prot because it was also observed when Y7 was incubated alone, and similar large products were observed when Y4 was incubated alone (see FIG. 14B, lane 7).

Figure 15A:
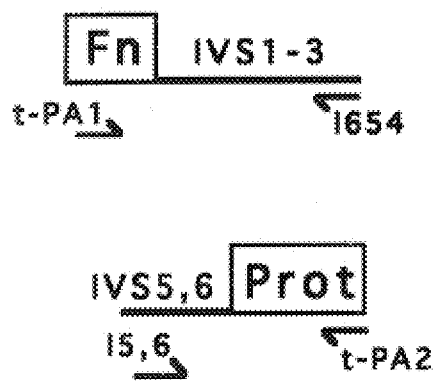
FIG. 15A depicts trans-splicing substrates according to the present invention.
Figure 15B:
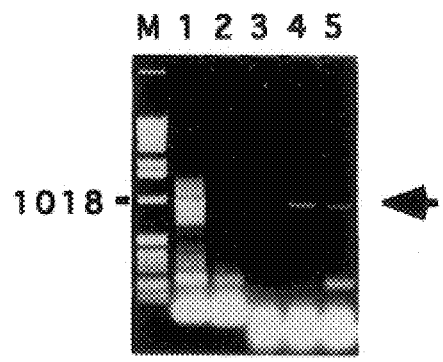
FIG. 15B shows a results of an RT-PCR reaction detecting the Fn(1–3) and (5,6)Prot substrates, generated by inverse splicing.

We analyzed purified products 1–5 by RT-PCR by using primers that amplify only recombinant RNAs. FIG. 15A shows the Fn(1–3) and (5,6)Prot recombinant RNAs, and the RT-PCR primers. FIG. 15B shows amplified DNAs from products 1–5. As can be seen, RT-PCR on product 1 produced an amplified DNA the expected size (1016 bp) of double-stranded Fn(1–3) (FIG. 15B, lane 1). RT-PCR analysis of product 2 produced three amplified DNAs that we did not analyze further, due to their low abundance (lane 2). Product 3 did not give rise to an amplification product (lane 3). Products 4 and 5 both yielded amplified DNAs the expected size (984 bp) of double-stranded (5,6)Prot (lanes 4 and 5).

Figure 15C:
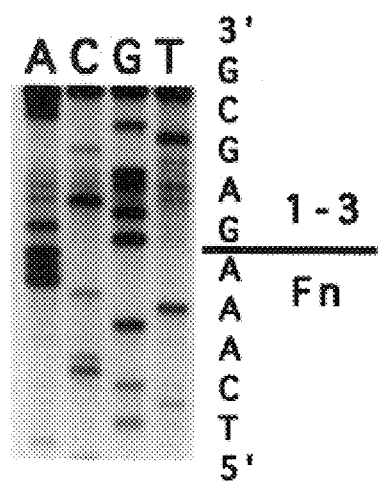
FIG. 15C shows the nucleotide sequence of the Fn(l-3) ligation point.
Figure 15D:
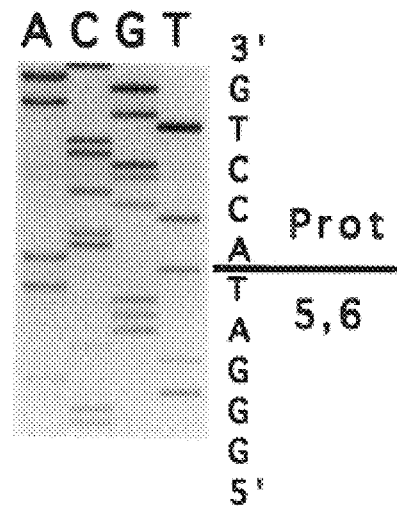
FIG. 15D shows the nucleotide sequence of the (5,6)Prot ligation point.

Both major amplifications products were cloned and analyzed by restriction mapping and sequencing. All 18 Fn(1–3) clones analyzed had the expected restriction map. Five clones were sequenced and were found to have accurately joined Fn and 1–3 sequences (FIG. 15C). Likewise, restriction mapping and sequencing of two (5,6)Prot recombinants showed that 5,6 and Prot sequencing of two (5,6) Prot recombinants showed that the 5,6 and Prot sequences had been accurately joined (FIG. 15D).

Having demonstrated that engineered Y-branched ribozymes insert specifically, our objective was to test the hypothesis that chimeric genes can be assembled by trans-splicing. The Fn(1–3) and (5,6)Prot RNAs were generated by in vitro transcription, mixed, and incubated under splicing conditions (FIG. 16). Two trans-splicing products (products 1 and 2) were characterized by RT-PCR (data not shown), using recombinant-specific primers (FIG. 16A). Product 1 did not yield amplified DNA; product 2 gave rise to amplified DNA the expected size (1204 bp) of Fn-Prot DNA. The amplified DNA was cloned, restriction mapped, and sequenced. Of 24 analyzed recombinants, 21 had the expected sequence; the remaining three had a deletion of a single adenosine residue (FIG. 16C). Although the mechanism of adenosine deletion is unknown, at least three mechanisms can be proposed based on known aspects of the group II intron splicing mechanism (see above).

EXAMPLE 2

Anti-sense Nucleic Acid Inhibits Inverse-splicing by a Flanked Internal Exon

Two different constructs were produced that encode flanked internal exons capable of both inverse- and trans-splicing. These constructs were prepared by isolating the Kringle-1 (K1) domain from the human t-PA gene and inserting this domain into appropriate inverse-splicing vectors.

Specifically, the cDNA clone of the human tissue plasminogen activator (t-PA) gene (pETPFR) was obtained from the ATCC collection (ATCC 40403; and U.S. Pat. No. 4,766,075). The entire cDNA clone was amplified by PCR using primers 5'-ACGATGCATGCTGGAGAGAAAACCTCTGCG (SEQ ID NO:3) and 5'-ACGATGCATTCTGTAGAGAAGCACTGCGCC (SEQ ID NO:4). TPA sequences from 70 base pairs (bp) upstream of the translation initiation site (AUG) to 88 bp downstream of the translation termination site (TGA) were amplified (SEQ ID NO:10). In addition, the primers added Nsi I sites to both ends of the amplified DNA. The amplified DNA was cut with Nsi I and ligated into the KS+ vector that had been cut with Pst I. A clone TPA-KS+, was isolated with the insert oriented such that in vitro transcription with $T_7$ RNA polymerase yields an RNA that is the same polarity as the tPA mRNA.

Separately, two unique restriction sites were added to the pINV1 plasmid (SEQ ID NO:11) by site directed mutagenesis, to facilitate insertion of portions of the tPA clone. A Kpn I site (GGTACC) was inserted at precisely the boundary between the end of the intron and the beginning of E3. An Xho I site was added to E5 by changing the sequence GTGGGA to a Xho I site (CTCGAG). Thus, the last seven bp of the exon were unchanged, but the six preceding base pairs were changed to create a Xho I site. The resulting plasmid is termed here INV-KX.

The region of the TPA cDNA clone that encodes the kringle-1 (Kp1) domain was amplified by PCR. The primers added a Kpn I site at the upstream end of the domain and a Xho I site to the downstream end. The amplified DNA was cut with Kpn I and Xho I and ligated into INV-KX such that the K1 sequences replaced the E3,E5 sequences.

Oligonucleotide splints were used in a site-directed mutagenesis experiment to change the sequences at the boundaries of the INV-KX derived introns and the K1 exon. The sequences were changed such that the intron sequences of domain 6 are directly followed by kringle domain sequences ACC AGG GCC and kringle sequences TCT GAG GGA precede the intron sequences of domain 1. In addition, the EBS 1 sequence in domain 1 was changed to TCCCTCA (this sequence is homologous to the last 7 nt of K1 (TGAGGGA)). Thus, the resulting transcript, contains complementary IBS1 and EBS1 sequences. The plasmid encoding this transcript is known as pY8. A related plasmid, which is identical to pY8 except that the KpnI site at the intron/exon boundary was not destroyed, was also isolated; This plasmid is known as pKK1. The transcript encoded by pKK1 is known as (IVS5,6)KKI(IVS1–3).

An second site-directed mutagenesis reaction was performed on pY8 to change the intron EBS2 site to be complementary to K1 IBS2 region. The plasmid produced in this experiment is known as pY9; the encoded transcript is (IVS5,6)Kl(IVSS1–3).

Figure 17:
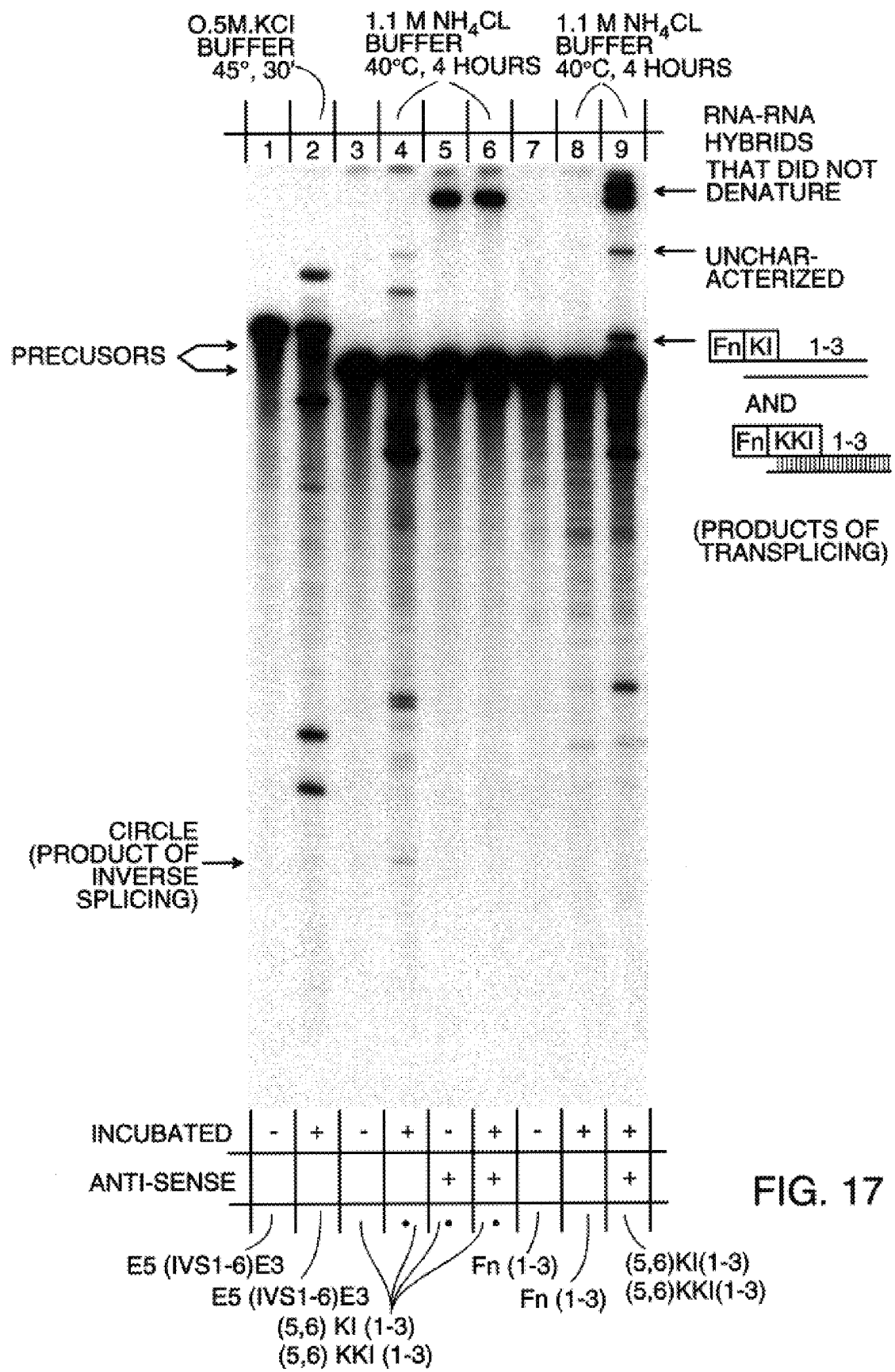
FIG. 17 presents the results of trans-splicing experiments in which cis-splicing by an intron-flanked internal exon is restricted by exposure to an anti-sense oligonucleotide.

The (IVS 5,6)K1(IVS 1–3) and (IVS 5,6)KK1(IVS 1–3) transcripts were produced by transcription of pY9 and pKK1; An inhibitory anti-sense RNA that hybridizes to the IVS 1–3 region and also to the 3' end of the K1 exon was produced by T3 transcription of pY9 digested with Apal I. Each transcript was then incubated under splicing conditions with and without the anti-sense RNA, and also with and without an Fn(1–3) transcript, prepared as described in Example 1, to which the K1 transcripts could splice. As is shown in FIG. 17, the antisense RNA completely blocked inverse splicing by either transcript, but allowed each transcript to splice to the Fn(1–3) RNA.

EXAMPLE 3

In Vivo Exon Shuffling

Figure 18:
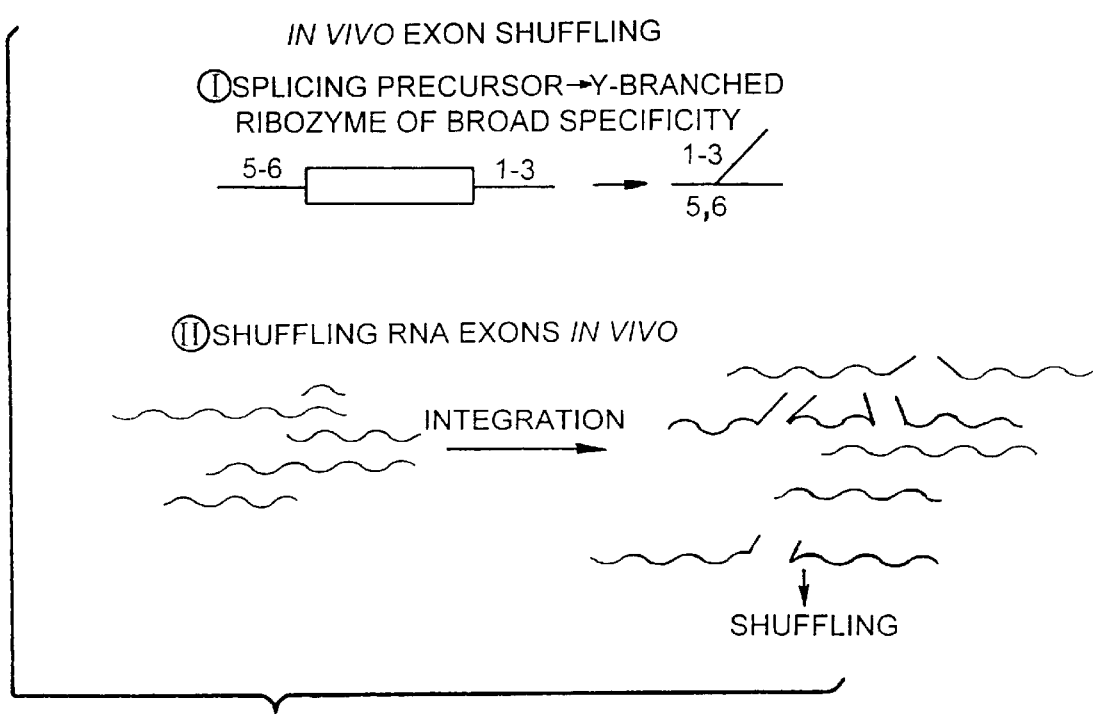
FIG. 18 is a schematic representation of an in vivo exon shuffling method according to the present invention.

As depicted in FIG. 18, exon shuffling according to the present invention can be made to occur in vivo. All that is required is expression in a cell of an inverse-splicing precursor that will produce a Y-branched ribozyme of broad specificity. Preferably, the inverse-splicing precursor is introduced into the cell in association with an inducible promoter, so that its expression may be initiated and terminated under controlled circumstances.

Once the Y-branched ribozyme is produced, it will integrate into other RNAs being expressed in the cell and will shuffle the "activated exons" created by its own integration. It will be appreciated that a population of ribozymes having different specificities may be employed rather than a single ribozyme of broad specificity.

A particularly preferred embodiment of this in vivo exon shuffling reaction is described in Example 11, where the shuffling is performed in a cell bearing a specialized integration construct, so that shuffling products may be integrated into the genome, expressed, and analyzed.

B. Exon Trapping

Figure 19:
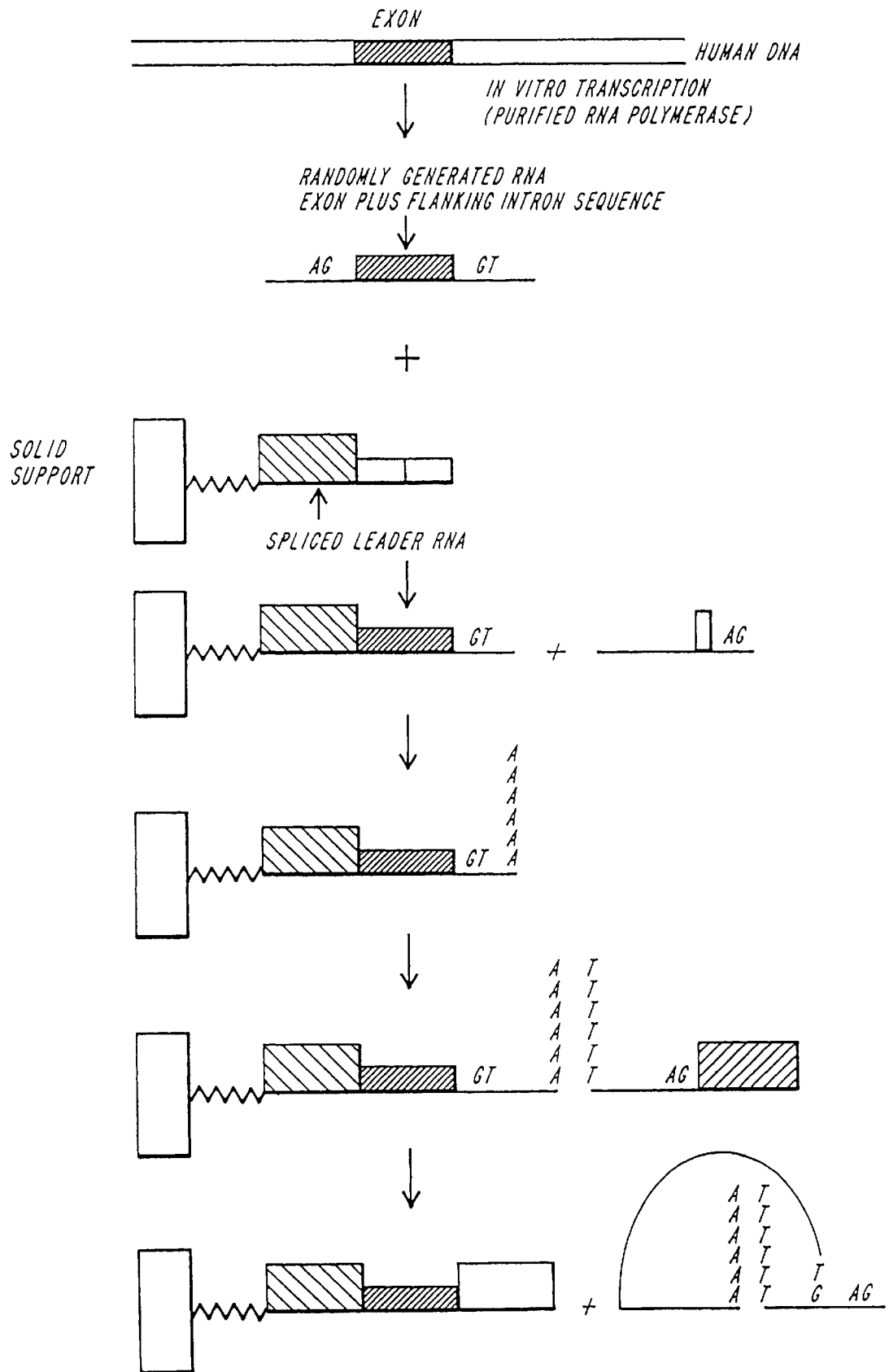
FIG. 19 illustrates an "exon-trap" assay for identifying exons from genomic DNA, utilizing trans-splicing mediated by discontinuous nuclear pre-mRNA intron fragments.

FIG. 19 illustrates an "exon-trap" assay for identifying exons (in the traditional use of the term) from genomic DNA, utilizing trans-splicing mediated by discontinuous nuclear pre-mRNA intron fragments. One advantage of this method is that the DNA does not have to be cloned prior to using the method. In contrast to prior techniques, the starting material of the exon-trap assay could ultimately be total human genomic DNA. In addition, the present method described herein is an in vitro method, and can be easily automated.

In the first step, purified RNA polymerase II is used to transcribe the target DNA. In the absence of the basal transcription factors, Pol II will randomly transcribe DNA (Lewis et al. (1982) *Enzymes* 15:109–153). FIG. 19 shows that some of these transcripts will contain individual exons flanked by intron sequences. Since human exons are small, typically less than 300 nt (Hawkins et al. (1988) *Nucleic Acids Res.* 16:9893–9908) and introns are large (up to 200,000 nt, Maniatis (1991) *Science* 251:33–34) most transcripts will contain either zero or one exon. In the illustrative embodiment, a spliced leader RNA of, for instance, trypanosome or nematode (Agabian (1990) *Cell* 61:1157–1160), is covalently linked to a solid support by its 5' end. The RNA generated by random transcription of the genomic DNA is mixed with the immobilized spliced leader and splicing is catalyzed using splicing extract. The resin is then washed to remove unwanted reaction products, such as unreacted RNA and the splicing extract.

Furthermore, in a subsequent step, an in vitro polyadenlyation reaction (for example, Ryner et al. (1989) *Mol. Cell. Biol.* 9:4229–4238) can be carried out which adds oligo-A (up to a length of 300 nt) to the 3' end of the RNA. FIG. 19 shows that an RNA transcript, generated by in vitro transcription of a plasmid having an oligo T stretch, followed by the 3' portion of an intron (including the branch acceptor site and the AG dinucleotide), followed by an exon, can be annealed to the immobilized polyadenylated RNA by hydrogen bonding between the poly-A and poly-T sequences. In vitro trans-splicing, catalyzed by splicing extract, will join the known 3' exon to the "trapped" exon. The RNA can then be stripped from the column, copied to DNA by reverse transcriptase and amplified by PCR using primers to the 5' leader and known 3' exon. The amplified DNA that contains a trapped exon primers to the 5' leader and known 3' exon. The amplified DNA that contains a trapped exon will be larger than the side product that results from splicing of the spliced leader exon to the known 3' exon. Thus, the amplified DNA that contains trapped exons can be selected by size.

Moreover, a "capping" reaction can be done to eliminate products that do not contain a trapped exon. After the step of mixing genomically derived RNA with the immobilized exon, a "capping RNA", with a 3' splice site and a 3' exon, can be added and splicing catalyzed by the addition of splicing extract. The 3' exon of the capping RNA is different from the 3' exon of the RNA shown with the oligo-T stretch. The capping RNA is one which will trans-splice very efficiently to any spliced leader RNA which has not already participated in a splicing reaction; but, will splice less efficiently to immobilized RNAs that have a trapped exon ligated to them as the capping RNA lacks a poly-T sequence to anneal to the trapped exon. Therefore, after the capping reaction, the step shown for splicing of the oligo-T containing construct will result, primarily, in the generation of the desired (leader/trapped exon/known exon) product and not in the generation of the unwanted (5' leader/3' known exon) product.

C. DNA Recombination

It should be understood that, although much of the discussion herein focusses on production of recombinant RNA molecules, the principles and techniques taught by the present invention are also applicable to manipulation of DNA sequences. Methods are available for linking splicing-competent intronic RNA sequences directly to single-stranded or double stranded DNA so that, in the language of the present invention, activated DNA exons are produced. These activated DNA exons can then be linked to one another, much as has been described herein for RNA exons, through trans-reactions mediated by the intronic sequences.

Figure 20:
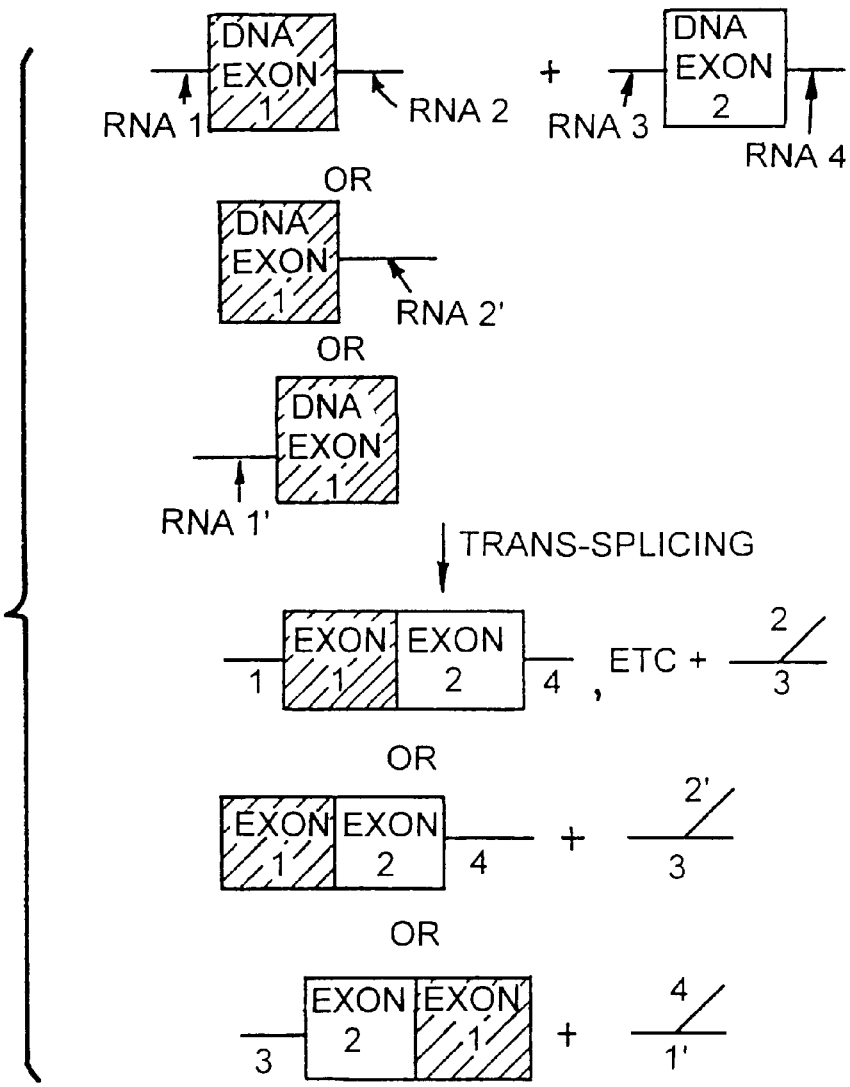
FIG. 20 is a schematic representation of trans-splicing reactions according to the present invention that utilize DNA exons.

FIG. 20 depicts various DNA "trans-splicing" reactions of the present invention. For convenience, the term "trans-splicing" is used herein to encompass any intron-mediated trans-reaction—i.e. any reaction between two distinct intron-linked exons—that leads to precise ligation of those exons, even though the term "splicing" has not traditionally been applied to reactions involving DNA (rather than RNA) exons. As shown in FIG. 20, intronic RNA sequences are linked to pieces of DNA in manner that allows the RNA elements to direct precise ligation of the DNA sequences to one another, with concomitant removal of the RNA elements. Specifically, at least RNA elements 2 and 3 (or 2' and 3 or 4 and 1') are selected to be capable of interacting with one another to form a functional intron that directs the trans-splicing reaction of the DNA exons. Preferably, the intron elements have been engineered as described herein to target the specific relevant exon sequences. If RNA elements 1 and 4 of FIG. 20 are also capable of interacting to form a functional intron, chains of ligated exons 1 and 2, in random order, can be produced. Also, it should be understood that the RNA elements depicted in FIG. 20 need not be continuous RNA molecules, so that components of the functional introns may themselves be provided in trans as desired (and as discussed above).

Any available method may be employed to attach intronic RNA sequences to DNA exons in order to practice the "trans-splicing" DNA recombination methods of the present invention. For example, RNA molecules may be ligated to DNA molecules through splint-mediated DNA-RNA ligation (see Moore et al. (1992) *Science* 256:992–997). As shown in FIG. 21A, a DNA molecule and an RNA molecule are brought within one bond length of one another by hybridization to the same nucleic acid splint molecule. The hybridized complex is then incubated with DNA ligase, which covalently links the DNA and RNA pieces to one another. In one preferred embodiment of DNA-RNA ligation as used herein, the DNA molecule is a double-stranded molecule in which the second strand (i.e. the strand to which the RNA molecule will not be linked) overhangs the first strand, so that the overhang acts as the splint to bring the RNA into register for ligation (see FIG. 21B).

Figure 21:
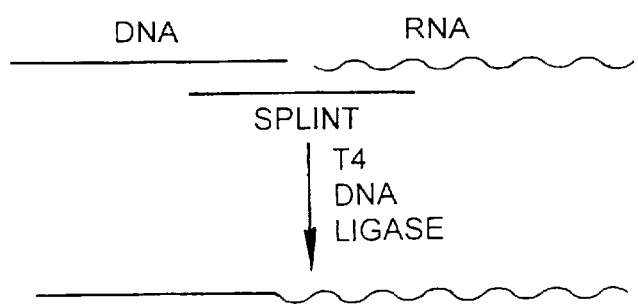
FIG. 21 presents schematic representations of splint-assisted DNA-RNA ligation methods.
Figure 21:
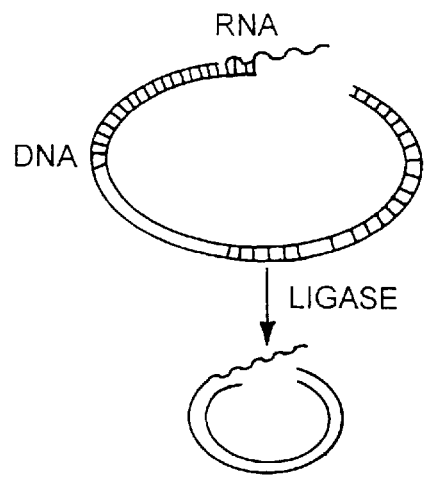

As an alternative to the DNA-RNA ligation methods depicted in FIG. 21, RNA molecules may be linked to DNA molecules through intron-mediated integration reactions in which the DNA molecule is cleaved and ligated to the RNA directly. Certain group II introns have been shown to integrate into DNA targets. For example, at least the aII group II intron can fully integrate into double-stranded DNA (Yang et al. (1996) *Nature* 381:332–335; see FIG. 22A); at least the aI2 group II intron can perform a first integration step, apparently equivalent to a reversal of the second step of splicing, so that a DNA strand is cleaved and the intron becomes linked to one of the resultant DNA pieces but not the other (Zimmerly et al. (1995) *Cell* 83:529–538; see FIG. 22B). Several other have been shown to perform such partial integrations into single-stranded DNA (Herschlag et al. (1990) *Nature* 344:405–409; Robertson et al. *Nature* 344:467–468; Morl et al (1992) *Cell* 70:803–810). Also, any intron capable of full insertion into a DNA target will perform only the first step of that insertion (analogous to a reversal of the second step of splicing) if the intron is presented to the target in linear, rather than lariat, form.

The DNA integration reactions catalyzed by aI1 (complete integration) and aI2 (partial integration) rely on an intron-encoded protein that has maturase, reverse transcriptase, and endonuclease activity. The endonuclease activity appears not to be required for intron integration into a DNA strand, but rather cleaves the complementary strand when the intron inserts into double-stranded DNA, thereby creating a 3'OH in the complementary strand that can serve as a reverse transcription primer so that the integrated intron can be copied into DNA (Zimmerly et al. (1995) *Cell* 83:529–538). The reverse transcriptase activity may also be dispensable.

According to the present invention, it will often be desirable to prevent reverse transcription of the integrated RNA into DNA, in order that the RNA remain available for "splicing" reactions. Accordingly, many preferred inventive methods are performed under conditions in which reverse transcription of integrated RNA is inhibited. For example, reverse transcriptase inhibitors may be employed (particularly in in vitro reactions). Alternatively or additionally, mutant proteins may be employed that lack the endonuclease and/or reverse transcriptase activities. Endonuclease-deficient mutant proteins have been described for at least the aI2 protein (the HHVR, ΔConZn, C-C/1, and C-C/2 derivatives described by Zimmerly et al. (1995) *Cell* 83:529–538); others can be readily generated using known mutagenesis techniques. Other approaches to avoiding reverse transcription include, for example, use of a reverse transcriptase-deficient protein (e.g. the YAHH version of the aI2 protein; Zimmerly et al. (1995) *Cell* 82:545–554), isolation of the target DNA strand (before or after linkage to the RNA intron element) away from the complementary strand, and use of an integrating ribozyme that does not require a protein co-factor. One particularly straightforward approach to inhibiting reverse transcriptase activity in in vitro reactions is to simply exclude dNTPs from the reaction; such dNTP exclusion does not interfere with the endonuclease activity of at least the aI2 protein (Zimmerly et al. (1995) *Cell* 83:529–538).

It will also often be desirable to minimize the effects of cis-splicing reactions capable of competing with the trans-splicing reaction(s) in issue. Various techniques can be used to prevent such cis-splicing reactions. For example, in some cases, it will be possible to utilize intron components that are only compatible with other components available in trans. Alternatively, cis components that would not participate in the desired trans- reaction can be specifically removed by, for example, RNAse H digestion, or can be inactivated by provision of a specific anti-sense probe (see, for example, Example 2).

Various embodiments of DNA trans-splicing reactions according to the present invention are depicted in FIGS. 23–33 and described below in Examples 4–11. Those of ordinary skill in the art will recognize that the depicted methods and reagents are merely certain preferred embodiments of the invention; various modifications of the presented embodiments can readily be made according to the teachings of this specification and the knowledge available in the art.

EXAMPLE 4

Intron-mediated Cleavage and Ligation of Single-stranded DNA Vectors

Figure 23:
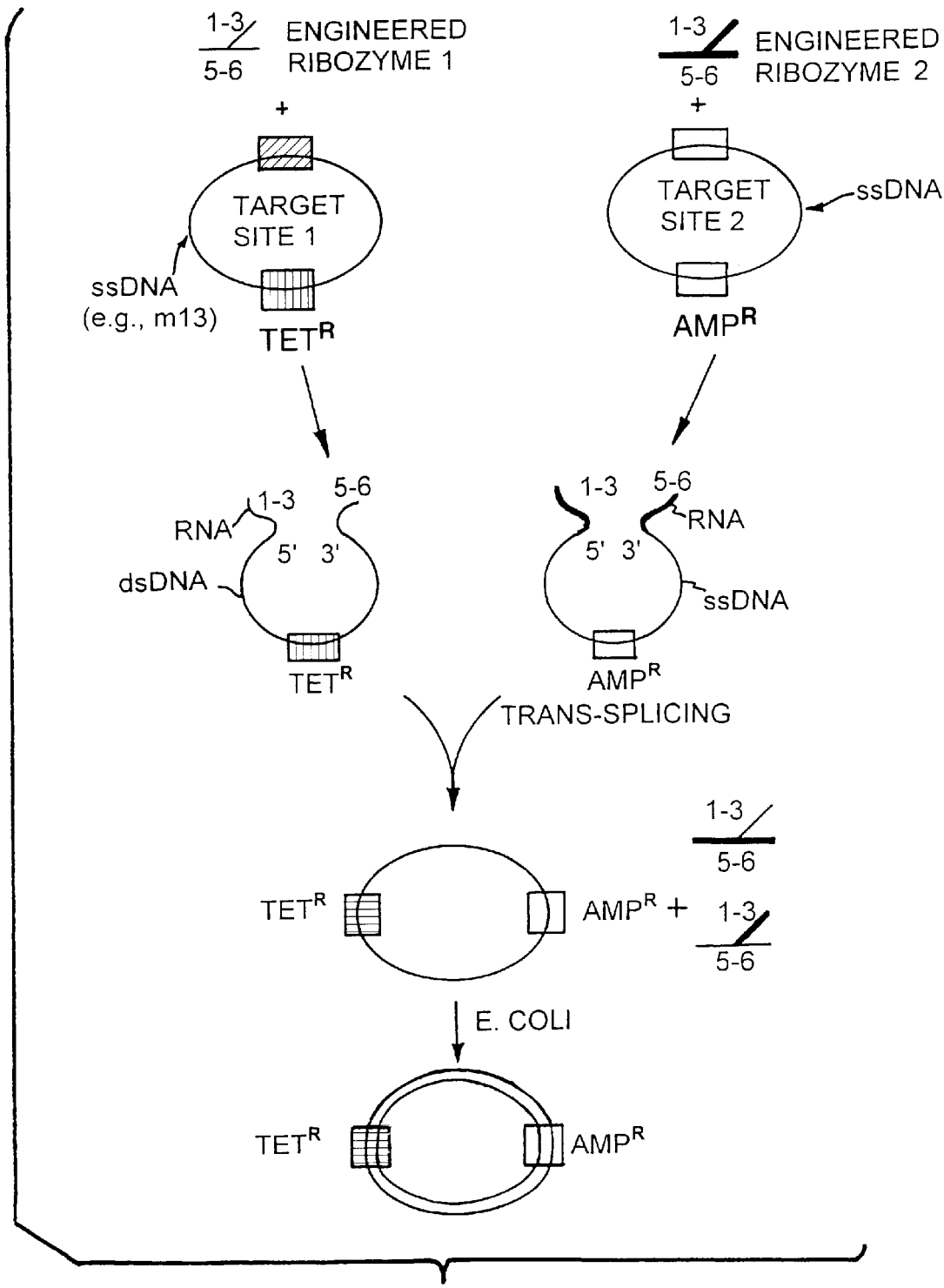
FIG. 23 presents a schematic representation of intron-mediated cleavage and ligation of single-stranded DNA vectors, according to the present invention.

In embodiment of the present invention, depicted in FIG. 23, two Y-branched ribozymes (e.g. derived from a group II intron such as aI5γ) are produced that are engineered to recognize target sites within a single-stranded DNA template. The elements of each Y-branched ribozyme are also selected to be compatible with one another for splicing (e.g. the 1–3 element of ribozyme 1 is compatible with the 5-6 elements of both ribozyme 1 and ribozyme 2; similarly, the 1–3 element of ribozyme 2 is compatible with both 5-6 elements).

The first single-stranded DNA template depicted in FIG. 23 includes sequences encoding a tetracycline resistance gene expressible in *E. coli*; the second single-stranded DNA template includes sequences encoding an ampicillin resistance gene. At least one of the single-stranded DNA templates also has an m13 origin of replication. Preferably, both single-stranded DNA templates have an m13 origin of replication, and are produced by infection and lysis of *E. coli*, as is known in the art.

The ribozymes shown in FIG. 23 are integrated into their respective target sites under "reverse-splicing" conditions, and the resultant DNA-RNA hybrid molecules are isolated. Mixed together, and allowed to "trans-splice". The single-stranded DNA trans-splicing product is then isolated and introduced into *E. coli*, where it may be converted into a double-stranded DNA vector or maintained as a single-stranded phage, as is known in the art. It will be appreciated that, as shown in the Figure, the trans-splicing reaction also produces "shuffled" ribozymes, in which ribozyme 1 element 1–3 is linked to ribozyme 2 element 5-6 and ribozyme 2 element 1–3 is linked to ribozyme I element 5-6.

EXAMPLE 5

Intron-mediated Cleavage and Ligation of Double-stranded DNA Vectors

Figure 24A:
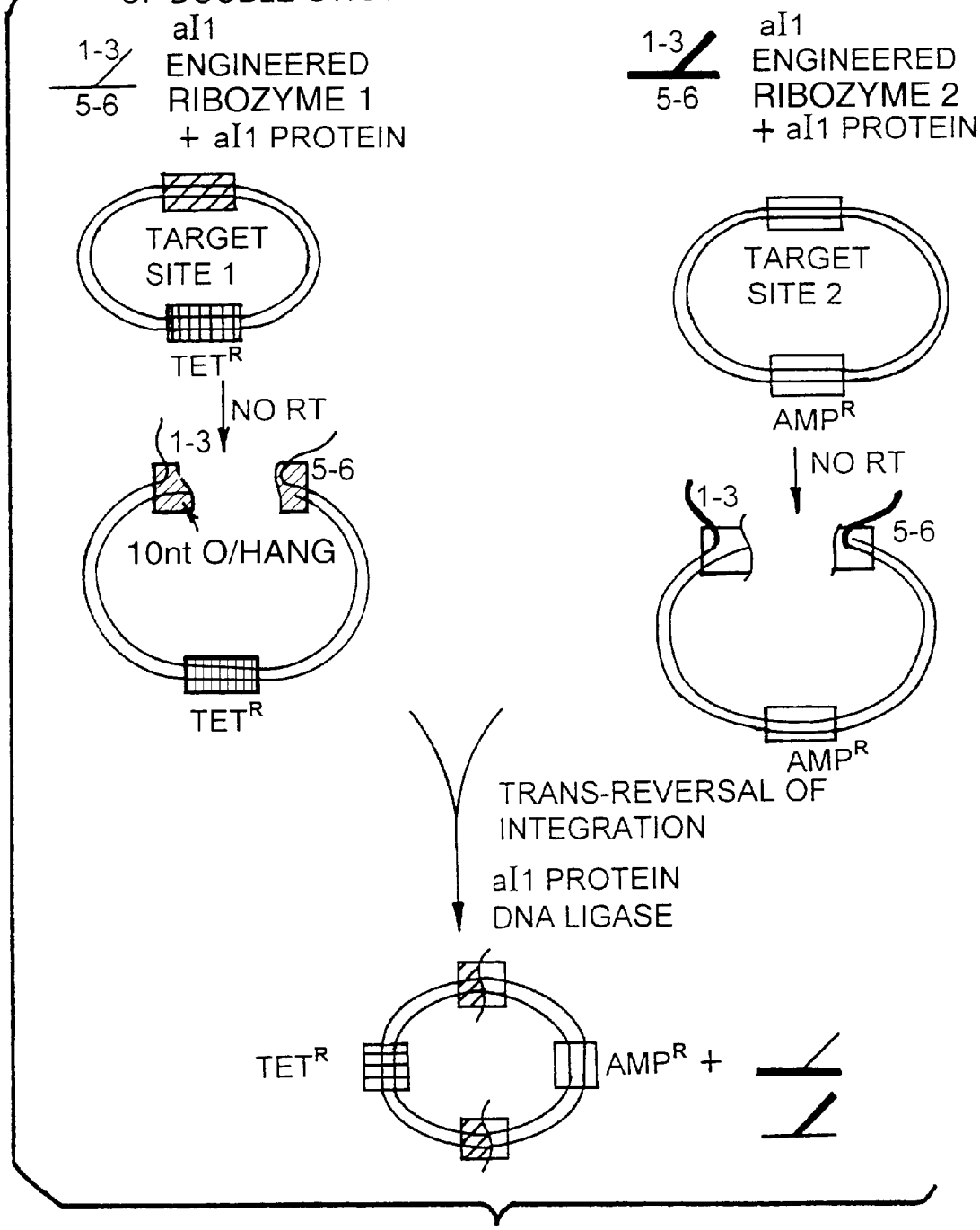
FIG. 24 presents schematic representations of three embodiments of intron-mediated cleavage and ligation of double-stranded DNA vectors according to the present invention.

FIG. 24 depicts another trans-splicing embodiment of the present invention, in which a group II intron, aI1, is utilized to cleave and ligate two double-stranded DNA vectors. As shown in FIG. 24A, two aI1-derived Y-branched ribozymes are engineered to insert into target sites in double-stranded DNA vectors. The integration reactions are performed in the presence of the aI1 protein, but under conditions that block reverse transcription. Accordingly, the ribozymes insert into one strand of the DNA and the other DNA strand is nicked by the endonuclease in a manner that produces a 10-nt 5' overhang. The ribozyme is not reverse transcribed into DNA. Also, because a Y-branched engineered ribozyme is employed instead of a lariat, the DNA target DNA strand is disrupted by the integration.

According to the method shown in FIG. 24A, the DNA-RNA hybrid products of the integration reactions are combined with one another in the presence of the aI1 protein and DNA ligase, and the integration reaction is allowed to reverse itself Because the ribozyme elements are selected to be compatible with one another (i.e. so that the 1–3 element of ribozyme 1 forms a splicing-competent intron with the 5-6 element of ribozyme 2 and vice-versa), trans-interactions will occur between the 1–3 element of ribozyme 1 and the 5,6 element of ribozyme 2 (and vice-versa) so that at least some of the time, the reversal of integration will produce the depicted trans-product. DNA ligase is added to seal the nicks that would otherwise be present in the complementary DNA strand (i.e. in the strand into which the ribozymes did not integrate).

The ligation reaction depicted in FIG. 24A is referred to as a "trans-reversal of integration" rather than a "trans-splicing" reaction because it is performed in the presence of the aI1 protein, and utilizes substrates in which the IBS1 (and/or IBS2) sites are double-stranded in the exons. It is clear that the aI1 intron can recognize and interact with double-stranded sites in the presence of its protein, but it may not be able to do so on its own. The aI1 intron does recognize single-stranded sites (e.g. in RNA) on its own. In fact, the presence of the aI1 protein alters the intron's natural preference for single-stranded RNA targets and allows it to select double-stranded DNA targets (Zimmerly et al. (1995) Cell 83:529–538). Thus, there are at least qualitative differences between the reactions catalyzed by the aI1 intron with double-stranded as compared with single-stranded targets, and the two types of reactions are distinguished herein for purposes of clarity. This distinction is not intended to imply a mechanistic difference between the two kinds of reactions, but rather is employed to achieve linguistic precision.

Figure 24B:
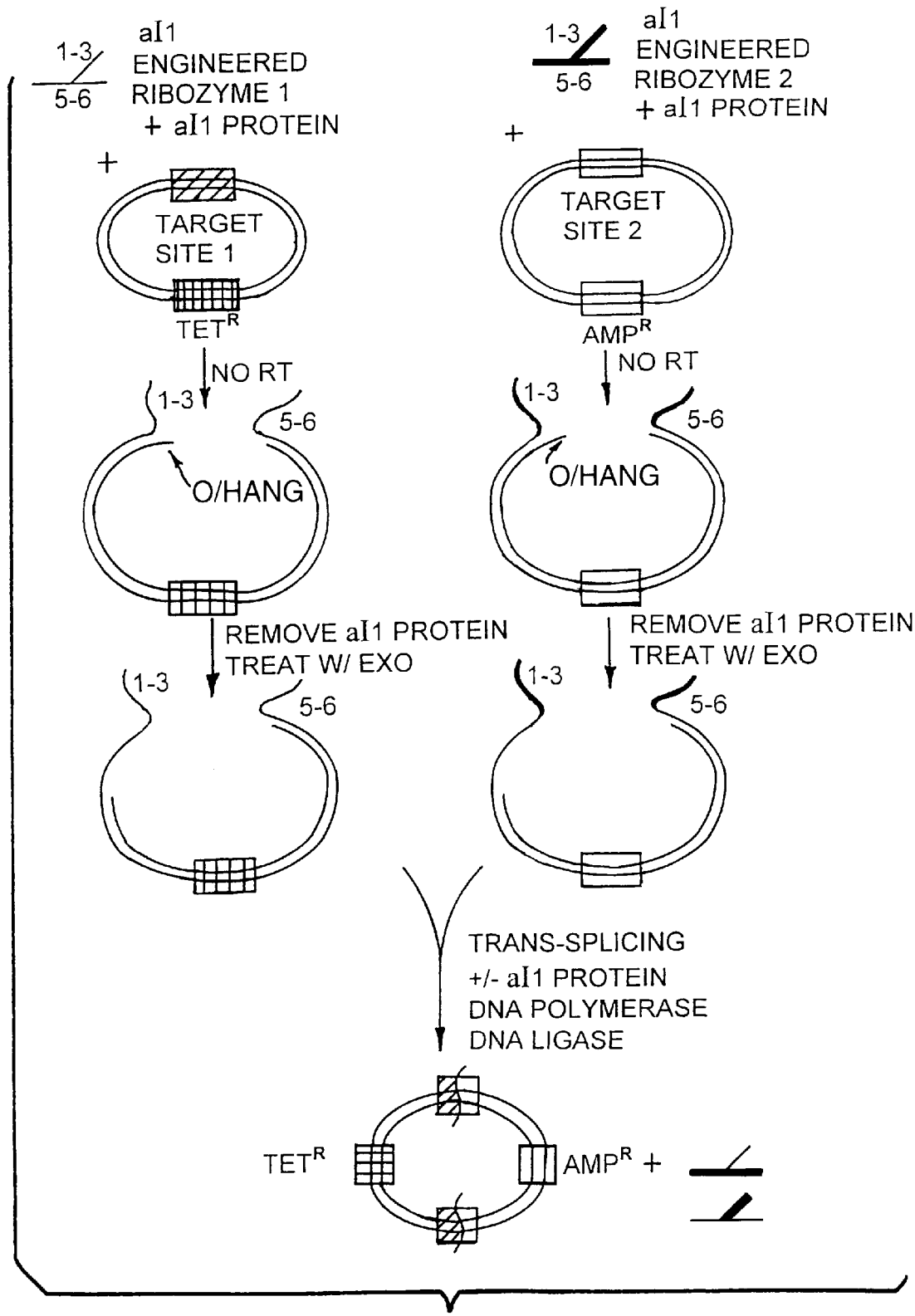

An alternative embodiment of the basic reaction depicted in FIG. 24A, one that achieves ligation by "trans-splicing" rather than "trans-ligation", is presented in FIG. 24B. As can be seen, the integration reaction is performed as in FIG. 24A, but is followed by an exonuclease step that removes the complementary DNA strand to the extent that at least IBS1, and optionally also IBS2, is uncovered. The exo-treated DNA-RNA hybrids are then combined and spliced together, either in the presence or absence of the aI1 protein (the aI1 protein may assist in the splicing reaction, but it is not necessary, as the aI1 intron is known to be capable of autocatalytic splicing). DNA polymerase is added to restore the regions of the complementary DNA strand that were removed by exonuclease digestion, and DNA ligase seals the final nicks.

Figure 24C:
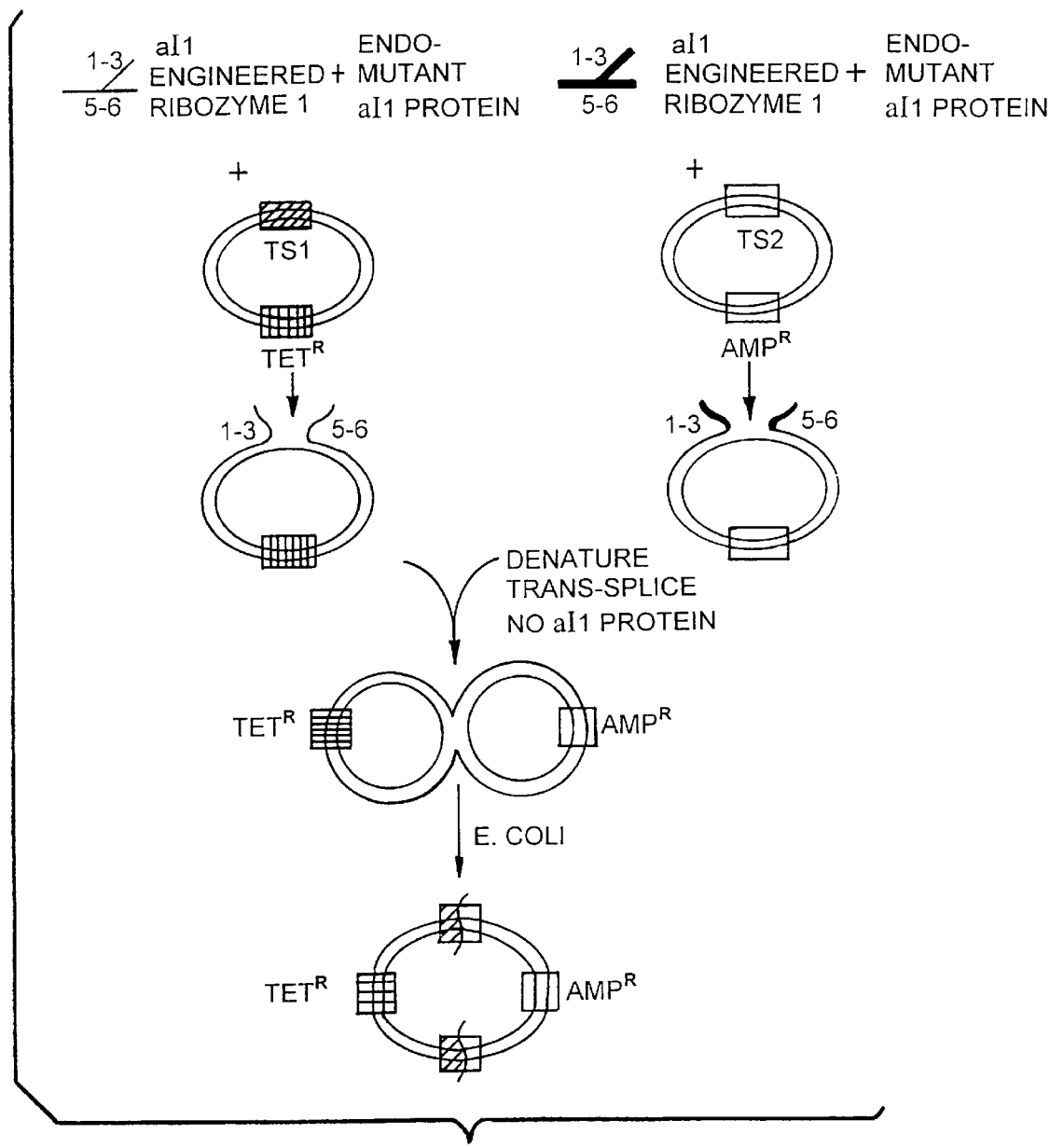

FIG. 24C presents yet a third embodiment of the basic reaction depicted in FIG. 24A. In this embodiment, the integration reactions are performed in the presence of a mutant aI1 protein that lacks endonuclease activity. Under such conditions, separate steps to inhibit reverse transcription need not be taken. Also, the integration reactions produce DNA-RNA hybrid molecules whose complementary strand is an intact circle. Ligation is then performed either by trans-reversal of integration (in the presence of the protein) or by trans-splicing (in its absence). As shown in FIG. 24C, ligation occurs by trans-splicing. A denaturation step is performed prior to the trans-splicing incubation, so that the IBS1 (and/or IBS2) sequence can be exposed. The resultant double-stranded DNA product molecule resembles a Holiday recombination intermediate and can be resolved into one or two DNA circles by passage through E. coli.

It should be noted that preferred embodiments of the reactions depicted in FIG. 24 are performed in vitro. However, such reactions could alternatively be performed in vivo if cell lines were produced that expressed inverse-splicing constructs capable of generating the Y-branched ribozymes and also expressed the aI1 protein.

EXAMPLE 6

Intron-catalyzed Shuffling of DNA Exons

As discussed above, the basic recombinatory principles of the present invention are just as applicable to DNA exons as to RNA exons, with the caveat that the introns' ability to recognize double-stranded DNA templates may be protein-dependent. The present Example demonstrates that exon shuffling of the sort described above in Example 1 may also be performed at the DNA level.

Figure 25A:
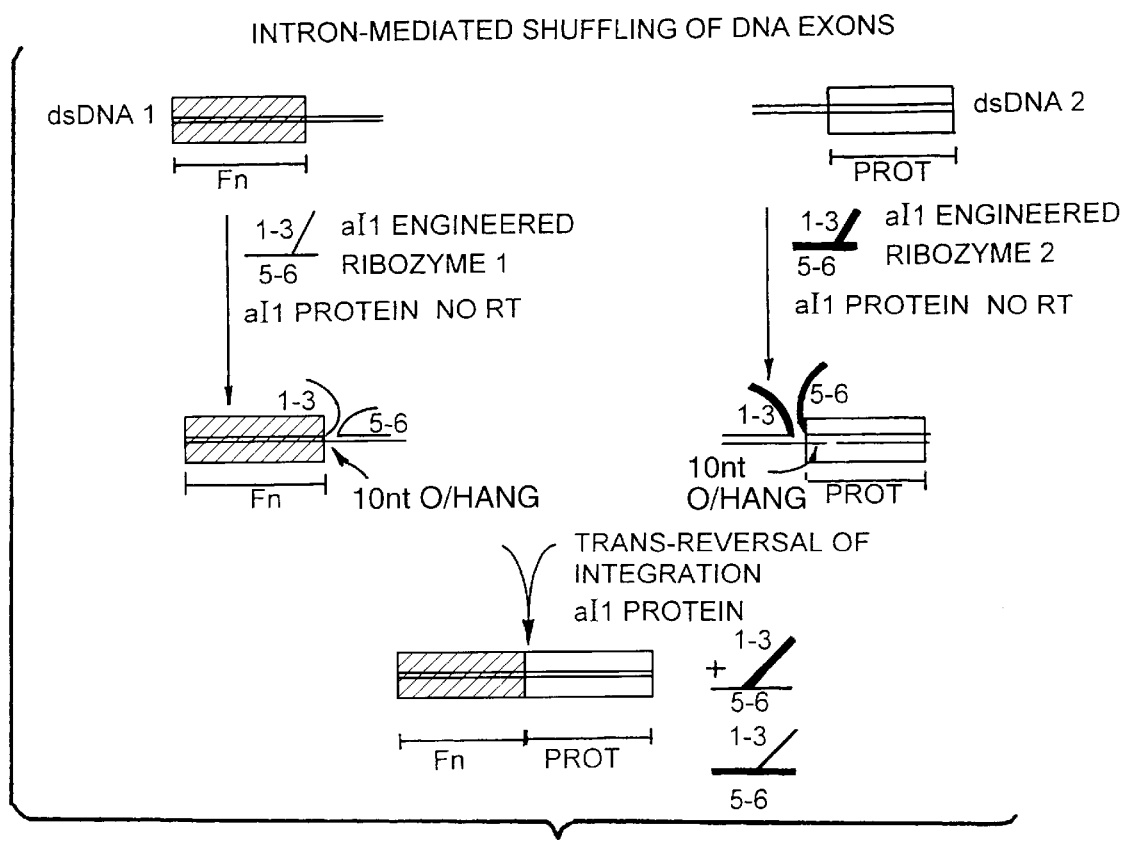
FIG. 25 presents schematic representations of two embodiments of intron-mediated shuffling of DNA exons, according to the present invention.
Figure 25B:
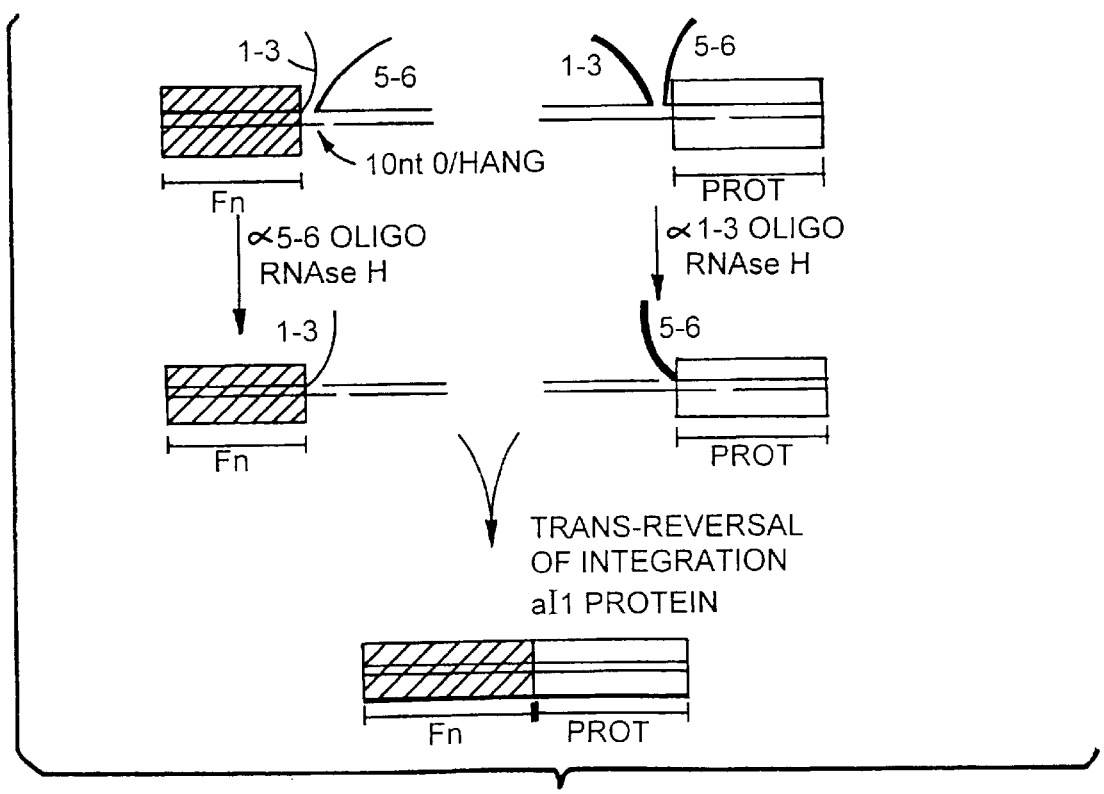

As shown in FIG. 25A, Y-branched aI1-type ribozymes can be engineered to insert immediately downstream of the t-PA Fn domain and immediately upstream of the T-PA Prot domain in DNA. Double-stranded DNAs containing these insertion sites can be prepared, for example, by PCR amplification of appropriate regions of the t-PA gene. Integration reactions are performed in the presence of the aI1 protein, and the resultant products are ligated together by trans-reversal of integration in the presence of the protein.

Where it is desirable to improve the efficiency of the trans-reversal of integration reaction as compared with the "cis" reversal reaction (which would produce the starting materials), it is useful to isolate each of the DNA-RNA hybrid products, deprotenate them (to remove any aI1 protein that may remain bound to the product after integration), and then mix them back together in the presence of more protein. Where it is desirable to favor the trans-reaction to the exclusion of the "cis" reaction, the steps diagramed in FIG. 25B can be performed. That is, each of the hybrid products can be isolated individually and hybridized with an oligodeoxyribonucleotide complementary to one element of the engineered ribozyme. Removal of one ribozyme element from each DNA-RNA hybrid product will prevent any "cis" reaction from occurring when the two products are mixed together.

It should be understood that the ligation reaction depicted in FIG. 25A can alternatively be performed as a trans-splicing reaction, in the absence of aI1 protein, with an appropriate denaturation step.

EXAMPLE 7

Cleavage and Ligation of Double-stranded DNA Exons Using the aI2 Group II Intron The present Example demonstrates that the sort of double-stranded DNA exon manipulation described above in Example 5 can also be performed with introns, such as the aI2 group II intron, that do not completely integrate into double-stranded DNA.

Figure 26:
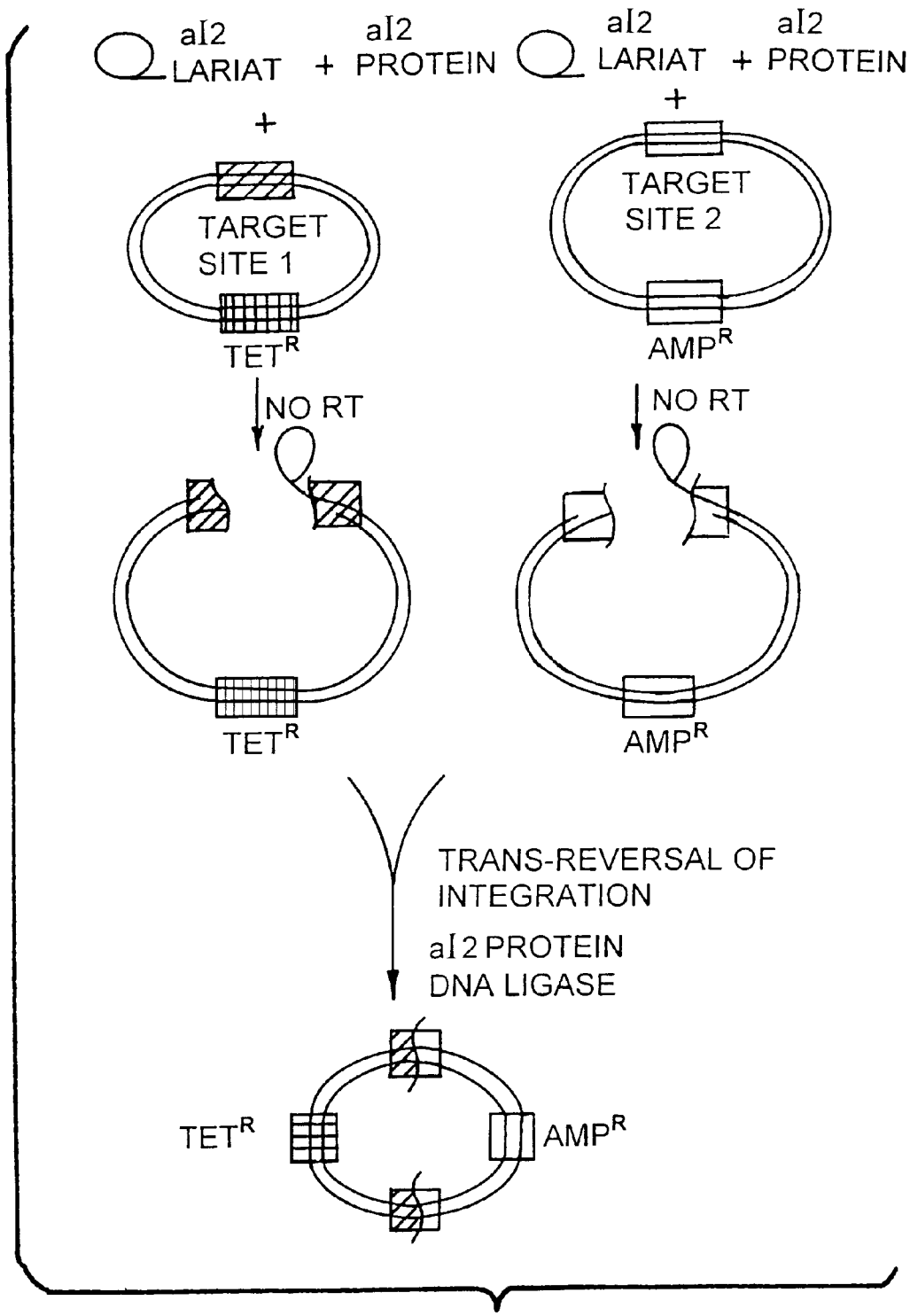
FIG. 26 presents a schematic representation of one embodiment of double-stranded DNA cleavage and ligation mediated by an aI2 group II intron, according to the present invention.

As shown in FIG. 26, an aI2-type lariat intron is designed to insert into a recognition site that is present in two different double-stranded DNA templates. The integration reactions are performed in the presence of the aI2 protein under conditions that block reverse transcription. The products of the integration reaction are then mixed with one another and ligation is performed either by trans-reversal of splicing (shown, no exonuclease step) or by trans-splicing (after an exonuclease step). Note that use of a lariat intron, rather than a Y-branched intron, requires that the insertion sites in the two double-stranded DNA targets be the same (or sufficiently similar that productive EBS1/IBS1, and optionally also EBS2/IBS2 is formed during the trans-reaction).

EXAMPLE 8

Chromosome Recombination

Figure 27:
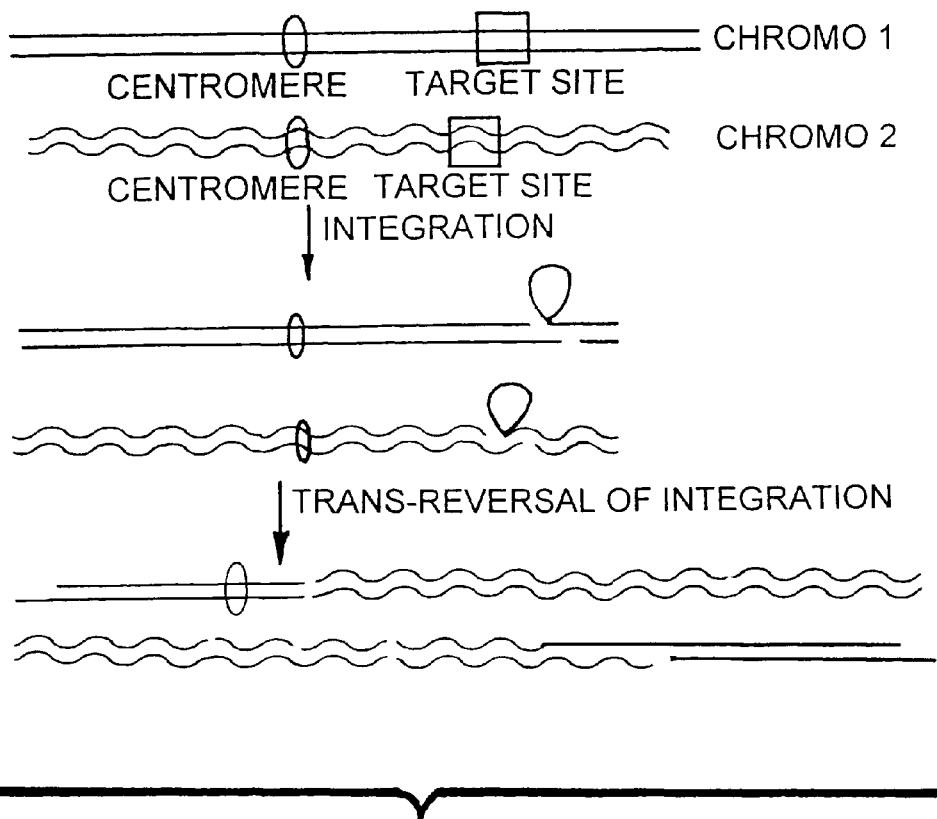
FIG. 27 presents a schematic representation of one embodiment of intron-mediated chromosomal recombination according to the present invention.

The trans-splicing DNA manipulation methods of the present invention may be performed in vivo to accomplish recombination of chromosomal regions. As shown in FIG. 27, a cell is generated that expresses both the aI2 protein and a splicing precursor that generates an aI2 lariat having a desired specificity. Preferably, one or both of these expressed factors is under the control of an inducible promoter, so that expression may be initiated and terminated under controlled circumstances. Also, the aI2 protein should be a version that has endonuclease activity, though it may lack reverse transcriptase activity.

When both the aI2 lariat and the aI2 protein are being expressed in the cell, the lariat will integrate at its recognition site in chromosomal DNA. Once it has integrated into sites in two different chromosomes, a trans-reversal of integration reaction will swap the relevant regions of the chromosomes. If it is desirable to select the chromosomal regions to be swapped, an aI2 lariat of high specificity can be engineered, and appropriate sites can be inserted into the chromosomes (according to standard techniques) prior to expression of the aI2 lariat and/or protein in the cell.

EXAMPLE 9

Intron-mediated DNA Insertion

Figure 28:
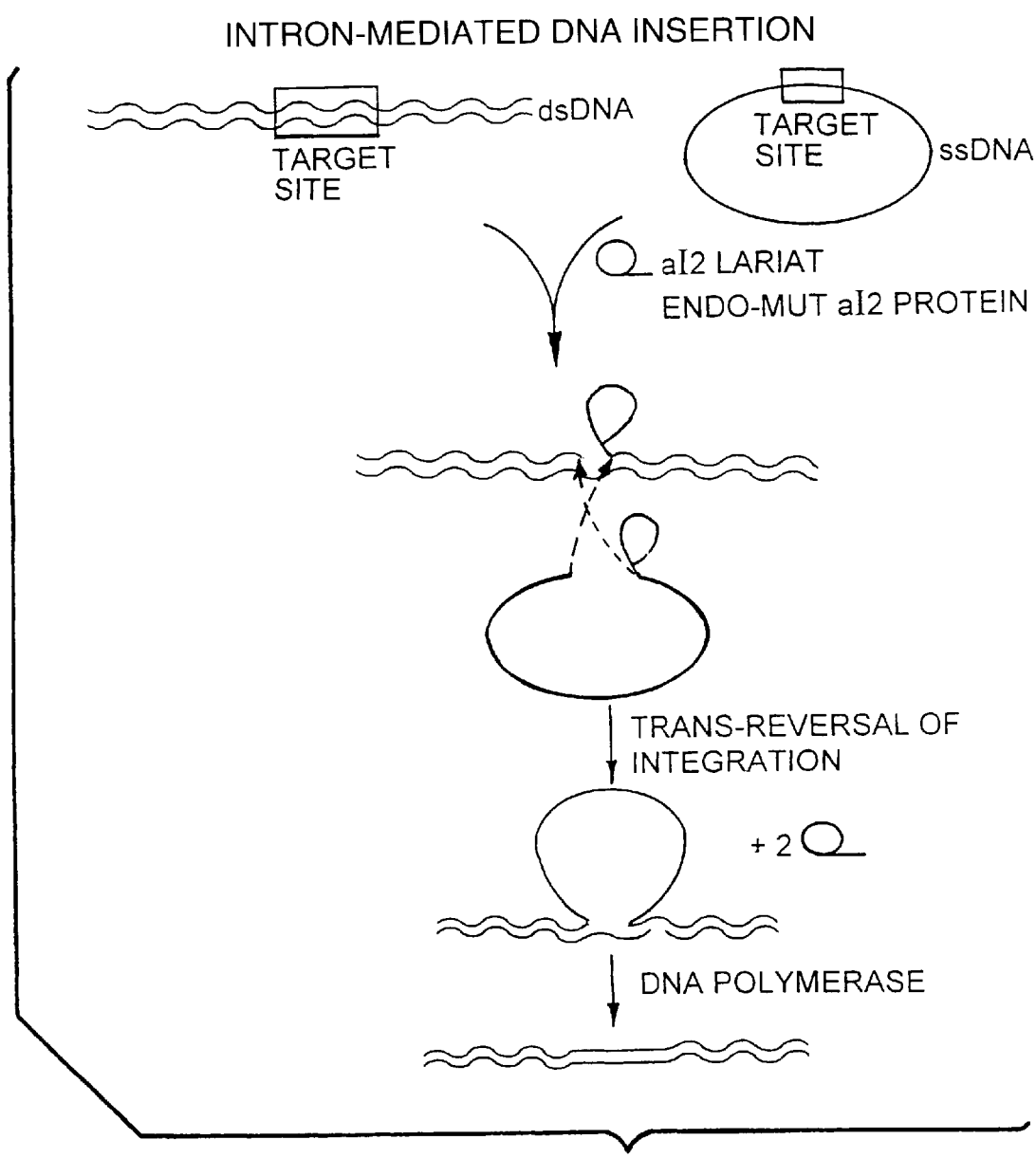
FIG. 28 presents a schematic representation of one embodiment of intron-mediated DNA cloning according to the present invention.

FIG. 28 depicts a trans-splicing reaction of the present invention that can be utilized to insert one DNA sequence into another in vivo or in vitro. As depicted, an aI2-type intron lariat is designed to insert at a specific target site that is present both in a double-stranded DNA target and in a single-stranded DNA target. The intron lariat is integrated into both targets in the presence of an endonuclease mutant version of the aI2 protein (although the presence of the protein may not be required for integration into the single-stranded DNA target). After integration, the DNA-RNA hybrid products interact with one another and undergo a tans-reversal of integration reaction so that the single-stranded DNA "exon" is inserted into the double-stranded DNA. Addition of DNA polymerase (or DNA replication in vivo) generates a fully double-stranded DNA molecule in which the sequences of the original single-stranded DNA target have been inserted into the double-stranded DNA target at a specific site.

It will be appreciated that these reactions can be performed in vivo if a cell is constructed that expresses the aI2 lariat (e.g. via expression of a splicing precursor) and the endonuclease mutant aI2 protein. Preferably, the expression of one or both of these factors is directed by an inducible promoter, so that splicing activity in the cell can be initiated and terminated under controlled circumstances. The single-stranded DNA template can be introduced into the cell (e.g., by infection) prior to expression of the aI2 lariat and/or protein. Alternatively, the reaction steps may be performed in vitro.

It will also be appreciated that use of a Y-branched, rather than a lariat, intron would allow insertion and recombination at two different target sites.

EXAMPLE 10

Intron-mediated DNA Cloning

Figure 29:
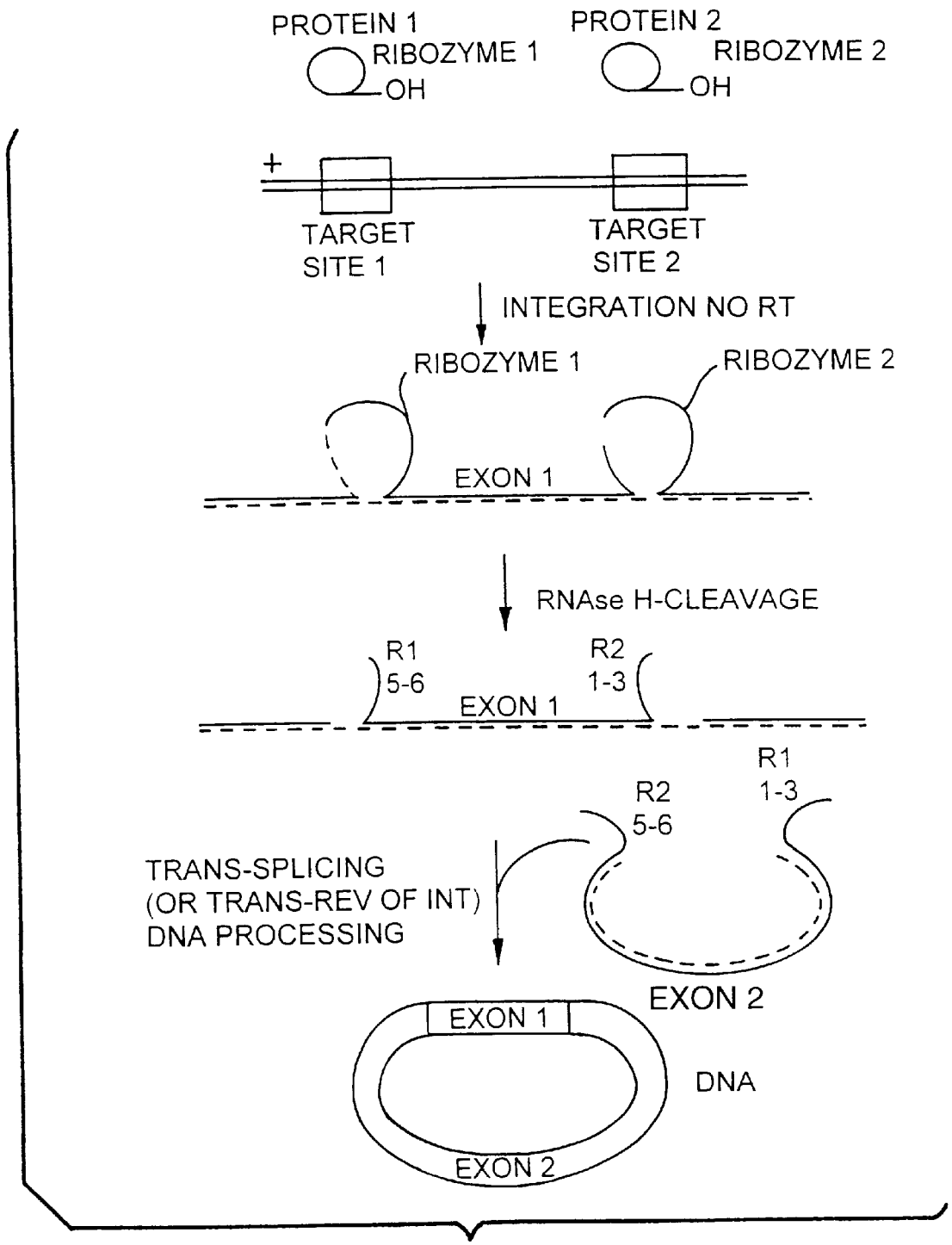
FIG. 29 presents a schematic representation of an intron-mediated DNA insertion method of the present invention.

FIG. 29 presents another embodiment of the trans-splicing methods of the present invention that allows single- or double-stranded DNA targets to be cleaved and ligated together. As depicted, two ribozymes are engineered as described herein (e.g. by alteration of at least their IBS 1 sites) to recognize desired target sites within a double-stranded DNA molecule. The ribozymes are depicted as lariats in FIG. 29 but alternatively could be Y-branched enzymes The DNA between the target sites, labeled "exon 1" in FIG. 29, becomes flanked by ribozyme sequences as a result of the integration reactions. An RNAse H cleavage reaction is then optionally performed in order to reduce the likelihood that the integrated ribozymes will splice themselves back out (i.e. to ensure that the trans-splicing reaction does not have to compete with a cis-splicing reaction). Ribozyme-flanked exon 1 is then mixed with a second exon, "exon 2" in FIG. 29, that is also flanked by appropriate ribozyme sequences. That is, the ribozyme sequences flanking exon 2 are selected to be competent to trans-splice with those flanking exon 1 so that the two exons will be linked to one another.

At certain points in FIG. 29, portions of nucleic acid molecules are depicted with dashed rather than solid lines. This dashing represents optional, or alternative, forms of the nucleic acids. For example, the exact form of the complementary DNA strand (i.e. the strand into which the ribozyme did not integrate) after ribozyme integration will depend on exactly how the reaction is performed. For example, when a protein component that has endonuclease activity is utilized, the complementary DNA strand will be nicked. On the other hand, when mutant versions of the protein that lack endonuclease activity are utilized, the complementary DNA strand is not broken during the integration reaction.

Also, a portion of ribozyme 1 is dashed after the integration reaction; this dashing is intended to indicate that ribozyme 1 may be an aI2-type ribozyme, capable of only partial integration into a double-stranded DNA template.

The optional RNAse H cleavage reaction depicted in FIG. 29 is performed by preparing DNA oligonucleotides complementary to portions of the integrated ribozymes that are not required for trans-splicing, hybridizing these oligonucleotides with the integrated ribozymes, and digesting the hybrids with RNAse H. Of course, it is particularly important that reverse transcription across the integrated ribozyme be prevented in reactions where the RNAse H step is to be performed; otherwise, digestion with RNAse H will remove the integrated ribozyme to the extent that it is hybridized with a reverse-transcribed DNA complement. It is, of course, important to leave a sufficient amount of intronic information both upstream and downstream of exon 1 that the trans-reaction can successfully.

Any of a variety of DNA targets may be employed as the second exon depicted in FIG. 29. Preferred targets include single- or double-stranded DNA cloning vectors such as are known in the art. Exon 2 may be linear or circular. Exon 2 may be linked to ribozyme elements by any available method. Preferred methods include ribozyme integration and splint-assisted DNA-RNA ligation.

FIG. 29 includes a step labeled "DNA processing". The details of this step will depend on the specifics of the constructs utilized. For example, it may be necessary to "chew back" and/or "fill in" regions of an exon 1 or exon 2 complementary strand. DNA ligation to seal the complementary strand may also be desirable. Of course, where the product recombinant DNA molecule is intended to be single-stranded (e.g., when exon 2 is a filamentous phase vector such as m13), such DNA processing steps are not required.

One particularly useful application of the method depicted in FIG. 29 is in isolation and analysis of genomic DNA sequences. For such applications, exon 1 is genomic DNA. One feature of the method that makes it desirable for this application is that reverse transcription and amplification steps are not required. Although such steps may be performed if desired, it will often be preferable to omit them as they can introduce errors into the sequence of the product DNA. Such errors can be problematic, particularly when the goal of a study is to identify and analyze the function of the cloned DNA sequence and/or any product it encodes.

Figure 30:
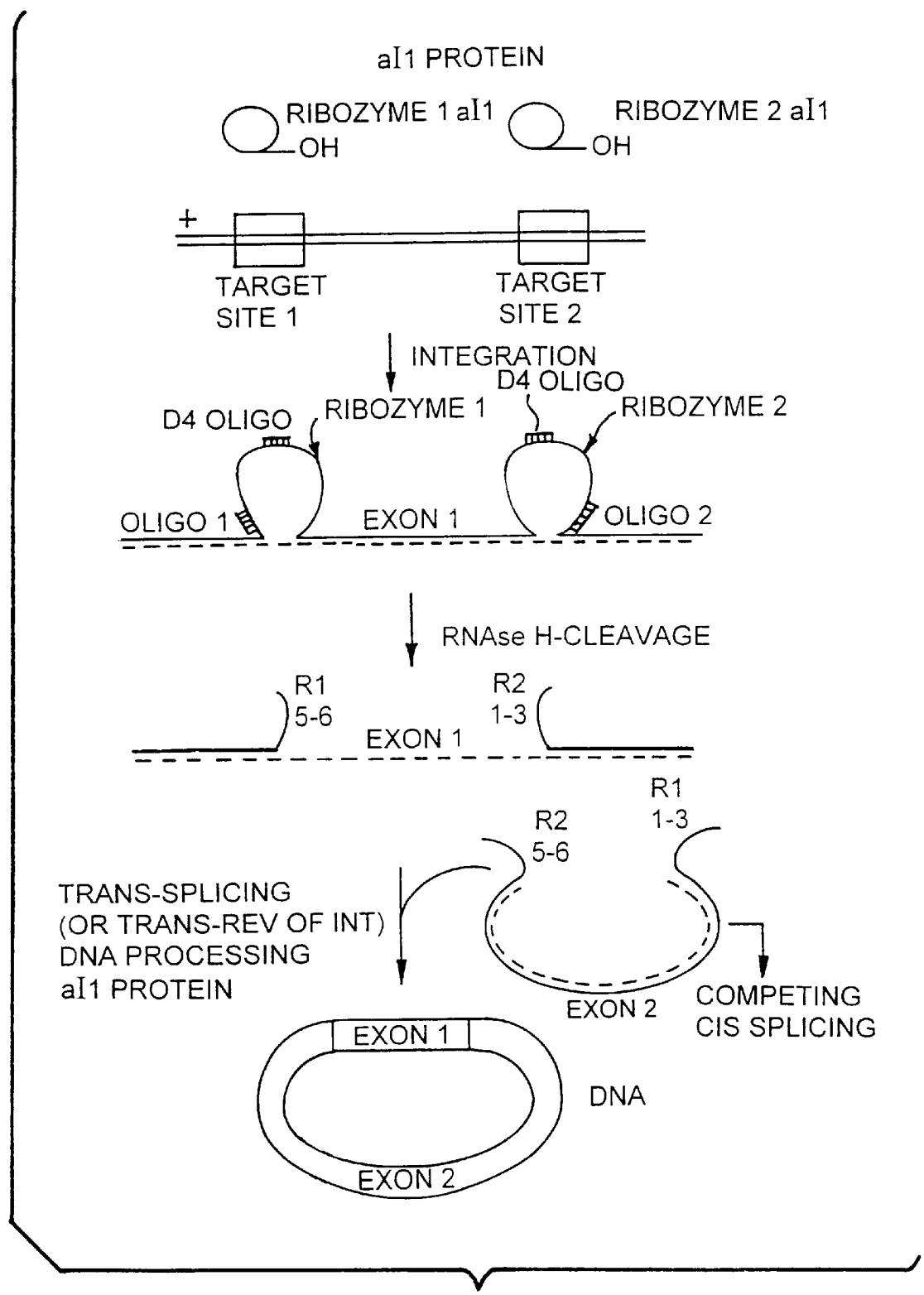
FIGS. 30 and 31 present alternative embodiments of the intron-mediated DNA cloning method of FIG. 29.

FIG. 30 presents one particular embodiment of the method shown in FIG. 29. As depicted in FIG. 30, both ribozymes are aI1-type ribozymes, capable of full integration. Under these circumstances, only a single protein factor (the aI1 protein) need be used. It will be appreciated that the two ribozymes depicted in FIG. 30 are not identical to one another. First of all, they will have been engineered to have different integration specificities, so at least their EBS 1 sites will differ. Furthermore, in order to simplify the RNAse H step, it is desirable to engineer the two ribozymes to include different sequences that can be specifically targeted for RNAse H digestion. As depicted in FIG. 30, three different oligonucleotides are utilized in the RNAse H reaction: one that hybridizes with domain 4 in both ribozymes, one that hybridizes with a region at or near the 5' end of ribozyme 1, and one that hybridizes with a region at or near the 3' end of ribozyme 2. In this version of the inventive method, ribozymnes 1 and 2 are engineered to differ from each other at the two regions to which the ribozyme-specific oligonucleotides hybridize.

In the reaction depicted in FIG. 30, exon 2, like exon 1, is flanked by aI1 ribozyme sequences. These ribozyme sequences can either splice with each other, and thus circularize exon 2, or can splice with the sequences flanking exon 1 to produce the desired recombinant product. Because the exon 2 circularization reaction is an intramolecular reaction, there is a risk that it will be favored over the intermolecular trans-reaction. Accordingly, it may be desirable to take steps to shift the competition. For example, larger concentrations of the flanked exon 2 reagent will increase the efficiency of the trans-reaction without affecting that of the cis reaction. Alternatively, the trans-reaction can be performed in two steps, one in the presence of an anti-sense oligonucleotide (DNA or RNA) that blocks one side of the cis reaction but allows one side of the trans reaction, and one in the absence of that oligonucleotide, so that the second side of the trans reaction (now a cis-splicing reaction) can occur.

Figure 31:
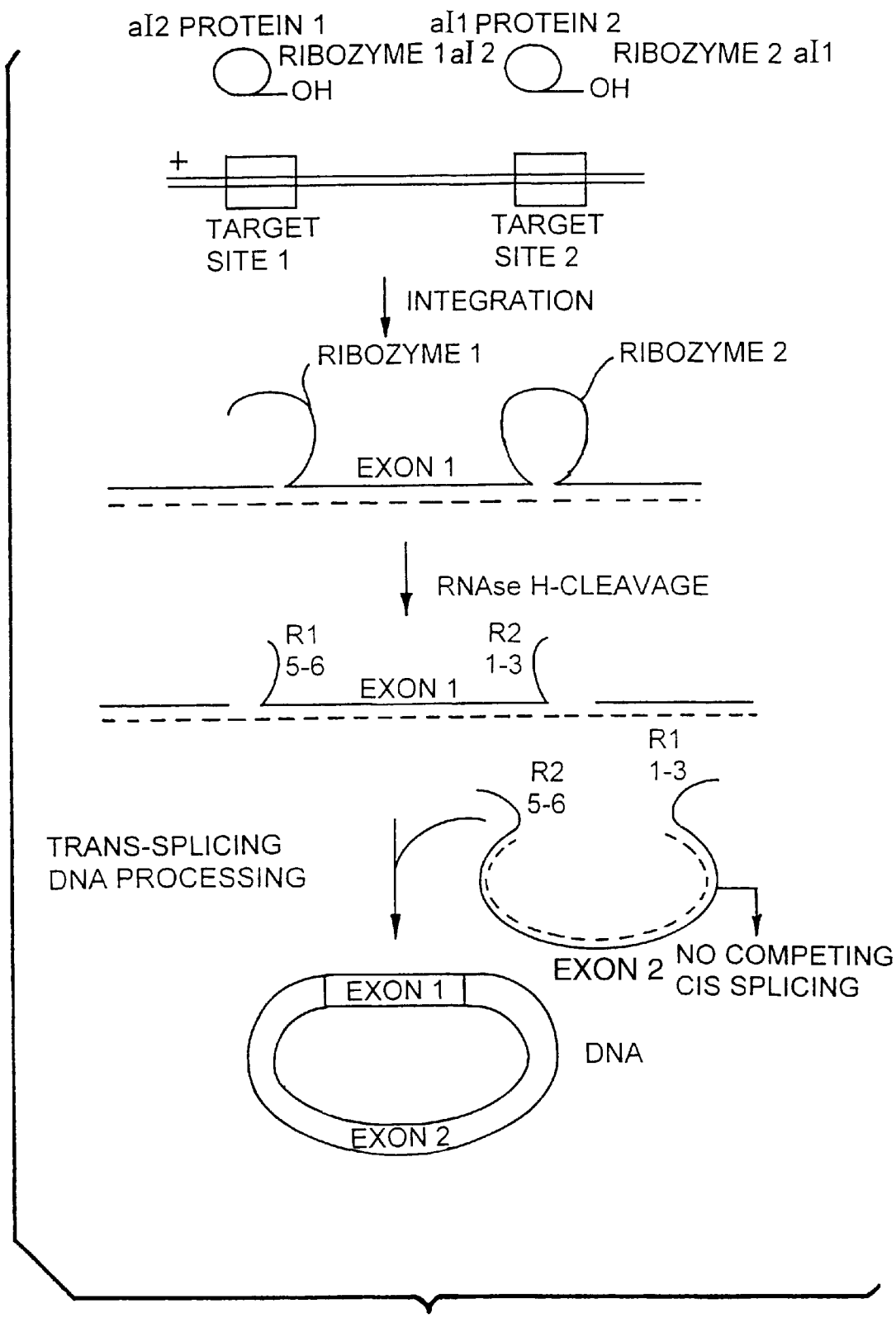
Figure 32:
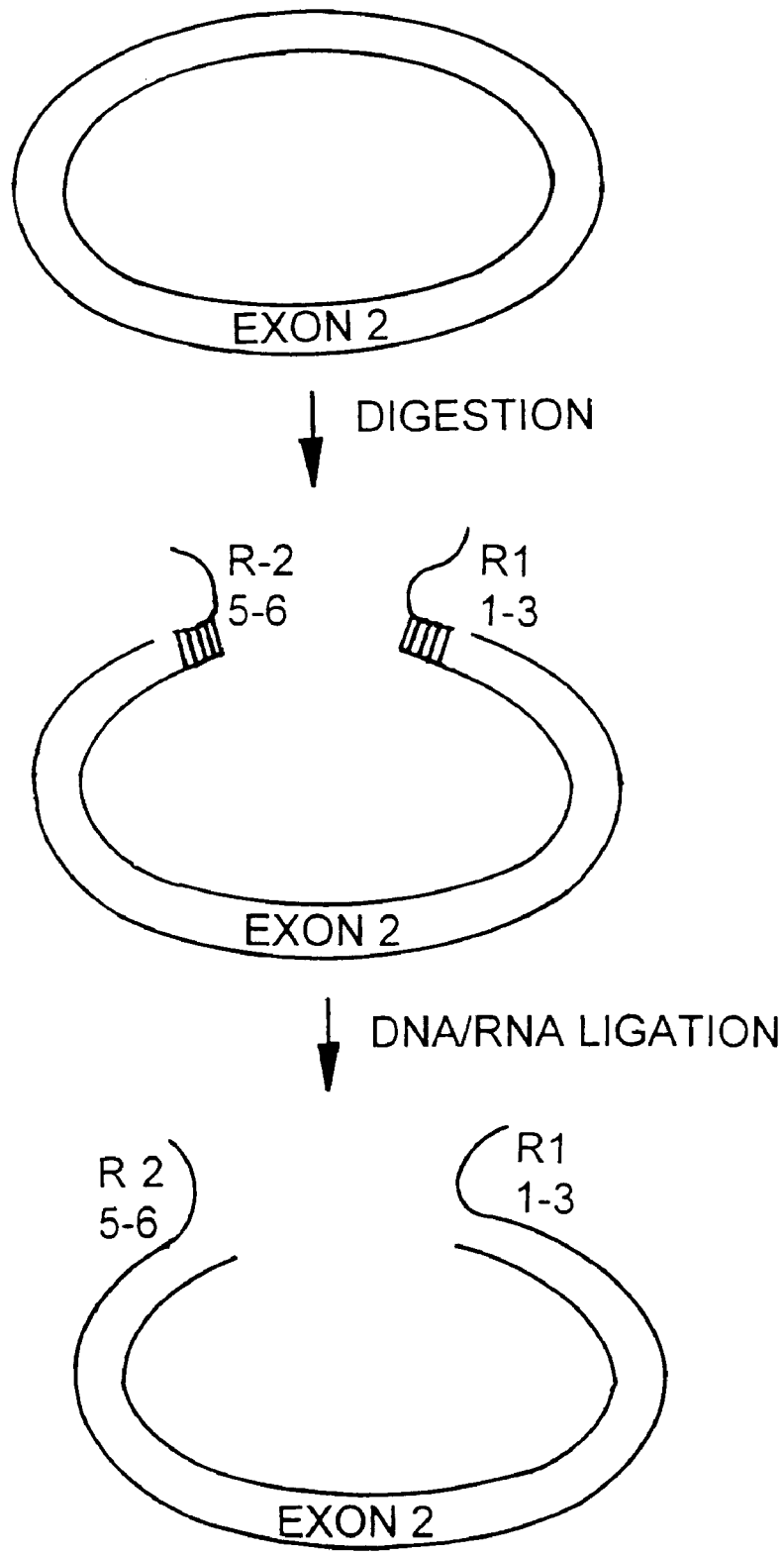
FIG. 32 presents one embodiment of a preferred splint-assisted DNA-RNA ligation method for use in accordance with the present invention.

FIG. 31 presents an alternative embodiment of the overall reaction scheme shown in FIG. 29. In FIG. 31, ribozyme 1 is an aI2-type ribozyme, whereas ribozyme 2 is an aI1-type ribozyme. The advantages of this approach include the relative increased simplicity in designing RNAse H oligonucleotides specific to each ribozyme and the absence of a competing cis-reaction when ribozyme-flanked exon 1 is incubated with ribozyme-flanked exon 2. Of course, it will be appreciated that the ribozyme designed to integrate downstream of exon 1 (and upstream of exon 2) must be aI1-type (or there will be no linkage between exon 1 and intron domains 1–3). Furthermore, where the ribozyme design to integrate upstream of exon 1 (and downstream of exon 2) is of the aI2-type (capable of only partial integration), it will not be possible to link exon 2 to intron domains 1–3 via an integration reaction. Preferably, this linkage is accomplished by splint-assisted DNA-RNA instead. FIG. 32 depicts the preferred method for this ligation reaction. As shown in FIG. 32, exon 2 DNA is cleaved in such a way as to leave both 5' and 3' overhangs on the complementary strand (the strand to which the ribozyme components will not be attached), which overhangs can act as the splint for DNA-RNA ligation.

EXAMPLE 11

Integration and Expression of Novel Genes in the Genome Mediated by Trans-splicing As has been discussed, the aI1 group II intron is capable of full insertion into double-stranded DNA. When steps are not taken to block reverse transcription of the inserted construct, the intron is copied into DNA. It has been proposed that this feature could provide a useful mode for integrating new sequences into an existing DNA molecule. Specifically, it has been proposed that desired sequences could be inserted into the domain 4 loop region of the aI1 intron (or into some other non-conserved region), the intron (along with the inserted sequences) could then be integrated into a target double-stranded DNA molecule, and the integrated sequences could be copied into DNA (see Yang et al. (1996) *Nature* 381:332–335, incorporated herein by reference). One interesting application for this integration system is the introduction of new sequences into expressible sites, e.g., in a genome. The present invention utilizes this integration system, in combination with the above-described RNA-based exon shuffling techniques, and provides a system by which novel genes, produced by exon shuffling, can be expressed and assayed in cells. This embodiment of the invention is depicted in FIG. 33.

Figure 33:
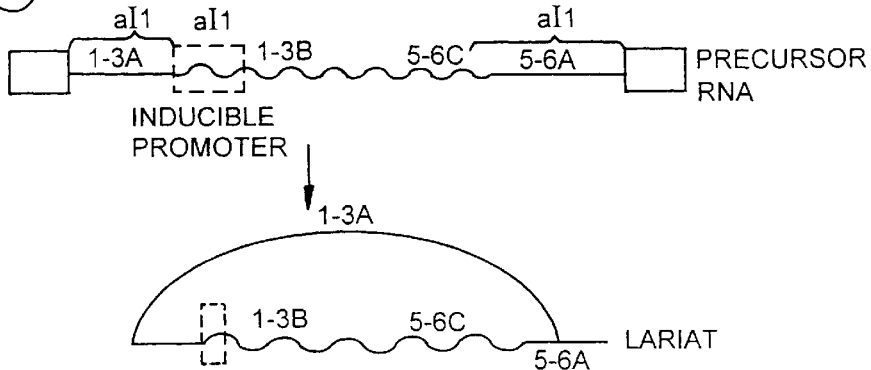
FIG. 33 presents a schematic representation of a trans-splicing method for integration and expression of novel genes in a genome according to the present invention.
Figure 33:
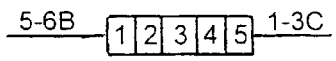
Figure 33:
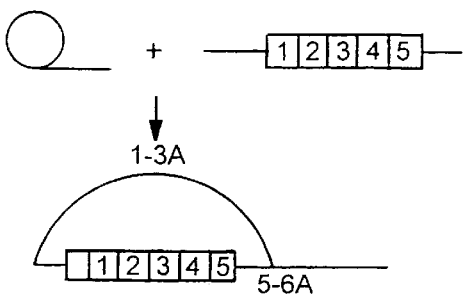
Figure 33:
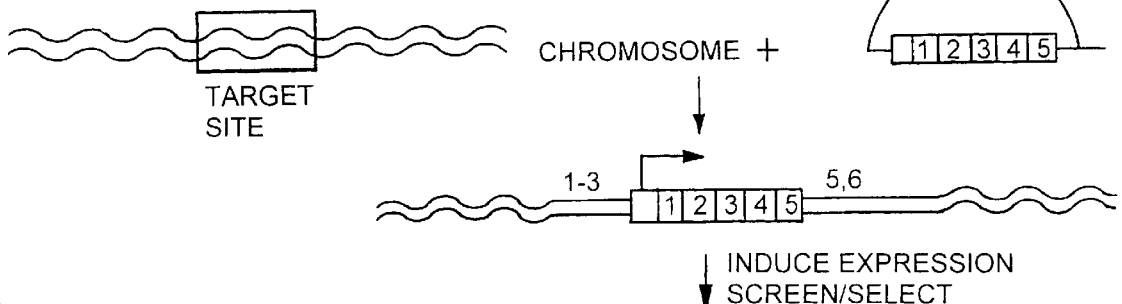

As shown in FIG. 33, a splicing precursor RNA is produced in which an incompatible intron elements are nested within the domain 4 loop of an aI1 intron. This splicing precursor splices to produce a lariat that includes the nested intron elements. The nested intron elements do not splice themselves out of the lariat because they are incompatible and therefore cannot undergo a splicing reaction. This lariat is then combined with an intron-flanked product of exon shuffling. The intron elements flanking the shuffled exons are compatible with the intron elements nested in the lariat, but not with each other. Under these circumstances, the only splicing reaction that the lariat and exon shuffling product can undergo is a trans-reaction in which the shuffled exons are specifically inserted within the domain 4 loop in the lariat, precisely replacing the previously-nested intron sequences. This new lariat is then an aI1 lariat with inserted gene sequences, and can be integrated into a specific site in double-stranded DNA as described above. It is preferred that the site be a genomic insertion site, and that the construct include an inducible promoter, so that effects of expressing the novel gene can be studied in vivo.

One preferred embodiment of the method depicted in FIG. 33 occurs entirely in vivo. Specifically, an aI1 intron carrying nested intron elements as discussed is first integrated into the genome of a host cell in which expression of the novel gene is to be analyzed. The cell is also designed to express the aI1 protein. The exon shuffling product is then also introduced into the cell, either because the shuffling itself occurs in the cell, or because a construct encoding the shuffled product is introduced into and expressed within the cell. Under these circumstances, trans-splicing and integration proceed within the cell, and the cell is analyzed to detect any effects of expressing the novel gene.

III. Cis-splicing Combination of Exons

In yet another embodiment, the combinatorial method can be carried out in a manner that utilizes the flanking intronic sequences in a cis-splicing reaction to generate a combinatorial gene library. As illustrated schematically in FIG. 34, the actual combinatorial event takes place at the DNA level through annealing of complementary sequences within the intron encoding fragments. Briefly, complementary DNA strands are synthesized which correspond to the exonic sequences and flanking intron fragments. As used herein, the term (+) strand refers to the single-stranded DNA that is of the same polarity as a trans-splicing RNA transcript. That is, intronic sequences flanking the 5' end of the exon represent a 3' fragment of an intron. Likewise, the term (−) strand refers to the single stranded DNA which is complementary to the (+) strand (e.g. of opposite polarity).

The 5' and 3' ends of each of the (+) and (−) strands are complementary and can therefore mediate concatenation of single-stranded DNA fragments to one and other through basepairing. In the exemplary illustration of FIG. 34, the exon sequences are flanked by group II domains 4–6 at on end, and domains 1–4 at the other. A library of combinatorial units representative of a number of different exons is generated, such as by PCR or digestion of double-stranded plasmid DNA, to include both (+) and (−) strands. The units are combined under denaturing conditions, and then renatured. Upon renaturation, the sequences corresponding to domain IV at the 3' end of one (+) strand unit can anneal with the complementary domain IV sequences at the 3' end of a (−) strand unit, resulting in concatenation of combinatorial units (see FIG. 34).

Double-stranded DNA can be generated from the concatenated single-stranded units by incubating with a DNA polymerase, dNTPs, and DNA ligase; and the resulting combinatorial genes subsequently cloned into an expression vector. In one instance, 5' terminal and 3' terminal combinatorial units can be used and the double-stranded genes can be amplified using PCR anchors which correspond to sequences in each of the two terminal units. The PCR primers can further be used to add restriction endonuclease cleavage sites which allow the amplified products to be conveniently ligated into the backbone of an expression vector. Upon transcription of the combinatorial gene, the intronic RNA sequences will drive ligation of the exonic sequences to produce an intron-less transcript.

Figure 34:
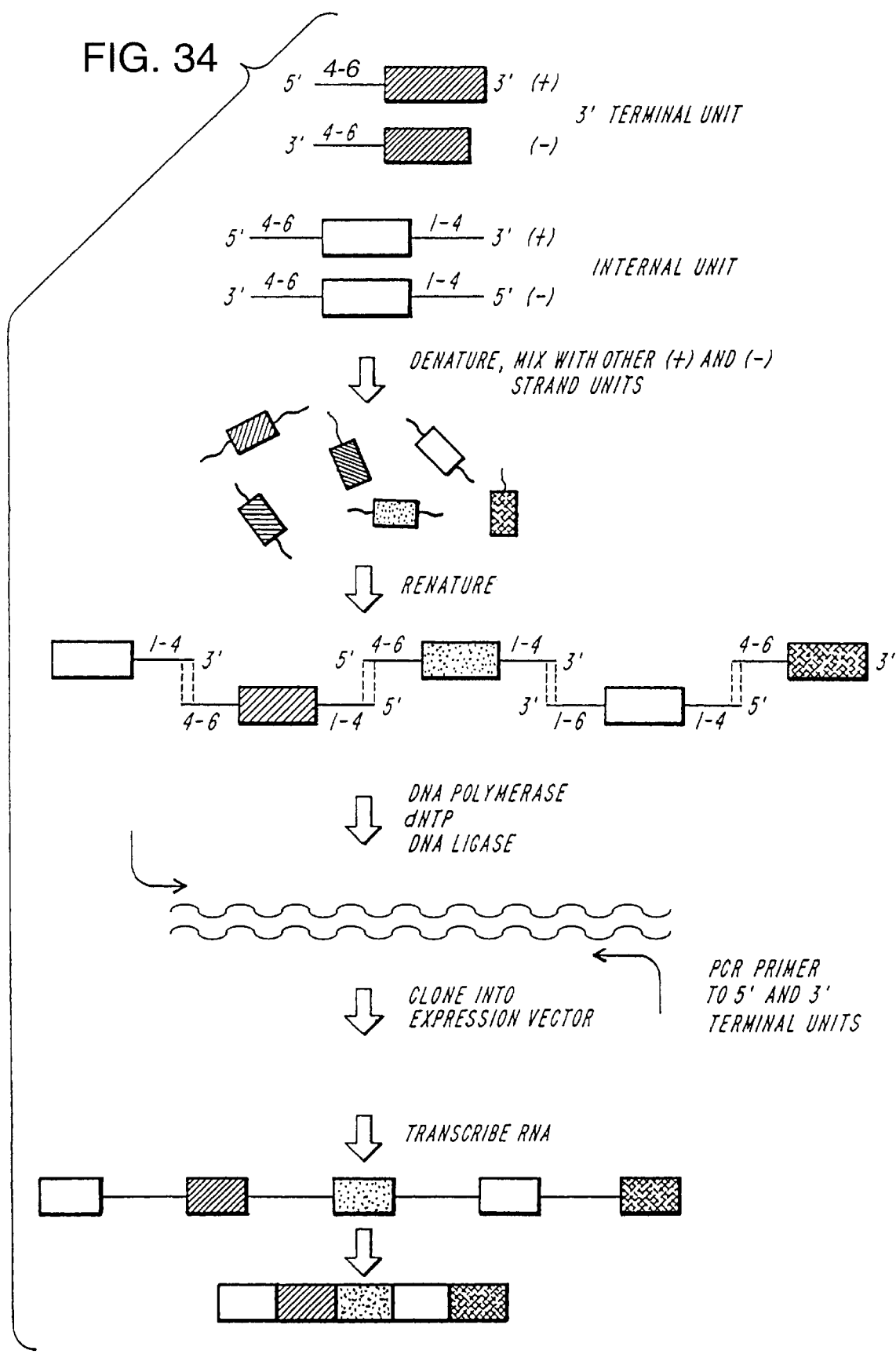
FIG. 34 is a schematic representation of an intron-mediated combinatorial method which relies on cis-splicing to ultimately form the chimeric genes.

While FIG. 34 demonstrates one embodiment which utilizes group II introns, the combinatorial process can be carried out in similar fashion using either group I intron sequences or nuclear pre-mRNA intron sequences.

IV. Circular RNA Transcripts

In addition to generating combinatorial gene libraries, certain splicing constructs of the present invention have a number of other significant uses. For instance, the present trans-splicing constructs can be used to produce circular RNA molecules. In particular, exon constructs flanked by either group II or nuclear pre-mRNA fragments can, under conditions which facilitate exon ligation by trans-splicing of the flanking intron sequences, drive the manufacture of circularly permuted exonic sequences in which the 5' and 3' ends of the same exon are covalently linked via a phosphodiester bond.

Circular RNA moieties generated in the present invention can have several advantages over the equivalent "linear" constructs. For example, the lack of a free 5' or 3' end may render the molecule less susceptible to degradation by cellular nucleases. Such a characteristic can be especially beneficial, for instance, in the use of ribozymes in vivo, as might be involved in a particular gene therapy. In the instance of generating ribozymes, the "exonic" sequences circularized are not true exons in the sense that they encode proteins, rather, the circularized sequences are themselves intronic in origin, and flanked by other trans-acting intron fragments.

However, the circularization of mature messenger-RNA transcripts can also be beneficial, by conferring increased stability as described above, as well as potentially increasing the level of protein translation from the transcript. To illustrate, a ribosome which has completed translation of a protein from the present circular transcript may continue to track around the transcript without dissociating from it, and hence renew synthesis of another protein. Alternatively, the ribosome may dissociate after translation is completed but, by design of the circular transcript, will disengage the transcript proximate to the start site and thereby provide an increased probability that the ribosome will rebind the transcript and repeat translation. Either scenario can provide a greater level of protein translation from the circular transcript relative to the equivalent linear transcript.

Figure 8A:
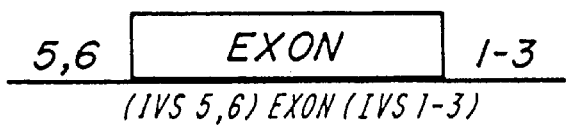
FIGS. 8A-C as illustrate how intronic ends of the same molecule can be brought together by a nucleic acid "bridge" which involves hydrogen bonding between the intronic fragments flanking an exon and a second discrete nucleic acid moiety.
Figure 8B:
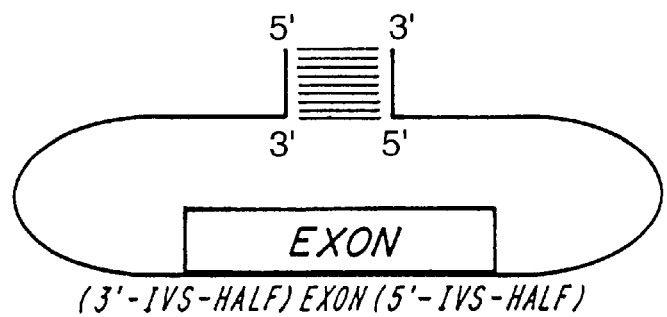
Figure 8C:
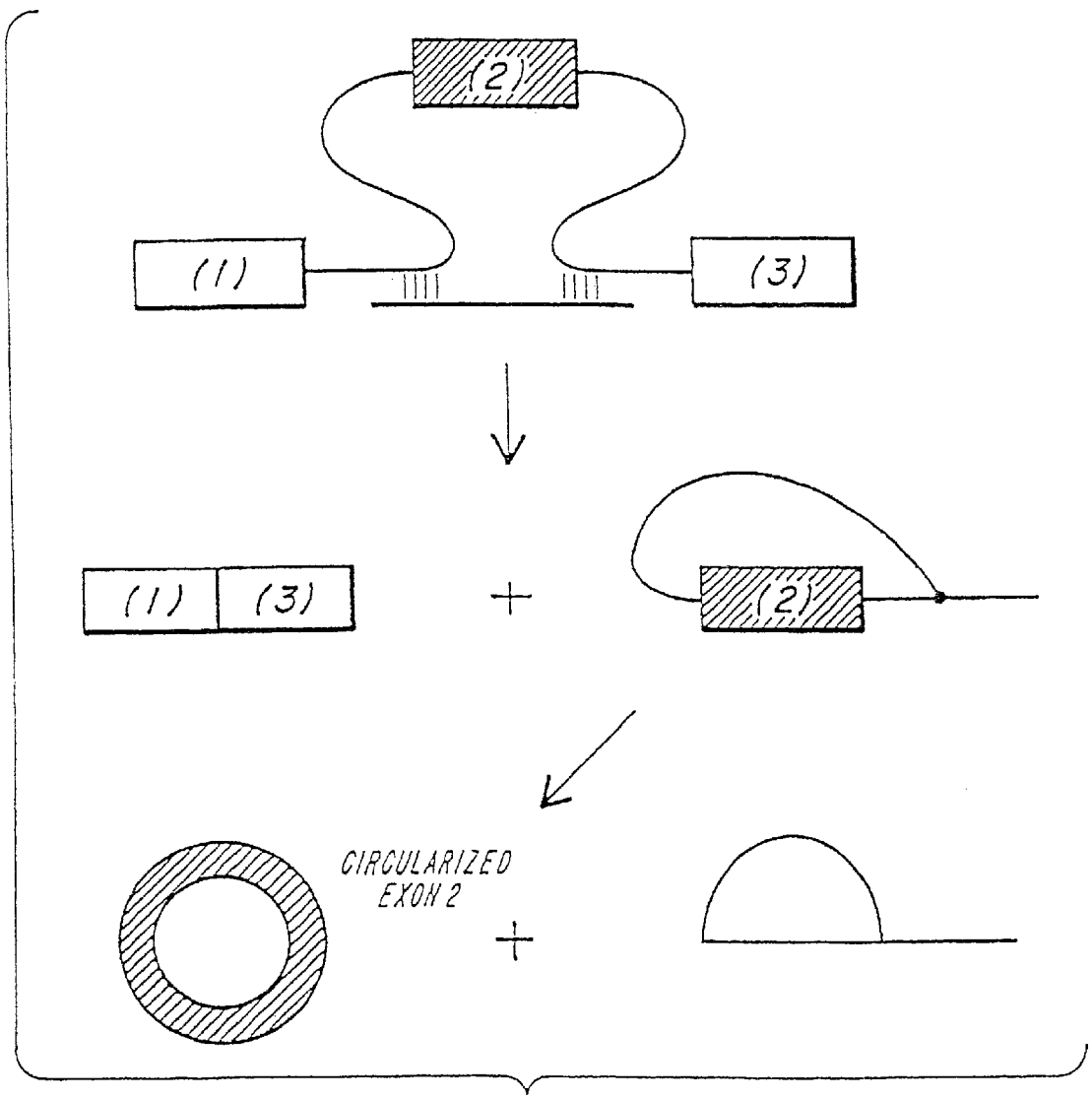
Figure 9:
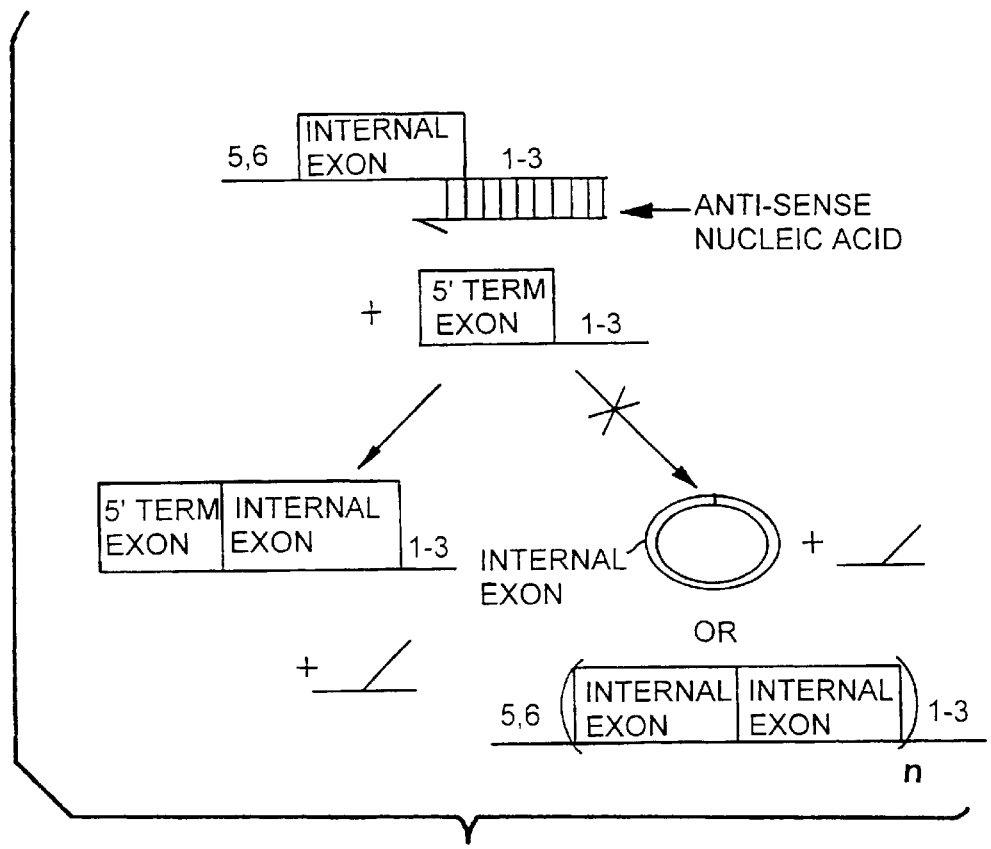
FIG. 9 is a schematic representation of the effects of an anti-sense nucleic acid in a trans-splicing reaction involving an intron-flanked internal exon.

FIGS. 8A–C depicts three examples of intron fragment constructs, designated (IVS5,6)-exon-(IVS1–3), and (3'-half-IVS)-exon-(5'-half-IVS), which, in addition to being capable of driving trans-splicing between heterologous exons as described above, can also be used to generate circular RNA transcripts. The (IVS5,6)-exon-(IVSI-3) transcript comprises the group II intron domains 5 and 6 at the 5' end of the exon, and domains 1–3 at the 3' end of the exon. The (3'-half-IVS)-exon-(5'-half-IVS) is a similar construct, but replaces the group II domains 5-6 and 1–3 with fragments corresponding to the 3'-half and 5'-half of a nuclear pre-mRNA intron. As described in Examples 12 and 15 below, each of these transcripts can be shown to drive intramolecular ligation of the exon's 5' and 3' end to form circular exons.

Figure 35:
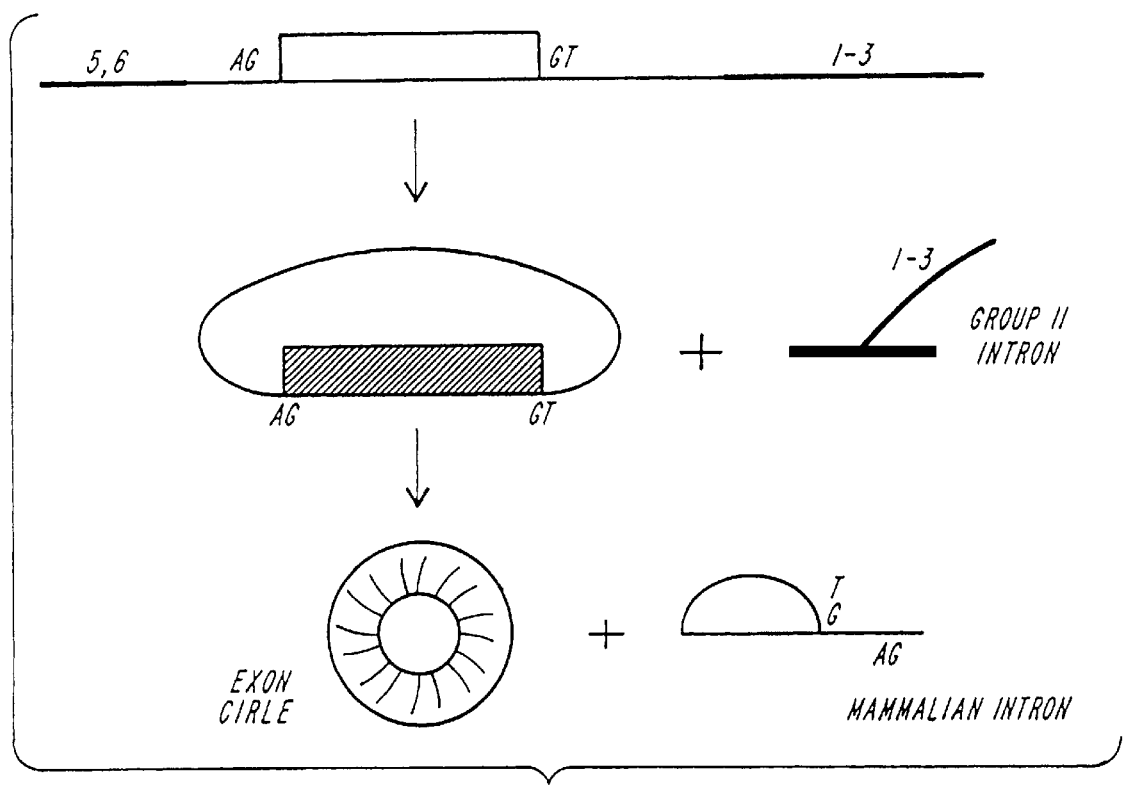
FIG. 35 shows how group II intronic fragments can be utilized to covalently join the ends of a nuclear pre-mRNA transcripts having flanking nuclear pre-mRNA intron fragments, such that the flanking nuclear pre-mRNA intron fragments can subsequently drive ligation of the 5' and 3' end of the exonic sequences.

Furthermore, as set forth in Example 15, a preferred embodiment of an exon construct using mammalian pre-mRNA intron sequences to generate circular transcripts provides an added structural element that brings together and 5' and 3' ends of flanking pre-mRNA intron fragments. The addition of such structural elements has been demonstrated to greatly improve the efficiency of the intramolecular splicing reaction. For example, the ends of the intronic fragments can be non-covalently linked as shown in FIGS. 8B and C, by hydrogen bonding between complementary sequences. Alternatively, the ends of the nuclear pre-mRNA intron fragments can be covalently closed. In an illustrative embodiment, FIG. 35 shows how group II intronic fragments can be utilized to covalentlyjoin the ends of the nuclear pre-mRNA transcripts having flanking nuclear pre-mRNA intron fragments, which subsequently drive ligation of the 5' and 3' end of the exonic sequences.

In yet another embodiment, the intronic ends can be brought together by a nucleic acid "bridge" which involves hydrogen bonding between the intronic fragments flanking the exon and a second discrete nucleic acid moiety. As illustrated in FIGS. 36A–C, such nucleic acid bridges can be formed a number of ways. Each of the splicing bridges shown differ from each other in either the orientation of the bridge oligonucleotide when base-paired to the flanking intron fragments, in the size of the bridging oligonucleotide, or both. For instance, the bridge oligonucleotide shown in FIG. 36A base-pairs in an orientation which can result in a stem-structure similar to the (3'IVS-half)-exon-(5'IVS-half) construct depicted in FIG. 8B. Moreover, when a bridge similar to one shown in FIG. 36C is used, and the 5' and 3' ends of the flanking introns base-pair some distance apart in the linear sequence of the bridge, the bridge oligonucleotide may itself comprise the branch acceptor site. For example, the bridge oligonucleotide can be an RNA transcript comprising the yeast branch site consensus sequence UAC-UAAC in a portion of the bridge sequence which does not base-pair with the intronic fragments of the exon construct.

Figure 8D:
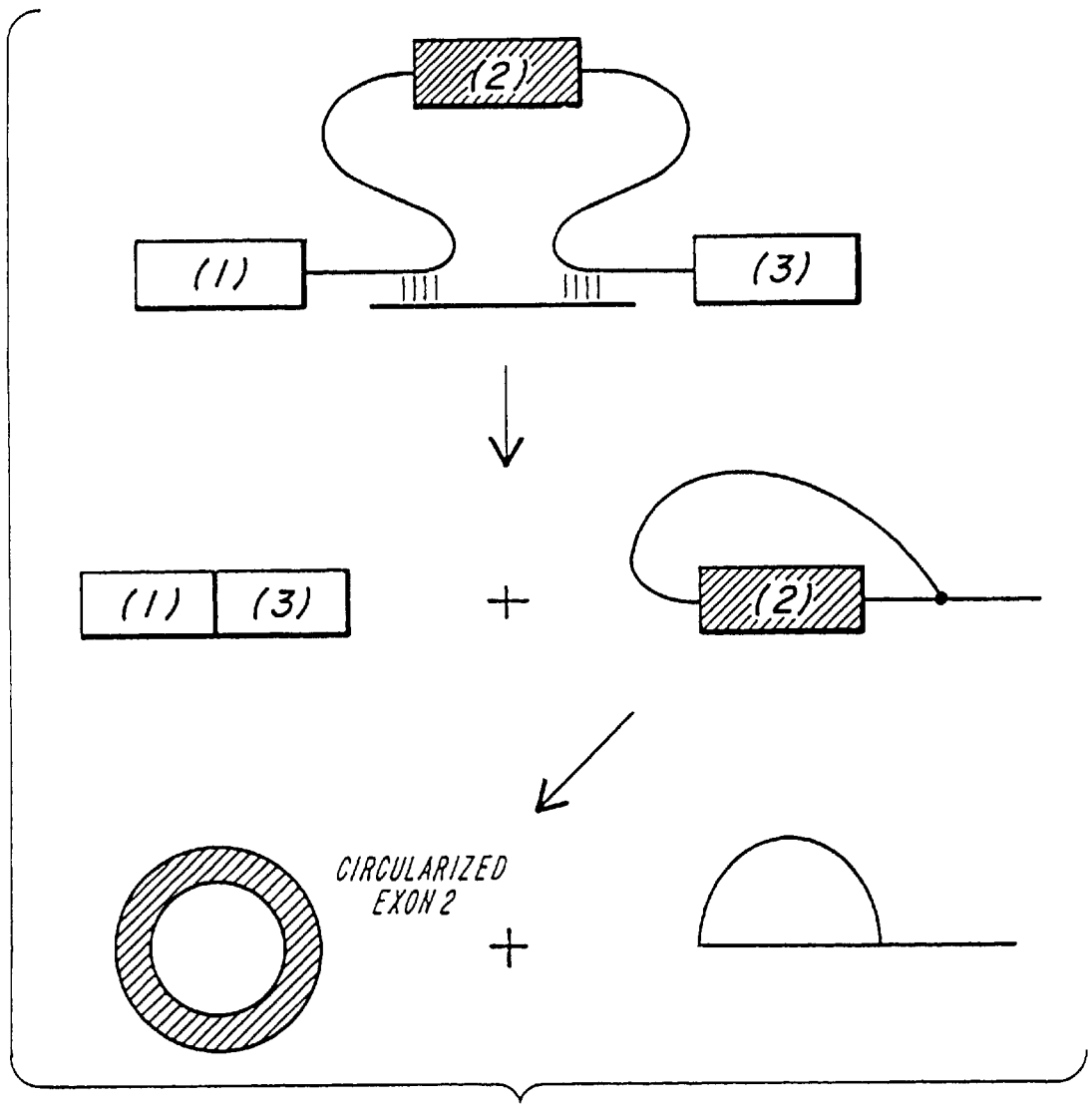
FIG. 8D shows, in an illustrative embodiment, how a nucleic acid bridge can be used to direct alternative splicing by "exon skipping".

Oligonucleotide bridges useful in driving the circularization of exon transcripts can also be used to direct alternative splicing by "exon skipping", which may be useful, for example, in disrupting expression of a particular protein. As shown in FIG. 8D, the splicing of exons 1 and 3 to each-other can be the result of an oligonucleotide which loops out exon 2, effectively bringing together two complementary halves of the intronic sequences flanking exons 1 and 3. As shown in FIG. 8D, exon 2 can, in fact, be spliced into a circular RNA.

Figure 37:
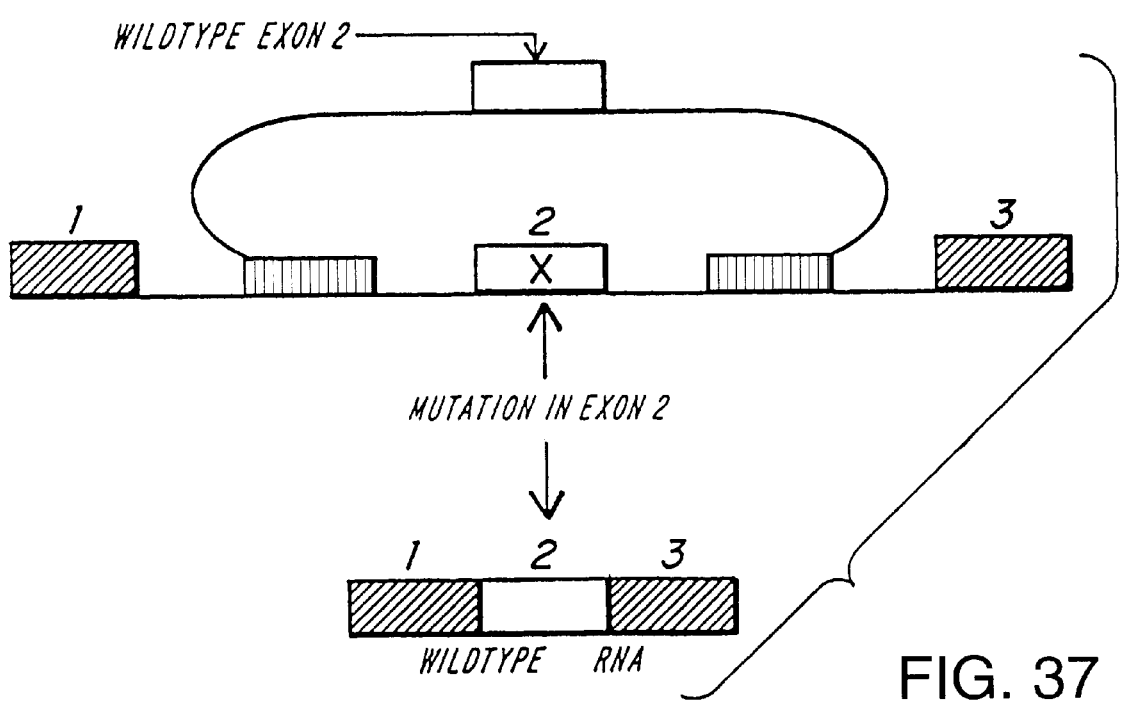
FIG. 37 illustrates a nucleic acid construct useful in mediating the alternate splicing of an exon through a trans-splicing-like mechanism.

Carrying the bridging nucleotide one step further, FIG. 37 illustrates the use of an exon construct useful in mediating the alternate splicing of an exon through a trans-splicing-like mechanism. For instance, a wild-type exon can be trans-spliced into an mRNA transcript so as to replace an exon in which a mutation has arisen. The wild-type exon construct comprises flanking intronic sequences which include sequences complementary to a portion of the continuous introns which connect exons 1, mutant exon 2, and exon 3. Thus, through a trans-splicing event as described above, some of the resulting mature mRNA transcripts will include the wild-type exon 2.

EXAMPLE 12

Group II Introns can Mediate Circularization of Exonic Sequences

The (IVS 5,6)-exon-(IVS 1–3) RNA transcript, shown in FIG. 8A, was synthesized from plasmid pINV1 (SEQ ID NO:1). The intronic sequences correspond to the half molecules generated by interruption of the 5 g intron of the yeast mitochondrial oxi3 gene in domain 4; and the exonic sequences are the exon sequences E5 and E3 which are naturally disposed at the 5' and 3' ends of the 5 g intron, respectively. To construct pINV1, the Sac I-Hind III fragment of pJDI5'-75 (Jarrell et al. (1988) *Mol. Cell Biol.* 8:2361–2366) was isolated and the Hind III site was filled in with Klenow fragment. This DNA was ligated to pJDI3'-673 (Jarrell et al., supra) that had been cleaved with SacI and SmaI. The RNA splicing substrates were made by in vitro transcription using T7 RNA polymerase.

Transcription, RNA purification, and splicing reactions were as described (Jarrell et al., supra). The E5-specific oligodexoynucleotide (5'-GTAGGATTAGATGCAGATAC-TAGAGC-3' [SEQ ID NO:12]) is identical to 26 nucleotides of the E5 region of the (IVS 5,6)exon(IVS 1–3) RNA. The E3-specific oligonucleotide (5'-GAGGACTTCAATAGTAGTATCCTGC-3' [SEQ ID NO:13]) is homologous to 25 nt of the E3 region.

To purify E3,E5(C), described below, for the reverse transcription reaction, a standard 100-$\mu$l transcription was done, with pINV1 as a template. The (IVS 5,6)E3,E5(IVS 1–3) RNA was concentrated by ethanol precipitation and was then incubated under the $(NH_4)_2SO_4$ splicing conditions for 1 hr. The E3E5(C) RNA was gel purified and dissolved in 30 $\mu$l of water. A 9-$\mu$l annealing reaction mixture was incubated at 65° C. for 3 min and then placed on ice. The annealing reacting mixture included 1 $\mu$l of the E3,E5(C) RNA plus 100 ng of the E3-specific oligonucleotide. As a control, an identical annealing reaction was done, except E3,E5(C) was not added. A buffer (4 $\mu$l) consisting of 0.25 M Tris-HCl (pH 8.5), 0.25 M KCl, 0.05 M dithiothreitol, and 0.05M $MgCl_2$ was added to both annealing reaction mixtures. Deoxynucleoside triphosphates were each added to a final concentration of 5 mM, followed by 40 units of RNasin (Promega) and 22 units of reverse transcriptase (Seikagaku America, Rockville, Md.). The final volume was adjusted to 20 $\mu$l with water. The mixture was incubated at 42° C. for 90 min.

Two polymerase chain reaction (PCR) experiments were done using as templates either 1 $\mu$l of the reverse transcription mixture that included E3,E5(C) or 1 $\mu$l of the control reverse transcription mixture, which lacked E3,E5(C). The PCRs were performed as described previously and were continued for 25 cycles. The E3- and E5-specific oligonucleotides, 300 ng each, were used as PCR primers. DNA sequencing was done with Sequence (United States Biochemical) according to the protocol provided by the manufacturer.

Group II intron excision can occur by transesterification (splicing) or by site-specific hydrolysis (cleavage). The former reaction is stimulated by $(NH_4)_2SO_4$, the control RNAs, E5(IVS 1–3) plus (IVS5,6)E3, trans-spliced to yield spliced exon S(E5-E3) and a Y branched intron [IVS(Y)]. Co-incubation in the presence of KC1 yielded free exons (E5 and E3) and a linear intron (IVS 1–3) as major products.

The (IVS 5,6)exon(IVS 1–3) precursor was also reactive. Most for the products could be identified based on their comigration with products of the control trans-reaction. In the present of $(NH_4)_2SO_4$, the IVS(Y) and some linear intron were liberated; several novel products were also generated. Among these was an RNA (E3,E5) the expected size of the linear excised exons (591 nt). A slower migrating RNA [E3,E5(C)] was also observed. At short times of incubation (1 min) E3,E5(C) and IVS(Y) were the predominant products. In contrast, E3,E5 did not accumulate to significant levels before 60 min, indicating that it was not an early product of the reaction. Analysis of E3,E5(C) demonstrated that is was circular spliced exons. E3,E5(C) accumulated in the presence of $(NH_4)_2SO_4$ but not in the presence of KCl. This was significant, given that spliced exons (E3-E5) are not only product of cis or trans splicing that accumulates in the presence of$(NH_4)_2SO_4$ but not in the presence of KCl. Thus, it was likely that E3,E5(C) resulted from splicing rather than hydrolysis.

E3,E5(C) and E3,E5 were purified and analyzed by denaturing gel electrophoresis. During the purification process some E3,E5(C) was converted to a faster migrating species that comigrated with E3,E5. The extent of conversion of E3,E5(C) to the faster migrating species was increased by incubation with the group II intron under conditions that promote site-specific hydrolysis of the spliced exons. These observations are consistent with E3,E5(C) being a circular RNA that can be broken by hydrolysis to yield (linear) E3,E5.

To demonstrate that E3,E5(C) contains spliced exons, a cDNA copy of purified E3,E5(C) RNA was made by reverse transcription. The reverse transcription was primed with an oligonucleotide homologous to 25 nt of E3. If E3,E5(C) is accurately spliced circular exons, its length is 591 nt. Reverse transcription of this circular RNA would yield cDNAs of variable lengths; in particular, multiple rounds of complete reverse transcription of the circular template would generate cDNAs that are >591 nt long. A sample of the reverse transcription reaction mixture was used as a template in a PCT. The E3-specific oligonucleotide and an oligonucleotide homologous to 26 nt of the E5 sequence of the expected cDNA were used as primers. If E3,E5(C) is the product of a splicing reaction, it will contain both E3 and E5 sequences and will yield amplification products in this PCR reaction. Analysis of the PCR products revealed that the major amplification product is the size expected [313 base pairs (bp)] for a PCR product derived from spliced exons. This product was not seen in a control PCR reaction. Two additional PCR products of about 900 bp and 1500 bp were also observed. Amplification of longer cDNAs generated by multiple rounds of reverse transcription of the circular E3,E5(C) template would yield a set PCR products each an integral multiple of 591 bp longer than the 313 bp indicating that the 900 bp and 1500 bp observed products were likely generated in this manner.

The 313-bp PCR product was purified and cloned into a plasmid vector. The nucleotide sequence of each of four independently isolated clones was determined by the dideoxy sequencing method, using the E3-specific oligonucleotide as a primer. The sequence showed that the PCR product contained both E5 and E3 sequences that were joined by accurate splicing.

EXAMPLE 13

Engineered Group II Introns Mediate Circularization of a Human Exon

A derivative of the yeast aI5γ group II intron was designed to be able to catalyze the production of a circular exon encoding the first Kringle domain (K1) of the human tissue plasminogen activator protein. The circular K1 exon is formed with high fidelity in vitro. Furthermore, the system is designed so that the circular exon consists entirely of human exon sequence.

Figure 38A:
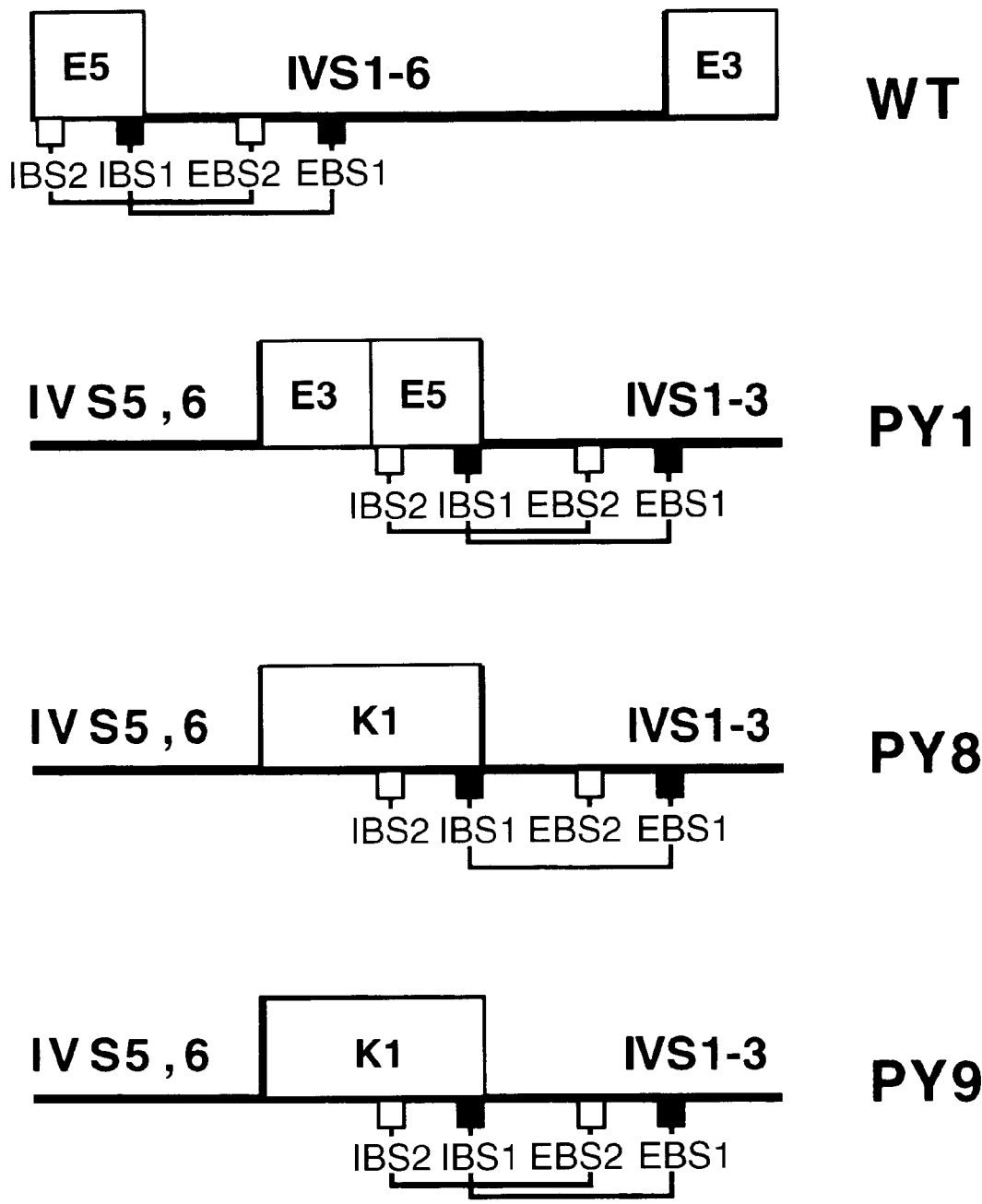
FIG. 38A depicts various RNA splicing substrates used in inverse splicing reactions to produce circular exons according to the present invention.

The four plasmid constructs utilized in this study are shown in FIG. 38A. pJD20 encodes the full-length aI5γ intron with its flanking 5' and 3' exons; pY1 is identical to pINV1 described above and encodes an inverse-splicing substrate that splices to yield an exon circle and a y-branched intron (Jarrell (1993) *PNAS* 90:8624–8627); pY8 and pY9 are plasmids that encode inverse-splicing constructs containing the human K1 exon. Both pY8 and pY9 were made by site-directed mutagenesis that deleted the KpnI site and precisely fused the K1 exon sequence to the last nucleotide of the group II intron domain 6. The group II intron sequences in pY8 were engineered so that the EBS1 site perfectly matches the appropriate region of the K1 exon (see FIG. 38B); there is also a two-base-pair interaction between IBS2 and EBS2. The group II intron sequences in pY9 were engineered so that there is perfect complementarily in both the EBS1-IBS1 and EBS2-IBS2 interactions (see FIG. 38B).

Since the EBS1-IBS1 interaction is essential and the EBS2-IBS2 interaction is important, but not essential, for cis or trans splicing, we compared the efficiency and accuracy of inverse splicing by the PY8 and PY9 RNAs (encoded by pY8 and pY9, respectively) in order to examine the roles of these interactions in inverse splicing. As described above, PY8 lacks the EBS2-IBS2 interaction, while PY9 has both interactions. In order that the splicing reactions could be compared quantitatively, the ΔG37° of the EBS1-IBS1 and EBS2-IBS2 interactions were calculated for each splicing precursor used (see FIG. 38B).

PY8 and PY9 splicing precursors (as well as the WT and PY1 splicing precursors) were prepared by in vitro transcription with T7 RNA polymerase (Phannacia, Stratagene). The in vitro transcription reactions were performed at 40° C. on plasmid templates that had been digested with HindIII restriction enzyme. The WT and PY1 transcripts were labeled with [α-$^{32}$P]UTP (given that intron aI5γ and its flanking exons are relatively A/T rich, splicing of UTP labeled substrate yields readily detectable spliced products) while PY8 and PY9 were labeled with [α-$^{32}$p]GTP (given that the human K1 exon is very G/C rich, when PY8 or PY9 were labeled with UTP we observed that products and intermediates that contain the K1 exon were barely detectable). The splicing precursor RNAs were then purified from an acrylamide gel and were incubated under splicing conditions (40 mM Tris-HCl (pH7.6), 100 mM MgCl$_2$, and either 1.5 M (NH$_4$)$_2$SO$_4$, 1.5 M NH$_4$Cl, or 1.5 M KCI; 45° C.).

Figure 39A:
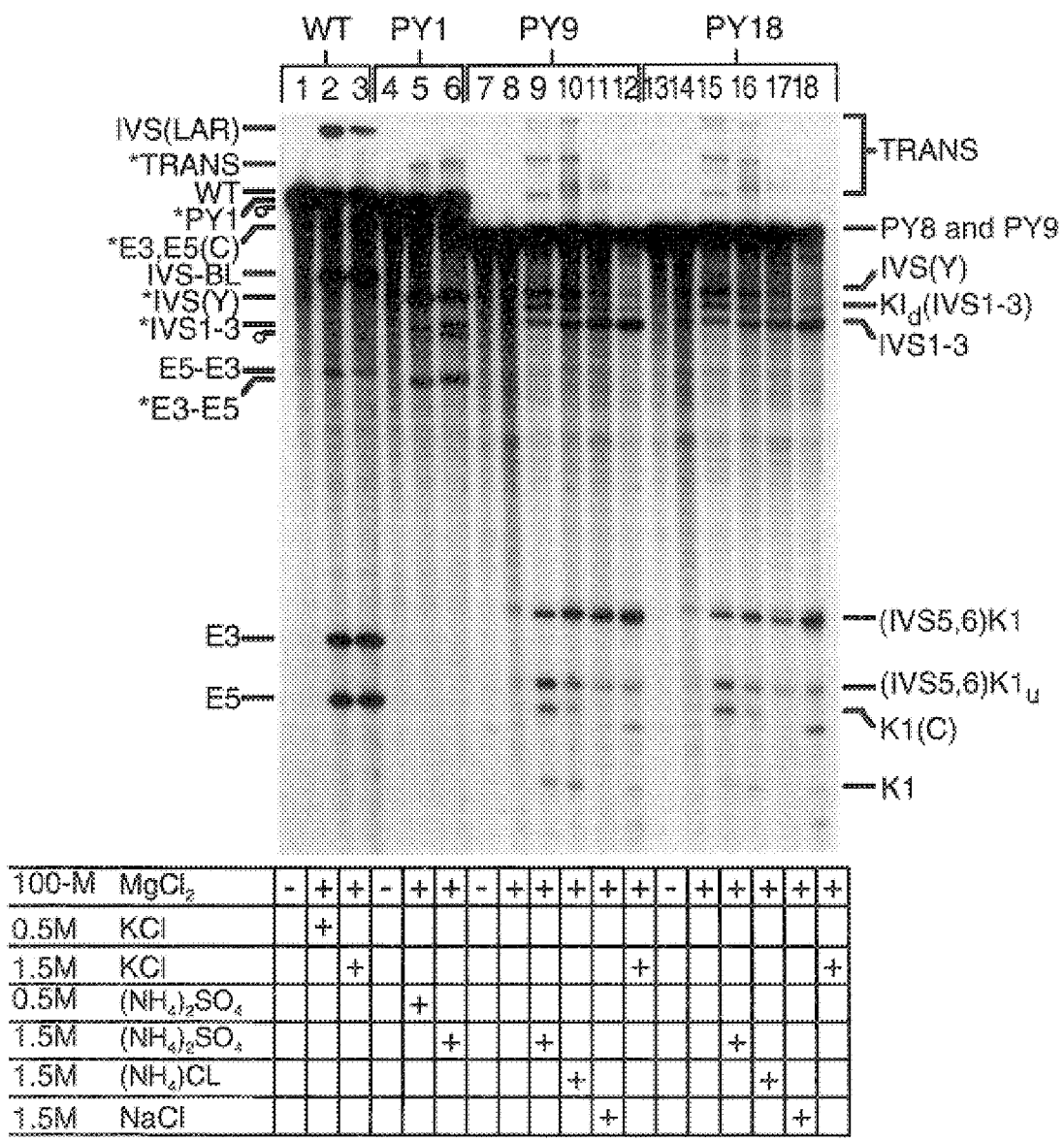
FIG. 39A shows the effects of various salts of monovalent cations on the splicing of particular substrates.

As shown in FIG. 39A, both PY8 and PY9 undergo inverse splicing to yield the excised exon circle [K1(C)] when incubated in splicing buffer (i.e., buffer that contains a monovalent cation salt). Neither gives the circular product when incubated in buffer lacking a monovalent cation (lanes 8 and 14). Of the four different sets of splicing conditions used, (NH$_4$)$_2$SO$_4$ (lanes 9 and 15) stimulates the most abundant production of the major products of inverse splicing, IVS(Y) and K1(C). The yield of those products is also high in NH$_4$Cl buffer (lanes 10 and 16), but the ratio of branched intron [IVS(Y)] to liner released intron (IVS 1–3) is reduced in that buffer. Little IVS(Y) or K1(C) is seen when PY8 or PY9 are incubated in the presence of NaCl (lanes 11 and 17) or KCl (anes 12 and 18).

Incubation of PY8 or PY9 under splicing conditions produces other products in addition to the inverse-splicing products discussed above. Products of trans splicing, labeled TRANS in FIG. 39A, are most abundant when the RNA is incubated in (NH$_4$)$_2$SO$_4$ or NH$_4$Cl, buffer. Schematic representations of the products observed in FIG. 39A are presented in FIG. 39B. The expected size of each product is given in nucleotides (nt). Two of the products, K1$_A$(IVS1–3) and (IVS5,6)K1$_u$, are produced by a cryptic cleavage event at a site within the K1 exon that resembles the last six nucleotides of that exon.

Figure 39B:
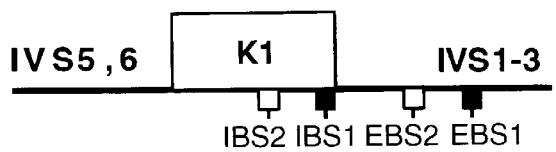
FIG. 39B gives schematic representations of the products observed in FIG. 39A.
Figure 39B:
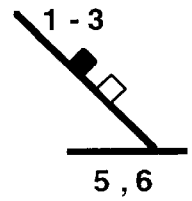
Figure 39B:
Figure 39B:
Figure 39B:
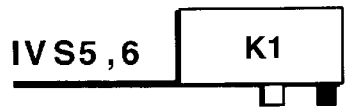
Figure 39B:
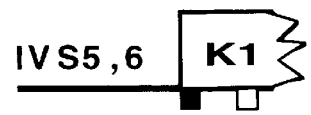
Figure 39B:
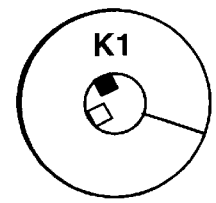
Figure 39B:
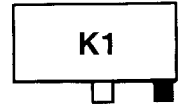

As shown in FIG. 39B, the two main products of splicing in both the NaCl or the KCl buffer were IVS 1–3 (line 4) and (IVS 5,6)K1 (line 5). These two products are generated when the first step of the two step splicing reaction occurs by hydrolysis rather than by transesterification. That (IVS 5,6)K1 accumulates to significant levels when either PY8 or PY9 is incubated in the presence of any of the four monovalent cation salts indicates that, for both substrates, there is a general reduction in the forward rate of the second step of splicing. There appears to be a correlation between the amount of branched intron that accumulates and the amount of released exon (both K1 and K1 (C)) that is seen; when the levels of IVS(Y) are high (e.g. lane 9) the levels of released K1 and K1(C) are also high. This suggests that RNAs that accomplish the first step of inverse splicing by branching (rather than by hydrolysis) are more likely to complete the second step of splicing than are RNAs that accomplish the first step by hydrolysis. That observation is consistent with the known observation that branched molecules catalyze the second step of cis splicing more efficiently than do liner molecules.

Time course experiments were performed to establish precursor-product relationships and to compare rates of splicing by the different substrates (data summarized in Table I). Although the desired products of inverse splicing were most abundant when PY9 or PY8 were incubated in (NH$_4$)$_2$SO$_4$ buffer, the reaction was slow in the presence of that salt. Inverse splicing of PY1, which contains yeast exon sequences, proceeds at a relative rate that is less than two-fold slower the rate observed for the WT (cis splicing) substrate; in contrast, PY8 and PY9 each splice at a rate about 20- to 30-fold slower than does WT in the (NH$_4$)$_2$SO$_4$ buffer. Interestingly, both PY8 and PY9 undergo inverse splicing at approximately the same rate in (NH4)$_2$SO$_4$ buffer even though PY8 lacks a strong EBS2-IBS2 pairing (−2.3 kcal), while PY9 has a strong EBS2-IBS2 pairing (−12.2 kcal).

The inverse splicing reaction was faster in the NH$_4$Cl buffer than in the (NH$_4$)$_2$SO$_4$ buffer. Although the relative yield to the desired products of inverse splicing is somewhat reduced in the NH$_4$Cl buffer, useful quantities of spliced product can be obtained relatively quickly upon incubation under these conditions.

Each of the products depicted in FIG. 39B was characterized individually. The K1(C) was gel purified from a 1.5M (NH$_4$)$_2$SO$_4$ splicing reaction and was characterized by reverse transcription and PCR amplification using K1-specific oligodeoxynucleotides (K1.Cir.1:anti-sense 5'-GCCAACGCGCTGCTGTTCCAG-3' [SEQ ID NO:14] and K1.Cir.2:sense 5'-GGCCAGACGCCATCAGGCTG-3' [SEQ ID NO:15]). The 241 bp amplification product was cloned into the pCR2.1® Vector (Invitrogeno® DNA Cloning® Kit Version D), and was sequenced (Amersham Sequenase® Version 2.0 DNA Sequencing Kit) across the splice junction. 8 independent clones of the PY8 K1(C) product were sequenced, as were 10 independent clones of the PY9 K1(c) product.

Y-branched products were characterized by debranching analyses. Specifically, IVS Y, K1$_A$(IVS1–3), and IVS1–3 were gel purified from 1.5 M (NH$_4$)$_2$SO$_4$ PY8 and PY9 splicing reactions. These products were incubated in HeLa cell extract (sl 00) (20 mM HEPES (pH8.0), 100 mM KCl, 8 mM EDTA, 20% Glycerol), which has debranching activity, for one hour a 30° C. for one hour. Proteins were then extracted from the reaction mixture and RNA products were precipitated and fractionated on a 4% denaturing polyacrylamide gel.

To further characterize the products of inverse splicing, PY8 (data not shown) and PY9 (FIG. 40A) were uniquely labeled at their 5' ends prior to splicing. Specifically, non-reactioactive PY9 was dephosphorylated with Phosphatase (Boehringer Mannheim) in calf intestinal phosphatase buffer (Boehringer Mannheim), and then [γ-$^{32}$P]ATP labeling was carried out using Polynucleotide Kinase (Pharmacia) in 1X one-phor-all kinase buffer (for 2 hours at 37° C.). The labeled RNA was then cleaned and precipitated, spliced in 1.5M (NH$_4$)$_2$SO$_4$, and run on a 4% acrylamide gel. Intermediates and products that contained the original 5' end of the splicing substrate were thereby identified. Three of the intermediates or products were found to harbor the original 5' end of the splicing substrate. Note that all three of those RNAs contain the IVS 5,6 sequence (FIG. 39B, lines 2, 5 and 6).

PY8 (data not shown) and PY9 (FIG. 40A, lane 8) were also uniquely labeled at their 3' ends prior to splicing. In this experiment, non-radioactive PY9 was made in vitro and purified by G25-Sephadex column elution. T4 RNA Ligase (Pharmacia) was used to label the 3'-end with [5'-$^{32}$P]pCp. The reaction was carried out with 0.25 mM ATP, 1% DMSO (Sigma) water in RNA Ligase buffer (0.5 M Tris hydrochloride [pH7.6], 0.15 M MgCl$_2$, 33 mM DTT). The reaction was incubated over night at 4° C. Labeled RNA was precipitated, spliced and run on a 4% acrylamide gel. Intermediates and products that contained the original 3' end of the splicing substrate were thus identified. Three of the intermediates or products were found to harbor the original 3' end of the splicing substrate. Note that all three of those RNAs contain the IVS 1–3 sequence (FIG. 39B, lines 2, 3 and 4). The only major products of inverse splicing that were not seen either when the substrate was 5' end labeled or when it was 3' end labeled were the circular form [K1(C)] and the linear form (K1) of the excised exon.

Figure 40A:
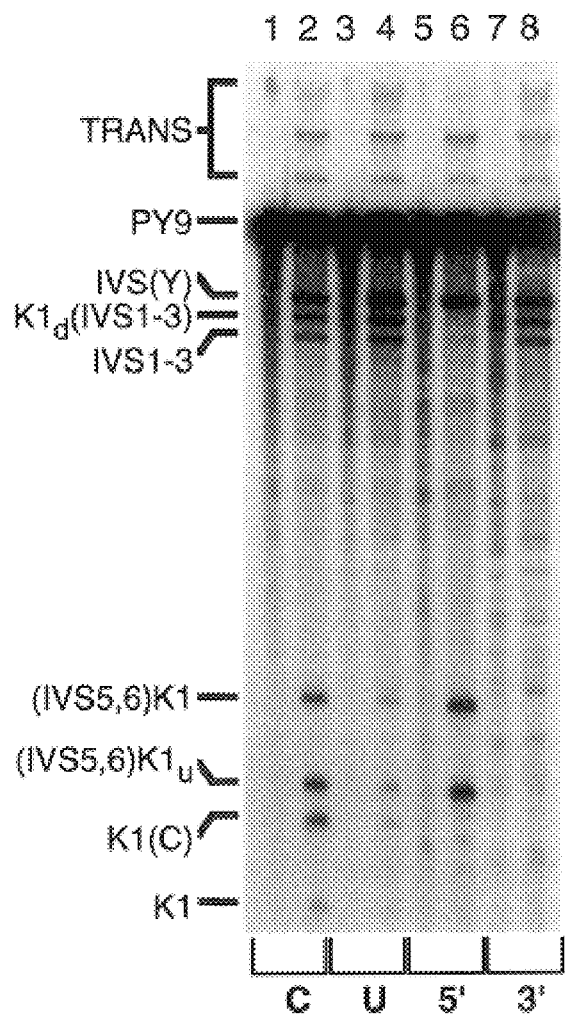
FIG. 40A shows splicing of 5' and 3' end-labeled PY9.

The product denoted as IVS(Y) in FIG. 40A contained both the original 5' and 3' ends of the splicing substrate. Furthermore, that product migrated with IVS(Y) generated by inverse splicing of the control substrate, PY1 (compare FIG. 38A, lanes 6 and 9). To confirm that product is IVS(Y), it was purified from an acrylamide gel and subjected to debranching as described above. As a control, IVS(Y) from PY1 was treated with the debranching activity. upon debranching a product that migrated with IVS 1–3 was seen, along with a second product that was the expected size of 5,6 (lane 2). These same two products were seen when IVS(Y) from PY8 (lane 4) or from PY9 (lane 6) was treated with the debranching activity, confirming that the product was indeed IVS(Y).

Figure 40B:
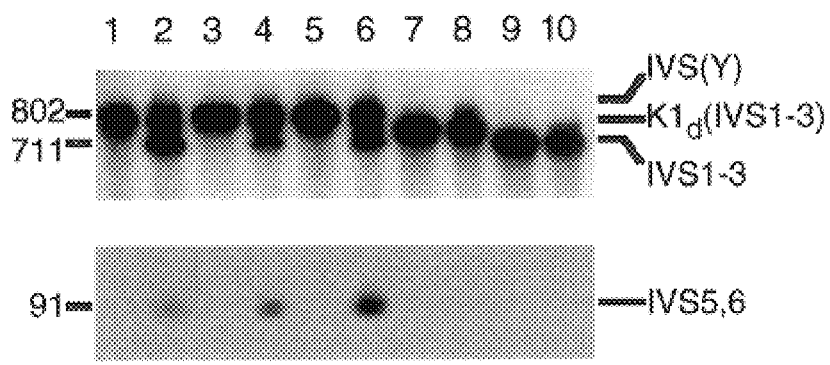
FIG. 40B shows debranching analyses of IVS(Y1), IVS(Y8), and IVS(Y9).

The K1$_A$(IVS 1–3) product was one of the two unexpected products. As part of the characterization of that product, we asked whether it was sensitive to debranching. We found that it was not sensitive to debranching (compare the treated sample [FIG. 40B, lane 8] to the untreated sample [FIG. 40B, lane 7]). Finally, as expected, the IVS 1–3 RNA was not sensitive to debranching (compare the treated sample [FIG. 40B, lane 9] to the untreated sample [FIG. 40B, lane 10]).

RNAase protection was used to analyze the four RNAs shown in lines 5–8 of FIG. 39B. The anti-sense probe that was used was complementary to the last 140 nt of the K1 exon as well as to the first 29nt of group 11 intron domain 1. This probe was generated by amplification of a 168nt region of the K1 exon of pY9 using anti-sense oligonucleotide I5–29 (5'-TATTATTTATGATAACTTTCAGACC-3' [SEQ ID NO:16]) and sense oligonucleotide K1.Cir.2 (5'-GGCCAGACGCCATCAGGCTG-3' [SEQ ID NO:15]). The product was agarose gel purified and cloned into pCR 2.1®Vector (Invitrogen®TA Cloning Kit Version D). Sequencing was carried out with Sequenase® (Amersham) to positively identify a clone with the PCR product in the anti-sense orientation with respect to the pY9 sequence.

RNAse protection studies were preformed as follows: pK1-ANTI-probe was cut with SpeI, transcribed and randomnly labeled with [a-$^{32}$P]UTP, and acrylamide gel purified. pY9 RNA was spliced in 1.5 M (NH$_4$)$_2$SO$_4$ and fractionated on a denaturing 4% acrylamide gel. The (IVS5, 6)K1, IVS(5,6)K1$_u$, K1 (C), and linear K1 products were purified and hybrizided to the probe over night at 37° C. in hybridization buffer: 40 mM pipes (pH 6.4), 1 mM EDTA (pH 8.0), 0.4 M NaCl, 8% formamide. The single stranded RNAs were degraded with RNAse A and RNAse T$_1$. The reaction proteins were denatured with 20% SDS and Proteinase K followed by phenol/chlorophorm extraction. The double stranded RNA was precipitated, dissolved in water and run on a 4% acrylamide gel.

Figure 40C:
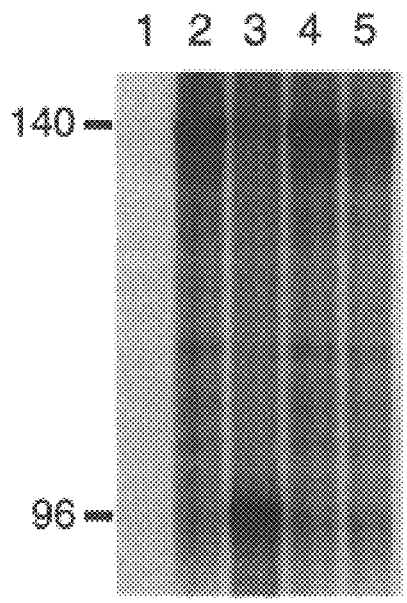
FIG. 40C shows RNAse protection mapping of the products.
Figure 40D:
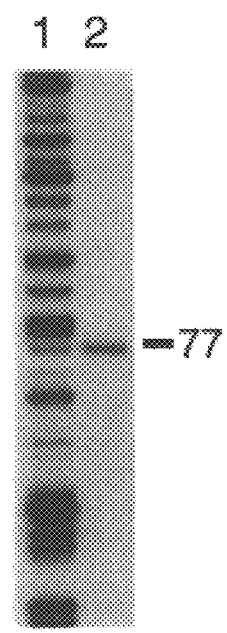
FIG. 40D shows primer extension mapping of the 5' end pfK1$_A$(IVS1–3).

The probe protected a 140 nt region of: (IVS 5,6)K1, K1(C) and K1, indicating that all three RNAs contained the last 140 nt of the K1 exon, but lacked the intron domain 1 sequences (see FIG. 40C, lanes 2,4 and 5, respectively). The probe protected a 96 nucleotide region of the (IVS 5,6) K1RNA, consistent with the hypothesis that RNA results from a cryptic cleavage event that occurs within the K1 exon just downstream of a sequence (5'-CGGGGA) that is complementary to the EBS I sequence of both the PY8 and PY9 intron.

As part of our characterization of the K1$_A$(IVS 1–3) and the (IVS 5,6)K1$_u$ RNAs, we measured the approximate length of both RNAs by comparing the electrophoretic mobility of those two RNAs with known RNA size standards (data not shown). We calculated that the length of K1$_A$(IVS 1–3) is approximately 760 nt, while the length of (IVS 5,6)K1$_u$ is approximately 300 nucleotides. Thus, the combined lengths of those RNAs (1060 nt) is approximately the length of the PY9 (or the PY8) precursor (1070 nt). Furthermore, our end labeling experiments (above) showed that (IVS 5,6)K1$_u$ contains the original 5' end of the precursor RNA while K1$_d$(IVS 1–3) contains the original 3' end of the precursor RNA. These data, along with the RNAase protection data (FIG. 40C, lane 2) suggested that (IVS 5,6)K1$_u$ was the upstream product of a cryptic cleavage event that occurs in the K1 exon, while K1$_d$(IVS 1–3) is the downstream product of that same cleavage event. To test that hypothesis, we used primer extension to map the 5' end of K1$_d$(IVS 1–3). The primer was complementary to nucleotides 5 to 29 of the intron. Extension of the primer produced a 77 nt extension product, as expected if K1$_d$(IVS 1–3) is the downstream product that is generated by cleavage of the K1 exon just downstream of the 5'-CGGGGA sequence.

The K1(C) RNA was further characterized by reverse transcription and PCR. Primers were designed that would amplify the K1 splice point sequence. Note that a pair of primers that is designed to amplify the circular K1 exon [K1(C)] will yield an amplification product when used in RT/PCR with K1(C). The two primers face toward each other, and the sequence that lies between them is amplified. In contrast, that same pair of primers will not amplify linear products that contain a single K1 exon (such as (IVS 5,6)K1) because the two primers face away from each other on the linear K1 exon.

Figure 41A:
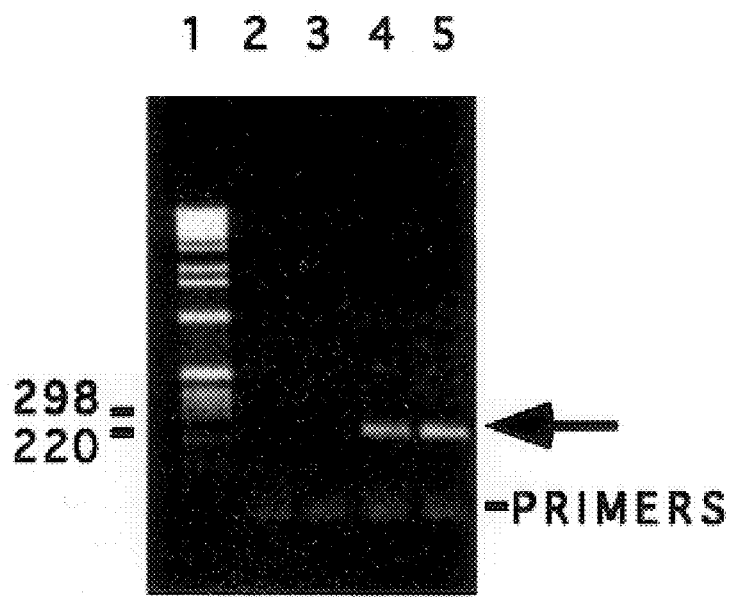
FIG. 41A shows RT-PCR analysis of products bands.

RT/PCR analysis of K1(C) from both PY9 (FIG. 41A, lane 4) and PY8 (FIG. 41A, lane 5) produced the same 244 base-pair amplification product. That product was not observed when either (IVS 5,6)K1 (FIG. 41A, lane 2) or (IVS 5,6)K1, (FIG. 41A, lane 3) was used as a template in an RT/PCR reaction. The 244 bp product was the size expected of a PCR product generated by amplification across the splice point of K1(C).

Figure 41B:
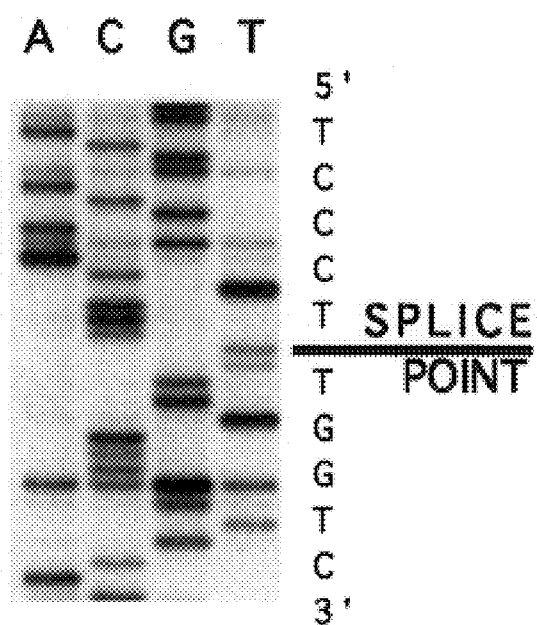
FIG. 41B gives the splice junction sequence.

For both PY8 and PY9, the amplified product was cloned into a plasmid vector and the nucleotide sequence of the splice point was determined. The splice point was sequenced in a total of 8% independently isolated PY8 clones and 10 independently isolated PY9 clones. In every case, the expected splice point sequence (5'-CCT/TGG) was observed (FIG. 41B).

Note that all of the inverse splicing substrates used in this study (PY1, PY8 and PY9) lack intron domain 4. Previous work has shown that domain 4 is not required for cis or trans splicing. Furthermore, the deletion of domain 4 (in PY1) does not seem to appreciably reduce the rate of inverse splicing (relative to the rate of cis splicing; see Table I). However, it was clear in previous studies that the deletion of domain 4 slows the rate of the second step of cis and trans splicing. Our current results clearly show that, for PY8 and PY9, when the first step of inverse splicing occurs by hydrolysis, the second step of splicing is slow (i.e. the products of the first step, IVS 1–3 and IVS 5,6)K1, accumulate to high levels). The above observations suggest that domain 4 sequences are also important for the rate of the second step of inverse splicing, but that the importance of the domain 4 sequences was not apparent until the yeast exon sequences of PY1 were replaced with human exon sequences (to yield PY8 and PY9). Thus, it may be desirable to add domain 4 sequences back to PY8 and PY9 RNAs in order to increase the rate of inverse splicing by these precursors.

TABLE I

| Overall Rates of Reaction from Semi-Log Plots | | | |
|---|---|---|---|
| Splicing Buffer Plasmid | KCl (min$^{-1}$) | NH$_4$Cl (min$^{-1}$) | (NR$_4$)$_2$SO$_4$ (min$^{-1}$) |
| Data Summary | | | |
| WT (10') | 0.0509 100% | 0.0408 80% | 0.0442 87% |
| INV (10') | 0.0425 83% | 0.0498 98% | 0.0242 48% |
| pY8 (60') | 0.01069 21% | 0.005735 11% | 0.0008356 2% |
| pY9 (60') | 0.001192 23% | 0.005035 10% | 0.001745 3% |
| Splicing Buffer Plasmid | KCl Y 1–3 | NH$_4$Cl Y 1–3 | (NH$_4$)$_2$SO$_4$ Y 1–3 |
| Ratio of Y-Branch to IVSI-3 | | | |
| INV (60') | 0.302 0.2818 1.020 | 1.599 0.4454 0.3096 | 2.233 0.7914 0.3583 |
| pY8 (120') | — | 0.9008 0.1634 0.1820 | 1.722 0.05785 0.03364 |
| pY9 (120') | — | 0.8879 0.1801 0.2070 | 2.019 0.09395 0.04711 |

EXAMPLE 14

Sequence Requirements for the Inverse Splicing Reaction

Inverse splicing provides an efficient means for production of Y-branched ribozymes. As shown above in Example 13, the group II intron can catalyze inverse splicing even when the EBS1 and/or EBS2 sites in the intron have been altered. Such inverse splicing reactions produce engineered ribozymes of altered specificity. We analyzed the sequence requirements for the inverse splicing reaction by engineering inverse splicing substrates with different EBS1, IBS1, EBS2, and IBS2 sequences.

Nine different inverse splicing precursors, PY1 through PY9, were produced (FIG. 42) PY1 through PY7 contained yeast exon sequences; PY8 and PY9 contained human sequences. PY1, PY8, and PY9 are described above in Example 13; the others were produced by site directed mutagenesis of encoding plasmids.

Figure 42B:
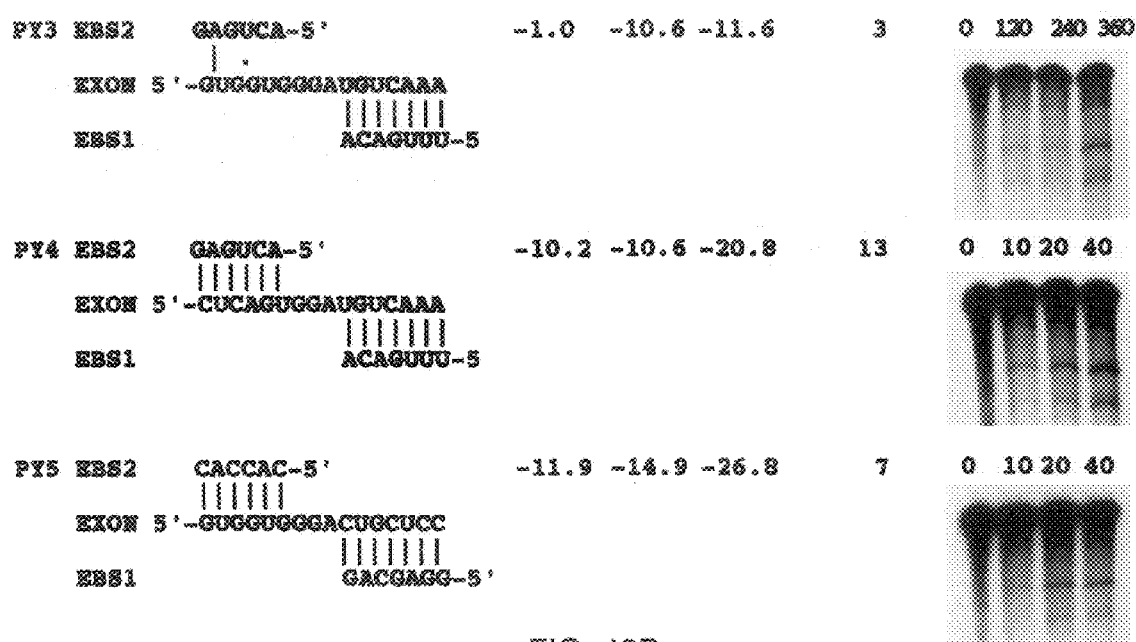
FIG. 42 summarizes data obtained in inverse splicing reactions with different EBS1-IBS1 and EBS2-IBS2 pairings. The calculated free energies of interaction are shown, as are the relative efficiencies of splicing. Time courses of splicing reactions, conducted under transesterification conditions, are also shown.
Figure 42C:
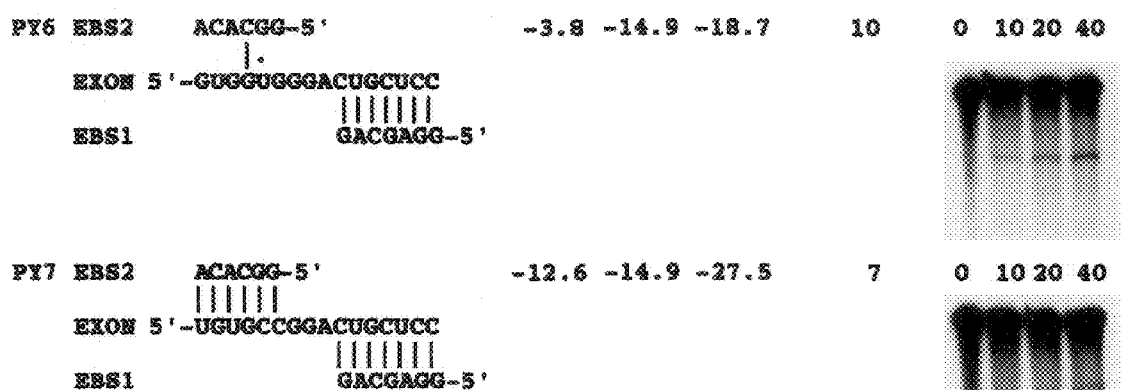
Figure 42D:
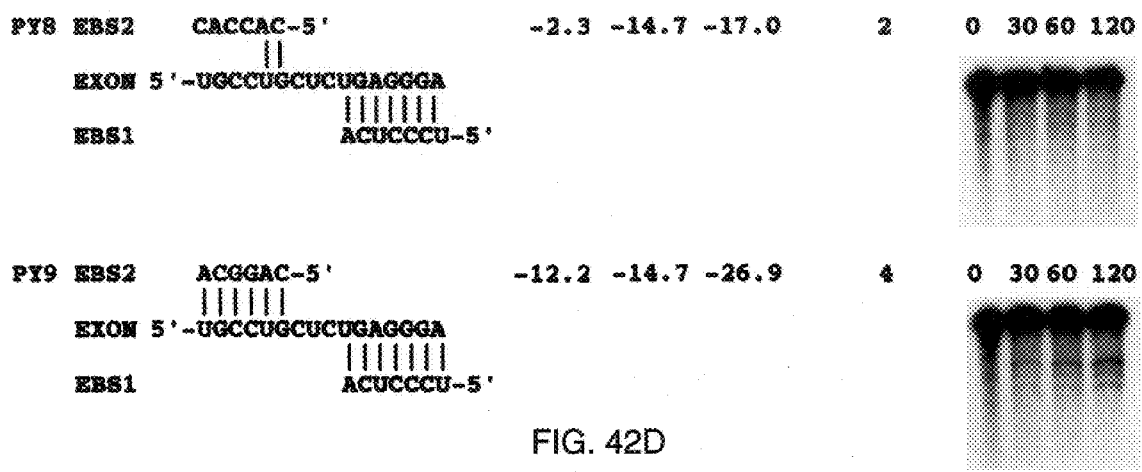

The EBS1-IBS1 and EBS2-IBS2 interactions for each of the nine precursors are shown in FIG. 42.

Figure 43:
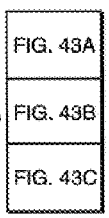
FIG. 43 is a table presenting the reaction rates and amounts of linear and lariat introns observed in inverse splicing reactions with the substrates summarized in FIG. 42.

Yeast exon sequences are shown in red. Standard Watson-Crick base pairs are indicated by dashes; G-U pairs are indicated by dots. FIG. 42 summarizes the base substitutions that were made using site-directed mutagenesis. Base substitutions shown in blue (PY2–PY4) were made to produce Y-branched ribozymes targeted to insert in the Fn txt RNA (Mikheeva et al. (1996) *PNAS* 93:7486–7490). At certain positions, the yeast and human exon sequences are identical. Thus, it was not necessary to mutate these nucleotides and they are shown in red (see for example nucleotide minus five of the PY2 exon). Base substitutions in PY5–PY7 are shown in green. For PY8 and PY9, the human exon sequences are shown in brown. For each precursor, the calculated free energy (Freier et al. (1986) *PNAS* 83:9373–9372) of (i) EBS1-IBS1, (ii) EBS2-IBS2, and (iii) the sum of these calculated values, are shown. The relative efficiency of splicing is also shown, along with an autoradiogram of representative time course data (incubation times are in minutes). The time course experiments were conducted under transesterification conditions, in buffer containing 1.5 M (NH$_4$)$_2$SO$_4$ (Jarrell et al. (1988) *J Biol. Chem.* 263:3432–3439); the most abundant product that is seen in the autoradiograms is the excised Y-branched intron. Analogous time courses were performed in NH$_4$Cl and KCl buffers. A summary of the reaction rate, amount of Y-branched intron, and amount of linear intron observed with each precursor in each salt condition is presented in FIG. 43.

Figure 44:
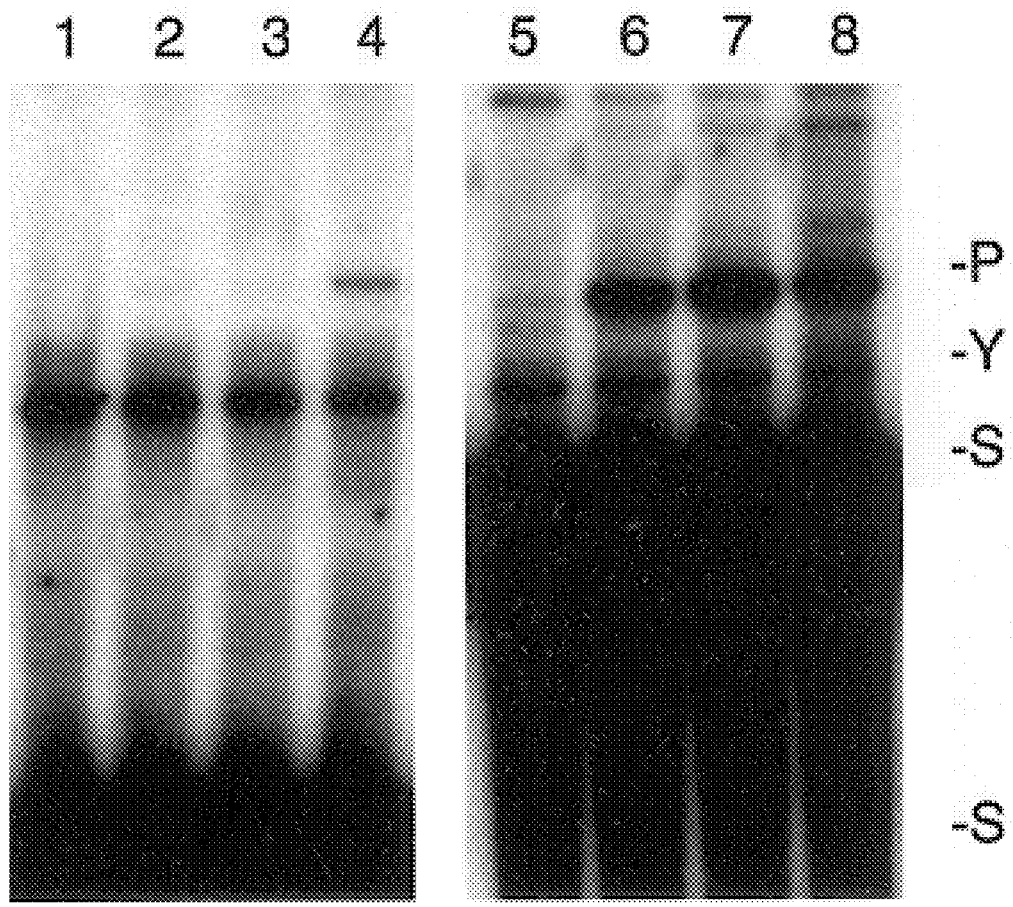
FIG. 44 shows integration of the Y2 ribozyme into the Fn txt.

We tested whether the Y2 ribozyme would in fact integrate into the Fn txt target RNA (note that the EBS1 site of Y2 is homologous to the target, but the EBS2 site is not). We found that Y2 integrates into the Fn txt less efficiently than Y1 integrates into its natural target, E5-E3 (FIG. 44). The targets and ribozymes were each present at approximately equimolar concentrations (about 1 μM each) (FIG. 44; P, products; Y, Y-branched ribozymes; S, substrates). The specific activity of the ribozymes was made lower than that of the substrates to ensure that the signal from unreacted ribozyme did not obscure the signal from product. Targets and ribozymes were mixed and incubated in splicing buffer for 2 hours at either 4° C. (lanes 1 and 5), 25° C. (lanes 2 and 6), 37° C. (lanes 3 and 7), or 45° C. (lanes 4 and 8). The Y2 and Fn txt RNAs were fractionated in lanes 1 through 4; the Y1 and E5-E3 RNAs were fractionated in lanes 5 through 8. Products the size of Fn(1–3)(1035 nt, lane 4) and E5(1–3) (1005 nt, lanes 6–8) were observed. The yield of E5(1–3) was clearly much greater than the yield of Fn(1–3). The efficiency of integration of Y2 might increase if its EBS2 site were also made perfectly homologous to the Fn txt target RNA.

Since data in the literature indicate that the EBS2-IBS2 interaction is not essential for group II intron cis splicing (Jacquier et al. (1987) Cell 50:17–29), we decided to change the pY2 EBS2 site, to make it homologous to the Fn txt target. We did not also change the IBS2 site of pY2. Our assumption was that the EBS2-IBS2 interaction would not be critical for inverse splicing since this interaction is not critical for cis splicing. We used site-directed mutagenesis to change the EBS2 site of pY2. This experiment produced the pY3 plasmid. The five nucleotides of the EBS2 site that were changed are shown in blue in FIG. 42, line 3. Note that the EBS2-IBS2 pairing of PY3 has an estimated free energy of about -1.0 kcalorie. Also note that the PY3 transcript splices about 30-fold less efficiently than does PY1 (see FIG. 42). We hypothesized that the splicing defects of PY3 would be rescued if its IBS2 sequence was changed so that base-pairing between EBS2 and IBS2 was fully restored. Thus, we generated the pY4 plasmid. Consistent with our hypothesis, transcripts from pY4 spliced in vitro as efficiently as did transcripts from pY2 (FIG. 42).

In a parallel set of experiments, three plasmids (pY5–pY7) were constructed from which Y-branched ribozymes (Y5–Y7), designed to insert into the Prot txt target (Mikheeva et al. (1996) *PNAS* 93:7486–7490, could be produced. As can be seen, PY5, PY6 and PY7 all spliced with approximately equal efficiency. One interpretation of our results (comparing PY3 with PY6) is that when the EBS1-IBS1 pairing is strong (PY6) then the EBS2-IBS2 interaction is not very important. However, when the EBS1-IBS1 pairing is weaker (PY3) the EBS2-IBS2 pairing is important.

Finally, plasmids pY8 and pY9 contain human exon sequences precisely flanked by group II intron sequences (all yeast exon sequences have been replaced with human exon sequences). The plasmids were made using standard recombinant DNA techniques, including site-directed mutagenesis. PY8 has a two base-pair EBS2-IBS2 interaction, while in PY9 the EBS2-IBS2 interaction has been fully restored. We made the PY8 and PY9 precursors in order to determine whether group II introns can be used to catalyze accurate production of particular circular human exons by inverse splicing. PY8 and PY9 splice more slowly that does PY1 (FIG. 42). This may indicate that the human exon sequences slow the rate of group II intron splicing. Alternately, the rate may be slowed because the human exon sequence is shorter than the yeast exon sequence (267 nt vs. 591 nt). That PY9 splices about two-fold more rapidly that does PY8 may result from the fact that PY9 has a stronger EBS2-IBS2 pairing.

Taken together, these results suggest that the wildtype EBS1-IBS 1 pairing is the optimal pairing, and that the EBS2-IBS2 interaction can be important for inverse splicing (compare PY3 with PY4). However, the EBS2-IBS2 pairing is not always critical for inverse splicing (compare PY6 with PY7). Finally, when the yeast exon sequences are completely replaced with human exon sequences, accurate inverse splicing occurs, although the rate of splicing is slowed.

EXAMPLE 15

Mammalian Nuclear Pre-mRNA Introns can Mediate Circularation of Exonic Sequences The BGINV plasmid (SEQ ID NO:17) was derived from plasmid HBT7. HBT7 has the first intron of the human β-globin gene, flanked by β-globin exon 1 and 2 sequences, cloned into the psp73 vector. To construct BGINV, HBT7 was cut at the unique BbvI site in the intron and at the unique BamnHI site, downstream of Exon 2. The ends were made blunt with klenow fragment. The DNA was diluted and ligase was added. A clone was isolated (BGUS) that has exon 1 and intron sequence, up to the filled BbvII site. In a separate experiment, HBT7 was cut with HindII and BbvI, the ends were filled in, and the DNA was diluted and ligated. A clone was isolated BGDS, that had intron sequence, beginning with the filled BbvI site, followed by exon 2 sequences. BGDS was cut with XhoI and SmaI and the fragment containing the intron and exon 2 sequences was gel purified. This DNA was ligated into BGUS that had been cleaved with XhoI and PvuII, to yield BGINV. The inverse-β-globin RNA can be transcribed from this plasmid in vitro using T7 polymerase.

BGINV was cut with EcoRI and RNA was transcribed in vitro using T7 polymerase. In vitro splicing reactions were performed as described in Hannon et al. (Hannon et al. (1990) *Cell*, 61:1247–1255), except that mammalian extract was used. The extract was prepared by the method of Dignam et al. (Dignam et al. (1983) *Nucl. Acids Res.* 11:1475–1489). Splicing extract is also commercially available (Promega cat.# E3980). Spliced products were separated by polyacrylamide gel electrophoresis and visualized by autoradiography.

The transcription reaction that generated the RNA that was used to create the circular precursor included GMP (final concentration, 0.8 mM); this was to ensure that some of the RNA transcripts initiated with GMP, instead of GTP, since a 5' phosphate is a substrate for ligase (while a 5' triphosphate is not). The transcript was purified from a polyacrylamide gel. Circular precursors were generated using a DNA oligonucleotide (5'-CGAGGCCGGTCTCCCAATTCGAGCTCGGTAC [SEQ ID NO:18]) to bring the ends of the RNA together, followed by the addition of DNA ligase to covalently join the ends (Moore et al. (1992) *Science* 256:992–997). The circular precursor was purified from a polyacrylamide gel. In vitro splicing reactions were done as described above.

The circular exon product was observed and characterized. This RNA was gel purified and a cDNA copy generated using the CIR-1 primer (5'-GAGTGGACAGATCCCCAAAGGACTC [SEQ ID NO:19]) which is specific to exon 2 sequences. The cDNA was amplified by PCR using the CIR-1 and CIR-2 (5'-GTGATGGCCTGGCTCACCTGGACAA [SEQ ID NO:20]) oligonucleotides as primers. A 145 nt product was observed. This amplification product is the expected size of a product generated from circular spliced exons.

The branched intermediate (generated by the first step of the reaction) was also observed and characterized. It was gel purified and treated with HeLa debranching enzyme (Ruskin et al. (1985) *Science* 229, 135–140). This treatment increased the rate of migration of the RNA through a denaturing polyacrylamide gel such that it migrated as a 553 nt RNA, consistent with the assignment of the product as the lariat intermediate.

V. Reagents for Molecular Biology

Molecular cloning of DNA currently relies heavily on restriction enzymes and DNA ligase to specifically cut and join molecules. The reverse-splicing introns or "ribozymes" of the present invention can fulfill these two functions; they can both cut and join RNA molecules, and thus can serve as useful tools for nucleic acid manipulation. In similar fashion to the activation of an exon by addition of flanking intronic fragments through the reversal of splicing the recombinant RNA technology described herein involves attacking a target RNA molecule with an intronic molecule and, by the reversal of splicing, cleaving the target into two pieces while simultaneously joining specific intron sequences to the cleaved ends of the target molecule. The newly formed exon construction can be purified, and appropriate exons ligated to each other through trans-splicing mediated by the intronic fragments. Alternatively, these recombinant RNA molecules can be cloned into a plasmid, and fresh RNA transcripts generated from these plasmids, with these second generation transcript being used in a trans-splicing reaction (see Example 1 and Mikheeva et al. (1996) *PNAS* 93:7486–7490). Thus, cleavage and ligation functions similar to those provided by restriction enzymes and ligase can be provided by RNA trans-splicing.

DNA restriction enzymes and DNA ligase are so routinely used for nucleic acid manipulation that the limitations of these reagents are seldom considered. Restriction enzymes typically recognize and cleave specific DNA sequences that are 4 to 6 basepairs in length. Although there are theoretically 4,096 different possible restriction enzymes that recognize 6 basepair sequences, only 78 such enzymes with distinct specificities are commercially available. One reason that most possible specificities are unavailable is that it is not feasible to engineer the sequence specificity of a restriction enzyme. Instead, micro-organisms must be identified that naturally produce enzymes with novel specificities. Often, it is difficult to obtain large quantities of pure active enzyme from these natural sources, leading to the second limitation, which is that restriction enzymes are often impure and the enzyme concentration is low. A third limitation is that certain classes of DNA sequences are not recognized by any known restriction enzyme. For example, there are no known enzymes that recognize sequences comprising only of A and C nucleotides, such as 5'-AACCAA. A fourth limitation is that DNA ligase only joins DNA molecules with compatible ends, making it often necessary to fill in or degrade 5' or 3' overhangs on DNA molecules before they can be joined by ligation. Finally, yet another limitation is that DNA ligation reactions are often not directional, leading to the generation of recombinant clones with inserts in the wrong orientation.

In contrast, the advantages of this system are that potentially any 3–8 nt sequence can be specifically targeted. Accordingly, whereas restriction enzymes are much more limited, recognizing only a small subset of, for example, the 4,096 possible 6 nt sequences present in DNA, the subject ribozymes can be generated for each of the 4,096 different sequences. Indeed, under appropriate reaction conditions, the efficiency of the reaction can be greatly influenced by the EBS2-IBS2 interation such that the specificity of the ribozyme is effectively 12–16 basepairs. Consequently, in the instance of the ribozyme which recognizes a specific 12 nucleotide target sequence, over 16 million different specificities are possible and can be assessed by the present invention. Note that because G:U basepairs are allowed basepairs are allowed in RNA, the specificity of a given inventive engineered ribozyme may be broader (especially under appropriate reaction conditions) than the particular sequence precisely targeted.

Moreover, in contrast to restriction enzymes which typically require palindromic sequences that may introduce ambiguity into the orientation of DNA sequences inserted at a restriction endonuclease cleavage site the subject ribozymes can be orientation specific. In addition, once an RNA is followed by, or preceded by, the correct intron sequences, any upstream molecule can be joined to any downstream molecule (see, for instance, Examples 19 and 20). In contrast, when molecular cloning is done with restriction enzymes, only molecules with compatible ends can be joined; for example, a molecule with EcoRI ends cannot be joined to a molecule with HindIII ends without first filling in the ends. Furthermore, molecules that are joined by trans-splicing are "seamless". That is, recognition sites do not have to be engineered into the target molecules in order to cleave and ligate the target molecule. Instead, the ribozyme is engineered to match the target. For instance, a library of reverse-splicing ribozymes can be generated to comprise every possible 6 nucleotide combination by manipulating intron sequences which interact with the "exon" target (e.g. the IBS1 for group II, and the IGS for group I). Thus, sequences can be precisely joined without adding, deleting or changing any nucleotides. Finally, for the autocatalytic introns, no enzymes need be added in order to catalyze the forward or reverse reactions. Instead, the RNAs are incubated together in a simple salt solution and other appropriate ions and the recombinant molecules are generated.

Accordingly, one aspect of the invention pertains to a preparation of a reverse-splicing intron which comprises two or more fragments of autocatalytic introns and catalyzes integration of at least a portion of the reverse-splicing construct into a substrate ribonucleic acid by a reverse-splicing reaction. For example, the autocatalytic intron fragments can be derived from one or more group II introns, and preferably are derived with exon binding site which have been altered by recombinant mutagenesis. In another illustrative embodiment, the autocatalytic intron fragments are derived from group I introns. Again, the specificity of the intron is preferably altered by recombinant mutagenesis of the internal guide sequence of group I intron fragments.

In one particular embodiment, as is apparent from the description throughout the present application, where the inventive reverse-splicing intron is derived from a group II intron, it may comprise a first segment having a 5' portion of a group II intron, which 5' portion includes an exon binding site; and a second segment comprising a 3' portion of a group II intron, which 3' portion includes a V motif, a branch site acceptor forming a phosphodiester bond with the 5' end of the first segment, and a nucleophilic group at the 3' end of the second segment for transesterifiing a phosphodiester bond of a ribonucleic acid. By this arrangement, the first and second segments together form an autocatalytic Y-branched intron which catalyzes integration of at least the first segment of the reverse-splicing intron into a substrate ribonucleic acid by a reverse-splicing reaction. In an exemplary embodiment, the 5' portion of the group II intron includes intron domains 5 and 6, and the 3' portion of the group II intron includes intron domains 1–3. It will be understood that the reverse-splicing construct can be a Y-branched lariat form of the group II intron, e.g., the first and second segments are contiguous via a covalent bond other than the phosphodiester bond formed with said branch site acceptor, or can be in the form of a Y-branched discontinuous intron, e.g., the first and second segments are covalently attached only at the branch site acceptor. Alternatively, the reverse-splicing construct can be linear.

The reverse-splicing intron can be represented by the general formula:

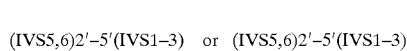

A wherein
(IVS1–3) represents a 5' portion of a group II intron.
(IVS5,6) represents a 3' portion of a group II intron, which position includes a branch site acceptor.
2'–5' represents a phosphodiester bond formed between a branch site acceptor of (IVS5,6) and the 5' end of (IVS1–3), and
A, if present, represents a phosphodiester bond between a 3' end of (IVS1–3) and a 5' end of (IVS5,6), wherein (IVS1–3) and (IVS5,6) together form an autocatalytic Y-branched intron which catalyzes integration of at least the (IVS1–3) fragment, if discontinuous with (IVS5,6), into a substrate ribonucleic acid by a reverse-splicing reaction.

In preferred embodiments, the exon binding site, e.g. EBS1 and/or EBS2, is altered (or deleted in certain instances) by recombinant mutagenesis. As a result, the exon binding site can be chosen to provide specific integration into a substrate ribonucleic acid at a selected intron binding site, such that the effective exon binding sequence can be from 3–16 nucleotides in length. Such altered reverse-splicing introns are referred to herein as "engineered ribozymes".

In yet another preferred embodiment, the reverse splicing intron is provided as a substantially pure preparation. By "substantially pure" it is meant that the construct has been isolated from, or otherwise substantially free of other polynucleotides, especially exonic sequences, normally associated with the intron. The term "substantially pure" or "substantially pure or purified preparations" are defined as encompassing preparations of the reversing splicing introns having less than 20% (by dry weight) contaminating protein or polynucleotides, and preferably having less than 5% contaminating protein or polynucleotides. By "purified", it is meant, when referring to a nucleic acid construct of the present invention, that the indicated molecule is present in the substantial absence of other biological macromolecules, such as other proteins or polynucleotides. The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 3000, can be present). The term "pure" as used herein preferably has the same numerical limits as "purified" immediately above. "Isolated" and "purified" do not encompass either natural materials in their native state or natural materials that have been separated into components (e.g. in an acrylarnide gel) but not obtained either as pure (e.g. lacking contaminating proteins or polynucleotides, or chromatography reagents such as denaturing agents and polymers, e.g. acrylamide or agarose) substances or solutions.

To further illustrate, a group II intron or portion thereof can be used to specifically cut and join RNA molecules (see Example 1, above). As described above, the group II intron splicing reaction is reversible. If an intron lariat, a product of the forward reaction, is incubated with spliced exons at high RNA concentration under the reaction conditions used for the forward reaction, the intron specifically inserts into the spliced exons, thus regenerating the precursor RNA (see FIG. 2). Likewise, as illustrated in FIG. 10, a Y-branched form of the intron, generated for example by an inverse splicing reaction, can also insert into spliced exons. When a Y-branched intron, such as the illustrated (VS5,6)$_{2'-5'}$(IVS 1–3) lariat, is used in a reverse-splicing reaction, the exon target is cleaved into two pieces. The upstream piece becomes joined to intron domains 1–3 and the downstream piece becomes joined to intron domains 5 and 6.

The 3–8 nucleotide EBS1 site on the ribozyne is the primary determinant of the specificity of the reverse reaction for group II introns. In the reverse reaction, EBS1 selects the site of integration by hydrogen bonding to it. The intron is subsequently inserted just downstream of this target sequence. By changing the nucleotide sequence of EBS1, the ribozyme can be targeted to insert downstream of any specific 3–8 nt sequence. Moreover, the manipulation of the EBS2:IBS2 interactions can also influence the efficiency of splicing and provide even greater specificity to the insertion site (e.g. by expanding the recognition sequence to, for example, 10–14 nucleotides; see Example 14, above). Likewise, manipulation of the IGS, and other secondary intron exon contacts analogous to EBS2, the specificity of a group I reverse splicing ribozyme, such as (IVS P1–P6.5–P10) can be controlled.

Figure 45:
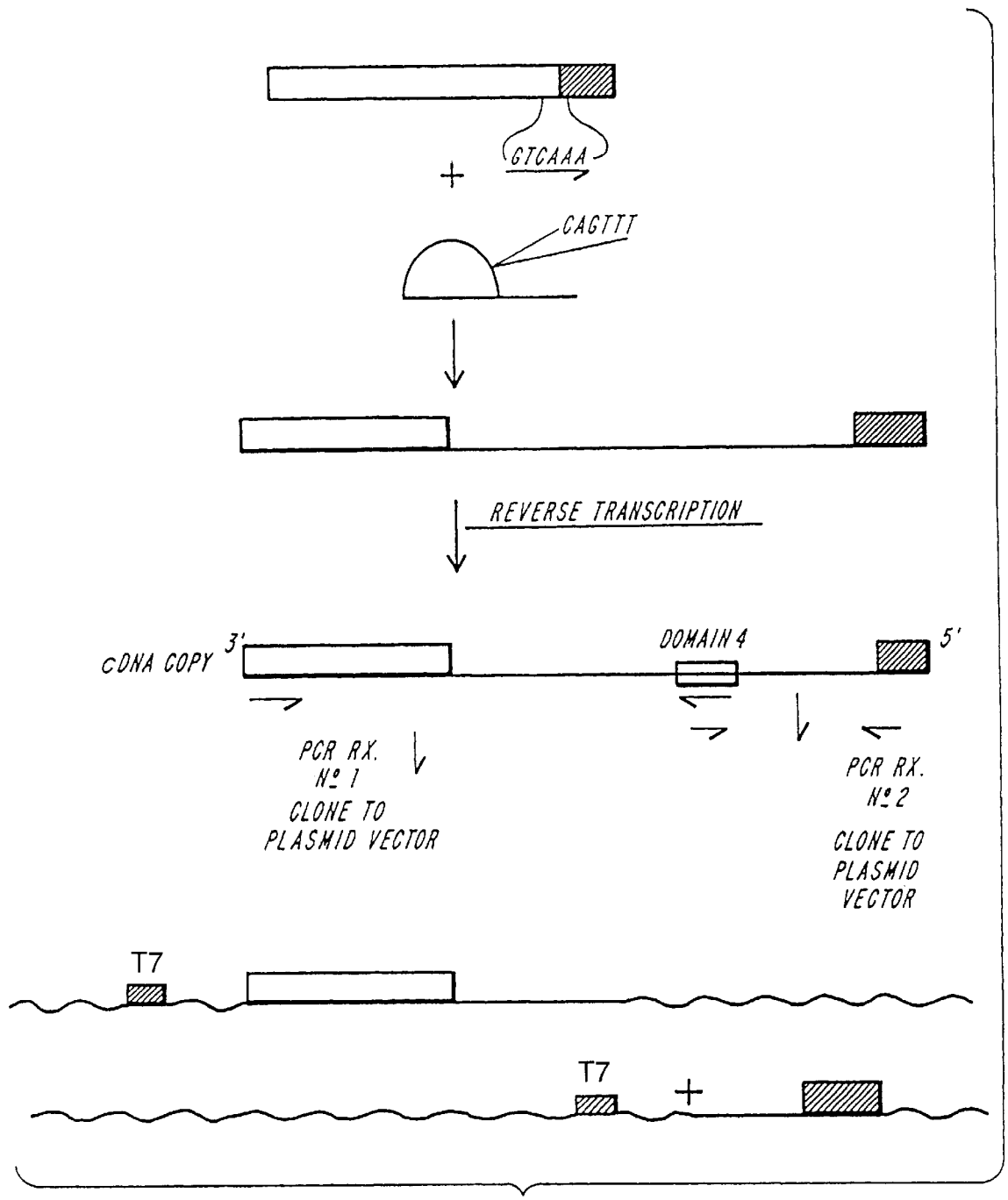
FIG. 45 depicts a further embodiment illustrating how a reverse-splicing ribozyme, such as the group II lariat IVS, can also be used to cleave and ligate target RNA molecules.

FIG. 45 depicts a further embodiment illustrating how an reverse-splicing ribozyme, such as the group II lariat IVS, can also be used to cleave and ligate target RNA molecules. The site directed mutagenesis is the same as described above (the EBS 1 and IBS 1 sequences are changed). The lariat ribozyme is generated by the forward reaction. The reverse reaction yields a single molecule with the intron specifically inserted in it. A cDNA copy is made by reverse transcriptase. Two different sets of PCR primers are used to amplify either the upstream portion of the interrupted target molecule, plus intron domains 1–3 or to amplify domains 5 and 6 and the downstream portion of the target molecule. Each of these amplified DNAs can be cloned into a plasmid to generate the same two constructs shown in FIG. 46.

Figure 47:
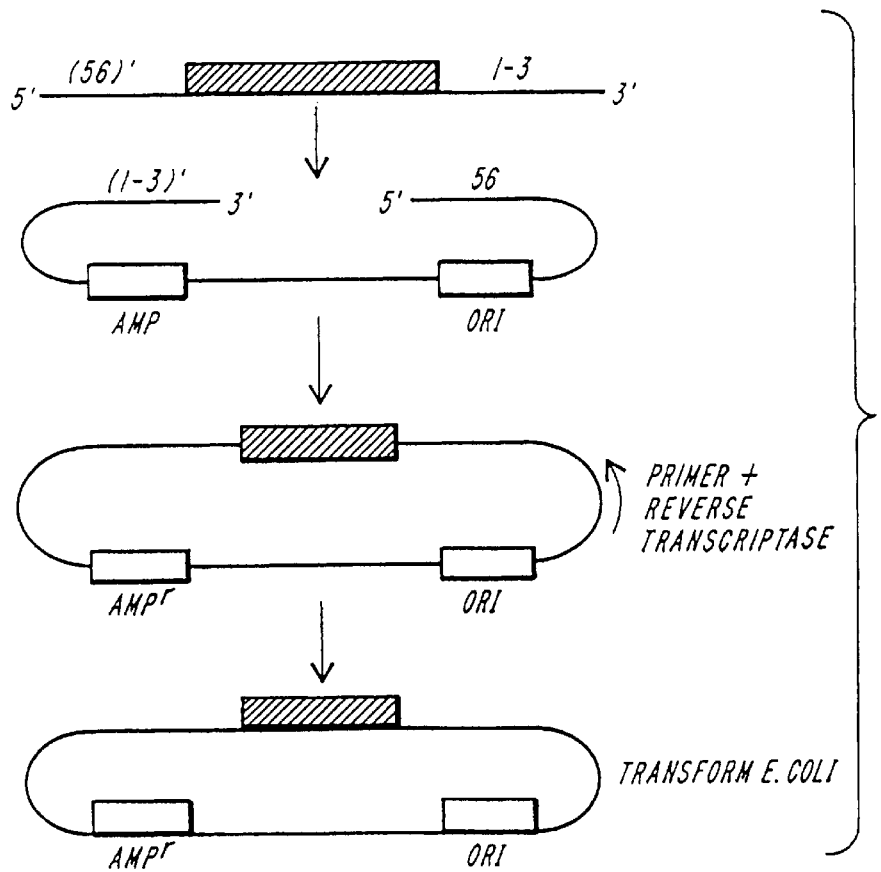
FIG. 47 depicts a method by which the present trans-splicing constructs can be used to manipulate nucleic acid sequences into a plasmid such as a cloning or expression vector.

In another illustrative embodiment, FIG. 47 depicts a method by which the present trans-splicing constructs can be used to manipulate nucleic acid sequences into a plasmid such as a cloning or expression vector. In such a scheme, the plasmid sequence is itself an exon being flanked at each end by intronic fragments capable of mediating a trans-splicing reaction. For example, as shown in FIG. 47, the plasmid can be generated as an RNA transcript comprising the backbone sequences of the plasmid, flanked at the 5' end with the group II domains 5 and 6, and at the 3' end with the group II domains 1–3. To generate such a transcript, a pre-plasmid can be utilized in which the 5' and 3' flanking sequences are joined with an intervening sequence including a T7 RNA promoter sequences and endonuclease cleavage site. The plasmid is linearized by cleavage at the endonuclease-sensitive site, and the linearized plasmid transcribed to RNA using standard techniques.

The nucleic acid sequences to be cloned into the plasmid are generated to similarly include flanking group II intron fragments. Mixing the two transcripts under trans-splicing conditions will therefore result in ligation of the nucleic acid of interest into the plasmid, in the appropriate orientation and at the correct site. Such a method is particularly amenable to the cloning of the above-described combinatorial gene libraries into replicable expression vectors. Furthermore, this trans-splicing technique of sub-cloning can be used effectively in random mutagenesis applications. For instance, the nucleic acid of interest can be first treated with actinic acid such that a discrete number of base modifications occur, and then ligated into the plasmid.

In addition to the RNA manipulations described herein, the inventive engineered ribozymes can be utilized to cleave and ligate DNA molecules. Many group II introns recognize single-stranded DNA, as an alternative to RNA, as an integration target (see, for example Herschlag (1990) *Nature* 344:405–409; Robertson et al (1990) *Nature* 344:467–468; Morl et al (1992) *Cell* 70:803–810; Zimmerly et al (1995) *Cell* 83:529–538); some also recognize double-stranded DNA (see, for example Yang et al (1996) *Nature* 381:332–335; Ziimmerly et al (1995) *Cell* 83:529–538). Accordingly, engineered ribozymes of the present invention may be integrated into DNA targets and linked to DNA "exons" than can then be linked to one another by splicing reactions, as described herein for RNA exons. Such inventive DNA manipulations as described in more detail above, in the section entitled "DNA Recombination".

Another aspect of the invention pertains to a kit for generating a Y-branched ribozyme of a particular specificity. In general, the kit can feature an expression vector containing a gene, whose expression product will give rise to a Y-branched ribozyme of the present invention. For instance, the transcript illustrated by FIG. 46, and described in further detail in Example 16 below, can be used to generate the Y-branch ribozymes of the present invention (see also above section on "Circular RNA Transcript"). For instance, a vector can be constructed containing such a gene having unique restriction enzyme sites immediately 5' to the IBS2 sequence and 3' to the EBS1 sequence, such that the EBS1 and (optionally) the EBS2 sequences can be altered by insertion of oligonucleotide cassettes. In another embodiment, the restriction sites can be placed immediately flanking the EBS1-EBS2 sites and another set of restriction sites used to flank the IBS1-IBS2 site such that 2 oligonucleotide are used to alter the EBS1 and EBS2 specifities. Where a continuous Y-branched lariat structure is desired, a construct as shown in the forward reaction of FIG. 2, e.g., exon1 -intron-exon2, can be used and appropriately manipulated to yield a certain specificity for the EBS1 and EBS2 recognition sequences.

Various considerations go into the design of an inventive engineered ribozyme having a desired specificity. For example, as mentioned above, both EBS1 and EBS2 may be designed to interact specifically with a selected target site. Alternatively, the EBS2 may have its wild-type sequence, or may be deleted altogether. Engineered ribozymes with targeted EBS1 and EBS2 sequences are expected to insert more efficiently (and specifically) into their target sites than are those ribozymes having only an engineered EBS1 site. Regardless of whether EBS1 alone or both EBS1 and EBS2 have been engineered, however, it should be borne in mind that G:U base pairs are allowed in RNA, so that ribozymes with G or U residues in their EBS1 and/or EBS2 sites may have broadened specificity.

Figure 48:
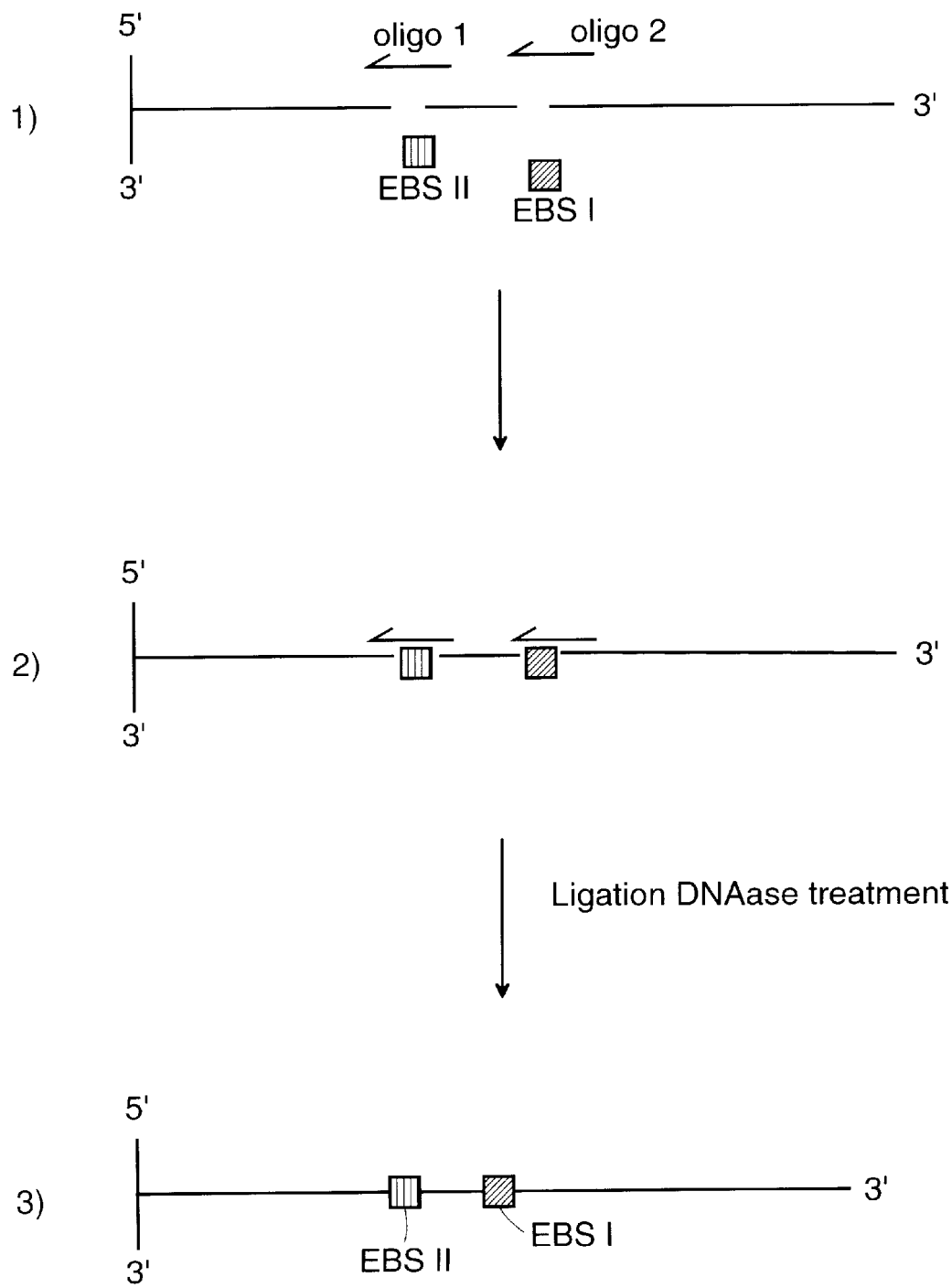
FIG. 48 depicts a preferred method of Y-branched ribozyme assembly according to the present invention.

As an alternative to the above-described splicing methods for generating engineered ribozymes of the present invention automated systems can be provided for scale-up production of quantities of the subject inverse-splicing constructs. An exemplary approach for high throughput production in commercial scale synthesis of the subject ribozymes is shown in FIG. 48. As can be seen with reference to that Figure, an automated system can be developed that relies on the fact that three pieces of the IVS(1–3) fragment (which flank EBS1 and EBS2 sequences) can be identical in each intron, and can consequently be produced in bulk by RNA synthesis procedures. For instance, T7 transcription processes have been scaled up to permit purification of milligram or greater quantities of RNA. Alternatively, such RNAs can be over produced in a bacterial or fungal host. Likewise, the EBS1 and EBS2 sequences can be generated easily by RNA solid phase synthesis. Similarly, two DNA oligonucleotides (1 and 2) can be synthesized by standard automated approaches. Each of the two DNA oligos is homologous to one of the EBS sequences, and to the flanking intron sequences. The mixture is annealed to produce DNA/RNA duplex, and the nicks in the RNA strand can be sealed using a DNA ligase. The DNA oligonucleotides are then removed by treatment with DNase I. Similar procedures using DNA/DNA pairs can be carried out in place of the use of restriction sites described above.

Figure 49:
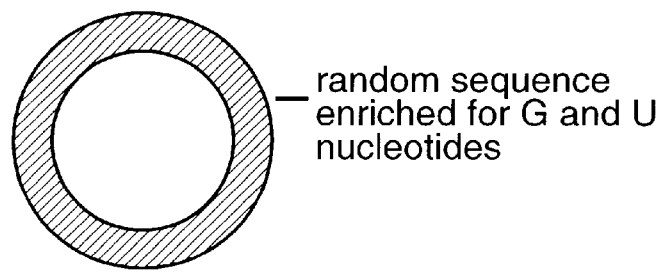
FIG. 49 is a schematic representation of a method for generating and selecting ribozymes according to the present invention.
Figure 49:
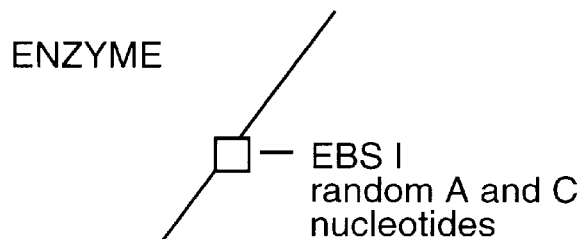
Figure 49:
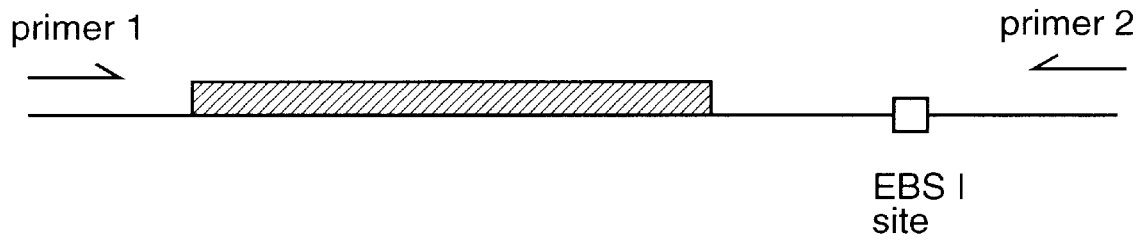

Rather than being produced one-at-a-time, as described above, inventive engineered ribozymes may be produced in as variegated populations. Because the genetic information that encodes the ribozyme and the enzymatic activity of the ribozyme reside in the same molecule, in vitro genetics can be used to produce a large number of engineered ribozymes, from which individual ribozymes may be selected if desired. For example, as shown in FIG. 49, a reverse-splicing target can be prepared that is enriched for G and U nucleotides. A population of ribozymes is then produced, in which the EBS 1 site is comprised of random combinations of A and C nucleotides (preferably, the EBS2 site has been deleted). The ribozyme population is incubated with the target under splicing conditions and, after the reversal reaction has been performed, DNA copies of the products are obtained by reverse transcription and PCR. The amplified DNA is cloned into a plasmid vector and individual clones are analyzed by DNA sequences to determine the sequence of the EBS1 site and of the last six nucleotides in the exon.

Still another embodiment of the present invention pertains to a library of reverse-splicing introns comprising a variegated population of Y-branched group II introns. In preferred embodiments, the variegated population is characterized as including at least 25 different Y-branched group II introns of unique specificity, more preferably at least 100 different Y-branched group II introns of unique specificity, and even more preferably from $10^3$ to $10^6$ different Y-branched group II introns of unique specificity. In one particular embodiment, 64 ribozymes that have only A and C residues in their EBS1 sites and that lack EBS2 sites, are prepared. Without wishing to be bound by any particular theory, we suggest that such ribozymes may have particularly high specificity due to the absence of Gs and Us from the EBS1 site.

In another particular embodiment, a set of 100 ribozymes is constructed with specificities representing all possible pairwise combinations of the following triplets: ACA, CCC, CCA, AAC, AAA, ACC, CAA, CAC, UUU, and GGG. Because of the ability of RNA to form G:U basepairs, this collection of ribozymes would consist of 64 that are uniquely targeted to a 6-nt IBS1 sequence; 32 that have affinity for 8 different IBS1 sequences, and 4 that have affinity for 64 different IBS 1 sequences, so that in total the set would have affinity for 576 different 6-nt sequences (1/7 of all possible 6-nt sequences).

EXAMPLE 16

Use of Group II Y-branched Lariats as Endonucleases/ligase

Figure 46:
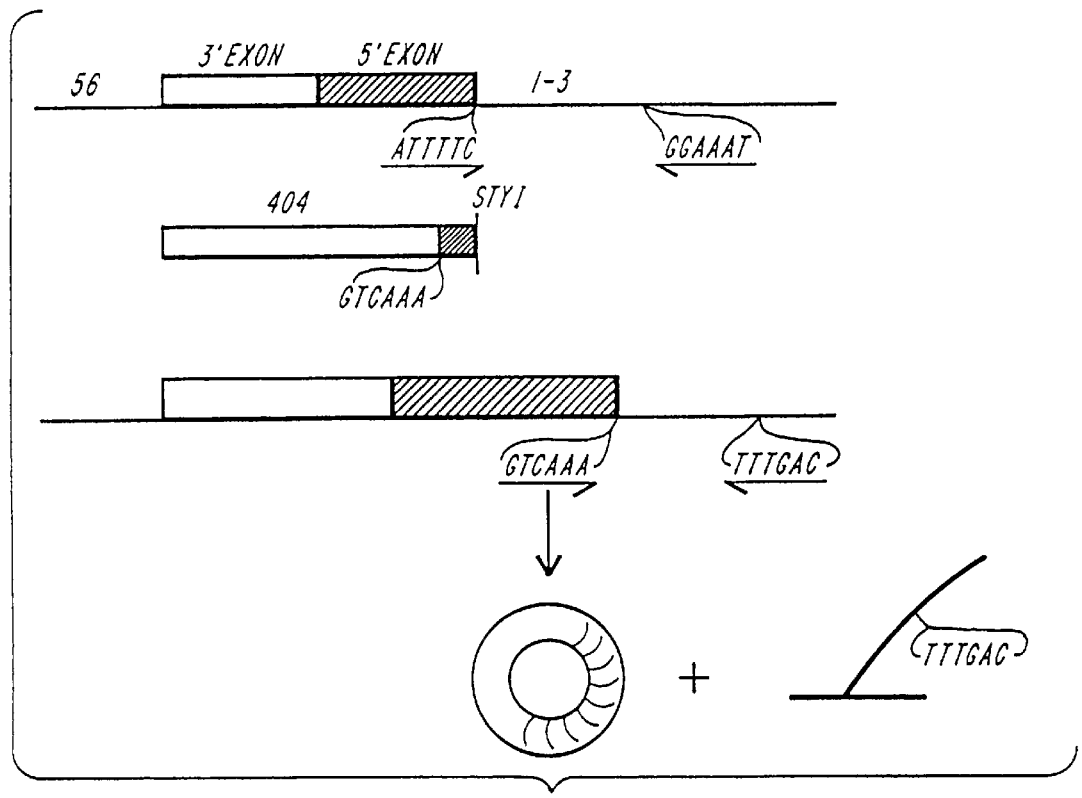
FIG. 46 is an exemplary illustration of the generation of recombinant Y-branched group II lariats.

FIG. 46 is an exemplary illustration of the use of these reactions to generate recombinant molecules. The last six nucleotides of the (IVS5,6)E4,E5(IVS1–3) RNA, which was generated by in vitro transcription of pINV1, are ATTTTC. The EBS 1 sequence of the flanking intron fragment is GGAAAT. As described in Example 19 below, inverse splicing of RNA transcribed from pINV1 yields a Y-branched intron with a wild-type EBS I sequence (GGAAA. FIG. 46 shows a 404 nt RNA (TPA S,F) that includes coding information for the signal sequence and growth factor domain of the TPA cDNA clone. This transcript was generated from plasmid TPA-KS+ that had been cut with Sty I. The goal was to attack TPA S,F with a Y-branched riboz yme such that the ribozyme inserted downstream of the GTCAAA sequence that is present at the end of the growth factor domain. In order to use pINV1 to generate a Y-branched ribozyte capable of attacking the TPA S,F RNA, the EBS I and IBS I sequences of pINVI were changed by site directed mutagenesis. The IBS 1 sequence was changed to GTCAAA (that is, to the same sequence present in the PTA transcript that is to be attacked), and the EBS 1 sequence was changed to TTTGAC in order that it be complementary to the mutated IBS 1 sequence. RNA was transcribed in vitro from this altered plasmid (termed here GrII-SIG) and incubated under splicing conditions to yield the excised Y-branched molecule (SIG-Y). This Y-branched intron is identical to that derived from (IVS5,6)E5,E3, (IVS1–3) in Example 19, except the EBS 1 sequence is TTTGAC. This Y-branched ribozyme was tested for its ability to insert specifically into TAP S,F RNA. As diagramed in FIG. 46, this RNA was incubated with the 404 nt target RNA under splicing conditions. Specific reversal generates a 1047 nt product that consists of the first 332 nt of the TPA-KS+ transcript ligated to intron domains 1–3. This 1047 nt product was gel purified and a cDNA copy was made by reverse transcription. The cDNA was amplified by PCR and cloned into a vector to yield plasmid SIG(IVS1–3). The smaller, 108 nt, product consists of intron domains 5 and 6 ligated to 72 nt of TPA, S,F. A cDNA copy of the smaller product can likewise be made by reverse transcription, amplified by PCR, and the amplified product cloned into a vector to yield plasmid (IVS5,6)StyI.

Following the success of the inverse splicing reaction, the role of the IBS2-EBS2 interaction was investigated with respect to efficiency of the reverse splicing reaction (see Example 14). Starting with the construct pINV1, oligonucleotide primer mutagenesis was used to alter the IBS 1 sequence to CTGCTCC and the EBS1 sequence to GGAGCAG. The EBS2 sequence was changed by oligonucleotide directed mutagenesis to the sequence GGCACA, while the IBS2 sequence was changed to the corresponding TGTGCC, to yield the construct pY7. Surprisingly, the reaction efficiency for the Y-branched ribozymes was several orders of magnitude better in the reversal of splicing reaction involving both the EBS1 and EBS2 interactions, relative to the Y-branch lariat having only a matched EBS1 interaction with the target RNA. Thus, despite the indication in the literature that the EBS2-IBS2 interaction is not essential for Group II intron splicing, the present data would indicate that this interaction is much more important to the efficiency of the reversal of splicing reaction. Consequently, as set out above, the subject reverse splicing ribozymes can be generated to be solely dependant on the EBS1/IBS1 interaction, e.g., by deletion or mismatch of the EBS2 with the target nucleic acid, or alternatively, can be generated to exploit all or a portion of the EBS2/IBS2 interaction by recombinantly engineering the sequence of the EBS2 sequence.

As suggested above, discrete inverse splicing introns can be generated for each of the potentially 4096 different 6 base sequences. However, since G:U base pairing is permissible in RNA, certain EBS1 sequences can give rise to specificity for more than one IBS1 target sequence. For instance, and EBS I of GGGGGG or UUUUUU could, in the absence of any contribution from EBS2/IBS2 interaction (e.g. EBS2 deleted) have an affinity for 64 different sequences. Accordingly, a library of 100 ribozymes with specificities that are derived from all pairwise combinations of the following triplets: ACA, CCC, CCA, AAC, AAA, ACC, CAA, CAC, UUU and GGG can be generated which recognize 576 different 6 nucleotide sequences. To illustrate, of this set of ribozyvmes, 64 would recognize one unique sequence each, 32 of the enzymes would recognize 8 different sequences each, and 4 would recognize 64 different sequences each. This library therefore represents, in specificity, approximately 1/7th of the total possible six nucleotide sequences, and would be expected, on average, have a corresponding recognition sequence (IBS1) approximately every 42 nucleotides. In contrast, the 78 or so restriction enzymes, on average have recognition sequences every 320 or so basepairs.

It is clear from this example that potentially any 4–8 nt RNA sequence can be attacked specifically by a Y-branch ribozyme that has been engineered to have the appropriate EBS 1 and (optionally) EBS2 sequence. The target molecule will be split into two pieces. Intron domains 1–3 will be ligated to the upstream piece, while domains 5 and 6 will be ligated to the downstream piece. Following reverse transcription and PCR, these recombinant molecules can each be cloned into a plasmid vector downstream, for example, of the 17 promoter. Synthesis of RNA from the plasmid will yield transcripts capable of trans-splicing. Thus, in the above example, the original 404 nt target RNA could be regenerated by trans splicing. Moreover, it is also true that transsplicing can be used to join the TPA sequences of SIG (IVS1–3) to any other RNA that has intron domains 5 and 6 upstream of it. The recombinant RNA molecule generated by such a trans-splicing reaction could be copied into cDNA, amplified by PCR and cloned into a plasmid vector.

EXAMPLE 17

Chromosome Disruption

Figure 50:
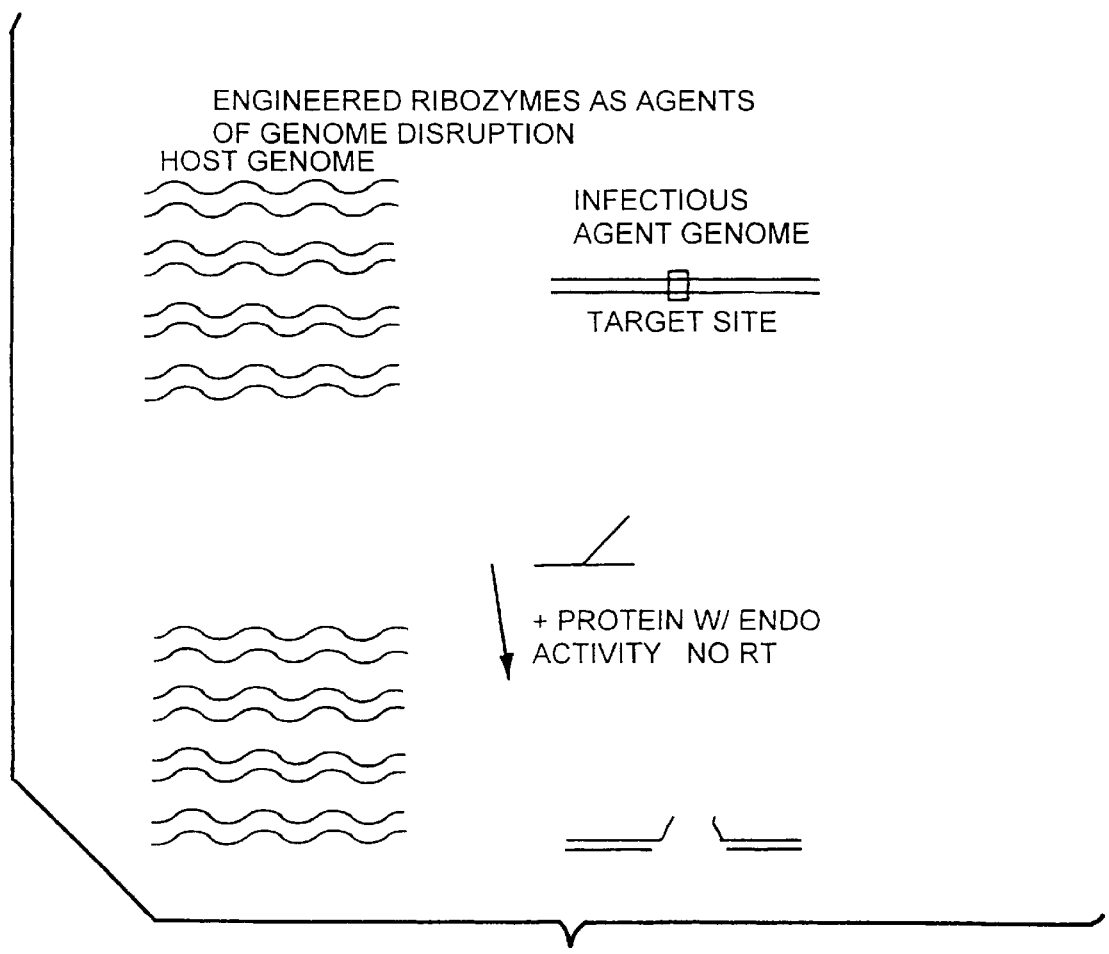
FIG. 50 is a schematic representation of a method for using engineered ribozymes as agents of genome disruption according to the present invention.

One application for engineered ribozymes of the present invention that are capable of partial integration into double-stranded DNA is as specific chromosome disruption agents. For example, FIG. 50 depicts an embodiment of the invention is which a ribozyme is engineered to recognize a sequence that is present in the genome of an infectious agent (e.g., a bacterium, fungus, or virus), but not in the genome of the host cell. The ribozyme is exposed to the cell in combination with its protein (which has endonuclease activity), but under conditions such that reverse transcription is prevented. The ribozyme therefore integrates (fully, as depicted, or partially, as would be the case with an aI2-type ribozyme) into the genome of the infectious agent, creating double-strand breaks. The host genome is unaffected.

VI. Generating Novel Genes and Gene Products

A major goal of the present combinatorial method is to increase the number of novel genes and gene products that can be created by exon shuffling in a reasonable period of time. As described herein, the exon portion of the present slicing constructs can encode a polypeptide derived from a naturally occurring protein, or can be artificial in sequence. The exon portion can also be nucleic acid sequences of other function, such as a sequence derived from a ribozyme. By accelerated molecular evolution through shuffling of such exons, a far greater population of novel gene products can be generated and screened in a meaningful period of time.

In one embodiment, the field of application of the present combinatorial method is in the generation of novel enzymatic activities, such as proteolytic enzymes. For example, combinatorial trans-splicing can be used to rapidly generate a library of potential thrombolytic agents by randomly shuffling the domains of several known blood serum proteins. In another embodiment, the trans-splicing technique can be used to generate a library of antibodies from which antibodies of particular affinity for a given antigen can be isolated. As described below, such an application can also be especially useful in grafting CDRs from one variable region to another, as required in the "humanization" of non-human antibodies. Similarly, the present technology can be extended to the immunoglobulin-super family, including the T-cell receptor, etc., to generate novel immunologically active proteins.

In another illustrative embodiment, the present trans-splicing method can be used to generate novel signal-transduction proteins which can subsequently be used to generate cells which have altered responses to certain biological ligands or stimuli. For instance, protein tyrosine kinases play an important role in the control of cell growth and differentiation. Ligand binding to the extracellular domain of receptor tyrosine kinases often provides an important regulatory step which determines the selectivity of intracellular signaling pathways. Combinatorial exon splicing can be used to shuffle, for example, intracellular domains of receptor molecules or signal transduction proteins, including SH2 domains, SH3 domains, kinase domains, phosphatase domains, and phospholipase domains. In another embodiment, variant of SH2 and SH3 domains are randomly shuffled with domains engineered as either protein kinase or phosphatase inhibitors and the combinatorial polypeptide library screened for the ability to block the function of, for example, the action of oncogenic proteins such as sic or ras.

As will be appreciated, the present invention allows shuffling of any exonic sequences. Thus, the invention provides methods by which novel genes, in which sequences encoding known protein domains can be precisely linked together inframe. Many different protein domains have been identified in the art (see, for example, Doolittle (1995) *Annu. Rev. Biochem.* 64:287–314, incorporated herein by reference), any of which is useful in the practice of the present invention.

Many techniques are known in the art for screening gene products of combinatorial libraries made by point mutations, and for screening cDNA libraries for gene products having a certain property. Such techniques will be generally applicable to screening the gene libraries generated by the present exon-shuffling methodology. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose producted was detected. For instance, in the case of shuffling intracellular domains, phenotypic changes can be detected and used to isolate cells expressing a combinatorially-derived gene product conferring the new phenotype. Likewise, interaction trap assays can be used in vivo to screen large polypeptide libraries for proteins able to bind a "bait" protein, or alternatively, to inhibit binding of two proteins.

For ribozymes, one illustrative embodiment comprises screening a ribozyme library for the ability of molecules to cleave an mRNA molecule and disrupt expression of a protein in such a manner as to confer some phenotypic change to the cell. Similarly, to assay the ability of novel autocatalytic introns to mediate splicing (e.g. see the group II domain shuffling described above) the ability of a combinatorial intron to mediate splicing between two exons can be detected by the ability to score for the protein product of two exons when accurately spliced.

In yet another screening assay, the gene product, especially if its a polypeptide, is displayed on the surface of a cell or viral particle, and the ability of particular cells or viral particles to bind another molecule via this gene product is detected in a "panning assay". For example, the gene library can be cloned into the gene for a surface membrane protein of a bacterial cell, and the resulting fusion protein detected on the surface of the bacteria (Ladner et al., WO 88/06630; Fuchs et al. (1991) *Bio/Technology* 9:1370–1371; and Goward et al. (1992) *TIBS* 18:136–140). In another embodiment, gene library is expressed as fusion protein on the surface of a viral particle. For instance, in the filamentous phase system, foreign peptide sequences can be expressed on the surface of infectious phase, thereby conferring two significant benefits. First, since these phage can be applied to affinity matrices at very high concentrations, large number of phase can be screened at one time. Second, since each infectious phage encodes the exon-shuffled gene product on its surface, if a particular phage is recovered from an affinity matrix in low yield, the phage can be amplified by another round of infection. The group of almost identical *E.coli* filamentous phages M13, fd, and fl are most often used in phase display libraries, as either of the phage gIII or gVIII coat proteins can be used to generate fusion proteins without disrupting the ultimate packaging of the viral particle (Ladner et al. PCT publication WO 90/02909; Garrard et al. PCT publication WO 92/09690; Marks et al. (1992) *J. Biol. Chem.* 267:16007–16010; Griffbhs et al. (1993) *EMBO J.* 12:725–734; Clackson et al. (1991) *Nature* 352:624–628; and Barbas et al. (1992) *PNAS* 89:4457–4461).

A. Antibody Repertoires

Mouse monoclonal antibodies are readily generated by the fusion of antibody-producing B lymphocytes with myeloma cells. However, for therapeutic applications, human monoclonal antibodies are preferred. Despite extensive efforts, including production of heterohybridomas, Epstein-Barr virus immortalization of human B cells, and "humanization" of mouse antibodies, no general method comparable to the Kohler-Milstein approach has emerged for the generation of human monoclonal antibodies.

Recently, however, techniques have been developed for the generation of antibody libraries in *E. coli* capable of expressing the antigen binding portions of immunoglobulin heavy and light chains. For example, recombinant antibodies have been generated in the form of fusion proteins containing membrane proteins such as peptidoglycan-associated lipoprotein (PAL), as well as fusion proteins with the capsular proteins of viral particles, or simply as secreted proteins which are able to cross the bacterial membrane after the addition of a bacterial leader sequence at their N-termini. (See, for example, Fuchs et al. (1991) *Bio/Technology* 9:1370–1372; Bettes et al. (1988) *Science* 240:1041–1043; Skerra et al. (1988) *Science* 240:1038–1041; Hay et al. (1992) *Hum. Antibod Hybridomas* 3:81–85; and Barbas et al. WO 92/18019.

The display of antibody fragments on the surface of filamentous phage that encode the antibody gene, and the selection of phage binding to a particular antigen, offer a powerful means of generating specific antibodies in vitro. Typically, phage antibodies (phAbs) have been generated and expressed in bacteria by cloning repertoires of rearranged heavy and light chain V-genes into filamentous bacteriophage. Antibodies of a particular specificity can be selected from the phAb library by panning with antigen. The present intron-mediated combinatorial approach can be applied advantageously to the production of recombinant antibodies by providing antibody libraries not readily accessible by any prior technique. For instance, in contrast to merely sampling combinations of $V_H$ and $V_L$ chains, the present method allows the complementarily-determining regions (CDRs) and framework regions (FRs) themselves to be randomly shuffled in order to create novel $V_H$ and $V_L$ regions which were not represented in the originally cloned rearranged V-genes.

Figure 51A:
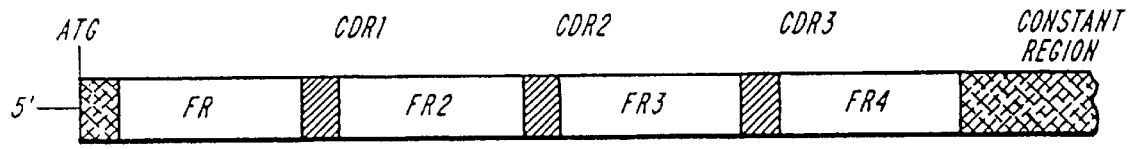
FIG. 51A is an illustration of the composite protein structure of the variable region of both heavy and light chains of an antibody.

Antibody variable domains consist of a β-sheet framework with three loops of hypervariable sequences (e.g. the CDRs) (see FIG. 51A), and the antigen binding site is shaped by loops from both heavy ($V_H$) and light ($V_L$) domains. The loops create antigen binding sites of a variety of shapes, ranging from flat surfaces to pockets. For human $V_H$ domains, the sequence diversity of the first two CDRs are encoded by a repertoire of about 50 germline $V_H$ segments (Tomlinson et al. (1992) *J. Mol. Biol.* 227:). The third CDR is generated from the combination of these segments with about 30 D and six J segments (Ichihara et al. (1988) *EMBO J* 7:4141–4150). The lengths of the first two CDRs are restricted, with the length being 6 amino acid residues for CDR1, 17 residues, and for CDR2. However, the length of CDR3 can differ significantly, with lengths ranging from 4 to 25 residues.

For human light chain variable domains, the sequence diversity of the first two CDRs and part of CDR3 are encoded by a repertoire of about 50 human $V_\kappa$ segments (Meindl et al. (1990) *Eur. J Immunol.* 20:1855–1863) and >10 $V_\lambda$ segments (Chuchana et al. (1990) *Eur. J Immunol.* 20:1317–1325; and Combriato et al. (1991) *Eur. J. Immunol.* 21:1513–1522). The lengths of the CDRs are as follows, CDR1=11–14 residues; CDR2=8 residues; and CDR3 ranges from 6 to 10 residues for $V_\kappa$ genes and 9 to 13 for $V_\lambda$ genes.

The present invention contemplates combinatorial methods for generating diverse antibody libraries, as well as reagents and kits for carrying out such methods. In one embodiment, the present combinatorial approach can be used to recombine both the framework regions and CDRs to generate a library of novel heavy and light chains. In another embodiment, trans-splicing can be used to shuffle only the framework regions which flank specific CDR sequences. While both schemes can be used to generate antibodies directed to a certain antigen, the later strategy is particularly amenable to being used for "humanizing" non-human monoclonal antibodies.

Figure 51B:
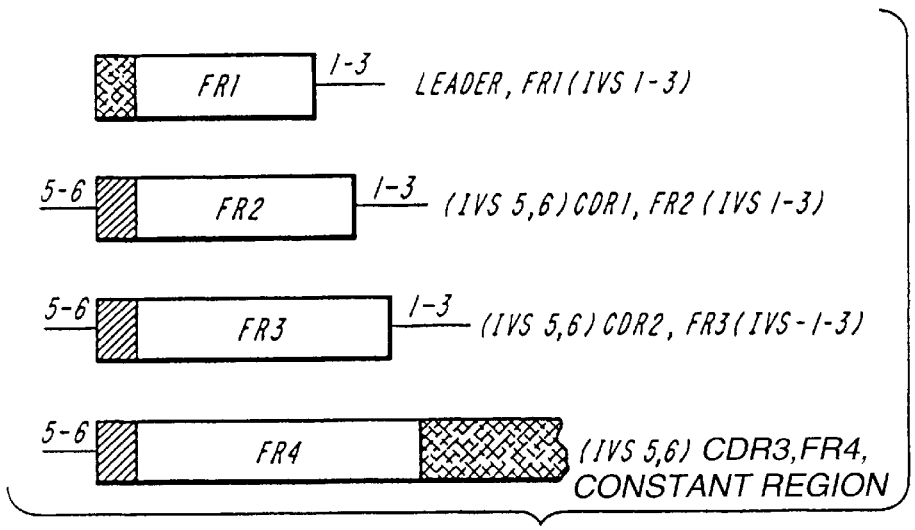
FIGS. 51B–C illustrate possible combinatorial constructs produced using antibody framework regions (FRs) and complementarity determining regions (CDRs).
Figure 51C:
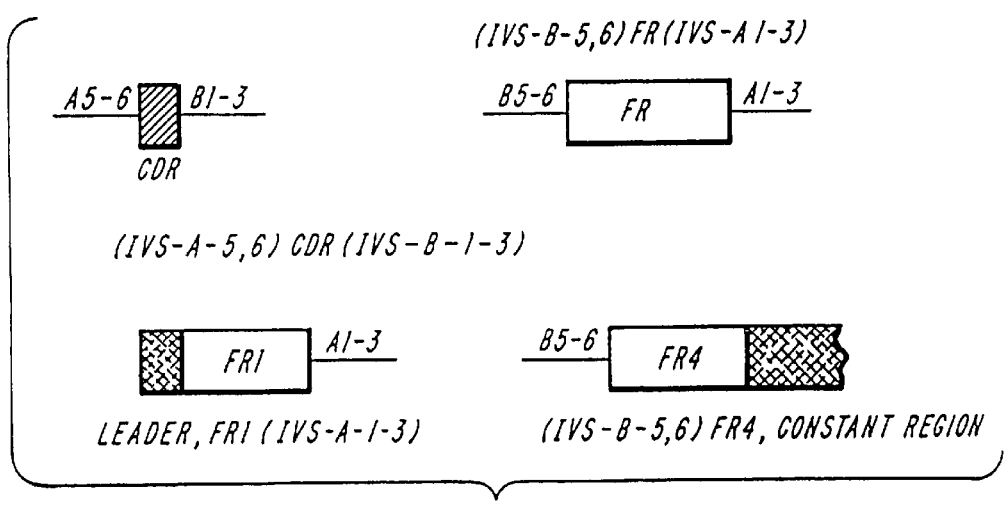

The combinatorial units useful for generating diverse antibody repertoires by the present trans-splicing methods comprise exon constructs corresponding to fragments of various immunoglobulin variable regions flanked by intronic sequences that can drive their ligation. As illustrated in FIG. 51B and 51C, the "exonic" sequences of the combinatorial units can be selected to encode essentially just a framework region or CDR, or can be generated to correspond to larger fragments which may include both CDR and FR sequences. The combinatorial units can be made by standard cloning techniques that manipulate DNA sequences into vectors which provide appropriate flanking intron fragments upon transcription. Alternatively, the combinatorial units can be generated using reverse-splicing, as described above, to specifically add intronic sequences to fragments of antibody transcripts.

Methods are generally known for directly obtaining the DNA sequence of the variable regions of any immunoglobulin chain by using a mixture of oligomer primers and PCR. For instance, mixed oligonucleotide primers corresponding to the 5' leader (signal peptide) sequences and/or FR1 sequences and a conserved 3' constant region primer have been used for PCR amplification of the heavy and light chain variable regions from a number of human antibodies directed to, for example, epitopes on HIV-I(gp 120, gp 42), digoxin, tetanus, immunoglobulins (rheumatoid factor), MHC class I and II proteins (Larrick et al. (1991) *Methods: Companion to Methods in Enzymology* 2:106–110). A similar strategy has also been used to amplify mouse heavy and light chain variable regions from murine antibodies, such as antibodies raised against human T cell antigens (CD3, CD6), carcino embryonic antigen, and fibrin (Larrick et al. (1991) *Bio Techniques* 11:152–156).

In the present invention, RNA is isolated from mature B cells of, for example, peripheral blood cells, bone marrow, or spleen preparations, using standard protocols. First-strand cDNA is synthesized using primers specific for the constant region of the heavy chain(s) and each of the κ and λ light chains. Using variable region PCR primers, such as those shown in Table II below, the variable regions of both heavy and light chains are amplified (preferably in separate reactions) and ligated into appropriate expression vectors. The resulting libraries of vectors (e.g. one for each of the heavy and light chains) contain a variegated population of variable regions that can be transcribed to generated mRNA enriched for $V_H$ and $V_L$ transcripts. Using the reversal of splicing reaction, group I or group II introns can be used which are designed to insert immediately downstream of specific nucleotide sites corresponding to the last (carboxy terminal) 2–3 amino acid residues of each framework region. For example, as depicted in FIG. 51B, a set of group II Y-branched lariats can be utilized to specifically insert flanking group II intron fragments between each CDR sequence and the FR sequence immediately upstream. The exon binding sequence (EBS1, and in some instances EBS2)

of each Y-branched lariat is manipulated to create a panel of Y lariats based on sequence analysis of known framework regions (FR1–4). The intronic addition can be carried out simultaneously for all three FR/CDR boundaries, or at fewer than all three boundaries. For instance, the RNA transcripts can be incubated with Y lariats which drive insertion at only the FR1/CDR1 and FR2/CDR2 boundaries. The resulting intron-containing fragments can be reverse transcribed using a domain VI primer, and the cDNA amplified using PCR primers complementary to a portion of domain VI, a portion of domain I, and the leader sequence. Thus, the Leader,FR1 (IVS 1–3) and (IVS 5,6)CDR1,FR2(IVS 1–3) constructs will be generated. Likewise, the RNA transcript can instead be incubated under reverse-splicing conditions with Y-branched lariats which are directed to insertion at the FR2/CDR2 and FR3/CDR3 boundaries, resulting in the (IVS 5,6)CDR2,FR3(IVS 1–3) and (IVS 5,6)CDR2,FR4 combinatorial units, which can then be isolated by reverse transcription and PCR using primers to sequences in domain I, domain VI, and the constant region.

TABLE II

Human Immunoglobulin Variable Region PCR Primers

5' End Sense

Human heavy chains
    Group A
        5'-GGGAATTCATGGACTGGACCTGGAGG(AG)TC(CT)-    (SEQ ID NO:21)
           TCT(GT)C-3'
    Group B
        5'-GGGAATTCATGGAG(CT)TTGGGCTGA(CG)CTGG(CG)-    (SEQ ID NO:22)
           TTTT-3'

Group C
        5'-GGGAATTCATG(AG)A(AC)(AC)(AT)ACT(GT)TG(GT)-    (SEQ ID NO:23)
           (AT)(CG)C(AT)(CT)(CG)CT(CT)CTG-3'

Human κ light chain
        5'-GGGAATTCATGGACATG(AG)(AG)(AG)(AGT)(CT)CC-    (SEQ ID NO:24)
           (ACT)(ACG)G(CT)(GT)CA(CG)CTT-3'

Human λ light chain
        5'-GGGAATTCATG(AG)CCTG(CG)(AT)C(CT)CCTCTC(CT)-    (SEQ ID NO:25)
           T(CT)CT(CG)(AT)(CT)C-3'

3' End sense constant region

Human IgM heavy chain
    5'-CCAAGCTTAGACGAGGGGGAAAAGGGTT-3'    (SEQ ID NO:26)

Human IgG1 heavy chain
    5'-CCAAGCTTGGAGGAGGGTGCCAGGGGG-3'    (SEQ ID NO:27)

Human λ light chain
    5'-CCAAGCTTGAAGCTCCTCAGAGGAGGG-3'    (SEQ ID NO:28)

Human κ light chain
    5'-CCAAGCTTTCATCAGATGGCGGGAAGAT-3'    (SEQ ID NO:29)

Murine Immunoglobulin Variable Region PCR Primers

5' End Sense

Leader (signal peptide) region (amino-acids -20 to -13)
    Group A
        5'-GGGGAATTCATG(GA)A(GC)TT(GC)(TG)GG(TC)T(AC)-    (SEQ ID NO:30)
           A(AG)CT(CT)G(GA)TT-3'

Group B
        5'-GGGGAATTCATG(GA)AATG(GC)A(GC)CTGGGT(CT)-    (SEQ ID NO:31)
           (TA)T(TC)CTCT-3'

Framework 1 region (amino acids 1 to 8)
        5'-GGGGAATTC(CG)AGGTG(CA)AGCTC(CG)(AT)(AG)(CG)-    (SEQ ID NO:32)
           A(AG)(CT)C(CG)GGG-3'

3' End sense constant region

Mouse γ constant region
        5'-GGAAGCTTA(TC)CTCCACACACAGG(AG)(AG)CCAGTG-    (SEQ ID NO:33)
           GATAGAC-3'

Mouse κ light chain (amino acids 116 to 122)
        5'-GGAAGCTTACTGGATGGTGGGAAGATGGA-3'    (SEQ ID NO:34)

Bases in parentheses represent substitutions at a given residue. EcoRI and HindIII sites are underlined.

The Leader, FR1 (IVS 1–3) transcripts can be linked to an insoluble resin by standard techniques, and each set of combinatorial units (CDR1/FR2, CDR2/FR3, CDR3/FR4) can be sequentially added to the resin-bound nucleic acid by incubation under trans-splicing conditions, with unbound reactants washed away between each round of addition. After addition of the (IVS 5,6)CDR3,FR4 units to the resin bound molecules, the resulting trans-spliced molecule can be released from the resin, reverse-transcribed and PCR amplified using primers for the leader sequence and constant region, and subsequently cloned into an appropriate vector for generating a screenable population of antibody molecules.

Taking the dissection of the variable regions one step further, a set of exon libraries can be generated for ordered combinatorial ligation much the same as above, except that each combinatorial unit is flanked at its 5' end with an intron fragment that is unable to drive a trans-splicing reaction with the intron fragment at its 3' end. As described above (section II) with regard to ordered gene assembly, each combinatorial unit is effectively protected from addition by another unit having identical flanking intron fragments. The 5' and 3' flanking intronic sequences can be of the same group, but from divergent enough classes (i.e. group IIA versus group IIB) or divided in such a way that intermolecular complementation and assembly of an active splicing complex cannot occur; or the intron fragments can simply be from different groups (e.g. group I versus group II).

As illustrated in FIG. 51C, the combinatorial units of FIG. 51B can be generated with Y lariats derived from group IIA intron fragments (hence the designation "IVS-A-5,6"). Each CDR is then split from the downstream framework region using a Y-branched lariat derived from a group IIB intron having a divergent enough domain V that neither combination of (IVS-A-5,6) and (IVS-B-1–3) or (IVS-B-5,6) and (IVS-A-1–3) results in a functional splicing complex. In order to avoid the need to determine the sequence of each of the cloned CDRs, the exon-binding sites of the IIB intron lariats can be constructed to match the much less variable nucleotide sequences corresponding to the first (amino terminal) 2-3 a.a. residues of each of the framework regions (FR2–4). The resulting constructs include internal exon units of the general formula (IVS-A-5,6) CDR (VIS-B-1–3) and (VIS-B-5,6) FR (IVS-A-1–3), with each CDR containing an extra 2–3 a.a. residues from the FR which previously flanked it. Thus, by sequentially adding each pool of combinatorial units to the resin-immobilized FR1, an ordered combinatorial ligation of variegated populations of CDRs and FRs can be carried out to produce a library of variable region genes in which both the CDRs and FRs have been independently randomized.

Furthermore, CDR combinatorial units can be generated which are completely random in sequence, rather than cloned from any antibody source. For instance, a plasmid similar to pINV1 (described herein) can be used to create a set of random CDR sequences of a given length and which are flanked by appropriate intronic fragments. In an illustrative embodiment, the plasmid includes restriction endonuclease sites in each of the 5' and 3' flanking intron sequences such that oligonucleotides having the CDR coding sequence can be cloned into the plasmid. For example, a degenerate oligonucleotide can be synthesized for CDRI which encodes all possible amino acid combinations for the 6 amino acid sequence. The nucleotide sequences which flank the CDR-encoding portion of the oligonucleotide comprise the flanking intron sequences necessary to allow ligation of the degenerate oligonucleotide into the plasmid and reconstitute a construct which would produce a spliceable transcript. To avoid creation of stop codons which can result when codons are randomly synthesized using nucleotide monomers, "dirty bottle" synthesis can instead be carried out using a set of nucleotide trimers which encode all 20 amino acids.

With slight modification, the present ordered combinatorial ligation can be used to efficiently humanize monoclonal antibodies of non-human origin. The CDRs from the monoclonal antibody can be recombined with human framework region libraries (e.g. an FR1 library, an FR2 library, etc.) to produce a combinatorial population of variable regions in which the CDR sequences are held constant, but each of the framework regions have been randomized. The variable regions can be subsequently fused with sequences corresponding to the appropriate human constant regions, and the antibodies resulting from heavy and light chain association can be screened for antigen binding using standard panning assays such as phage display. In contrast to contemporary humanization schemes which require the practitioner to prejudicially choose a particular human scaffold into which the CDRs are grafted, the present technique provides a greater flexibility in choosing appropriate human framework regions which do not adversely affect antigen binding by the resultant chimeric antibody.

To illustrate, the variable regions of both the heavy and light chains of a mouse monoclonal antibody can be cloned using primers as described above. The sequence of each CDR can be obtained by standard techniques. The CDRs can be cloned into vectors which provide appropriate flanking intronic sequences, or alternatively, isolated by reverse-splicing with Y-branched lariats designed to insert precisely at each FR/CDR and CDR/FR boundary. As described above, the particular intronic fragments provided with each murine CDR and each human FR construct can be selected to disfavor multiple ligations at each step of addition to a resin bound nucleic acid. The library of human heavy chain leader, FRI(IVS-A-1–3) constructs can be immobilized on a resin, and in a first round of ligation, the heavy chain murine (IVS-A-5,6) CDR1 (IVS-B-1–3) construct is added under trans-splicing conditions. Un-ligated combinatorial units are washed away, and the library of human heavy chain (IVS-B-5,6) FR2 (IVS-A-1–3) units are admixed and trans-spliced to the resin-bound nucleic acids terminating with the murine CDR construct. This process is carried out for the remaining murine CDR and human FR units of the heavy chain, and a similar process is used to construct combinatorial light chain chimeras as well. The resulting chimeric heavy and light chains can be cloned into a phage display library, and the phAbs screened in a panning assay to isolate humanized antibodies (and their genes) which bind the antigen of interest.

B. Combinatorial Enzyme Libraries

Plasminogen activators (PAs) are a class of serine proteases that convert the proenzyme plasminogen into plasmin, which then degrades the fibrin network of blood clots. The plasminogen activators have been classified into two immunologically unrelated groups, the urokinase-type PAs (u-PA) and the tissue-type PA (tPA), with the later activator being the physiological vascular activator. These proteins, as well as other proteases of the fibrinolytic pathway, are composed of multiple structural domains which appear to have evolved by genetic assembly of individual subunits with specific structural and/or functional properties. For instance, the amino terminal region of tPA is composed of multiple structural/functional domains found in other plasma proteins, including a "finger-like domain"

homologous to the finger domains of fibronectin, an "epidermal growth factor domain" homologous to human EGF, and two disulfide-bonded triple loop structures, commonly referred to as "kringle domains," homologous to the kringle regions in plasminogen. The region comprising residues 276–527 (the "catalytic domain" is homologous to that of other serine proteases and contains the catalytic triad. In addition, the gene for tPA encodes a signal secretion peptide which directs secretion of the protein into the extracellular environment, as well as a prosequence which is cleaved from the inactive form of the protease (the "plasminogen") to active tPA during the fibrinolytic cascade.

These distinct domains in tPA are involved in several functions of the enzyme, including its binding to fibrin, stimulation of plasminogen activation by fibrin, and rapid in vivo clearance. Approaches used to characterize the functional contribution of these structural domains include isolation of independent structural domains as well as the production of variant proteins which lack one or more domains. For example, the fibrin selectivity of tPA is found to be mediated by its affinity for fibrin conferred by the finger-like domain and by at least one of the kringle domains.

The present combinatorial method can be used to generate novel plasminogen activators having superior thrombolytic properties, by generating a library of proteins by RNA-splicing mediated shuffling of the domains of plasma proteins (see, for example, Example 1, above, and Examples 18–21, below). As described below, one mode of generating the combinatorial library comprises the random trans-splicing of a mixture of exons corresponding to each of the domains of the mature tPA protein. Briefly, a cDNA clone of tPA was obtained and, through the use of specific PCR amplimers, each of the 5 protein domains was amplified and isolated. Each of these amplified domains was then separately cloned into a plasmid as an exon module such that the 5' end of the exon is preceded by group II domains 5-6, and the 3' end of the exon is followed by group II domains 1–3. In addition, the IBS 1 site of each of the exon was mutated in order to facilitate base pairing with the EBS 1 sequence of the 3' flanking intron fragment. Transcription of the resulting construct thus produces RNA transcripts of the general formula (IVS 5,6)-Exon-(IVS 1–3). Mixture of these transcripts under trans-splicing conditions can result in random ligation of the exons to one and other and assembly of the combinatorial gene library which can subsequently be screened for fibrinolytic activity.

Moreover, combinatorial units can be generated from other proteins, including proteins having no catalytic role in blood clotting or fibrinolysis. For example, a library of catalytic domains can be generated from other thrombolytic proteases, blood clotting factors, and other proteases having peptidic activity similar to the typsin-like activity of tPA. Likewise, libraries of splicing constructs can be derived from EGF-like domains, finger-like domains, kringle domains, and calcium-binding domains from a vast array of proteins which contain such moieties.

Preferred combinatorial units include domains of the vampire bat DSPAxl protein, a plasminogen activator with high fibrin binding activity (see Gulba et al. (1995) *Fibrinolysis* 9 Supp. 1:91–96, incorporated by reference). Shuffling one of these domains with domains of the human t-PA protein might produce a novel plasminogen activator with desirable characteristics as a human therapeutic.

EXAMPLE 18

Construction of Plasmid GrII-Sig

Two oligonucleotide primers were used to change the IBS 1 sequence of pINV1 to TGTCAAA and the EBS 1 sequence to TTTGACA. Thus, the last seven nucleotides of E5 were changes to the sequence of the last 7 nucleotides of TPA fibronectin finger like domain and the EBS 1 sequence was made complementary. The resulting plasmid is termed here GrII-Sig.

EXAMPLE 19

Construction of Plasmid SIG(IVS1–3)

The plasmid SIG(IVS1–3) contains the first two protein domains of TPA (the signal sequence and the finger domain) followed by group II intron domains 1–3. It was made by the reversal of splicing. Plasmid Gril-Sig (Example 18) was linearized with Hind III and RNA made using $T_7$ polymerase in vitro. The RNA was incubated under self splicing conditions for two hours and the products fractionated on an acrylamide gel. The Sig(Y) molecule (a Y-branched lariat intron comprising domains 5 and 6 joined to domains 1 through 3 by a 2'–5' phosphodiester bond) was gel purified. This molecule was the "enzyme" used for the reverse-splicing reaction. The substrate was made by cutting TPA-KS$^+$ DNA (Example 2) with Sty I, which cuts 17 bp downstream of the end of the finger domain. A 404 nt RNA was made using $T_7$ polymerase. The enzyme and substrate were mixed and incubated under splicing conditions for two hours. By the reversal of splicing, the Sig(Y) RNA attacked the substrate to yield the signal plus finger region followed by intron domains 1 through 3. A cDNA copy of the molecule was made using reverse transcriptase and amplified by PCR. It was cloned into the PBS vector in the $T_7$ orientation. The clones analyzed each showed precise joining of the coding sequence to the group II intron sequence. Thus, the nucleotide sequence of the EBS1 was sufficient to direct exact integration of the intronic IVS(1–3) fragment.

EXAMPLE 20

Construction of Other Shuffling Clones

Clones with each of the other three protein domains (growth factor (GF) domain, kringle 2 (K2) domain and catalytic (cat) domain), flanked by group II intron sequences, can also be made by either standard cloning methods or by the reversal of splicing method, as described above, to yield constructs corresponding to (IVS5,6)FG (IVS1–3), (IVS5,6)K2(IVS1–3), and (IVS5,6)cat or (IVS5, 6)cat(IVS1–3).

To further illustrate, the plasmid (IVS5.6)cat was generated by reversal of splicing as in Example 19. Briefly, the Y-branched intron of the pY7 construct (see Example 16) was generated by cutting the pY7 plasmid with Hindi, producing RNA with $T_7$, and incubating the RNA under self-splicing conditions for 1.5 hours. The products were fractioned on an acylamide gel. The Y7 molecule (a Y-branched intron) was gel purified. This molecule was used for the reverse-splicing reaction. The substrate for this reaction was generated by cutting a plasmid containing the tPA catalytic domain with HindiII and transcribing the linear plasmid with T7. The Y-branched enzyme and tPA substrate RNAs were mixed and incubated under reverse-splicing conditions for 4 hours. By the reversal of splicing, the Y7 RNA attacked the substrate at a site (IBS 1) just upstream of the coding sequence for the catalytic domain to yield intron domains 5 and 6 followed by the tPA protease domain. A cDNA copy of the molecule was made using reverse transcriptase and amplified by PCR. It was cloned into a PBS vector in the T7 orientation. Two independent clones were characterized by DNA sequence analysis. Both clones had the group II intron sequences precisely joined to the tPA sequences. Thus, the nucleotide sequence of the fusion protein was 5'-ATCCGGAT/ACCTGCGG (SEQ ID NO:___) (intron/exon, respectively).

EXAMPLE 21

Generation of Library

RNA transcripts are made for each of the tPA combinatorial units, SIG(IVS1–3), (IVS5,6)K1(IVS1–3), (VS5,6)K2 (IVS1–3), (IVS5,6)GF(IVS-3), and (IVS5,6)cat. The transcripts are mixed and incubated under trans-splicing conditions. The resulting combinatorial RNA molecules can be reverse-transcribed to cDNA using primers complementary to sequences in the intron domains I-III, and the cDNA amplified by PCR using a similar primer and a primer to the tPA signal sequence. The amplified cDNAs can subsequently be cloned into suitable expressions vectors to generate an expressions library, and the library screened for fibrinolytic activity by standard assays.

All of the above-cited references and publications are hereby incorporated by reference.

EQUIVALENTS

Those skilled in the art will recognize, or be able to ascertain using no more than routine experimentation, numerous equivalents to the specific methods and reagents described herein. Such equivalents are considered to be within the scope of this invention and are covered by the following claims.

I claim:

1. A method of producing a recombinant DNA molecule, the method comprising steps of:
   providing a first DNA/RNA hybrid molecule comprising a first DNA linked to a first splicing component;
   providing a second DNA/RNA hybrid molecule comprising a second DNA linked to a second splicing component, which second splicing component is selected so that, when the first and second DNA/RNA hybrid molecules are admixed together, trans-splicing between the first and second splicing components covalently links the first DNA with the second DNA to form a single, recombinant DNA molecule; and
   admixing the first and second DNA/RNA hybrid molecules together so that the recombinant DNA molecule is produced by trans-splicing.

2. The method of claim 1 wherein the first DNA is single-stranded.

3. The method of claim 2 wherein the second DNA is single-stranded.

4. The method of claim 2 wherein the second DNA is double-stranded.

5. The method of claim 1 wherein the first DNA is double-stranded.

6. The method of claim 5 wherein the second DNA is single-stranded.

7. The method of claim 5 wherein the second DNA is double-stranded.

8. The method of claim 7 wherein the step of providing a second DNA/RNA hybrid molecule comprises:
   integrating a third splicing ribozyme into a third target site in a second DNA molecule;
   integrating a fourth splicing ribozyme into a fourth target site in the second DNA molecule, the fourth target site being removed from the third target site, so that DNA between the third and fourth target sites constitutes the second DNA and is flanked by splicing components as a result of integration by the third and fourth ribozymes.

9. The method of claim 1 wherein the step of providing a first DNA/RNA hybrid molecule comprises:
   providing a first DNA/RNA hybrid molecule comprising a first DNA flanked by first and third splicing components.

10. The method of claim 1 or claim 9 wherein the step of providing a second DNA/RNA hybrid molecule comprises;
    providing a second DNA/RNA hybrid molecule comprising a second DNA flanked by second and first splicing components.

11. The method of claim 10 wherein the step of providing a second DNA/RNA hybrid comprises;
    ligating at least one of the second and fourth splicing components the second DNA by oligonucleotide-bridge-mediated DNA/RNA ligation.

12. The method of claim 9 wherein the step of providing a first DNA/RNA hybrid molecule comprises:
    integrating a first splicing ribozyme into a first target site in a DNA molecule;
    integrating a second splicing ribozyme into a second target site in the DNA molecule, the second target site being located at a distance removed from the first target site, so that DNA between the first and second target sites constitutes the first DNA and is flanked by splicing components as a result of integration by the first and second ribozyme.

13. The method of claim 12 wherein the first splicing ribozyme constitutes a lariat intron.

14. The method of claim 13 wherein the first splicing ribozyme constitutes a lariat group II intron.

15. The method of claim 14 wherein the group II intron is selected from the group consisting of aI5γ, bI1, aI1 and aI2.

16. The method of claim 14 wherein the first splicing ribozyme constitutes a lariat group II intron whose EBS1 site has been engineered to recognize the first target site, which first target site is distinct from the target site into which the intron would naturally integrate without having been so engineered.

17. The method of claim 12 wherein the first splicing ribozyme constitutes a Y-branched RNA molecule.

18. The method of claim 17 wherein the Y-branched RNA molecule comprises:
    a first arm comprising at least domains 1–3 of a group II intron; and
    a second arm comprising at least domains 5-6 of the group II intron, the first and second arms being covalently linked to one another via a 2'–5' phosphodiester linkage to the group II intron branch-point residue in domain 6.

19. The method of claim 18 wherein the group II intron EBS1 site has been engineered to recognize the first target site, which first target site is distinct from the target site into which the intron would naturally integrate had the EBS1 site not been so engineered.

* * * * *

```
                         SEQUENCE LISTING (1) GENERAL INFORMATION:

(iii) NUMBER OF SEQUENCES: 46

(2) INFORMATION FOR SEQ ID NO:1:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "group I intron Element R
            consensus"

(xi) SEQUENCE DESCRIPTION: SEQ ID NO:1:

SYUCARMGAC UANANG                                                      16

(2) INFORMATION FOR SEQ ID NO:2:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "group I intron Element S
            consensus sequence"

(xi) SEQUENCE DESCRIPTION: SEQ ID NO:2:

AAGAUAGUCY                                                             10

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA primer"

(vii) IMMEDIATE SOURCE:
        (B) CLONE: t-PA1

(xi) SEQUENCE DESCRIPTION: SEQ ID NO:3:
```

```
ACGATGCATG CTGGAGAGAA AACCTCTGCG                                              30

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA primer"

(vii) IMMEDIATE SOURCE:
        (B) CLONE: t-PA2

(xi) SEQUENCE DESCRIPTION: SEQ ID NO:4:

ACGATGCATT CTGTAGAGAA GCACTGCGCC                                              30

(2) INFORMATION FOR SEQ ID NO:5:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA primer"

(vii) IMMEDIATE SOURCE:
        (B) CLONE: I654

(xi) SEQUENCE DESCRIPTION: SEQ ID NO:5:

ACGAAGCTTC CTATAGTATA AGTTAGCAGA T                                            31

(2) INFORMATION FOR SEQ ID NO:6:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA primer"

(vii) IMMEDIATE SOURCE:
        (B) CLONE: I5,6

(xi) SEQUENCE DESCRIPTION: SEQ ID NO:6:

GCGAATTCGA GCTCGTGAGC CGTAT                                                   25

(2) INFORMATION FOR SEQ ID NO:7:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA primer"

(vii) IMMEDIATE SOURCE:
        (B) CLONE: t-PA(-49)

(xi) SEQUENCE DESCRIPTION: SEQ ID NO:7:

ACGGGTACCG AAAGGGAAGG AGCAAGCCGT G                                            31
```

(2) INFORMATION FOR SEQ ID NO:8:

(i) SEQUENCE CHARACTERISTICS:
        (A) LENGTH: 16 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "Ribozyme"

(vii) IMMEDIATE SOURCE:
        (B) CLONE: last 16 nt of Fn in Y4

(xi) SEQUENCE DESCRIPTION: SEQ ID NO:8:

```
CUCAGUGCCU GUCAAA                                                16
```

(2) INFORMATION FOR SEQ ID NO:9:

(i) SEQUENCE CHARACTERISTICS:
        (A) LENGTH: 16 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "Ribozyme"

(vii) IMMEDIATE SOURCE:
        (B) CLONE: last 16 nt of K2 in Y7

(xi) SEQUENCE DESCRIPTION: SEQ ID NO:9:

```
UGUGCCCUCC UGCUCC                                                16
```

(2) INFORMATION FOR SEQ ID NO:10:

(i) SEQUENCE CHARACTERISTICS:
        (A) LENGTH: 1848 base pairs
        (B) TYPE: nucleic acid
        (C) STRANDEDNESS: double
        (D) TOPOLOGY: linear (ii) MOLECULE TYPE: cDNA (vii) IMMEDIATE SOURCE:
        (B) CLONE: amplified t-PA clone (xi) SEQUENCE DESCRIPTION: SEQ ID NO:10:

```
GCTGGAGAGA AAACCTCTGC GAGGAAAGGG AAGGAGCAAG CCGTGAATTT AAGGGACGCT        60

GTGAAGCAAT CATGGATGCA ATGAAGAGAG GGCTCTGCTG TGTGCTGCTG CTGTGTGGAG       120

CAGTCTTCGT TTCGCCCAGC CAGGAAATCC ATGCCCGATT CAGAAGAGGA GCCAGATCTT       180

ACCAAGTGAT CTGCAGAGAT GAAAAACGC AGATGATATA CCAGCAACAT CAGTCATGGC        240

TGCGCCCTGT GCTCAGAAGC AACCGGGTGG AATATTGCTG GTGCAACAGT GGCAGGGCAC       300

AGTGCCACTC AGTGCCTGTC AAAAGTTGCA GCGAGCCAAG GTGTTTCAAC GGGGGCACCT       360

GCCAGCAGGC CCTGTACTTC TCAGATTTCG TGTGCCAGTG CCCCGAAGGA TTTGCTGGGA       420

AGTGCTGTGA AATAGATACC AGGGCCACGT GCTACGAGGA CCAGGGCATC AGCTACAGGG       480

GCACGTGGAG CACAGCGGAG AGTGGCGCCG AGTGCACCAA CTGGAACAGC AGCGCGTTGG       540

CCCAGAAGCC CTACAGCGGG CGGAGGCCAG ACGCCATCAG GCTGGGCCTG GGAACCACA        600

ACTACTGCAG AAACCCAGAT CGAGACTCAA AGCCCTGGTG CTACGTCTTT AAGGCGGGGA       660

AGTACAGCTC AGAGTTCTGC AGCACCCCTG CCTGCTCTGA GGGAAACAGT GACTGCTACT       720

TTGGGAATGG GTCAGCCTAC CGTGGCACGC ACAGCCTCAC CGAGTCGGGT GCCTCCTGCC       780
```

```
TCCCGTGGAA TTCCATGATC CTGATAGGCA AGGTTTACAC AGCACAGAAC CCCAGTGCCC     840

AGGCACTGGG CCTGGGCAAA CATAATTACT GCCGGAATCC TGATGGGGAT GCCAAGCCCT     900

GGTGCCACGT GCTGAAGAAC CGCAGGCTGA CGTGGGAGTA CTGTGATGTG CCCTCCTGCT     960

CCACCTGCGG CCTGAGACAG TACAGCCAGC CTCAGTTTCG CATCAAAGGA GGGCTCTTCG    1020

CCGACATCGC CTCCCACCCC TGGCAGGCTG CCATCTTTGC CAAGCACAGG AGGTCGCCCG    1080

GAGAGCGGTT CCTGTGCGGG GGCATACTCA TCAGCTCCTG CTGGATTCTC TCTGCCGCCC    1140

ACTGCTTCCA GGAGAGGTTT CCGCCCCACC ACCTGACGGT GATCTTGGGC AGAACATACC    1200

GGGTGGTCCC TGGCGAGGAG GAGCAGAAAT TTGAAGTCGA AAAATACATT GTCCATAAGG    1260

AATTCGATGA TGACACTTAC GACAATGACA TTGCGCTGCT GCAGCTGAAA TCGGATTCGT    1320

CCCGCTGTGC CCAGGAGAGC AGCGTGGTCC GCACTGTGTG CCTTCCCCCG GCGGACCTGC    1380

AGCTGCCGGA CTGGACGGAG TGTGAGCTCT CCGGCTACGG CAAGCATGAG GCCTTGTCTC    1440

CTTTCTATTC GGAGCGGCTG AAGGAGGCTC ATGTCAGACT GTACCCATCC AGCCGCTGCA    1500

CATCACAACA TTTACTTAAC AGAACAGTCA CCGACAACAT GCTGTGTGCT GGAGACACTC    1560

GGAGCGGCGG GCCCCAGGCA AACTTGCACG ACGCCTGCCA GGGCGATTCG GGAGGCCCCC    1620

TGGTGTGTCT GAACGATGGC CGCATGACTT TGGTGGGCAT CATCAGCTGG GGCCTGGGCT    1680

GTGGACAGAA GGATGTCCCG GGTGTGTACA CAAAGGTTAC CAACTACCTA GACTGGATTC    1740

GTGACAACAT GCGACCGTGA CCAGGAACAC CCGACTCCTC AAAAGCAAAT GAGATCCCGC    1800

CTCTTCTTCT TCAGAAGACA CTGCAAAGGC GCAGTGCTTC TCTACAGA               1848

(2) INFORMATION FOR SEQ ID NO:11:

(i) SEQUENCE CHARACTERISTICS:
        (A) LENGTH: 4542 base pairs
        (B) TYPE: nucleic acid
        (C) STRANDEDNESS: double
        (D) TOPOLOGY: circular (ii) MOLECULE TYPE: other nucleic acid
        (A) DESCRIPTION: /desc = "plasmid DNA"

(vii) IMMEDIATE SOURCE:
        (B) CLONE: pINV1

(xi) SEQUENCE DESCRIPTION: SEQ ID NO:11:

TCGCGCGTTT CGGTGATGAC GGTGAAAACC TCTGACACAT GCAGCTCCCG GAGACGGTCA      60

CAGCTTGTCT GTAAGCGGAT GCCGGGAGCA GACAAGCCCG TCAGGGCGCG TCAGCGGGTG     120

TTGGCGGGTG TCGGGCTGG CTTAACTATG CGGCATCAGA GCAGATTGTA CTGAGAGTGC     180

ACCATATGCG GTGTGAAATA CCGCACAGAT GCGTAAGGAG AAAATACCGC ATCAGGCGAC     240

GCGCCCTGTA GCGGCGCATT AAGCGCGGCG GGTGTGGTGG TTACGCGCAG CGTGACCGCT     300

ACACTTGCCA GCGCCCTAGC GCCCGCTCCT TTCGCTTTCT TCCCTTCCTT TCTCGCCACG     360

TTCGCCGGCT TTCCCCGTCA AGCTCTAAAT CGGGGGCTCC CTTTAGGGTT CCGATTTAGT     420

GCTTTACGGC ACCTCGACCC CAAAAAACTT GATTAGGGTG ATGGTTCACG TAGTGGGCCA     480

TCGCCCTGAT AGACGGTTTT TCGCCCTTTG ACGTTGGAGT CCACGTTCTT TAATAGTGGA     540

CTCTTGTTCC AAACTGGAAC AACACTCAAC CCTATCTCGG TCTATTCTTT TGATTTATAA     600

GGGATTTTGC CGATTTCGGC CTATTGGTTA AAAAATGAGC TGATTTAACA AAAATTTAAC     660

GCGAATTTTA ACAAAATATT AACGCTTTAC AATTTCGCCA TTCGCCATTC AGGCTGCGCA     720

ACTGTTGGGA AGGGCGATCG GTGCGGGCCT CTTCGCTATT ACGCCAGCTG GCGAAAGGGG     780
```

```
GATGTGCTGC AAGGCGATTA AGTTGGGTAA CGCCAGGGTT TTCCCAGTCA CGACGTTGTA    840

AAACGACGGC CAGTGAATTG TAATACGACT CACTATAGGG CGAATTCGAG CTCGTGAGCC    900

GTATGCGATG AAAGTCGCAC GTACGGTTCT TACCGGGGGA AAACTTGTAA AGGTCTACCT    960

ATCGGGATAC TATGTATTAT CAATGGGTGC TATTTTCTCT TTATTTGCAG GATACTACTA   1020

TTGAAGTCCT CAAATTTTAG GTTTAAACTA TAATGAAAAA TTAGCTCAAA TTCAATTCTG   1080

ATTAATTTTC ATTGGGGCTA ATGTTATTTT CTTCCCAATG CATTTCTTAG GTATTAATGG   1140

TATGCCTAGA AGAATTCCTG ATTATCCTGA TGCTTTCGCA GGATGAAATT ATGTCGCTTC   1200

TATTGGTTCA TTCATTGCAC TATTATCATT ATTCTTATTT ATCTATATTT TATATGATCC   1260

TCTAGAGTCG ACCTGCAGGC ATGCAAGCTG GGATCACAT  CATATGTATA TTGTAGGATT   1320

AGATGCAGAT ACTAGAGCAT ATTTCCTATC CGCACTGATG ATTATTGCAA TTCCAACAGG   1380

AATTAAAATC TTTTCTTGAT TAGCCCTGAT CTACGGTGGT TCAATTAGAT TAGCACTACC   1440

TATGTTATAT GCAATTGCAT TCTTATTCTT ATTCACAATG GGTGGTTTAA CTGGTGTTGC   1500

CTTAGCTAAC GCCTCATTAG ATGTGGCATT CCACGATACT TACTACGTGG TGGGACATTT   1560

TCGAGCGGTC TGAAAGTTAT CATAAATAAT ATTTACCATA TAATAATGGA TAAATTATAT   1620

TTTTATCAAT ATAAGTCTAA TTACAAGTGT ATTAAAATGG TAACATAAAT ATGCTAAGCT   1680

GTAATGACAA AAGTATCCAT ATTCTTGACA GTTATTTTAT ATTATAAAAA AAAGATGAAG   1740

GAACTTTGAC TGATCTAATA TGCTAACGA  AAGTGAATCA AATGTTATAA AATTACTTAC   1800

ACCACTAATT GAAAACCTGT CTGATATTCA ATTATTATTT ATTATTATAT AATTATATAA   1860

TAATAAATAA AATGGTTGAT GTTATGTATT GGAAATGAGC ATACGATAAA TCATATAACC   1920

ATTAGTAATA TAATTTGAGA GCTAAGTTAG ATATTTACGT ATTTATGATA AAACAGAATA   1980

AACCCTATAA ATTATTATTA TTAATAATAA AAAATAATAA TAATACCAAT ATATATATTA   2040

TTTAATTTAT TATTATTATA TTAATAAAAT TTAATATATA TTATAAATAA TTATTGGATT   2100

AAGAAATATA ATATTTTATA GAAATTTTCT TTATATTTAG AGGGTAAAAG ATTGTATAAA   2160

AAGCTAATGC CATATTGTAA TGATATGGAT AAGAATTATT ATTCTAAAGA TGAAAATCTG   2220

CTAACTTATA CTATAGGGGG GATCCTCTAG AGTCGACCTG CAGGCATGCA AGCTTTTGTT   2280

CCCTTTAGTG AGGGTTAATT TCGAGCTTGG CGTAATCATG GTCATAGCTG TTTCCTGTGT   2340

GAAATTGTTA TCCGCTCACA ATTCCACACA ACATACGAGC CGGAAGCATA AAGTGTAAAG   2400

CCTGGGGTGC CTAATGAGTG AGCTAACTCA CATTAATTGC GTTGCGCTCA CTGCCCGCTT   2460

TCCAGTCGGG AAACCTGTCG TGCCAGCTGC ATTAATGAAT CGGCCAACGC GCGGGGAGAG   2520

GCGGTTTGCG TATTGGGCGC TCTTCCGCTT CCTCGCTCAC TGACTCGCTG CGCTCGGTCG   2580

TTCGGCTGCG GCGAGCGGTA TCAGCTCACT CAAAGGCGGT AATACGGTTA TCCACAGAAT   2640

CAGGGGATAA CGCAGGAAAG AACATGTGAG CAAAAGGCCA GCAAAAGGCC AGGAACCGTA   2700

AAAAGGCCGC GTTGCTGGCG TTTTTCCATA GGCTCCGCCC CCCTGACGAG CATCACAAAA   2760

ATCGACGCTC AAGTCAGAGG TGGCGAAACC CGACAGGACT ATAAAGATAC CAGGCGTTTC   2820

CCCCTGGAAG CTCCCTCGTG CGCTCTCCTG TTCCGACCCT GCCGCTTACC GGATACCTGT   2880

CCGCCTTTCT CCCTTCGGGA AGCGTGGCGC TTTCTCATAG CTCACGCTGT AGGTATCTCA   2940

GTTCGGTGTA GGTCGTTCGC TCCAAGCTGG GCTGTGTGCA CGAACCCCCC GTTCAGCCCG   3000

ACCGCTGCGC CTTATCCGGT AACTATCGTC TTGAGTCCAA CCCGGTAAGA CACGACTTAT   3060

CGCCACTGGC AGCAGCCACT GGTAACAGGA TTAGCAGAGC GAGGTATGTA GGCGGTGCTA   3120
```

-continued

```
CAGAGTTCTT GAAGTGGTGG CCTAACTACG GCTACACTAG AAGGACAGTA TTTGGTATCT      3180

GCGCTCTGCT GAAGCCAGTT ACCTTCGGAA AAAGAGTTGG TAGCTCTTGA TCCGGCAAAC      3240

AAACCACCGC TGGTAGCGGT GGTTTTTTTG TTTGCAAGCA GCAGATTACG CGCAGAAAAA      3300

AAGGATCTCA AGAAGATCCT TTGATCTTTT CTACGGGGTC TGACGCTCAG TGGAACGAAA      3360

ACTCACGTTA AGGGATTTTG GTCATGAGAT TATCAAAAAG GATCTTCACC TAGATCCTTT      3420

TAAATTAAAA ATGAAGTTTT AAATCAATCT AAAGTATATA TGAGTAAACT TGGTCTGACA      3480

GTTACCAATG CTTAATCAGT GAGGCACCTA TCTCAGCGAT CTGTCTATTT CGTTCATCCA      3540

TAGTTGCCTG ACTCCCCGTC GTGTAGATAA CTACGATACG GGAGGGCTTA CCATCTGGCC      3600

CCAGTGCTGC AATGATACCG CGAGACCCAC GCTCACCGGC TCCAGATTTA TCAGCAATAA      3660

ACCAGCCAGC CGGAAGGGCC GAGCGCAGAA GTGGTCCTGC AACTTTATCC GCCTCCATCC      3720

AGTCTATTAA TTGTTGCCGG GAAGCTAGAG TAAGTAGTTC GCCAGTTAAT AGTTTGCGCA      3780

ACGTTGTTGC CATTGCTACA GGCATCGTGG TGTCACGCTC GTCGTTTGGT ATGGCTTCAT      3840

TCAGCTCCGG TTCCCAACGA TCAAGGCGAG TTACATGATC CCCCATGTTG TGCAAAAAAG      3900

CGGTTAGCTC CTTCGGTCCT CCGATCGTTG TCAGAAGTAA GTTGGCCGCA GTGTTATCAC      3960

TCATGGTTAT GGCAGCACTG CATAATTCTC TTACTGTCAT GCCATCCGTA AGATGCTTTT      4020

CTGTGACTGG TGAGTACTCA ACCAAGTCAT TCTGAGAATA GTGTATGCGG CGACCGAGTT      4080

GCTCTTGCCC GGCGTCAATA CGGGATAATA CCGCGCCACA TAGCAGAACT TTAAAAGTGC      4140

TCATCATTGG AAAACGTTCT TCGGGGCGAA AACTCTCAAG GATCTTACCG CTGTTGAGAT      4200

CCAGTTCGAT GTAACCCACT CGTGCACCCA ACTGATCTTC AGCATCTTTT ACTTTCACCA      4260

GCGTTTCTGG GTGAGCAAAA ACAGGAAGGC AAAATGCCGC AAAAAAGGGA ATAAGGGCGA      4320

CACGGAAATG TTGAATACTC ATACTCTTCC TTTTTCAATA TTATTGAAGC ATTTATCAGG      4380

GTTATTGTCT CATGAGCGGA TACATATTTG AATGTATTTA GAAAAATAAA CAAATAGGGG      4440

TTCCGCGCAC ATTTCCCCGA AAAGTGCCAC CTGACGTCTA AGAAACCATT ATTATCATGA      4500

CATTAACCTA TAAAAATAGG CGTATCACGA GGCCCTTTCG TC                        4542
```

(2) INFORMATION FOR SEQ ID NO:12:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA primer"

(vii) IMMEDIATE SOURCE:
        (B) CLONE: E5-specific oligonucleotide (xi) SEQUENCE DESCRIPTION: SEQ ID NO:12:

```
GTAGGATTAG ATGCAGATAC TAGAGC                                            26
```

(2) INFORMATION FOR SEQ ID NO:13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA primer"

(vii) IMMEDIATE SOURCE:
              (B) CLONE: E3-specific oligonucleotide (xi) SEQUENCE DESCRIPTION: SEQ ID NO:13:

GAGGACTTCA ATAGTATCCT GC                                                    22

(2) INFORMATION FOR SEQ ID NO:14:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "DNA primer"

(vii) IMMEDIATE SOURCE:
              (B) CLONE: K1.Cir.1:anti-sense (xi) SEQUENCE DESCRIPTION: SEQ ID NO:14:

GCCAACGCGC TGCTGTTCCA G                                                     21

(2) INFORMATION FOR SEQ ID NO:15:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "DNA primer"

(vii) IMMEDIATE SOURCE:
              (B) CLONE: K1.Cir.2:sense (xi) SEQUENCE DESCRIPTION: SEQ ID NO:15:

GGCCAGACGC CATCAGGCTG                                                       20

(2) INFORMATION FOR SEQ ID NO:16:

(i) SEQUENCE CHARACTERISTICS:
              (A) LENGTH: 25 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "DNA primer"

(vii) IMMEDIATE SOURCE:
              (B) CLONE: I5-29

(xi) SEQUENCE DESCRIPTION: SEQ ID NO:16:

TATTATTTAT GATAACTTTC AGACC                                                 25

(2) INFORMATION FOR SEQ ID NO:17:

(i) SEQUENCE CHARACTERISTICS:
              (A) LENGTH: 2939 base pairs
              (B) TYPE: nucleic acid
              (C) STRANDEDNESS: double
              (D) TOPOLOGY: circular (ii) MOLECULE TYPE: other nucleic acid
              (A) DESCRIPTION: /desc = "plasmid DNA"

(vii) IMMEDIATE SOURCE:
              (B) CLONE: BGINV

-continued (xi) SEQUENCE DESCRIPTION: SEQ ID NO:17:

```
TATAGTGTCA CCTAAATCGT ATGTGTATGA TACATAAGGT TATGTATTAA TTGTAGCCGC      60
GTTCTAACGA CAATATGTCC ATATGGTGCA CTCTCAGTAC AATCTGCTCT GATGCCGCAT     120
AGTTAAGCCA GCCCCGACAC CCGCCAACAC CCGCTGACGC GCCCTGACGG GCTTGTCTGC     180
TCCCGGCATC CGCTTACAGA CAAGCTGTGA CCGTCTCCGG GAGCTGCATG TGTCAGAGGT     240
TTTCACCGTC ATCACCGAAA CGCGCGAGAC GAAAGGGCCT CGTGATACGC CTATTTTTAT     300
AGGTTAATGT CATGATAATA ATGGTTTCTT AGACGTCAGG TGGCACTTTT CGGGGAAATG     360
TGCGCGGAAC CCCTATTTGT TTATTTTTCT AAATACATTC AAATATGTAT CCAGAGTATG     420
AGTATTCAAC ATTTCCGTGT CGCCCTTATT CCCTTTTTTG CGAGAGTATG AGTATTCAAC     480
ATTTCCGTGT CGCCCTTATT CCCTTTTTTG CGGCATTTTG CCTTCCTGTT TTTGCTCACC     540
CAGAAACGCT GGTGAAAGTA AAAGATGCTG AAGATCAGTT GGGTGCACGA GTGGGTTACA     600
TCGAACTGGA TCTCAACAGC GGTAAGATCC TTGAGAGTTT TCGCCCCGAA GAACGTTTTC     660
CAATGATGAG CACTTTTAAA GTTCTGCTAT GTGGCGCGGT ATTATCCCGT ATTGACGCCG     720
GGCAAGAGCA ACTCGGTCGC CGCATACACT ATTCTCAGAA TGACTTGGTT GAGTACTCAC     780
CAGTCACAGA AAAGCATCTT ACGGATGGCA TGACAGTAAG AGAATTATGC AGTGCTGCCA     840
TAACCATGAG TGATAACACT GCGGCCAACT TACTTCTGAC AACGATCGGA GGACCGAAGG     900
AGCTAACCGC TTTTTTGCAC AACATGGGGG ATCATGTAAC TCGCCTTGAT CGTTGGGAAC     960
CGGAGCTGAA TGAAGCCATA CCAAACGACG AGCGTGACAC CACGATGCCT GTAGCAATGG    1020
CAACAACGTT GCGCAAACTA TTAACTGGCG AACTACTTAC TCTAGCTTCC CGGCAACAAT    1080
TAATAGACTG GATGGAGGCG GATAAAGTTG CAGGACCACT TCTGCGCTCG GCCCTTCCGG    1140
CTGGCTGGTT TATTGCTGAT AAATCTGGAG CCGGTGAGCG TGGGTCTCGC GGTATCATTG    1200
CAGCACTGGG GCCAGATGGT AAGCCCTCCC GTATCGTAGT TATCTACACG ACGGGGAGTC    1260
AGGCAACTAT GGATGAACGA AATAGACAGA TCGCTGAGAT AGGTGCCTCA CTGATTAAGC    1320
ATTGGTAACT GTCAGACCAA GTTTACTCAT ATATACTTTA GATTGATTTA AAACTTCATT    1380
TTTAATTTAA AAGGATCTAG GTGAAGATCC TTTTTGATAA TCTCATGACC AAAATCCCTT    1440
AACGTGAGTT TTCGTTCCAC TGAGCGTCAG ACCCCGTAGA AAAGATCAAA GGATCTTCTT    1500
GAGATCCTTT TTTTCTGCGC GTAATCTGCT GCTTGCAAAC AAAAAAACCA CCGCTACCAG    1560
CGGTGGTTTG TTTGCCGGAT CAAGAGCTAC CAACTCTTTT TCCGAAGGTA ACTGGCTTCA    1620
GCAGAGCGCA GATACCAAAT ACTGTCCTTC TAGTGTAGCC GTAGTTAGGC CACCACTTCA    1680
AGAACTCTGT AGCACCGCCT ACATACCTCG CTCTGCTAAT CCTGTTACCA GTGGCTGCTG    1740
CCAGTGGCGA TAAGTCGTGT CTTACCGGGT TGGACTCAAG ACGATAGTTA CCGGATAAGG    1800
CGCAGCGGTC GGGCTGAACG GGGGGTTCGT GCACACAGCC CAGCTTGGAG CGAACGACCT    1860
ACACCGAACT GAGATACCTA CAGCGTGAGC ATTGAGAAAG CGCCACGCTT CCCGAAGGGA    1920
GAAAGGCGGA CAGGTATCCG GTAAGCGGCA GGGTCGGAAC AGGAGAGCGC ACGAGGGAGC    1980
TTCCAGGGGG AAACGCCTGG TATCTTTATA GTCCTGTCGG GTTTCGCCAC CTCTGACTTG    2040
AGCGTCGATT TTTGTGATGC TCGTCAGGGG GGCGGAGCCT ATGGAAAAAC GCCAGCAACG    2100
CGGCCTTTTT ACGGTTCCTG GCCTTTTGCT GGCCTTTTGC TCACATGTTC TTTCCTGCGT    2160
TATCCCCTGA TTCTGTGGAT AACCGTATTA CCGCCTTTGA GTGAGCTGAT ACCGCTCGCC    2220
GCAGCCGAAC GACCGAGCGC AGCGAGTCAG TGAGCGAGGA AGCGGAAGAG CGCCCAATAC    2280
GCAAACCGCC TCTCCCCGCG CGTTGGCCGA TTCATTAATG CAGGTTAACC TGGCTTATCG    2340
```

```
AAATTAATAC GACTCACTAT AGGGAGACCG GCCTCGAGCA GCTGAAGCTT TGGGTTTCTG    2400

ATAGGCACTG ACTCTCTCTG CCTATTGGTC TATTTTCCCA CCCTTAGGCT GCTGGTGGTC    2460

TACCCTTGGA CCCAGAGGTT CTTTGAGTCC TTTGGGGATC TGTCCACTCC TGATGCTGTT    2520

ATGGGCAACC CTAAGGTGAA GGCTCATGGC AAGAAAGTGC TCGGTGCCTT TAGTGATGGC    2580

CTGGCTCACC TGGACAACCT CAAGGGCACC TTTGCCACAC TGAGTGAGCT GCACTGTGAC    2640

AAGCTGCACG TGGATCCCCC TGAAGCTTGC TTACATTTGC TTCTGACACA ACTGTGTTCA    2700

CTAGCAACCT CAAACAGACA CCATGGTGCA CCTGACTCCT GAGGAGAAGT CTGCCGTTAC    2760

TGCCCTGTGG GGCAAGGTGA ACGTGGATGA AGTTGGTGGT GAGGCCCTGG GCAGGTTGGT    2820

ATCAAGGTTA CAAGACAGGT TTAAGGAGAC CAATAGAAAC TGGGCATGTG GAGACAGAGA    2880

AGACTCTTGG GATCCCCGGG TACCGAGCTC GAATTCATCG ATGATATCAG ATCTGGTTC    2939
```

(2) INFORMATION FOR SEQ ID NO:18:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA oligonucleotide"

(vii) IMMEDIATE SOURCE:
        (B) CLONE: DNA oligonucleotide used as splint for
            ligation of RNA ends (xi) SEQUENCE DESCRIPTION: SEQ ID NO:18:

```
CGAGGCCGGT CTCCCAATTC GAGCTCGGTA C                                      31
```

(2) INFORMATION FOR SEQ ID NO:19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA primer"

(vii) IMMEDIATE SOURCE:
        (B) CLONE: CIR-1

(xi) SEQUENCE DESCRIPTION: SEQ ID NO:19:

```
GAGTGGACAG ATCCCCAAAG GACTC                                             25
```

(2) INFORMATION FOR SEQ ID NO:20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA primer"

(vii) IMMEDIATE SOURCE:
        (B) CLONE: CIR-2

(xi) SEQUENCE DESCRIPTION: SEQ ID NO:20:

```
GTGATGCCTG GCTCACCTGG ACAA                                              24
```

(2) INFORMATION FOR SEQ ID NO:21:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA primer"

(vii) IMMEDIATE SOURCE:
        (B) CLONE: Group A human heavy chain (xi) SEQUENCE DESCRIPTION: SEQ ID NO:21:

GGGAATTCAT GGACTGGACC TGGAGGRTCY TCTK                                  34

(2) INFORMATION FOR SEQ ID NO:22:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA primer"

(vii) IMMEDIATE SOURCE:
        (B) CLONE: Group B human heavy chain (xi) SEQUENCE DESCRIPTION: SEQ ID NO:22:

GGGAATTCAT GGAGYTTGGG CTGASCTGGS TTTT                                  34

(2) INFORMATION FOR SEQ ID NO:23:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA primer"

(vii) IMMEDIATE SOURCE:
        (B) CLONE: Group C human heavy chain (xi) SEQUENCE DESCRIPTION: SEQ ID NO:23:

GGGAATTCAT GRAMMWACTK TGKWSWYSCT YCTG                                  34

(2) INFORMATION FOR SEQ ID NO:24:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA primer"

(vii) IMMEDIATE SOURCE:
        (B) CLONE: Human kappa light chain (xi) SEQUENCE DESCRIPTION: SEQ ID NO:24:

GGGAATTCAT GGACATGRRR DYCCHVYKCA SCTT                                  34

(2) INFORMATION FOR SEQ ID NO:25:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA primer"

(vii) IMMEDIATE SOURCE:
        (B) CLONE: Human lambda light chain (xi) SEQUENCE DESCRIPTION: SEQ ID NO:25:

GGGAATTCAT GRCCTGSWCY CCTCTCYTYC TSWYC                         35

(2) INFORMATION FOR SEQ ID NO:26:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA primer"

(vii) IMMEDIATE SOURCE:
        (B) CLONE: Human IgM heavy chain (xi) SEQUENCE DESCRIPTION: SEQ ID NO:26:

CCAAGCTTAG ACGAGGGGGA AAAGGGTT                                 28

(2) INFORMATION FOR SEQ ID NO:27:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA primer"

(vii) IMMEDIATE SOURCE:
        (B) CLONE: Human IgG1 heavy chain (xi) SEQUENCE DESCRIPTION: SEQ ID NO:27:

CCAAGCTTGG AGGAGGGTGC CAGGGGG                                  27

(2) INFORMATION FOR SEQ ID NO:28:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA primer"

(vii) IMMEDIATE SOURCE:
        (B) CLONE: Huam lambda light cjain (xi) SEQUENCE DESCRIPTION: SEQ ID NO:28:

CCAAGCTTGA AGCTCCTCAG AGGAGGG                                  27

(2) INFORMATION FOR SEQ ID NO:29:

(i) SEQUENCE CHARACTERISTICS:
        (A) LENGTH: 33 base pairs
        (B) TYPE: nucleic acid

```
        (C) STRANDEDNESS: single
        (D) TOPOLOGY: linear (ii) MOLECULE TYPE: other nucleic acid
        (A) DESCRIPTION: /desc = "DNA primer"

(vii) IMMEDIATE SOURCE:
        (B) CLONE: Group A murine leader region (xi) SEQUENCE DESCRIPTION: SEQ ID NO:29:

GGGGAATTCA TGRASTTSKG GYTMARCTKG RTT                                  33

(2) INFORMATION FOR SEQ ID NO:30:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA primer"

(vii) IMMEDIATE SOURCE:
        (B) CLONE: Group B murine leader region (xi) SEQUENCE DESCRIPTION: SEQ ID NO:30:

GGGGAATTCA TGRAATGSAS CTGGGTYWTY CTCT                                 34

(2) INFORMATION FOR SEQ ID NO:31:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA primer"

(vii) IMMEDIATE SOURCE:
        (B) CLONE: Murine framework 1 region (xi) SEQUENCE DESCRIPTION: SEQ ID NO:31:

GGGGAATTCS AGGTGMAGCT CSWRSARYCS GGG                                  33

(2) INFORMATION FOR SEQ ID NO:32:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA primer"

(vii) IMMEDIATE SOURCE:
        (B) CLONE: Murine gamma constant region (xi) SEQUENCE DESCRIPTION: SEQ ID NO:32:

GGAAGCTTAY CTCCACACAC AGGRRCCAGT GGATAGAC                             38

(2) INFORMATION FOR SEQ ID NO:33:

(i) SEQUENCE CHARACTERISTICS:
        (A) LENGTH: 28 base pairs
        (B) TYPE: nucleic acid
        (C) STRANDEDNESS: single
        (D) TOPOLOGY: linear
```

-continued

```
        (ii) MOLECULE TYPE: other nucleic acid
              (A) DESCRIPTION: /desc = "DNA primer"

(vii) IMMEDIATE SOURCE:
              (B) CLONE: Murine kappa light chain (xi) SEQUENCE DESCRIPTION: SEQ ID NO:33:

GGAAGCTTAC TGGATGGTGG GAAGATGG                                            28

(2) INFORMATION FOR SEQ ID NO:34:

(i) SEQUENCE CHARACTERISTICS:
              (A) LENGTH: 16 base pairs
              (B) TYPE: nucleic acid
              (C) STRANDEDNESS: Not Relevant
              (D) TOPOLOGY: unknown (ii) MOLECULE TYPE: other nucleic acid
              (A) DESCRIPTION: /desc = "DNA"

(vii) IMMEDIATE SOURCE:
              (B) CLONE: nucleotide sequence of fusion point (xi) SEQUENCE DESCRIPTION: SEQ ID NO:34:

ATCCGGATAC CTGCGG                                                         16

(2) INFORMATION FOR SEQ ID NO:35:

(i) SEQUENCE CHARACTERISTICS:
              (A) LENGTH: 10 base pairs
              (B) TYPE: nucleic acid
              (C) STRANDEDNESS: single
              (D) TOPOLOGY: unknown (ii) MOLECULE TYPE: other nucleic acid
              (A) DESCRIPTION: /desc = "RNA"

(vii) IMMEDIATE SOURCE:
              (B) CLONE: ligated rRNA exons (xi) SEQUENCE DESCRIPTION: SEQ ID NO:35:

CUCUCUUAAG                                                                10

(2) INFORMATION FOR SEQ ID NO:36:

(i) SEQUENCE CHARACTERISTICS:
              (A) LENGTH: 13 base pairs
              (B) TYPE: nucleic acid
              (C) STRANDEDNESS: single
              (D) TOPOLOGY: both (ii) MOLECULE TYPE: other nucleic acid
              (A) DESCRIPTION: /desc = "Ribozyme"

(vii) IMMEDIATE SOURCE:
              (B) CLONE: attack point for reverse group I splicing
                    reaction (xi) SEQUENCE DESCRIPTION: SEQ ID NO:36:

GGCUCUCUAA AAA                                                            13

(2) INFORMATION FOR SEQ ID NO:37:

(i) SEQUENCE CHARACTERISTICS:
              (A) LENGTH: 33 base pairs
              (B) TYPE: nucleic acid
              (C) STRANDEDNESS: single
              (D) TOPOLOGY: Not Relevant (ii) MOLECULE TYPE: other nucleic acid
              (A) DESCRIPTION: /desc = "Ribozyme"
```

```
    (vii) IMMEDIATE SOURCE:
          (B) CLONE: Group IIB intron domain V (xi) SEQUENCE DESCRIPTION: SEQ ID NO:37:

RAGCURAUGA NNNNAAANUN UCAYGUMUUG UUY                               33

(2) INFORMATION FOR SEQ ID NO:38:

(i) SEQUENCE CHARACTERISTICS:
        (A) LENGTH: 34 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "Ribozyme"

(vii) IMMEDIATE SOURCE:
        (B) CLONE: Group IIA intron domain V (xi) SEQUENCE DESCRIPTION: SEQ ID NO:38:

RAGCNNNRUR CRRNGAAANY YGYANGYNNN GUUY                              34

(2) INFORMATION FOR SEQ ID NO:39:

(i) SEQUENCE CHARACTERISTICS:
        (A) LENGTH: 10 base pairs
        (B) TYPE: nucleic acid
        (C) STRANDEDNESS: double
        (D) TOPOLOGY: Not Relevant (ii) MOLECULE TYPE: other nucleic acid
        (A) DESCRIPTION: /desc = "DNA construct"

(vii) IMMEDIATE SOURCE:
        (B) CLONE: Fn(1-3) ligation point (xi) SEQUENCE DESCRIPTION: SEQ ID NO:39:

TCAAAGAGCG                                                         10

(2) INFORMATION FOR SEQ ID NO:40:

(i) SEQUENCE CHARACTERISTICS:
        (A) LENGTH: 10 base pairs
        (B) TYPE: nucleic acid
        (C) STRANDEDNESS: double
        (D) TOPOLOGY: Not Relevant (ii) MOLECULE TYPE: other nucleic acid
        (A) DESCRIPTION: /desc = "DNA construct"

(vii) IMMEDIATE SOURCE:
        (B) CLONE: (5,6)Prot ligation point (xi) SEQUENCE DESCRIPTION: SEQ ID NO:40:

GGGATACCTG                                                         10

(2) INFORMATION FOR SEQ ID NO:41:

(i) SEQUENCE CHARACTERISTICS:
        (A) LENGTH: 16 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "RNA"

(vii) IMMEDIATE SOURCE:
        (B) CLONE: PY1 exon sequence
```

```
       (xi) SEQUENCE DESCRIPTION: SEQ ID NO:41:

GUGGUGGGAC AUUUUC                                                    16

(2) INFORMATION FOR SEQ ID NO:42:

(i) SEQUENCE CHARACTERISTICS:
            (A) LENGTH: 15 base pairs
            (B) TYPE: nucleic acid
            (C) STRANDEDNESS: single
            (D) TOPOLOGY: Not Relevant (ii) MOLECULE TYPE: other nucleic acid
            (A) DESCRIPTION: /desc = "RNA"

(vii) IMMEDIATE SOURCE:
            (B) CLONE: PY2 and PY3 exon sequence (xi) SEQUENCE DESCRIPTION: SEQ ID NO:42:

GUGGUGGAUG UCAAA                                                     15

(2) INFORMATION FOR SEQ ID NO:43:

(i) SEQUENCE CHARACTERISTICS:
            (A) LENGTH: 16 base pairs
            (B) TYPE: nucleic acid
            (C) STRANDEDNESS: single
            (D) TOPOLOGY: Not Relevant (ii) MOLECULE TYPE: other nucleic acid
            (A) DESCRIPTION: /desc = "RNA"

(vii) IMMEDIATE SOURCE:
            (B) CLONE: PY4 exon sequence (xi) SEQUENCE DESCRIPTION: SEQ ID NO:43:

GUGGUGGGAU GUCAAA                                                    16

(2) INFORMATION FOR SEQ ID NO:44:

(i) SEQUENCE CHARACTERISTICS:
            (A) LENGTH: 15 base pairs
            (B) TYPE: nucleic acid
            (C) STRANDEDNESS: single
            (D) TOPOLOGY: Not Relevant (ii) MOLECULE TYPE: other nucleic acid
            (A) DESCRIPTION: /desc = "RNA"

(vii) IMMEDIATE SOURCE:
            (B) CLONE: PY5 and PY6 exon sequence (xi) SEQUENCE DESCRIPTION: SEQ ID NO:44:

CUCGUGGAUG UCAAA                                                     15

(2) INFORMATION FOR SEQ ID NO:45:

(i) SEQUENCE CHARACTERISTICS:
            (A) LENGTH: 16 base pairs
            (B) TYPE: nucleic acid
            (C) STRANDEDNESS: single
            (D) TOPOLOGY: Not Relevant (ii) MOLECULE TYPE: other nucleic acid
            (A) DESCRIPTION: /desc = "RNA"

(vii) IMMEDIATE SOURCE:
            (B) CLONE: PY7 exon sequence (xi) SEQUENCE DESCRIPTION: SEQ ID NO:45:
```

-continued

```
UGUGCCGGAC UGCUCC                                                    16

(2) INFORMATION FOR SEQ ID NO:46:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "RNA"

(vii) IMMEDIATE SOURCE:
        (B) CLONE: PY8 and PY9 exon sequence (xi) SEQUENCE DESCRIPTION: SEQ ID NO:46:

UGCCUGCUCU GAGGGA                                                    16
```